(12) United States Patent
Buchanan et al.

(10) Patent No.: US 10,117,889 B2
(45) Date of Patent: Nov. 6, 2018

(54) ANTIBODIES SPECIFIC FOR LOX1 AND USE IN TREATMENT OF CARDIOVASCULAR DISORDERS

(71) Applicant: MedImmune Limited, Cambridge (GB)

(72) Inventors: Andrew Buchanan, Cambridge (GB); Matthieu Chodorge, Cambridge (GB); Peter Cariuk, Cambridge (GB); Johanna Husmark, Macclesfield (GB); Clare Balendran, Molndal (SE); Deepesh Pandey, Baltimore, MD (US); Fumin Chang, Baltimore, MD (US); Daniel E. Berkowitz, Baltimore, MD (US); Lewis H. Romer, Baltimore, MD (US)

(73) Assignee: MedImmune Limited, Cambridge (GB)

(*) Notice: Subject to any disclaimer, the term of this patent is extended or adjusted under 35 U.S.C. 154(b) by 0 days.

(21) Appl. No.: 15/516,115

(22) PCT Filed: Sep. 30, 2015

(86) PCT No.: PCT/EP2015/072644
§ 371 (c)(1),
(2) Date: Mar. 31, 2017

(87) PCT Pub. No.: WO2016/050889
PCT Pub. Date: Apr. 7, 2016

(65) Prior Publication Data
US 2017/0304343 A1    Oct. 26, 2017

Related U.S. Application Data

(60) Provisional application No. 62/058,254, filed on Oct. 1, 2014.

(51) Int. Cl.
| | |
|---|---|
| *C07K 16/28* | (2006.01) |
| *A61K 39/395* | (2006.01) |
| *A61P 9/10* | (2006.01) |
| *A61P 9/12* | (2006.01) |
| *A61P 9/04* | (2006.01) |
| *A61K 31/7068* | (2006.01) |
| *C07K 16/30* | (2006.01) |
| *C12N 5/095* | (2010.01) |
| *G01N 33/574* | (2006.01) |
| *C12N 5/00* | (2006.01) |
| *G01N 33/00* | (2006.01) |
| *A61K 39/00* | (2006.01) |
| *C07K 14/47* | (2006.01) |

(52) U.S. Cl.
CPC ........ *A61K 31/7068* (2013.01); *A61K 39/395* (2013.01); *A61P 9/04* (2018.01); *A61P 9/10* (2018.01); *A61P 9/12* (2018.01); *C07K 16/2851* (2013.01); *C07K 16/30* (2013.01); *C12N 5/0695* (2013.01); *G01N 33/574* (2013.01); *A61K 2039/505* (2013.01); *C07K 14/47* (2013.01); *C07K 2317/76* (2013.01); *C07K 2318/00* (2013.01); *C12N 5/00* (2013.01); *G01N 33/00* (2013.01)

(58) Field of Classification Search
None
See application file for complete search history.

(56) References Cited

U.S. PATENT DOCUMENTS

| 2008/0241134 A1 | 10/2008 | Kobayashi et al. |
| 2009/0311271 A1 | 12/2009 | Harnish et al. |

FOREIGN PATENT DOCUMENTS

| EP | 2444492 A1 | 4/2012 |
| WO | WO 2014/205300 A2 | 12/2014 |
| WO | WO 2014/205302 A2 | 12/2014 |

OTHER PUBLICATIONS

Mehta et al, 2011. Cardiovasc Drugs Ther. 25:495-500.*
Kunik, et al., "Structural consensus among antibodies defines the antigen binding site", PLoS Comput Biol. 2012;8(2):e1002388, p. 1-12.
Oganesyan, et al., "Structural characterization of a human Fc fragment engineered for lack of effector functions", Acta Crystallogr D Biol Crystallogr. Jun. 2008;D64, p. 700-704.
De Vos, et al., "Specific targeting of atherosclerotic plaques in ApoE(-/-) mice using a new Camelid sdAb binding the vulnerable plaque marker LOX-1", Mol Imaging Biol. Oct. 2014;16(5), p. 690-698.

* cited by examiner

*Primary Examiner* — Zachary C Howard

(57) ABSTRACT

This disclosure provides LOX1 (LOX1) binding proteins such as anti-LOX1 antibodies, and compositions and methods for making these binding proteins. In certain aspects the LOX1-binding proteins provided herein, inhibit, or antagonize LOX1 activity. In addition, the disclosure provides compositions and methods for diagnosing and treating conditions associated with atherosclerosis, thrombosis, coronary artery disease (CAD), ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia, cancer and other LOX1-mediated diseases and conditions.

Figure 1A:
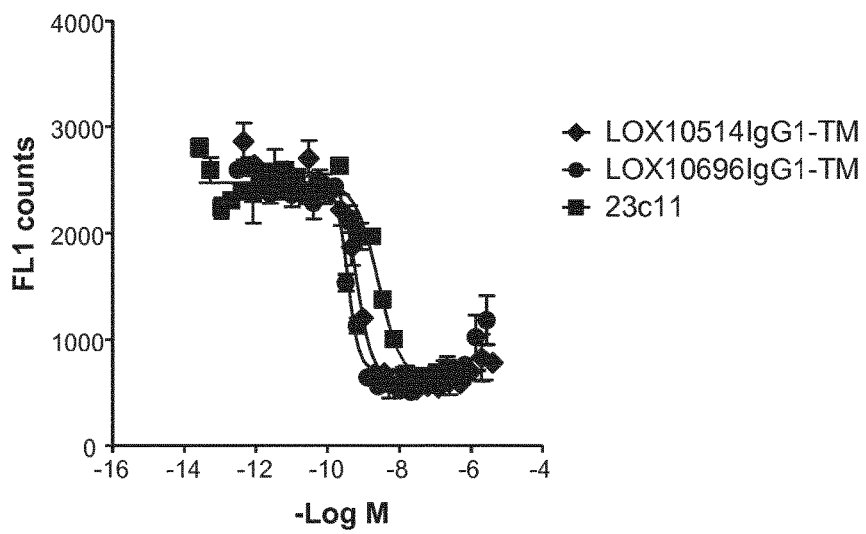

20 Claims, 22 Drawing Sheets
Specification includes a Sequence Listing.

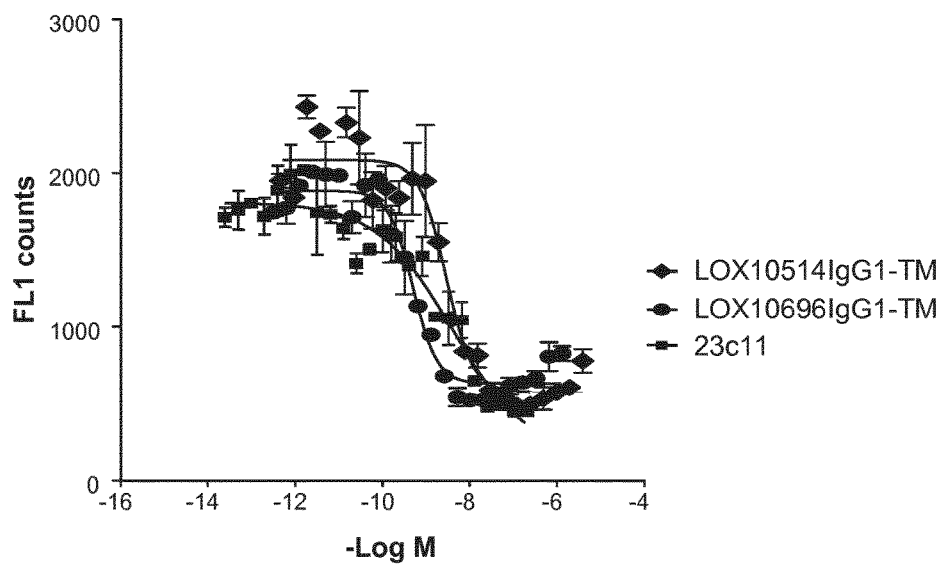
Figure 2A
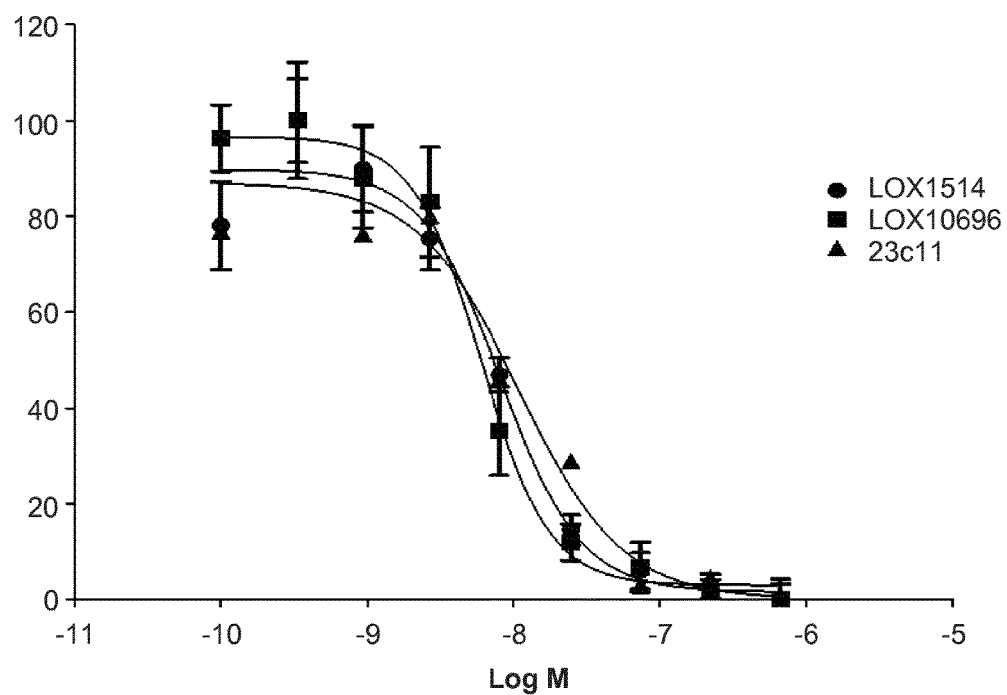
Figure 2B (ROS)

FIGURE 9E Superoxide Production in HAEC with Luminol Analog

SEQUENCE LISTING

<160> NUMBER OF SEQ ID NOS: 82

<210> SEQ ID NO 1
<211> LENGTH: 5
<212> TYPE: PRT
<213> ORGANISM: Artificial Sequence
<220> FEATURE:
<223> OTHER INFORMATION: Lox514 CDR-1 Heavy Chain sequence

<400> SEQUENCE: 1

Glu Leu Ser Met His
1               5

<210> SEQ ID NO 2
<211> LENGTH: 17
<212> TYPE: PRT
<213> ORGANISM: Artificial Sequence
<220> FEATURE:
<223> OTHER INFORMATION: LX5140110 CDR-2 Heavy Chain sequence

<400> SEQUENCE: 2

Gly Phe Asp Pro Glu Asp Phe Lys Tyr His Thr His Gln Lys Phe Gln
1               5                   10                  15

Gly

<210> SEQ ID NO 3
<211> LENGTH: 20
<212> TYPE: PRT
<213> ORGANISM: Artificial Sequence
<220> FEATURE:
<223> OTHER INFORMATION: LX5140110 CDR-3 Heavy Chain sequence

<400> SEQUENCE: 3

Val Trp Gly Thr Gln Gly Lys Gly Val Arg Gly Trp Asp Tyr Tyr Tyr
1               5                   10                  15

Gly Met Asp Val
            20

<210> SEQ ID NO 4
<211> LENGTH: 129
<212> TYPE: PRT
<213> ORGANISM: Artificial Sequence
<220> FEATURE:
<223> OTHER INFORMATION: LX5140110 Heavy Chain sequence

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Phe Lys Tyr His Thr His Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Leu Val Trp Gly Thr Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser

<210> SEQ ID NO 5
<211> LENGTH: 17
<212> TYPE: PRT
<213> ORGANISM: Artificial Sequence
<220> FEATURE:
<223> OTHER INFORMATION: Lox514 CDR-2 Heavy Chain sequence

<400> SEQUENCE: 5

Gly Phe Asp Pro Glu Asp Gly Glu Thr Ile Tyr Ala Gln Lys Phe Gln
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: LX5140011 CDR-2 Heavy Chain sequence

<400> SEQUENCE: 6

Gly Phe Asp Pro Glu Asp Trp Glu Tyr Ala Tyr Asp Gln Lys Phe Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: LX5140014 CDR-2 Heavy Chain sequence

<400> SEQUENCE: 7

Gly Phe Asp Pro Glu Asp Tyr Thr Ile Arg Val Gly Gln Lys Phe Gln
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: LX5140016 CDR-2 Heavy Chain sequence

<400> SEQUENCE: 8

Gly Phe Asp Pro Glu Asp Trp Gln Thr His Thr Ala Gln Lys Phe Gln
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: LX5140038 CDR-2 Heavy Chain sequence

<400> SEQUENCE: 9

Gly Phe Asp Pro Glu Asp Trp Thr Ile His Val Asp Gln Lys Phe Gln
1               5                   10                  15

Gly

```
<210> SEQ ID NO 10
<211> LENGTH: 17
<212> TYPE: PRT
<213> ORGANISM: Artificial Sequence
<220> FEATURE:
<223> OTHER INFORMATION: LX5140094 CDR-2 Heavy Chain sequence

<400> SEQUENCE: 10

Gly Phe Asp Pro Glu Asp Trp Gln Tyr His Val Ser Gln Lys Phe Gln
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: LX5140108 CDR-2 Heavy Chain sequence

<400> SEQUENCE: 11

Gly Phe Asp Pro Glu Asp Trp Ser Asn His Val Ser Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: LX5140092 CDR-2 Heavy Chain sequence

<400> SEQUENCE: 12

Gly Phe Asp Pro Glu Asp Trp Lys Tyr His Leu Ser Gln Lys Phe Gln
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: LX5140093 CDR-2 Heavy Chain sequence

<400> SEQUENCE: 13

Gly Phe Asp Pro Glu Asp Trp Ala Tyr His Gln Ala Gln Lys Phe Gln
1               5                   10                  15

Gly

<210> SEQ ID NO 14
<211> LENGTH: 20
<212> TYPE: PRT
<213> ORGANISM: Artificial Sequence
<220> FEATURE:
<223> OTHER INFORMATION: LX5140011 CDR-3 Heavy Chain sequence

<400> SEQUENCE: 14

Pro Asn Gly Gln Gln Gly Lys Gly Val Arg Gly Trp Asp Tyr Tyr Tyr
1               5                   10                  15

Gly Met Asp Val
            20

<210> SEQ ID NO 15
<211> LENGTH: 20
<212> TYPE: PRT
```

<213> ORGANISM: Artificial Sequence
<220> FEATURE:
<223> OTHER INFORMATION: LX5140108 CDR-3 Heavy Chain sequence

<400> SEQUENCE: 15

```
Ser Thr Gly Arg Gln Gly Lys Gly Val Arg Gly Trp Asp Tyr Tyr Tyr
1               5                   10                  15

Gly Met Asp Val
            20
```

<210> SEQ ID NO 16
<211> LENGTH: 20
<212> TYPE: PRT
<213> ORGANISM: Artificial Sequence
<220> FEATURE:
<223> OTHER INFORMATION: LX5140092_D CDR-3 Heavy Chain sequence

<400> SEQUENCE: 16

```
Pro Asp Gly Thr His Gln Gly Gly Val Arg Gly Trp Asp Tyr Tyr Tyr
1               5                   10                  15

Gly Met Asp Val
            20
```

<210> SEQ ID NO 17
<211> LENGTH: 20
<212> TYPE: PRT
<213> ORGANISM: Artificial Sequence
<220> FEATURE:
<223> OTHER INFORMATION: LX5140092_N CDR-3 Heavy Chain sequence

<400> SEQUENCE: 17

```
Pro Asn Gly Thr His Gln Gly Gly Val Arg Gly Trp Asp Tyr Tyr Tyr
1               5                   10                  15

Gly Met Asp Val
            20
```

<210> SEQ ID NO 18
<211> LENGTH: 20
<212> TYPE: PRT
<213> ORGANISM: Artificial Sequence
<220> FEATURE:
<223> OTHER INFORMATION: LX5140093_D CDR-3 Heavy Chain sequence

<400> SEQUENCE: 18

```
Pro Asp Gly Gln Gln Gly Lys Gly Val Arg Gly Trp Asp Tyr Tyr Tyr
1               5                   10                  15

Gly Met Asp Val
            20
```

<210> SEQ ID NO 19
<211> LENGTH: 129
<212> TYPE: PRT
<213> ORGANISM: Artificial Sequence
<220> FEATURE:
<223> OTHER INFORMATION: LX5140011 Heavy Chain sequence

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45
```

Gly Gly Phe Asp Pro Glu Asp Trp Glu Tyr Ala Tyr Asp Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
                100                 105                 110

Tyr Tyr Gly Met Asp Val Trp Gly Gln Gly Thr Thr Val Thr Val Ser
            115                 120                 125

Ser

<210> SEQ ID NO 20
<211> LENGTH: 129
<212> TYPE: PRT
<213> ORGANISM: Artificial Sequence
<220> FEATURE:
<223> OTHER INFORMATION: LX5140014 Heavy Chain sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Tyr Thr Ile Arg Val Gly Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
                100                 105                 110

Tyr Tyr Gly Met Asp Val Trp Gly Gln Gly Thr Thr Val Thr Val Ser
            115                 120                 125

Ser

<210> SEQ ID NO 21
<211> LENGTH: 129
<212> TYPE: PRT
<213> ORGANISM: Artificial Sequence
<220> FEATURE:
<223> OTHER INFORMATION: LX5140016 Heavy Chain sequence

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Gln Thr His Thr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys

```
                    85                  90                  95

Ala Thr Pro Asn Gly Gln Gln Gly Lys Gly Val Arg Gly Trp Asp Tyr
                100                 105                 110

Tyr Tyr Gly Met Asp Val Trp Gly Gln Gly Thr Thr Val Thr Val Ser
            115                 120                 125

Ser

<210> SEQ ID NO 22
<211> LENGTH: 129
<212> TYPE: PRT
<213> ORGANISM: Artificial Sequence
<220> FEATURE:
<223> OTHER INFORMATION: LX5140038 Heavy Chain sequence

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Trp Thr Ile His Val Asp Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
                100                 105                 110

Tyr Tyr Gly Met Asp Val Trp Gly Gln Gly Thr Thr Val Thr Val Ser
            115                 120                 125

Ser

<210> SEQ ID NO 23
<211> LENGTH: 129
<212> TYPE: PRT
<213> ORGANISM: Artificial Sequence
<220> FEATURE:
<223> OTHER INFORMATION: LX5140094 Heavy Chain sequence

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Trp Gln Tyr His Val Ser Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Gln Gln Gly Lys Gly Val Arg Gly Trp Asp Tyr
                100                 105                 110

Tyr Tyr Gly Met Asp Val Trp Gly Gln Gly Thr Thr Val Thr Val Ser
            115                 120                 125
```

Ser

<210> SEQ ID NO 24
<211> LENGTH: 129
<212> TYPE: PRT
<213> ORGANISM: Artificial Sequence
<220> FEATURE:
<223> OTHER INFORMATION: LX5140108 Heavy Chain sequence

<400> SEQUENCE: 24

Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Trp Ser Asn His Val Ser Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Leu Thr Ser Thr Gly Arg Gln Gly Lys Gly Val Arg Gly Trp Asp Tyr
            100                 105                 110
Tyr Tyr Gly Met Asp Val Trp Gly Gln Gly Thr Thr Val Thr Val Ser
        115                 120                 125
Ser

<210> SEQ ID NO 25
<211> LENGTH: 129
<212> TYPE: PRT
<213> ORGANISM: Artificial Sequence
<220> FEATURE:
<223> OTHER INFORMATION: LX5140092_D Heavy Chain sequence

<400> SEQUENCE: 25

Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Trp Lys Tyr His Leu Ser Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Pro Asp Gly Thr His Gly Gly Val Arg Gly Trp Asp Tyr
            100                 105                 110
Tyr Tyr Gly Met Asp Val Trp Gly Gln Gly Thr Thr Val Thr Val Ser
        115                 120                 125
Ser

<210> SEQ ID NO 26
<211> LENGTH: 129
<212> TYPE: PRT

<213> ORGANISM: Artificial Sequence
<220> FEATURE:
<223> OTHER INFORMATION: LX5140092_N Heavy Chain sequence

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Lys Tyr His Leu Ser Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asn Gly Thr His Gly Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser
```

<210> SEQ ID NO 27
<211> LENGTH: 129
<212> TYPE: PRT
<213> ORGANISM: Artificial Sequence
<220> FEATURE:
<223> OTHER INFORMATION: LX5140093_D Heavy Chain sequence

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Trp Ala Tyr His Gln Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Asp Gly Gln Gln Gly Lys Gly Val Arg Gly Trp Asp Tyr
            100                 105                 110

Tyr Tyr Gly Met Asp Val Trp Gly Gln Gly Thr Thr Val Thr Val Ser
        115                 120                 125

Ser
```

<210> SEQ ID NO 28
<211> LENGTH: 129
<212> TYPE: PRT
<213> ORGANISM: Artificial Sequence
<220> FEATURE:
<223> OTHER INFORMATION: LX5140093_N Heavy Chain sequence

<400> SEQUENCE: 28

```
Gln Val Gln Leu Val Gln Ser Gly Ala Glu Val Lys Lys Pro Gly Ala
```

```
                1               5                  10                  15
        Ser Val Lys Val Ser Cys Lys Val Ser Gly Tyr Thr Leu Thr Glu Leu
                        20                  25                  30

Ser Met His Trp Val Arg Gln Ala Pro Gly Lys Gly Leu Glu Trp Met
                        35                  40                  45

Gly Gly Phe Asp Pro Glu Asp Trp Ala Tyr His Gln Ala Gln Lys Phe
                        50                  55                  60

Gln Gly Arg Val Thr Met Thr Glu Asp Thr Ser Thr Asp Thr Ala Tyr
        65                  70                  75                  80

Met Glu Leu Ser Ser Leu Arg Ser Glu Asp Thr Ala Val Tyr Tyr Cys
                        85                  90                  95

Ala Thr Pro Asn Gly Gln Gln Gly Lys Gly Val Arg Gly Trp Asp Tyr
                        100                 105                 110

Tyr Tyr Gly Met Asp Val Trp Gly Gln Gly Thr Thr Val Thr Val Ser
                        115                 120                 125

Ser

<210> SEQ ID NO 29
<211> LENGTH: 129
<212> TYPE: PRT
<213> ORGANISM: Artificial Sequence
<220> FEATURE:
<223> OTHER INFORMATION: Lox514 Heavy Chain sequence

<400> SEQUENCE: 29

Gln Val Gln Leu Val Gln Ser Gly Ala Glu Val Lys Lys Pro Gly Ala
        1               5                  10                  15

Ser Val Lys Val Ser Cys Lys Val Ser Gly Tyr Thr Leu Thr Glu Leu
                        20                  25                  30

Ser Met His Trp Val Arg Gln Ala Pro Gly Lys Gly Leu Glu Trp Met
                        35                  40                  45

Gly Gly Phe Asp Pro Glu Asp Gly Glu Thr Ile Tyr Ala Gln Lys Phe
                        50                  55                  60

Gln Gly Arg Val Thr Met Thr Glu Asp Thr Ser Thr Asp Thr Ala Tyr
        65                  70                  75                  80

Met Glu Leu Ser Ser Leu Arg Ser Glu Asp Thr Ala Val Tyr Tyr Cys
                        85                  90                  95

Ala Thr Pro Asn Gly Gln Gln Gly Lys Gly Val Arg Gly Trp Asp Tyr
                        100                 105                 110

Tyr Tyr Gly Met Asp Val Trp Gly Arg Gly Thr Thr Val Thr Val Ser
                        115                 120                 125

Ser

<210> SEQ ID NO 30
<211> LENGTH: 14
<212> TYPE: PRT
<213> ORGANISM: Artificial Sequence
<220> FEATURE:
<223> OTHER INFORMATION: Lox514 CDR-1 Light Chain sequence

<400> SEQUENCE: 30

Thr Gly Ser Ser Ser Asn Ile Gly Ala Gly Tyr Asp Val His
        1               5                  10

<210> SEQ ID NO 31
<211> LENGTH: 7
<212> TYPE: PRT
<213> ORGANISM: Artificial Sequence
```

```
<220> FEATURE:
<223> OTHER INFORMATION: Lox514 CDR-2 Light Chain sequence

<400> SEQUENCE: 31

Gly Asn Ser Asn Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Lox514 CDR-3 Light Chain sequence

<400> SEQUENCE: 32

Gln Ser Tyr Asp Ser Ser Leu Ser Gly Trp Val
1               5                   10

<210> SEQ ID NO 33
<211> LENGTH: 111
<212> TYPE: PRT
<213> ORGANISM: Artificial Sequence
<220> FEATURE:
<223> OTHER INFORMATION: LX5140110 Light Chain sequence

<400> SEQUENCE: 33

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu
            100                 105                 110

<210> SEQ ID NO 34
<211> LENGTH: 10
<212> TYPE: PRT
<213> ORGANISM: Artificial Sequence
<220> FEATURE:
<223> OTHER INFORMATION: LX5140094 CDR-3 Light Chain sequence

<400> SEQUENCE: 34

Gln Ser Tyr Asp Ser Met Tyr Arg Phe Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: LX5140093 CDR-3 Light Chain sequence

<400> SEQUENCE: 35

Gln Ser Tyr Asp Ser Ser His Arg Ala Trp Ala
1               5                   10
```

```
<210> SEQ ID NO 36
<211> LENGTH: 110
<212> TYPE: PRT
<213> ORGANISM: Artificial Sequence
<220> FEATURE:
<223> OTHER INFORMATION: LX5140094 Light Chain sequence

<400> SEQUENCE: 36
```

Gln Ser Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Met
                85                  90                  95

Tyr Arg Phe Gly Phe Gly Gly Gly Thr Lys Leu Thr Val Leu
            100                 105                 110

```
<210> SEQ ID NO 37
<211> LENGTH: 111
<212> TYPE: PRT
<213> ORGANISM: Artificial Sequence
<220> FEATURE:
<223> OTHER INFORMATION: LX5140093 Light Chain sequence

<400> SEQUENCE: 37
```

Gln Ser Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

His Arg Ala Trp Ala Phe Gly Gly Gly Thr Lys Leu Thr Val Leu
            100                 105                 110

```
<210> SEQ ID NO 38
<211> LENGTH: 5
<212> TYPE: PRT
<213> ORGANISM: Artificial Sequence
<220> FEATURE:
<223> OTHER INFORMATION: Lox696 CDR-1 Heavy Chain sequence

<400> SEQUENCE: 38
```

Asp Tyr Ala Met His
1               5

```
<210> SEQ ID NO 39
<211> LENGTH: 17
<212> TYPE: PRT
<213> ORGANISM: Artificial Sequence
```

```
<220> FEATURE:
<223> OTHER INFORMATION: Lox696 CDR-2 Heavy Chain sequence

<400> SEQUENCE: 39

Gly Ile Ser Trp Asn Ser Gly Ser Ile Gly Tyr Ala Asp Ser Val Lys
1               5                   10                  15

Gly

<210> SEQ ID NO 40
<211> LENGTH: 11
<212> TYPE: PRT
<213> ORGANISM: Artificial Sequence
<220> FEATURE:
<223> OTHER INFORMATION: LX6960073_G82bS_gl CDR-3 Heavy Chain sequence

<400> SEQUENCE: 40

Glu Gly Ser Trp Asn Tyr Asp Ala Leu Asp Ile
1               5                   10

<210> SEQ ID NO 41
<211> LENGTH: 120
<212> TYPE: PRT
<213> ORGANISM: Artificial Sequence
<220> FEATURE:
<223> OTHER INFORMATION: LX6960073_G82bS_gl Heavy Chain sequence

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ser Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Trp Asn Tyr Asp Ala Leu Asp Ile Trp Gly Gln
            100                 105                 110

Gly Thr Met Val Thr Val Ser Ser
        115                 120

<210> SEQ ID NO 42
<211> LENGTH: 17
<212> TYPE: PRT
<213> ORGANISM: Artificial Sequence
<220> FEATURE:
<223> OTHER INFORMATION: LX6960067_ng11 CDR-2 Heavy Chain sequence

<400> SEQUENCE: 42

Gly Val Ser Leu Gln Glu Leu Tyr Thr Gly Tyr Ala Asp Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: LX6960086_ng11 CDR-2 Heavy Chain sequence
```

<400> SEQUENCE: 43

Gly Ile Ser Trp Asn Ser Pro Asp Arg Tyr Met Asp Asp Ser Val Lys
1               5                   10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Lox696 CDR-3 Heavy Chain sequence

<400> SEQUENCE: 44

Glu Gly Asn Trp Asn Tyr Asp Ala Phe Asp Ile
1               5                   10

<210> SEQ ID NO 45
<211> LENGTH: 11
<212> TYPE: PRT
<213> ORGANISM: Artificial Sequence
<220> FEATURE:
<223> OTHER INFORMATION: LX6960067_ngl1 CDR-3 Heavy Chain sequence

<400> SEQUENCE: 45

Glu Gly Ser Trp Asn Tyr Asp Ala Phe Asp Ile
1               5                   10

<210> SEQ ID NO 46
<211> LENGTH: 11
<212> TYPE: PRT
<213> ORGANISM: Artificial Sequence
<220> FEATURE:
<223> OTHER INFORMATION: LX6960073_ngl1 CDR-3 Heavy Chain sequence

<400> SEQUENCE: 46

Glu Gly Ser Trp Asn Tyr Asp Ala Leu Asp Ile
1               5                   10

<210> SEQ ID NO 47
<211> LENGTH: 11
<212> TYPE: PRT
<213> ORGANISM: Artificial Sequence
<220> FEATURE:
<223> OTHER INFORMATION: LX6960101_ngl1 CDR-3 Heavy Chain sequence

<400> SEQUENCE: 47

Glu Gly Asn Trp Asn Tyr Asp Ala Phe Asp Val
1               5                   10

<210> SEQ ID NO 48
<211> LENGTH: 120
<212> TYPE: PRT
<213> ORGANISM: Artificial Sequence
<220> FEATURE:
<223> OTHER INFORMATION: LX6960067_ngl1 Heavy Chain sequence

<400> SEQUENCE: 48

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

```
Ser Gly Val Ser Leu Gln Glu Leu Tyr Thr Gly Tyr Ala Asp Ser Val
    50                  55                  60

Lys Gly Arg Phe Thr Val Ser Gly Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ser Trp Asn Tyr Asp Ala Phe Asp Ile Trp Gly Arg
                100                 105                 110

Gly Thr Thr Val Thr Val Ser Ser
            115                 120

<210> SEQ ID NO 49
<211> LENGTH: 120
<212> TYPE: PRT
<213> ORGANISM: Artificial Sequence
<220> FEATURE:
<223> OTHER INFORMATION: LX6960071_ng11 Heavy Chain sequence

<400> SEQUENCE: 49

Gln Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asp Ser Leu Arg Ala Glu Asp Thr Ala Val Tyr Tyr Cys
                 85                  90                  95

Ala Arg Glu Gly Asn Trp Asn Tyr Asp Ala Phe Asp Ile Trp Gly Arg
                100                 105                 110

Gly Thr Thr Val Thr Val Ser Ser
            115                 120

<210> SEQ ID NO 50
<211> LENGTH: 120
<212> TYPE: PRT
<213> ORGANISM: Artificial Sequence
<220> FEATURE:
<223> OTHER INFORMATION: LX6960073_ng11 Heavy Chain sequence

<400> SEQUENCE: 50

Gln Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Ser Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Gly Leu Arg Ala Glu Asp Thr Ala Val Tyr Tyr Cys
                 85                  90                  95

Ala Arg Glu Gly Ser Trp Asn Tyr Asp Ala Leu Asp Ile Trp Gly Arg
                100                 105                 110
```

```
Gly Thr Thr Val Thr Val Ser Ser
        115                 120

<210> SEQ ID NO 51
<211> LENGTH: 120
<212> TYPE: PRT
<213> ORGANISM: Artificial Sequence
<220> FEATURE:
<223> OTHER INFORMATION: LX6960086_ng11 Heavy Chain sequence

<400> SEQUENCE: 51

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Pro Asp Arg Tyr Met Asp Asp Ser Val
    50                  55                  60

Lys Gly Arg Phe Thr Ile Ser Arg Asp Asn Ala Gln Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Glu Gly Asn Trp Asn Tyr Asp Ala Phe Asp Ile Trp Gly Arg
            100                 105                 110

Gly Thr Thr Val Thr Val Ser Ser
        115                 120

<210> SEQ ID NO 52
<211> LENGTH: 120
<212> TYPE: PRT
<213> ORGANISM: Artificial Sequence
<220> FEATURE:
<223> OTHER INFORMATION: LX6960101_ng11 Heavy Chain sequence

<400> SEQUENCE: 52

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Gly Leu Arg Ala Glu Asp Thr Ala Val Tyr Tyr Cys
                85                  90                  95

Ala Arg Glu Gly Asn Trp Asn Tyr Asp Ala Phe Asp Val Trp Gly Arg
            100                 105                 110

Gly Thr Thr Val Thr Val Ser Ser
        115                 120

<210> SEQ ID NO 53
<211> LENGTH: 120
<212> TYPE: PRT
<213> ORGANISM: Artificial Sequence
<220> FEATURE:
<223> OTHER INFORMATION: LX6960073_g1 Heavy Chain sequence
```

<400> SEQUENCE: 53

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ser Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Gly Leu Arg Ala Glu Asp Thr Ala Val Tyr Tyr Cys
                85                  90                  95

Ala Arg Glu Gly Ser Trp Asn Tyr Asp Ala Leu Asp Ile Trp Gly Gln
            100                 105                 110

Gly Thr Met Val Thr Val Ser Ser
        115                 120

<210> SEQ ID NO 54
<211> LENGTH: 120
<212> TYPE: PRT
<213> ORGANISM: Artificial Sequence
<220> FEATURE:
<223> OTHER INFORMATION: Lox696 Heavy Chain sequence

<400> SEQUENCE: 54

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asn Trp Asn Tyr Asp Ala Phe Asp Ile Trp Gly Arg
            100                 105                 110

Gly Thr Thr Val Thr Val Ser Ser
        115                 120

<210> SEQ ID NO 55
<211> LENGTH: 14
<212> TYPE: PRT
<213> ORGANISM: Artificial Sequence
<220> FEATURE:
<223> OTHER INFORMATION: LX6960073_G82bS_gl CDR-1 Light Chain sequence

<400> SEQUENCE: 55

Thr Gly Thr Ser Ser Asp Val Gly Gly Tyr Asn Tyr Val Ser
1               5                   10

<210> SEQ ID NO 56
<211> LENGTH: 7
<212> TYPE: PRT
<213> ORGANISM: Artificial Sequence
<220> FEATURE:
<223> OTHER INFORMATION: LX6960073_G82bS_gl CDR-2 Light Chain sequence

<400> SEQUENCE: 56

Asp Val Ser Lys Arg Pro Ser
1               5

<210> SEQ ID NO 57
<211> LENGTH: 11
<212> TYPE: PRT
<213> ORGANISM: Artificial Sequence
<220> FEATURE:
<223> OTHER INFORMATION: LX6960073_G82bS_gl CDR-3 Light Chain sequence

<400> SEQUENCE: 57

Met Gly Gly Met Gly Arg Ser Thr Asn Trp Val
1               5                   10

<210> SEQ ID NO 58
<211> LENGTH: 111
<212> TYPE: PRT
<213> ORGANISM: Artificial Sequence
<220> FEATURE:
<223> OTHER INFORMATION: LX6960073_G82bS_gl Light Chain sequence

<400> SEQUENCE: 58

Gln Ser Ala Leu Thr Gln Pro Ala Ser Val Ser Gly Ser Pro Gly Gln
1               5                   10                  15

Pro Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Gly Met Gly Arg
                85                  90                  95

Ser Thr Asn Trp Val Phe Gly Gly Gly Thr Lys Leu Thr Val Leu
            100                 105                 110

<210> SEQ ID NO 59
<211> LENGTH: 14
<212> TYPE: PRT
<213> ORGANISM: Artificial Sequence
<220> FEATURE:
<223> OTHER INFORMATION: LX6960116_ngl1 CDR-1 Light Chain sequence

<400> SEQUENCE: 59

Thr Gly Thr Ser Asn Asp Val Gly Gly Tyr Asn Tyr Val Ser
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Lox696 CDR-2 Light Chain sequence

<400> SEQUENCE: 60

Asp Val Ser Asn Arg Pro Ser
1               5

```
<210> SEQ ID NO 61
<211> LENGTH: 11
<212> TYPE: PRT
<213> ORGANISM: Artificial Sequence
<220> FEATURE:
<223> OTHER INFORMATION: Lox696 CDR-3 Light Chain sequence

<400> SEQUENCE: 61

Ser Ser Tyr Thr Ser Ser Ser Thr Asn Trp Val
1               5                   10

<210> SEQ ID NO 62
<211> LENGTH: 11
<212> TYPE: PRT
<213> ORGANISM: Artificial Sequence
<220> FEATURE:
<223> OTHER INFORMATION: LX6960067_ngl1 CDR-3 Light Chain sequence

<400> SEQUENCE: 62

Leu Gly Arg Thr Trp Ser Ser Thr Asn Trp Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: LX6960071_ngl1 CDR-3 Light Chain sequence

<400> SEQUENCE: 63

Met Gly Ser Met Gly Arg Ser Thr Asn Trp Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: LX6960094_ngl1 CDR-3 Light Chain sequence

<400> SEQUENCE: 64

Ala Gln Arg Thr Val Ser Ser Thr Asn Trp Val
1               5                   10

<210> SEQ ID NO 65
<211> LENGTH: 111
<212> TYPE: PRT
<213> ORGANISM: Artificial Sequence
<220> FEATURE:
<223> OTHER INFORMATION: LX6960067_ngl1 Light Chain sequence

<400> SEQUENCE: 65

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Leu Gly Arg Thr Trp Ser
                85                  90                  95
```

```
Ser Thr Asn Trp Val Phe Gly Gly Gly Thr Lys Leu Thr Val Leu
            100                 105                 110
```

<210> SEQ ID NO 66
<211> LENGTH: 111
<212> TYPE: PRT
<213> ORGANISM: Artificial Sequence
<220> FEATURE:
<223> OTHER INFORMATION: LX6960071_ng11 Light Chain sequence

<400> SEQUENCE: 66

```
Gln Ser Ala Leu Thr Gln Pro Ala Ser Val Ser Gly Ser Pro Gly Gln
1               5                   10                  15

Pro Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Ser Met Gly Arg
                85                  90                  95

Ser Thr Asn Trp Val Phe Gly Gly Gly Thr Lys Leu Thr Val Leu
            100                 105                 110
```

<210> SEQ ID NO 67
<211> LENGTH: 111
<212> TYPE: PRT
<213> ORGANISM: Artificial Sequence
<220> FEATURE:
<223> OTHER INFORMATION: LX6960073_ng11 Light Chain sequence

<400> SEQUENCE: 67

```
Gln Ser Ala Leu Thr Gln Pro Ala Ser Val Ser Gly Ser Pro Gly Gln
1               5                   10                  15

Pro Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Gly Met Gly Arg
                85                  90                  95

Ser Thr Asn Trp Val Phe Gly Gly Gly Thr Lys Leu Thr Val Leu
            100                 105                 110
```

<210> SEQ ID NO 68
<211> LENGTH: 111
<212> TYPE: PRT
<213> ORGANISM: Artificial Sequence
<220> FEATURE:
<223> OTHER INFORMATION: LX6960094_ng11 Light Chain sequence

<400> SEQUENCE: 68

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
```

```
                    20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Gln Arg Thr Val Ser
                85                  90                  95

Ser Thr Asn Trp Val Phe Gly Gly Gly Thr Lys Leu Thr Val Leu
                100                 105                 110

<210> SEQ ID NO 69
<211> LENGTH: 111
<212> TYPE: PRT
<213> ORGANISM: Artificial Sequence
<220> FEATURE:
<223> OTHER INFORMATION: LX6960116_ng11 Light Chain sequence

<400> SEQUENCE: 69

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Met Gly Ser Met Gly Arg
                85                  90                  95

Ser Thr Asn Trp Val Phe Gly Gly Gly Thr Lys Leu Thr Val Leu
                100                 105                 110

<210> SEQ ID NO 70
<211> LENGTH: 111
<212> TYPE: PRT
<213> ORGANISM: Artificial Sequence
<220> FEATURE:
<223> OTHER INFORMATION: Lox696 Light Chain sequence

<400> SEQUENCE: 70

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Asn Trp Val Phe Gly Gly Gly Thr Lys Leu Thr Val Leu
                100                 105                 110
```

```
<210> SEQ ID NO 71
<211> LENGTH: 17
<212> TYPE: PRT
<213> ORGANISM: Artificial Sequence
<220> FEATURE:
<223> OTHER INFORMATION: Lox514 VH CDR2
<220> FEATURE:
<221> NAME/KEY: misc_feature
<222> LOCATION: (7)..(7)
<223> OTHER INFORMATION: Xaa is Gly, Trp, Tyr, or Phe
<220> FEATURE:
<221> NAME/KEY: misc_feature
<222> LOCATION: (8)..(8)
<223> OTHER INFORMATION: Xaa is Glu, Thr, Gln, Ser, Lys, or Ala
<220> FEATURE:
<221> NAME/KEY: misc_feature
<222> LOCATION: (9)..(9)
<223> OTHER INFORMATION: Xaa is Thr, Tyr, Ile, or Asn
<220> FEATURE:
<221> NAME/KEY: misc_feature
<222> LOCATION: (10)..(10)
<223> OTHER INFORMATION: Xaa is Ile, Ala, Arg, or His
<220> FEATURE:
<221> NAME/KEY: misc_feature
<222> LOCATION: (11)..(11)
<223> OTHER INFORMATION: Xaa is Tyr, Val, Thr, Leu, or Gln
<220> FEATURE:
<221> NAME/KEY: misc_feature
<222> LOCATION: (12)..(12)
<223> OTHER INFORMATION: Xaa is Ala, Asp, Gly, Ser, or His

<400> SEQUENCE: 71

Gly Phe Asp Pro Glu Asp Xaa Xaa Xaa Xaa Xaa Xaa Gln Lys Phe Gln
1               5                   10                  15

Gly

<210> SEQ ID NO 72
<211> LENGTH: 20
<212> TYPE: PRT
<213> ORGANISM: Artificial Sequence
<220> FEATURE:
<223> OTHER INFORMATION: Lox514 VH CDR3
<220> FEATURE:
<221> NAME/KEY: misc_feature
<222> LOCATION: (1)..(1)
<223> OTHER INFORMATION: Xaa is Pro, Ser, or Val
<220> FEATURE:
<221> NAME/KEY: misc_feature
<222> LOCATION: (2)..(2)
<223> OTHER INFORMATION: Xaa is Asn, Thr, Trp, or Asp
<220> FEATURE:
<221> NAME/KEY: misc_feature
<222> LOCATION: (4)..(4)
<223> OTHER INFORMATION: Xaa is Gln, Arg, or Thr
<220> FEATURE:
<221> NAME/KEY: misc_feature
<222> LOCATION: (5)..(5)
<223> OTHER INFORMATION: Xaa is Gln or His
<220> FEATURE:
<221> NAME/KEY: misc_feature
<222> LOCATION: (6)..(6)
<223> OTHER INFORMATION: Xaa is Gly or Gln
<220> FEATURE:
<221> NAME/KEY: misc_feature
<222> LOCATION: (7)..(7)
<223> OTHER INFORMATION: Xaa is Lys or Gly

<400> SEQUENCE: 72

Xaa Xaa Gly Xaa Xaa Xaa Xaa Gly Val Arg Gly Trp Asp Tyr Tyr Tyr
1               5                   10                  15

Gly Met Asp Val
            20
```

```
<210> SEQ ID NO 73
<211> LENGTH: 11
<212> TYPE: PRT
<213> ORGANISM: Artificial Sequence
<220> FEATURE:
<223> OTHER INFORMATION: Lox514 VL CDR3
<220> FEATURE:
<221> NAME/KEY: misc_feature
<222> LOCATION: (6)..(6)
<223> OTHER INFORMATION: Xaa is Ser or Met
<220> FEATURE:
<221> NAME/KEY: misc_feature
<222> LOCATION: (7)..(7)
<223> OTHER INFORMATION: Xaa is Leu, Tyr, or His
<220> FEATURE:
<221> NAME/KEY: misc_feature
<222> LOCATION: (8)..(8)
<223> OTHER INFORMATION: Xaa is Ser or Arg
<220> FEATURE:
<221> NAME/KEY: misc_feature
<222> LOCATION: (9)..(9)
<223> OTHER INFORMATION: Xaa is Gly, Ala, or no amino acid
<220> FEATURE:
<221> NAME/KEY: misc_feature
<222> LOCATION: (10)..(10)
<223> OTHER INFORMATION: Xaa is Trp or Phe
<220> FEATURE:
<221> NAME/KEY: misc_feature
<222> LOCATION: (11)..(11)
<223> OTHER INFORMATION: Xaa is Val, Gly, or Ala

<400> SEQUENCE: 73

Gln Ser Tyr Asp Ser Xaa Xaa Xaa Xaa Xaa Xaa
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Lox696 VH CDR2
<220> FEATURE:
<221> NAME/KEY: misc_feature
<222> LOCATION: (2)..(2)
<223> OTHER INFORMATION: Xaa is Ile or Val
<220> FEATURE:
<221> NAME/KEY: misc_feature
<222> LOCATION: (4)..(4)
<223> OTHER INFORMATION: Xaa is Trp or Leu
<220> FEATURE:
<221> NAME/KEY: misc_feature
<222> LOCATION: (5)..(5)
<223> OTHER INFORMATION: Xaa is Asn or Gln
<220> FEATURE:
<221> NAME/KEY: misc_feature
<222> LOCATION: (6)..(6)
<223> OTHER INFORMATION: Xaa is Ser or Glu
<220> FEATURE:
<221> NAME/KEY: misc_feature
<222> LOCATION: (7)..(7)
<223> OTHER INFORMATION: Xaa is Gly, Leu, or Pro
<220> FEATURE:
<221> NAME/KEY: misc_feature
<222> LOCATION: (8)..(8)
<223> OTHER INFORMATION: Xaa is Ser, Tyr, or Asp
<220> FEATURE:
<221> NAME/KEY: misc_feature
<222> LOCATION: (9)..(9)
<223> OTHER INFORMATION: Xaa is Ile, Thr, or Arg
<220> FEATURE:
<221> NAME/KEY: misc_feature
<222> LOCATION: (10)..(10)
<223> OTHER INFORMATION: Xaa is Gly or Tyr
<220> FEATURE:
<221> NAME/KEY: misc_feature
<222> LOCATION: (11)..(11)
```

<223> OTHER INFORMATION: Xaa is Tyr or Met
<220> FEATURE:
<221> NAME/KEY: misc_feature
<222> LOCATION: (12)..(12)
<223> OTHER INFORMATION: Xaa is Ala or Asp

<400> SEQUENCE: 74

Gly Xaa Ser Xaa Xaa Xaa Xaa Xaa Xaa Xaa Xaa Asp Ser Val Lys
1               5                   10                  15
Gly

<210> SEQ ID NO 75
<211> LENGTH: 11
<212> TYPE: PRT
<213> ORGANISM: Artificial Sequence
<220> FEATURE:
<223> OTHER INFORMATION: Lox696 VH CDR3
<220> FEATURE:
<221> NAME/KEY: misc_feature
<222> LOCATION: (3)..(3)
<223> OTHER INFORMATION: Xaa is Asn or Ser
<220> FEATURE:
<221> NAME/KEY: misc_feature
<222> LOCATION: (9)..(9)
<223> OTHER INFORMATION: Xaa is Phe or Leu
<220> FEATURE:
<221> NAME/KEY: misc_feature
<222> LOCATION: (11)..(11)
<223> OTHER INFORMATION: Xaa is Ile or Val

<400> SEQUENCE: 75

Glu Gly Xaa Trp Asn Tyr Asp Ala Xaa Asp Xaa
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Lox696 VL CDR1
<220> FEATURE:
<221> NAME/KEY: misc_feature
<222> LOCATION: (5)..(5)
<223> OTHER INFORMATION: Xaa is Ser or Asn

<400> SEQUENCE: 76

Thr Gly Thr Ser Xaa Asp Val Gly Gly Tyr Asn Tyr Val Ser
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Lox696 VL CDR2
<220> FEATURE:
<221> NAME/KEY: misc_feature
<222> LOCATION: (4)..(4)
<223> OTHER INFORMATION: Xaa is Asn or Lys

<400> SEQUENCE: 77

Asp Val Ser Xaa Arg Pro Ser
1               5

<210> SEQ ID NO 78
<211> LENGTH: 11
<212> TYPE: PRT
<213> ORGANISM: Artificial Sequence
<220> FEATURE:
<223> OTHER INFORMATION: Lox696 VL CDR3

```
<220> FEATURE:
<221> NAME/KEY: misc_feature
<222> LOCATION: (1)..(1)
<223> OTHER INFORMATION: Xaa is Ser, Leu, Met, or Ala
<220> FEATURE:
<221> NAME/KEY: misc_feature
<222> LOCATION: (2)..(2)
<223> OTHER INFORMATION: Xaa is Ser, Gly, or Gln
<220> FEATURE:
<221> NAME/KEY: misc_feature
<222> LOCATION: (3)..(3)
<223> OTHER INFORMATION: Xaa is Tyr, Arg, Ser, or Gly
<220> FEATURE:
<221> NAME/KEY: misc_feature
<222> LOCATION: (4)..(4)
<223> OTHER INFORMATION: Xaa is Thr or Met
<220> FEATURE:
<221> NAME/KEY: misc_feature
<222> LOCATION: (5)..(5)
<223> OTHER INFORMATION: Xaa is Ser, Trp, Gly, or Val
<220> FEATURE:
<221> NAME/KEY: misc_feature
<222> LOCATION: (6)..(6)
<223> OTHER INFORMATION: Xaa is Ser or Arg

<400> SEQUENCE: 78

Xaa Xaa Xaa Xaa Xaa Xaa Ser Thr Asn Trp Val
1               5                   10

<210> SEQ ID NO 79
<211> LENGTH: 50
<212> TYPE: DNA
<213> ORGANISM: Artificial Sequence
<220> FEATURE:
<223> OTHER INFORMATION: Top Ad-shNontargeted synthetic primer

<400> SEQUENCE: 79
caccgatgga ttgcacgcag gttctcgaaa gaacctgcgt gcaatccatc                50

<210> SEQ ID NO 80
<211> LENGTH: 50
<212> TYPE: DNA
<213> ORGANISM: Artificial Sequence
<220> FEATURE:
<223> OTHER INFORMATION: Bottom Ad-shNontargeted synthetic primer

<400> SEQUENCE: 80
aaaagatgga ttgcacgcag gttctttcga gaacctgcgt gcaatccatc                50

<210> SEQ ID NO 81
<211> LENGTH: 50
<212> TYPE: DNA
<213> ORGANISM: Artificial Sequence
<220> FEATURE:
<223> OTHER INFORMATION: Top LOX1sh synthetic primer

<400> SEQUENCE: 81
caccgcttca ctctctcatt cttagcgaac taagaatgag agagtgaagc                50

<210> SEQ ID NO 82
<211> LENGTH: 50
<212> TYPE: DNA
<213> ORGANISM: Artificial Sequence
<220> FEATURE:
<223> OTHER INFORMATION: Bottom LOX1sh synthetic primer

<400> SEQUENCE: 82
aaaagcttca ctctctcatt cttagttcgc taagaatgag agagtgaagc                50
```

ANTIBODIES SPECIFIC FOR LOX1 AND USE IN TREATMENT OF CARDIOVASCULAR DISORDERS

CROSS-REFERENCE TO RELATED APPLICATIONS

This patent application is a U.S. National Stage application of International Patent Application No. PCT/EP2015/072644, filed on Sep. 30, 2015, which claims the benefit of U.S. Provisional Patent Application No. 62/058,254, filed Oct. 1, 2014, which is incorporated by reference herein in its entirety.

REFERENCE TO SEQUENCE LISTING SUBMITTED ELECTRONICALLY

The content of the electronically submitted sequence listing in ASCII text file (Name: LOX1-100-US-PCTSequenceListing.txt; Size: 50,937 bytes; and Date of Creation: Mar. 30, 2017) filed with the application is incorporated herein by reference in its entirety.

BACKGROUND

This disclosure provides Lectin-like oxidized low density lipoprotein receptor-1 (LOX1) binding proteins and methods for the use of such binding proteins, e.g., for the treatment, prevention and/or amelioration of a disease or condition associated with LOX1 including, e.g., vascular dysfunction, atherosclerosis (plaque progression, rupture and/or thrombosis) coronary artery disease (CAD), ischemia (e.g., myocardial ischemia), infarction (e.g., myocardial infarction), stroke and acute coronary syndrome (ACS).

Atherosclerosis is a complex disease that results from the accumulation of lipids, macrophages and fibrous elements as lesions in the arterial wall. The lesions develop into complex plaques that narrow the artery lumen and are a focus of chronic inflammation. The plaques are vulnerable to rupture triggering thrombosis that results in adverse cardiovascular events including stroke and myocardial infarction. Atherosclerosis is the primary cause of coronary artery disease, stroke and peripheral vascular disease and therefore represents the most common cause of morbidity worldwide (World Health Organization 2011).

Lectin-like oxidized low density lipoprotein receptor-1 (LOX1) is a disulphide linked type II transmembrane protein. It was first identified as a major receptor of oxidized low density lipoprotein (oxLDL) (Kume et al., 70th Scientific Sessions of the American Heart Association Ser. 96, 1997). The receptor consists of a short N terminal cytoplasmic domain, transmembrane domain, neck domain and a C-type lectin domain (CTLD), with the structure of the CTLD has been solved (Ohki et al., Structure 13:905-917 (2005)). In addition, LOX1 can be proteolytically cleaved in the neck domain releasing soluble LOX1 (sLOX1). LOX1 is a class E scavenger receptor and binds multiple ligands including oxLDL, C-reactive protein (CRP), phosphatidylserine, advanced glycation end products (AGEs), small dense lipoproteins (sdLDL), oxidized HDL, N4-oxononanoyl lysine (ONL), heat shock proteins (hsp), *Chlamydia pneumoniae*, platelets, leukocytes and apoptotic cells. Many of these ligands, particularly oxLDL, are associated with atherosclerosis. Multiple signal transduction pathways are associated with LOX1 activation including RhoA/Rac1, nitrogen monoxide, p38MAPK, protein kinase B and C, ERK1/2, and NFκB. See, e.g., Taye et. al., *Eur J Clin Invest.* 43(7):740-5 (2013).

Preclinical evidence implicates LOX1 in the promotion of vascular dysfunction, plaque progression, rupture and thrombosis, atherosclerosis and inflammatory conditions. See, e.g., Ulrich-Merzenich et al., *Expert Opin Ther Targets.* 17(8):905-19 (2013). For example, whereas LOX1 knockout mice have reduced aortic atherosclerosis and decreased vessel wall collagen deposition (Mehta et al., *Circ. Res.* 100:1634-1642 (2007)), LOX1 overexpression increased atherosclerotic plaque formation (Inoue et al., *Circ. Res.* 97:176-84 (2005); and White et al., *Cardiovascular pathology* 20:369-73 (2011)) with LOX1 expression observed on the vulnerable plaque shoulders and associated with macrophage accumulation, apoptosis, and MMP-9 expression (Li et al., *Cir. Cardio. Imaging* 3:464-72 (2010)). Neutralizing LOX1 antibodies restored acetylcholine induced coronary arteriolar dilation (Xu et al., *Arterioscler. Thromb. Vasc. Biol.* 27(4) 871-877 (2007)) and reduced intimal thickening after balloon injury in rats (Hinagata et al., *Cardiovasc. Res.* 69:263-71 (2006)). LOX1 expression in humans is not constitutive but dynamically inducible by proinflammatory stimuli. In the atherosclerotic plaque LOX1 is expressed on endothelial cells, smooth muscle cells and macrophages. Interestingly serum sLOX1 has been proposed to be diagnostic of plaque instability and rupture in acute coronary syndrome (ACS) patients (Nakamura et al., *J. Pharm. Biomed. Anal.* 51:158-163 (2010)); to be predictive of ACS recurrence or death (Kume et al., 70th Scientific Sessions of the American Heart Association Ser. 96, 1997); and is associated with increasing number of complex lesions (Zhao et al., *Clin. Cardiol.* 34:172-177 (2011)).

Atherosclerosis related mortality continues to rise due to the increasing prevalence of hypertension, diabetes, dyslipidemia and life-style characteristics (such as smoking and obesity) which are risk factors for atherosclerosis. Intervention with standard of care treatments including: platelet inhibitors, anti-hypertensives, HMG CoA reductases inhibitors (statins), thrombolytic agents, percutaneous arterial dilation, stenting or coronary artery bypass surgery have had significant clinical benefit. However, despite the use of preventative strategies and treatment there are still large numbers of patients who suffer from secondary major adverse cardiovascular events (MACE). Therefore there is a need for new therapeutics that can be used alone or in combination with the standard of care.

BRIEF SUMMARY

The disclosure provides LOX1-binding proteins and their methods of use. In particular aspects, the LOX1-binding proteins disclosed herein reduce, inhibit or block LOX1-binding to one or more of its ligands. In some aspects, the LOX1-binding proteins reduce, inhibit or block LOX1-binding with oxidized low density lipoprotein (oxLDL), C-reactive protein (CRP) and/or advanced glycation end products (AGEs). In some aspects, the disclosure provides methods of using LOX1-binding proteins for the treatment, prevention and/or amelioration of a disease or condition associated with LOX1 expression and/or reduced HDL-mediated signaling. The disclosure also provides methods of using LOX1-binding proteins for the treatment, prevention and/or amelioration of acute coronary syndrome (ACS), myocardial infarction (MI) or coronary artery disease (CAD) or a condition associated with ACS, MI or CAD. In some aspects, the disclosure provides methods of using LOX1-binding proteins for the treatment, prevention and/or amelioration of a disease or condition selected from the group including, but not limited to: atherosclerosis, thrombosis, coronary artery disease (CAD), ischemia (e.g., myocardial ischemia), infarction (e.g., myocardial infarction), acute coronary syndrome (ACS), stroke, reperfusion injury, restenosis, peripheral vascular disease, hypertension, heart failure, inflammation, angiogenesis, preeclampsia and cancer.

In some aspects, the LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3, wherein the set of CDRs is identical to, or has a total of 18 or fewer (e.g., 1, 2, 3, 4, 5, 6, 7, 8, 9, 10, 11, 12, 13, 14, 15, 16, 17 or 18) amino acid substitutions, deletions, and/or insertions from a reference set of CDRs in which: (a) VH-CDR1 has the amino acid sequence of SEQ ID NO:1; (b) VH-CDR2 has the amino acid sequence of SEQ ID NO:5; (c) VH-CDR3 has the amino acid sequence of SEQ ID NO:14; (d) VL-CDR1 has the amino acid sequence of SEQ ID NO:30; (e) VL-CDR2 has the amino acid sequence of SEQ ID NO:31; and (f) VL-CDR3 has the amino acid sequence of SEQ ID NO:32.

In some aspects, the LOX1-binding protein comprises a set of six complementary determining regions (CDRs): heavy chain variable region (VH)-CDR1, VH-CDR2, VH-CDR3, and light chain variable region (VL)-CDR1, VL-CDR2 and VL-CDR3, wherein the set of CDRs is identical to, or has a total of one, two, three, four, five, six, seven, eight or fewer amino acid substitutions, deletions, and/or insertions from a reference set of CDRs in which: (a) VH-CDR1 has the amino acid sequence of SEQ ID NO:1; (b) VH-CDR2 has the amino acid sequence of SEQ ID NO:2; (c) VH-CDR3 has the amino acid sequence of SEQ ID NO:3; (d) VL-CDR1 has the amino acid sequence of SEQ ID NO:30; (e) VL-CDR2 has the amino acid sequence of SEQ ID NO:31; and (f) VL-CDR3 has the amino acid sequence of SEQ ID NO:32.

In some aspects, the LOX1-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3 wherein the set of CDRs is identical to, or has a total of one, two, three, four, five, six, seven, eight or fewer amino acid substitutions, deletions, and/or insertions from a reference set of CDRs in which: (a) VH-CDR1 has the amino acid sequence of SEQ ID NO:38; (b) VH-CDR2 has the amino acid sequence of SEQ ID NO:39; (c) VH-CDR3 has the amino acid sequence of SEQ ID NO:40; (d) VL-CDR1 has the amino acid sequence of SEQ ID NO:55; (e) VL-CDR2 has the amino acid sequence of SEQ ID NO:56; and (f) VL-CDR3 has the amino acid sequence of SEQ ID NO:57.

In further aspects, the LOX1-binding protein comprises a set of six CDRs: VH-CDR1, VH-CDR2, VH-CDR3, VL-CDR1, VL-CDR2 and VL-CDR3 wherein: (a) VH-CDR1 has the amino acid sequence of SEQ ID NO:1; (b) VH-CDR2 has the amino acid sequence of SEQ ID NO:2; (c) VH-CDR3 has the amino acid sequence of SEQ ID NO:3; (d) VL-CDR1 has the amino acid sequence of SEQ ID NO:30; (e) VL-CDR2 has the amino acid sequence of SEQ ID NO:31; and (f) VL-CDR3 has the amino acid sequence of SEQ ID NO:32.

In further aspects, the LOX1-binding protein comprises a set of six CDRs: VH-CDR1, VH-CDR2, VH-CDR3, VL-CDR1, VL-CDR2 and VL-CDR3 wherein: (a) VH-CDR1 has the amino acid sequence of SEQ ID NO:38; (b) VH-CDR2 has the amino acid sequence of SEQ ID NO:39; (c) VH-CDR3 has the amino acid sequence of SEQ ID NO:44; (d) VL-CDR1 has the amino acid sequence of SEQ ID NO:55; (e) VL-CDR2 has the amino acid sequence of SEQ ID NO:60; and (f) VL-CDR3 has the amino acid sequence of SEQ ID NO:61.

In further aspects, the LOX1-binding protein comprises a set of six CDRs: VH-CDR1, VH-CDR2, VH-CDR3, VL-CDR1, VL-CDR2 and VL-CDR3 wherein: (a) VH-CDR1 has the amino acid sequence of SEQ ID NO:38; (b) VH-CDR2 has the amino acid sequence of SEQ ID NO:39; (c) VH-CDR3 has the amino acid sequence of SEQ ID NO:40; (d) VL-CDR1 has the amino acid sequence of SEQ ID NO:55; (e) VL-CDR2 has the amino acid sequence of SEQ ID NO:56; and (f) VL-CDR3 has the amino acid sequence of SEQ ID NO:57.

In some aspects, the LOX1-binding protein comprises a heavy chain variable region (VH) having at least 90, 95, 97, 98 or 99% sequence identity to SEQ ID NO:4 and/or a light chain variable region (VL) having at least 90, 95, 97, 98 or 99% sequence identity to SEQ ID NO:33.

In some aspects, the LOX1-binding protein comprises a VH having at least 90, 95, 97, 98 or 99% sequence identity to SEQ ID NO:41 and/or a VL having at least 90, 95, 97, 98 or 99% sequence identity to SEQ ID NO:58.

In some aspects, the LOX1-binding protein comprises a heavy chain variable region (VH) having at least 90, 95, 97, 98 or 99% sequence identity to SEQ ID NOs:4, 19-29, 41, or 48-54; and a light chain variable region (VL) having at least 90, 95, 97, 98 or 99% sequence identity to SEQ ID NOs:33, 36, 37, 58 or 65-70.

In some aspects, the LOX1-binding protein comprises a heavy chain variable region (VH) having at least 90, 95, 97, 98 or 99% sequence identity and a light chain variable region (VL) having at least 90, 95, 97, 98 or 99% sequence identity to a VH and a VL selected from: (a) a VH having the amino acid sequence of SEQ ID NO:4 and a VL having the amino acid sequence of SEQ ID NO:33; (b) a VH having the amino acid sequence of SEQ ID NO:29 and a VL having the amino acid sequence of SEQ ID NO:33; (c) a VH having the amino acid sequence of SEQ ID NO:41 and a VL having the amino acid sequence of SEQ ID NO:58; and (d) a VH having the amino acid sequence of SEQ ID NO:54 and a VL having the amino acid sequence of SEQ ID NO:70.

In some aspects, the LOX1-binding protein comprises a heavy chain variable region (VH) and a light chain variable region (VL), wherein the VH sequence is identical to, or has a total of 15 or fewer (e.g., 1, 2, 3, 4, 5, 6, 7, 8, 9, 10, 11, 12, 13, 14 or 15) amino acid substitutions, deletions, and/or insertions from a reference VH sequence of SEQ ID NO:4, 19-28, or 29, and wherein the VL sequence is identical to, or that has a total of 6 or fewer (e.g., 1, 2, 3, 4, 5, or 6) amino acid substitutions, additions and/or deletions from a reference VL sequence of SEQ ID NO:33, 36 or 37.

In some aspects, the LOX1-binding protein comprises a heavy chain variable region (VH) selected from the group consisting of: a VH comprising SEQ ID NO:4, 19-29, 41, or 48-54; and a light chain variable region (VL) selected from the group consisting of a VL comprising SEQ ID NO:33, 36, 37, 58 or 65-70.

In some aspects, the LOX1-binding protein comprises a heavy chain variable region (VH) and a light chain variable region (VL) selected from the group consisting of: (a) a VH having the amino acid sequence of SEQ ID NO:4 and a VL having the amino acid sequence of SEQ ID NO:33; (b) a VH having the amino acid sequence of SEQ ID NO:29 and a VL having the amino acid sequence of SEQ ID NO:33; (c) a VH having the amino acid sequence of SEQ ID NO:41 and a VL having the amino acid sequence of SEQ ID NO:58; and (d) a VH having the amino acid sequence of SEQ ID NO:54 and a VL having the amino acid sequence of SEQ ID NO:70.

In some aspects, the LOX1-binding protein comprises a heavy chain variable region (VH) comprising the amino acid sequence of SEQ ID NO:4 and a light chain variable region (VL) comprising the amino acid sequence of SEQ ID NO:33.

In some aspects, the LOX1-binding protein comprises a heavy chain variable region (VH) selected from a VH containing a VH-CDR1 having the amino acid sequence of SEQ ID NO:1, a VH-CDR2 having the amino acid sequence of SEQ ID NO:2, 5-12, or 13, and a VH-CDR3 having the amino acid sequence of SEQ ID NO:3, 14-17 or 18; and a light chain variable region (VL) selected from a VL containing a VL-CDR1 having the amino acid sequence of SEQ ID NO:30, a VL-CDR2 having the amino acid sequence of SEQ ID NO:31, and a VL-CDR3 having the amino acid sequence of SEQ ID NO:32, 34 or 35.

In some aspects, the LOX1-binding protein comprises a heavy chain variable region (VH) and a light chain variable region (VL), wherein the VH sequence is identical to, or has a total of one, two, three, four, five, six, seven, eight or fewer amino acid substitutions, deletions, and/or insertions from a reference VH sequence of SEQ ID NO:41, 48-53 or 54, and wherein the VL sequence is identical to, or that has a total of one, two, three, four, five, six, seven, eight or fewer amino acid substitutions, additions and/or deletions from a reference VL sequence of SEQ ID NO:58, 65-69 or 70.

In some aspects, the LOX1-binding protein comprises a heavy chain variable region (VH) selected from a VH containing a VH-CDR1 having the amino acid sequence of SEQ ID NO:38, a VH-CDR2 having the amino acid sequence of SEQ ID NO:39, 42, or 43, and a VH-CDR3 having the amino acid sequence of SEQ ID NO:40, 44-46 or 47; and a light chain variable region (VL) selected from a VL containing a VL-CDR1 having the amino acid sequence of SEQ ID NO:55 or 59, a VL-CDR2 having the amino acid sequence of SEQ ID NO:56 or 60, and a VL-CDR3 having the amino acid sequence of SEQ ID NO:57, 61-63, or 64.

In some aspects, the LOX1-binding protein comprises a set of CDRs: VH-CDR1, VH-CDR2, VH-CDR3, VL-CDR1, VL-CDR3 and VL-CDR3 as described in Table 1, FIG. 4 or FIG. 5 (e.g. a set of CDRs from Lox514, LX5140011, LX5140014, LX5140016, LX5140038, LX5140094, LX5140108, LX5140110, LX5140092, LX5140092_D, LX5140093, LX5140093_D, Lox696, LX6960067_ng1, LX6960071_ng1, LX6960073_ng1, LX6960086_ng1, LX6960094_ng1, LX6960101_ng1, LX6960102_ng1, LX6960116_ng1, LX6960073_gl, or LX6960073_G82bs_gl).

In some additional aspects, the LOX1-binding protein comprises a heavy chain variable region (VH) and light chain variable region (VL) as described in Table 1, FIG. 4 or FIG. 5 (e.g. a VH and VL from Lox514, LX5140011, LX5140014, LX5140016, LX5140038, LX5140094, LX5140108, LX5140110, LX5140092, LX5140092_D, LX5140093, LX5140093_D, Lox696, LX6960067_ng1, LX6960071_ng1, LX6960073_ng1, LX6960086_ng1, LX6960094_ng1, LX6960101_ng1, LX6960102_ng1, LX6960116_ng1, LX6960073_gl, or LX6960073_G82bs_gl).

In some aspects, the isolated LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3 wherein: (a) VH-CDR1 comprises the amino acid sequence: ELS MH (SEQ ID NO: 1); (b) VH-CDR2 comprises the amino acid sequence: G F D P E D HX1 HX2 HX3 HX4 HX5 HX6 Q K F Q G, wherein HX1 is selected from the group consisting of G, W, Y and F, HX2 is selected from the group consisting of E, T, Q, K, A, and S, HX3 is selected from the group consisting of T, Y, I, and N, HX4 is selected from the group consisting of I, A, R and H, HX5 is selected from the group consisting of Y, V, T, L and Q, and HX6 is selected from the group consisting of A, D, G, S and H (SEQ ID NO: 71); (c) VH-CDR3 comprises the amino acid sequence: HX7 HX8 G HX9 HX10 HX11 HX12 G V R G W D Y Y Y G M D V, wherein HX7 is selected from the group consisting of P, S and V, HX8 is selected from the group consisting of N, W, D, and T, HX9 is selected from the group consisting of Q, R and T, HX10 is selected from the group consisting of Q and H, HX11 is selected from the group consisting of G and Q, and HX12 is selected from the group consisting of K and G (SEQ ID NO: 72); (d) VL-CDR1 comprises the amino acid sequence: T G S S S N I G A G Y D V H (SEQ ID NO: 30); (e) VL-CDR2 comprises the amino acid sequence: G N S N R P S (SEQ ID NO: 31); and (f) VL-CDR3 comprises the amino acid sequence: Q S Y D S LX1 LX2 LX3 LX4 LX5 LX6, wherein LX1 is selected from the group consisting of M and S, LX2 is selected from the group consisting of L, Y and H, LX3 is selected from the group consisting of S and R, LX4 is selected from the group consisting of A and G or is omitted (no amino acid), LX5 is selected from the group consisting of W and F, and LX6 is selected from the group consisting of V, G and A (SEQ ID NO: 73).

In some aspects, the LOX1-binding protein binds the same epitope as a LOX-1 binding protein (e.g. a LOX-1 antibody or fragment thereof) comprising a heavy chain variable region (VH) and a light chain variable region (VL) described in Table 1, FIG. 4 or FIG. 5, including a LOX-1 binding protein (e.g. a LOX-1 antibody or fragment thereof) comprising a VH sequence of SEQ ID NO:4 and a VL sequence of SEQ ID NO:33.

In other aspects, the disclosure provides LOX1-binding proteins (e.g., antibodies such as, full length LOX1-antibodies, LOX1-binding antibody fragments, and variants and derivatives thereof), that compete or cross-compete for binding to LOX1 with a LOX-1 binding protein (e.g. a LOX-1 antibody or fragment thereof) comprising a heavy chain variable region (VH) and a light chain variable region (VL) described in Table 1, FIG. 4 or FIG. 5, including a LOX-1 binding protein (e.g. a LOX-1 antibody or fragment thereof) comprising a VH sequence of SEQ ID NO:4 and a VL sequence of SEQ ID NO:33.

In some aspects, the LOX1-binding protein binds the same epitope as an antibody comprising a VH sequence of SEQ ID NO:4 and a VL sequence of SEQ ID NO:33.

In other aspects, the disclosure provides LOX1-binding proteins (e.g., antibodies such as, full length LOX1-antibodies, LOX1-binding antibody fragments, and variants and derivatives thereof), that compete or cross-compete for binding to LOX1 with an antibody comprising a VH sequence of SEQ ID NO:4 and a VL sequence of SEQ ID NO:33.

In some aspects, the LOX1-binding proteins disclosed herein reduce, inhibit or antagonize LOX1 activity. In some aspects, the LOX1-binding protein has at least one property selected from the group consisting of: (a) reduces or inhibits binding of oxLDL, C-reactive protein (CRP) and/or advanced glycation end products (AGEs) to LOX1 as determined by any suitable assay including an assay disclosed herein (see, e.g., Example 10, assays 1, 2 and/or 3 or Example 11); (b) decreases or inhibits RhoA/Rac1, nitrogen monoxide (NO), p38MAPK, protein kinase B and C, ERK1/2, and/or NFκB signaling in an endothelial cell expressing cell surface LOX1 as determined by any suitable assay including an assay disclosed herein (see, e.g., Example 11); (c) decreases or inhibits caspase-8, caspase-9, and/or BAX activity in an endothelial cell expressing cell surface LOX1 as determined by any suitable assay including an assay disclosed herein; (d) binds to LOX1 having the single nucleotide polymorphism K167N as determined by any suitable assay including an assay disclosed herein (see, e.g., Example 10, assays 1, 2 and/or 3 or Example 11); (e) reduces or inhibits oxLDL internalization as determined by any suitable assay including an assay disclosed herein (see, e.g., Example 10, assay 4 or Example 11); (f) reduces or inhibits oxLDL-induced LOX1 signaling as determined by any suitable assay including an assay disclosed herein (see, e.g., Example 10, assay 5 or Example 11); (g) binds to LOX1 with a dissociation constant (KD) of about 150 pM to about 600 pM (e.g. about 400 pM) as determined by BIACORE or KinExA; (h) binds to LOX1 with a Kon rate of about $1 \times 10^5$ $M^{-1} s^{-1}$ to about $6 \times 10^6$ $M^{-1} s^{-1}$ (e.g. about $5 \times 10^5$ $M^{-1} s^{-1}$) as determined by BIACORE; and (i) binds to LOX1 with a Koff rate of about $1 \times 10^{-4}$ $s^{-1}$ to about $3 \times 10^{-4}$ $s^{-1}$ (e.g. about $2.3 \times 10^{-4}$ $s^{-1}$) as determined by BIACORE.

In additional aspects, the LOX1-binding protein is an antibody. In some aspects, the antibody is a monoclonal antibody, a recombinant antibody, a human antibody, a humanized antibody, a chimeric antibody, a bi-specific antibody, a multi-specific antibody, or an LOX1-binding antibody fragment. In some aspects the antibody is a LOX1 binding antibody fragment selected from the group consisting of: a Fab fragment, a Fab' fragment, a F(ab')$_2$ fragment, a Fv fragment, a diabody, and a single chain antibody molecule.

In some aspects, the LOX1-binding protein is an antibody that comprises an IgG1 heavy chain immunoglobulin constant region. In some aspects, the IgG1 constant region comprises a mutation that decreases effector function. In further aspects, the IgG1 constant region comprises the triple mutation L234F/L235E/P331S, that results in an effector null IgG1.

The disclosure provides an isolated nucleic acid or a set of nucleic acids encoding a LOX1-binding protein (e.g. a LOX-1 antibody or fragment thereof). Also provided is a vector or set of vectors containing the nucleic acids or set of nucleic acids, and host cells transformed with the isolated nucleic acids or vectors. In some aspects, the host cell is a mammalian host cell such as, a NS0 murine myeloma cell, a PER.C6® human cell, or a Chinese hamster ovary (CHO) cell. Host cells and hybridomas producing LOX1-binding proteins (e.g. a LOX-1 antibody or fragment thereof) are also provided.

The disclosure also provides a method for making an LOX1-binding protein disclosed herein. In some aspects, the method comprises culturing a host cell or hybridoma capable of expressing the LOX1-binding protein (e.g. a LOX-1 antibody or fragment thereof) under suitable conditions and optionally provides a method for isolating the LOX1-binding protein secreted from the host cell or hybridoma. And the disclosure additionally provides the LOX1-binding protein (e.g. a LOX-1 antibody or fragment thereof) isolated using these methods.

Also provided are pharmaceutical compositions comprising a LOX1-binding protein (e.g. a LOX-1 antibody or fragment thereof) and a pharmaceutically acceptable carrier. Methods for treating, preventing and/or ameliorating a condition associated with LOX1, elevated LOX1 activity and/or elevated LOX1 expression levels, including, for example, atherosclerosis, thrombosis, coronary artery disease (CAD), ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and/or cancer in a subject are also provided herein. In some aspects, the methods comprise administering to a subject in need thereof, a pharmaceutical composition comprising an effective amount of a LOX1-binding protein.

In some aspects, the LOX1-binding protein is administered alone. In other aspects, the LOX1-binding protein is administered as a combination therapy. In some aspects, the LOX1-binding protein is administered as a combination therapy to the standard of care treatment/therapy.

Also provided is a method of reducing LOX1 activity in a subject comprising administering an effective amount of a LOX1-binding protein to a subject in need thereof.

Additionally provided are methods of treating, preventing, and/or ameliorating atherosclerosis. In some instances, the method comprises administering a LOX1-binding protein (e.g., an anti-LOX1 antibody or fragment thereof in a pharmaceutical composition described herein) to a subject having atherosclerosis. In other aspects, the subject to which the LOX1-binding protein is administered is at risk of developing atherosclerosis. In some aspects, the subject has a proatherogenic condition. In further aspects, the proatherogenic condition is systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or bacterial infection. Also provided are methods of decreasing atherosclerosis. In some instances, the disclosure provides a method of decreasing atherosclerosis in a subject that comprises administering a LOX1-binding protein to a subject having atherosclerosis.

Also provided are methods of treating, preventing, and/or ameliorating thrombosis. In some instances, the method comprises administering a LOX1-binding protein (e.g., an anti-LOX1 antibody or fragment thereof) to a subject having thrombosis. In other aspects, the subject to which the LOX1-binding protein is administered is at risk of developing thrombosis. In some aspects the thrombosis is an arterial thrombosis. In further aspects, the thrombosis is an arterial thrombosis.

The disclosure also provides methods of treating, preventing, and/or ameliorating coronary artery disease (CAD) or a condition associated with CAD. In some instances, the method comprises administering a LOX1-binding protein (e.g., an anti-LOX1 antibody or fragment thereof in a pharmaceutical composition described herein) to a subject having CAD. In other aspects, the subject to which the LOX1-binding protein (e.g., an anti-LOX1 antibody or fragment thereof) is administered is at risk of developing CAD. In some aspects, the subject has a proatherogenic condition. In further aspects, the proatherogenic condition is systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or bacterial infection.

The disclosure also provides methods of treating, preventing, and/or ameliorating ischemia or a condition associated with ischemia. In some instances, the method comprises administering a LOX1-binding protein (e.g., an anti-LOX1 antibody or fragment thereof in a pharmaceutical composition described herein) to a subject having ischemia. In other aspects, the subject to which the LOX1-binding protein (e.g., an anti-LOX1 antibody or fragment thereof) is administered is at risk of developing ischemia. In some aspects, the subject has myocardial ischemia. In other aspects, the subject is at risk of developing myocardial ischemia. In additional aspects, the subject has systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or a bacterial infection.

Also provided are methods of treating, preventing, and/or ameliorating an infarction or a condition associated with an infarction. In some instances, the method comprises administering a LOX1-binding protein (e.g., an anti-LOX1 antibody or fragment thereof in a pharmaceutical composition described herein) to a subject having an infarction. In other aspects, the subject to which the LOX1-binding protein (e.g., an anti-LOX1 antibody or fragment thereof) is administered is at risk of developing an infarction. In some aspects, the subject has a myocardial infarction. In other aspects, the subject is at risk of developing a myocardial infarction. In additional aspects, the subject has ischemia, systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or a bacterial infection.

The disclosure also provides methods of treating, preventing, and/or ameliorating acute coronary syndrome (ACS) or a condition associated with ACS. In some instances, the method comprises administering a LOX1-binding protein (e.g., an anti-LOX1 antibody or fragment thereof in a pharmaceutical composition described herein) to a subject having ACS. In other aspects, the subject to which the LOX1-binding protein (e.g., an anti-LOX1 antibody or fragment thereof) is administered is at risk of developing ACS. In some aspects, the subject has elevated soluble LOX1 (sLOX1) serum levels or elevated LOX1 activity. In additional aspects, the subject has atherosclerosis.

The disclosure also provides methods of treating, preventing, and/or ameliorating a stroke or a condition associated with a stroke. In some instances, the method comprises administering a LOX1-binding protein (e.g., an anti-LOX1 antibody or fragment thereof in a pharmaceutical composition described herein) to a subject that has had a stroke. In other aspects, the subject to which the LOX1-binding protein is administered is at risk of having a stroke. In some aspects, the subject has elevated sLOX serum levels and/or elevated LOX1 activity. In additional aspects, the subject has atherosclerosis.

Also provided are methods of treating, preventing, and/or ameliorating reperfusion injury or a condition associated with reperfusion injury. In some instances, the method comprises administering a LOX1-binding protein (e.g., an anti-LOX1 antibody or fragment thereof in a pharmaceutical composition described herein) to a subject having reperfusion injury. In other aspects, the subject to which the LOX1-binding protein (e.g., an anti-LOX1 antibody or fragment thereof) is at risk of developing reperfusion injury. In some aspects, the subject is about to have surgery. In other aspects, the subject has had surgery. In some aspects the surgery is transplantation or coronary bypass surgery. In additional aspects the patient has, or is at risk of developing, myocardial ischemia-reperfusion injury. In further aspects the method decreases myocardial injury, reduces serum creatine kinase-MB isoenzyme (CK-MB) and serum malondialdehyde (MDA) levels, reduces cardiomyocyte size, reduces leukocyte infiltration at the site of the injury, and/or reduces cardiac dysfunction (e.g., reduces left ventricular pressure (LVP) and increases left ventricular end-diastolic pressure (LVEDP). In further aspects, the method increases heart stroke volume, fractional shortening, and/or injection fraction.

The disclosure also provides methods of treating, preventing, and/or ameliorating restenosis or a condition associated with restenosis. In some instances, the method comprises administering a LOX1-binding protein (e.g., an anti-LOX1 antibody or fragment thereof in a pharmaceutical composition described herein) to a subject having restenosis. In other aspects, the subject to which the LOX1-binding protein is administered is at risk of developing restenosis. In some aspects, the subject is about to have surgery. In other aspects, the subject has had surgery. In some aspects the surgery is an endovascular procedure is vascular surgery, cardiac surgery or angioplasty. In additional aspects the restenosis, the procedure is transplantation or coronary bypass surgery. In additional aspects the treated, prevented, and/or ameliorated restenosis is in-stent restenosis or post-angioplasty restenosis.

In additional aspects, the disclosure provides methods of treating, preventing, and/or ameliorating peripheral vascular disease (PVD) or a condition associated with PVD. In some instances, the method comprises administering a LOX1-binding protein (e.g., an anti-LOX1 antibody or fragment thereof in a pharmaceutical composition described herein) to a subject having PVD. In other aspects, the subject to which the LOX1-binding protein is administered is at risk of developing PVD. In some aspects, the subject has elevated sLOX serum levels and/or elevated LOX1 activity. In additional aspects, the subject has atherosclerosis.

The disclosure also provides methods of treating, preventing, and/or ameliorating inflammation or a condition associated with inflammation. In some instances, the method comprises administering a LOX1-binding protein (e.g., an anti-LOX1 antibody or fragment thereof in a pharmaceutical composition described herein) to a subject with inflammation. In further aspects, the subject has chronic inflammation. In some aspects, the subject has elevated oxLDL and/or sLOX serum levels and/or elevated LOX1 activity. In additional aspects, the subject has atherosclerosis.

The disclosure also provides methods of treating, preventing, and/or ameliorating preeclampsia or a condition associated with preeclampsia. In some instances, the method comprises administering a LOX1-binding protein (e.g., an anti-LOX1 antibody or fragment thereof in a pharmaceutical composition described herein) to a subject with preeclampsia or eclampsia. In further aspects, the subject has high blood pressure and large amounts of protein in the urine. In some aspects, the subject has elevated oxLDL and/or sLOX serum levels and/or elevated LOX1 activity. In additional aspects, the subject has swelling in the feet, legs and/or hands.

In additional aspects, the disclosure provides methods of stabilizing an atherosclerotic plaque in a subject. In some instances, the method comprises administering a LOX1-binding protein (e.g., an anti-LOX1 antibody such as, a full length LOX1-antibody, a LOX1-binding antibody fragment, and variants and derivatives thereof) to a subject in need thereof. In some aspects the method reduces the signaling of the RhoA/Rac1, nitrogen monoxide, p38MAPK, protein kinase B and C, ERK1/2, and/or NFκB signal transduction pathway in the plaque. In other aspects, the method decreases apoptosis in the plaque. In further aspects, the method decreases caspase 8, caspase 9 and/or BAX activity and/or increases BCL-2 activity in the plaque. In other aspects, the method decreases the levels of an adhesion molecule or cytokine produced by the plaque. In further aspects, the method decreases E-selectin, P-selectin, ICAM-1, VCAM-1, MCP1 and/or CD40/CD40L expression by the plaque. In additional aspects, the method decreases atherosclerotic plaque size or formation, macrophage accumulation and/or MMP (e.g., MMP9) expression in the atherosclerotic plaque. In additional aspects, the method results in decreased progression or regression of the plaque.

Also provided are methods of reducing the loss of vascular tone in a subject. In some instances, the method comprises administering a LOX1-binding protein (e.g., an anti-LOX1 antibody such as, a full length LOX1-antibody and a LOX1-binding antibody fragment, and variants and derivatives thereof) to a subject in need thereof. In some aspects the method reduces the loss of vascular tone. In further aspects, the method reduces the loss of vascular tone in a subject through regulating HDL driven NO production (ability of antibody to stimulate endothelial NO production. Additionally provided are methods of improving vascular tone in a subject. In some instances, the method comprises administering a LOX1-binding protein to a subject in need thereof.

Additionally provided are methods of treating, preventing, and/or ameliorating cancer. In some instances the disclosure provides a method of treating, preventing, and/or ameliorating cancer in a subject that comprises administering a LOX1-binding protein (e.g., an anti-LOX1 antibody or fragment thereof) to a subject having cancer. In some aspects, the subject has a cancer selected from the group consisting of: breast cancer, colon cancer, ovarian cancer, melanoma, cervical cancer, lung cancer, uterine cancer, kidney cancer, and pancreatic cancer.

Also provided are methods of inhibiting tumor cell proliferation, migration or invasion. In some instances the disclosure provides a method of antagonizing LOX1 activity that comprises contacting a LOX1-binding protein (e.g., an anti-LOX1 antibody or fragment thereof) with a tumor cell expressing LOX1. In some aspects the tumor cell is from a cancer selected from the group consisting of: breast cancer, colon cancer, ovarian cancer, melanoma, cervical cancer, lung cancer, uterine cancer, kidney cancer, and pancreatic cancer. In some aspects the tumor cell is from a cancer line.

The disclosure additionally provides methods of reducing or inhibiting angiogenesis. In some aspects the method of reducing or inhibiting angiogenesis comprises administering a LOX1-binding protein (e.g., an anti-LOX1 antibody or fragment thereof) to a subject in need thereof. In some aspects the subject has a condition associated with pathological angiogenesis. In additional aspects the disclosure provides a method of inhibiting angiogenesis that comprises contacting a LOX1-binding protein (e.g., an anti-LOX1 antibody or fragment thereof) with a cell expressing LOX1. In some aspects the cell is an endothelial cell. In further aspects the endothelial cell is a coronary endothelial cell. In some aspects the method is performed in vitro. In other aspects the method is performed in vivo.

Additionally provided are methods of blocking or reducing LOX1 activity. In some aspects the disclosure provides methods of blocking LOX1 activity comprising administering a LOX1-binding protein (e.g., an anti-LOX1 antibody or fragment thereof) that reduces or inhibits the interaction between LOX1 and a LOX1-binding protein such as, oxLDL, AGEs, and/or CRP. In some aspects, LOX1 is expressed on the surface of an endothelial cell, macrophage, smooth muscle vascular cell and/or platelet. In some aspects the cell is an endothelial cell such as, a coronary endothelial cell. In additional aspects, the cell is a vascular smooth muscle cell, macrophage, or platelet. In other aspects the cell is part of an atherosclerotic tissue. In some aspects, the method is performed in vivo. In other aspects, the method is performed in vitro. In some aspects the blocked or reduced LOX1 activity is the binding and/or taking up (e.g. internalization) of oxLDL. In additional aspects, the blocked or reduced LOX1 activity is the induction of the p38 (MAPK), p44/42 MAPK, protein kinase C (PKC), protein kinase B (PKB), protein tyrosine kinase (PTK), transcription factor NF-KB and/or AP1 signaling pathway. In additional aspects the blocked or reduced LOX1 activity is the induction of apoptosis. In further embodiments, the induction of apoptosis is mediated by caspase-9, caspase-3 and/or Bcl-2. In additional aspects the blocked or reduced LOX1 activity is the expression of the A and B chains of PDFG and/or heparin-binding EGF-like protein (HB-EGF) in endothelial cells expressing LOX1. In some aspects, the blocked or reduced LOX1 activity is a LOX1 activity induced by oxLDL binding to LOX1.

Additionally provided are methods of blocking or reducing LOX1 activity in a pathological condition associated with increased LOX1 activity levels or LOX1 expression levels (e.g. sLOX1 serum protein levels). In some instances, the method comprises administering a LOX1-binding protein (e.g., an anti-LOX1 antibody or fragment thereof) to a subject having increased LOX1 activity or LOX1 expression levels (e.g. sLOX1 serum protein levels). In some aspects the pathological condition is systemic lupus erythematosus (SLE), diabetes, hypertension, hyperglycemia, heart failure, vascular injury, transplantation, dyslipidemia (hyperlipidemia), inflammation, (e.g., chronic inflammation and endotoxin induced inflammation) or bacterial infection. In some aspects, the subject has elevated serum levels of OxLDL. In some aspects, the subject has elevated serum levels of OxLDL, 15 lipoxygenase modified LDL, 15 lipoxygenase modified HDL, glyoxidized LDL, lysophosphatidylcholinesterase (LPC) and/or palmitic acid. In additional aspects, the subject has elevated serum levels of TNF alpha, IL1, interferon gamma, LPS (lipopolysaccharide), CRP, angiotensin II, endothelin I, and/or AGEs. In additional aspects, the subject has elevated serum levels of soluble LOX1 (sLOX1). In some aspects, the subject has a single nucleotide polymorphism (SNP) in the LOX1 gene. In some aspects, the SNP in the LOX1 gene is the LOX1 K167N variant.

Also provided are methods of agonizing or increasing a high-density lipoprotein (HDL) activity. In some aspects, the disclosure provides a method of increasing or agonizing an HDL activity by administering a LOX1-binding protein (e.g., an anti-LOX1 antibody or fragment thereof) to a subject in need thereof. In some aspects the increased HDL activity is the promotion of HDL-mediated endothelial NO production. In some aspects, the increased HDL activity is the inhibition of the NFKB signaling activity of the endothelial cell. In some aspects, the increase HDL activity is the promotion of endothelial cell repair. In some aspects, the increase HDL activity is the reduction of inflammation.

BRIEF DESCRIPTION OF THE
DRAWINGS/FIGURES

FIG. 1 shows inhibition of oxLDL, AGE-BSA and CRP binding to human LOX1 (hLOX1) by antibodies LOX514 and LOX696. Binding of DyLight 649 labeled ox-LDL (FIG. 1A) or DyLight 649 labeled AGE-BSA (FIG. 1B) to hLOX1 transfected cells or binding of biotin labeled C-Reactive Protein (CRP) to recombinant hLOX1(FIG. 1C) was measured in the presence of LOX514 ("LOX10514-IgG1-TM") (diamonds), LOX696 ("LOX10696-IgG1-TM") (circles) or 23C11 (squares), a commercially available mouse anti-LOX-1 antibody. Representative plots are shown in FIGS. 1A, 1B and 1C illustrating dose-dependent inhibition of oxLDL, AGE-BSA and CRP binding, respectively, by LOX514 and LOX696. In addition, LOX514 and LOX696 also block the binding of DyLight 649 labeled ox-LDL to hLOX1 K167N transfected cells (FIG. 1D) confirming that these antibodies bind and block oxLDL binding to the LOX1 SNP K167N variant. These results demonstrate specific, multi-ligand inhibition of LOX1 binding to oxLDL, AGE-BSA and CRP by antibodies LOX514 and LOX696; and that LOX514 and LOX696 functionally cross react with the common LOX1 SNP K167N variant. M=molar concentration of antibody; bars denote standard error.

FIG. 2 shows inhibition of oxLDL internalization and oxLDL-dependent reactive oxygen species (ROS) generation by antibodies LOX514 and LOX696. Cypher 5E labeled ox-LDL internalization (FIG. 2A) or oxLDL-dependent ROS generation (FIG. 2B) in human LOX1 transfected cells was measured in the presence of LOX514 ("LOX10514-IgG1-TM") (diamonds), LOX696 ("LOX10696-IgG1-TM") (circles) or 23C11 (squares), a commercially available mouse anti-LOX-1 antibody. Representative plots are shown in FIGS. 2A and 2B illustrating dose-dependent inhibition of oxLDL internalization and oxLDL-dependent signaling, respectively, by LOX514 and LOX696. For oxLDL-dependent ROS generation in hLOX1 transfected cells, the relative fluorescent units (RFU) of the amount of Carboxy-dichlorofluorescein (DCF) generated in the assay with LOX514, LOX696 and 23C11, as averaged for three replicates, is shown (FIG. 2B). These results demonstrate that antibodies LOX514 and LOX696 inhibit oxLDL internalization and oxLDL-dependent LOX-1 signaling. M=molar concentration of antibody; bars denote standard error.

Figure 3A:
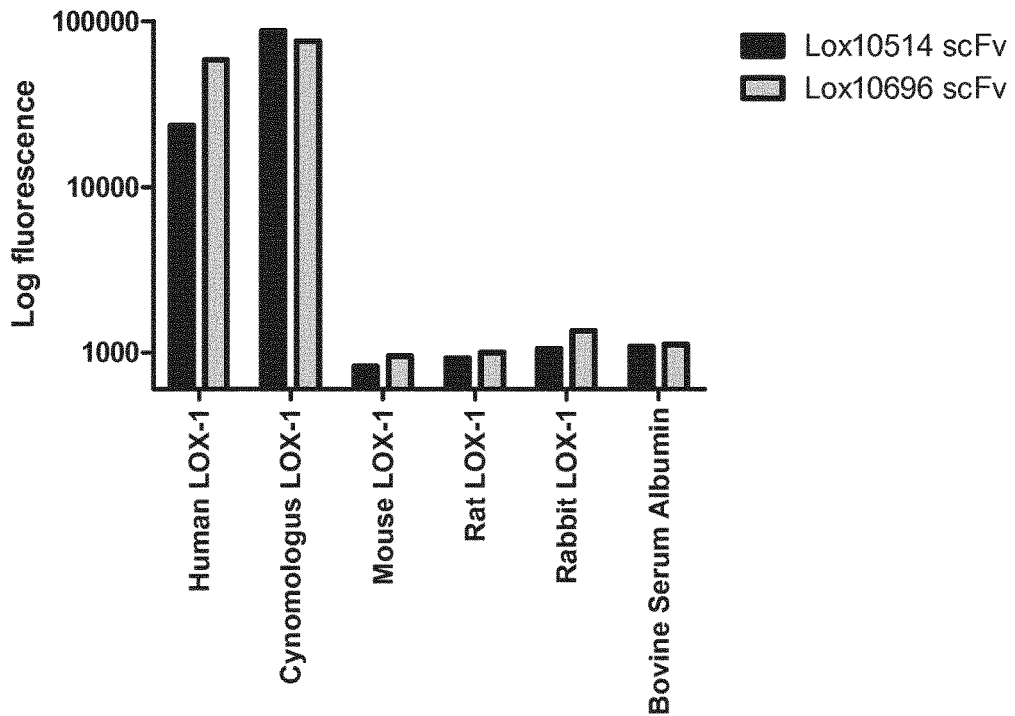
Figure 3B:
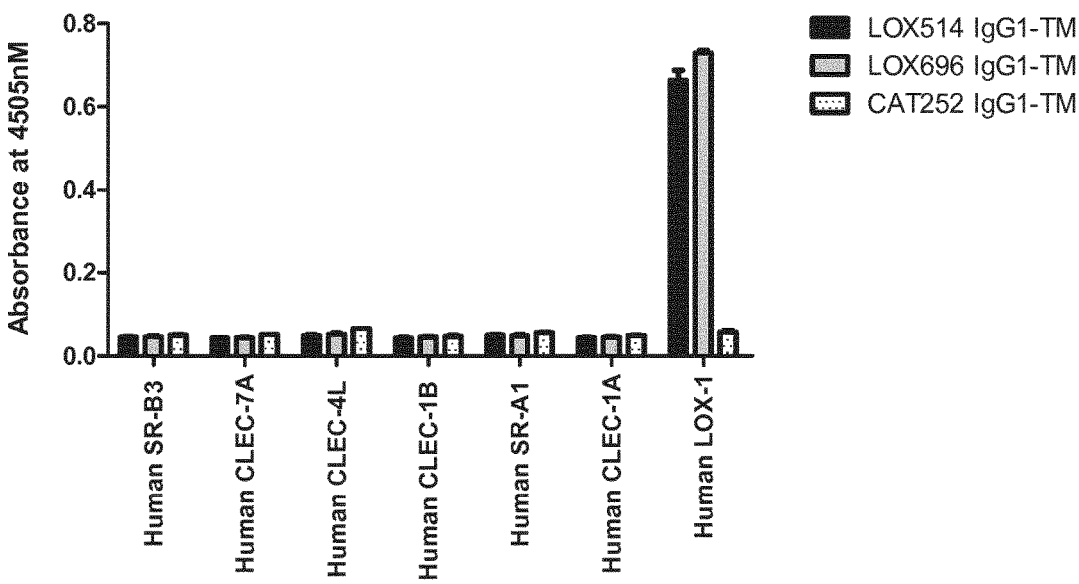

FIG. 3 shows the species cross reactivity of anti-LOX1 antibodies, LOX514 and LOX696. Cross-reactivity of anti-human LOX1 antibodies to various LOX1 species orthologs was assessed using a scFv binding ELISA. As shown in FIG. 3A, LOX514 ("LOX10514") and LOX696 ("LOX10696") bind to human and cynomolgus LOX1 but not to mouse, rat or rabbit LOX1 orthologs or Bovine Serum Albumin (negative control). The specificity of LOX514 and LOX696 to other human C type lectin and scavenger receptors related to LOX-1 was also assessed using an IgG binding ELISA. As shown in FIG. 3B, LOX514 ("LOX10514 IgG1-TM") and LOX696 ("LOX10696 IgG1-TM") bind only to human LOX1 and do not bind to human CLEC-7A, CLEC-1A, CLEC-4L, CLEC-1B, SR-A1 or SR-B3. As expected, CAT252 IgG1-TM, an isotype control antibody, did not bind to any of the human C type lectin and scavenger receptors tested. CLEC-7A=C-type lectin domain family 7 member A (also known as Dectin-1); CLEC-1A=C-type lectin domain family 1 member A; CLEC-4L=C-type lectin domain family 4 member L (also known as DC-SIGN); CLEC-1B=C-type lectin domain family 1 member B (also known as CLEC-2); SR-A1=Macrophage scavenger receptor types I and II (also known as MSR); SR-B3=Platelet glycoprotein 4 (also known as CD36). Bars denote standard error.

Figure 4A:
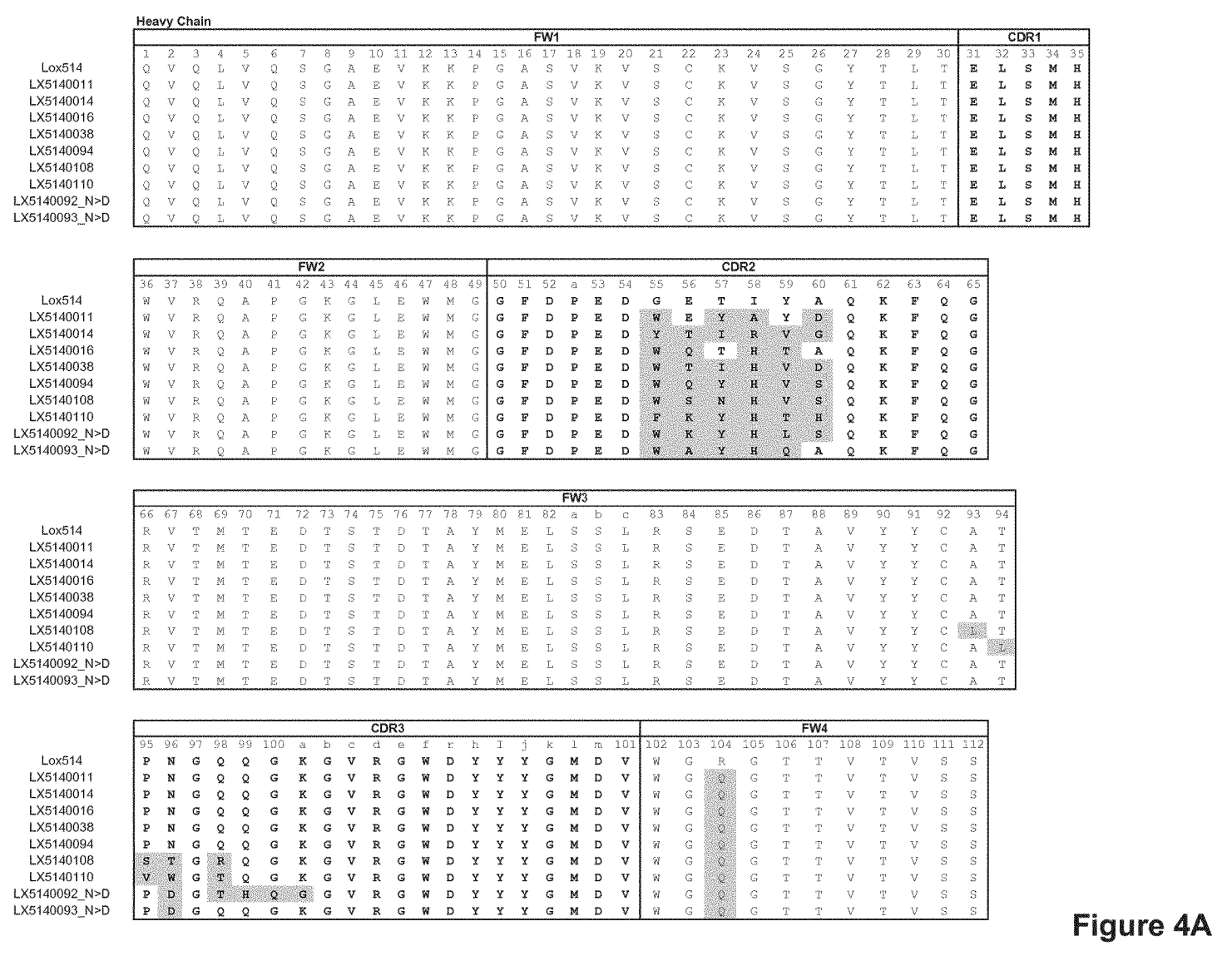
Figure 4B:
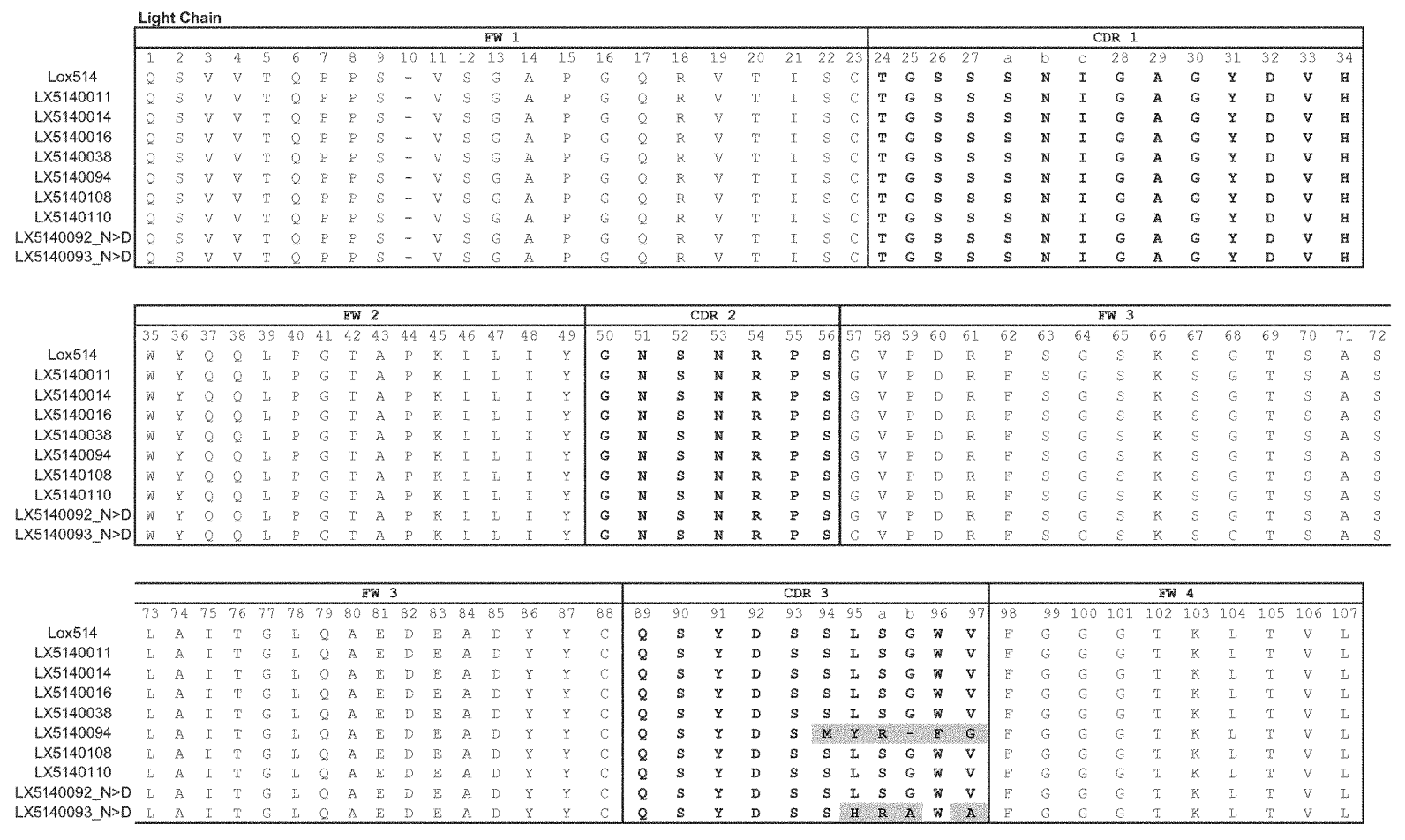

FIG. 4 shows a comparison between LOX514 and several optimized LOX514 antibodies. Amino acid sequence alignments of the heavy chain variable region (VH) (FIG. 4A) or the light chain variable region (VL) (FIG. 4B) between LOX514 and optimized LOX514 antibodies are shown. Differences from LOX514 VH or VL are highlighted. FW=framework; CDR=complementary determining regions.

Figure 5A:
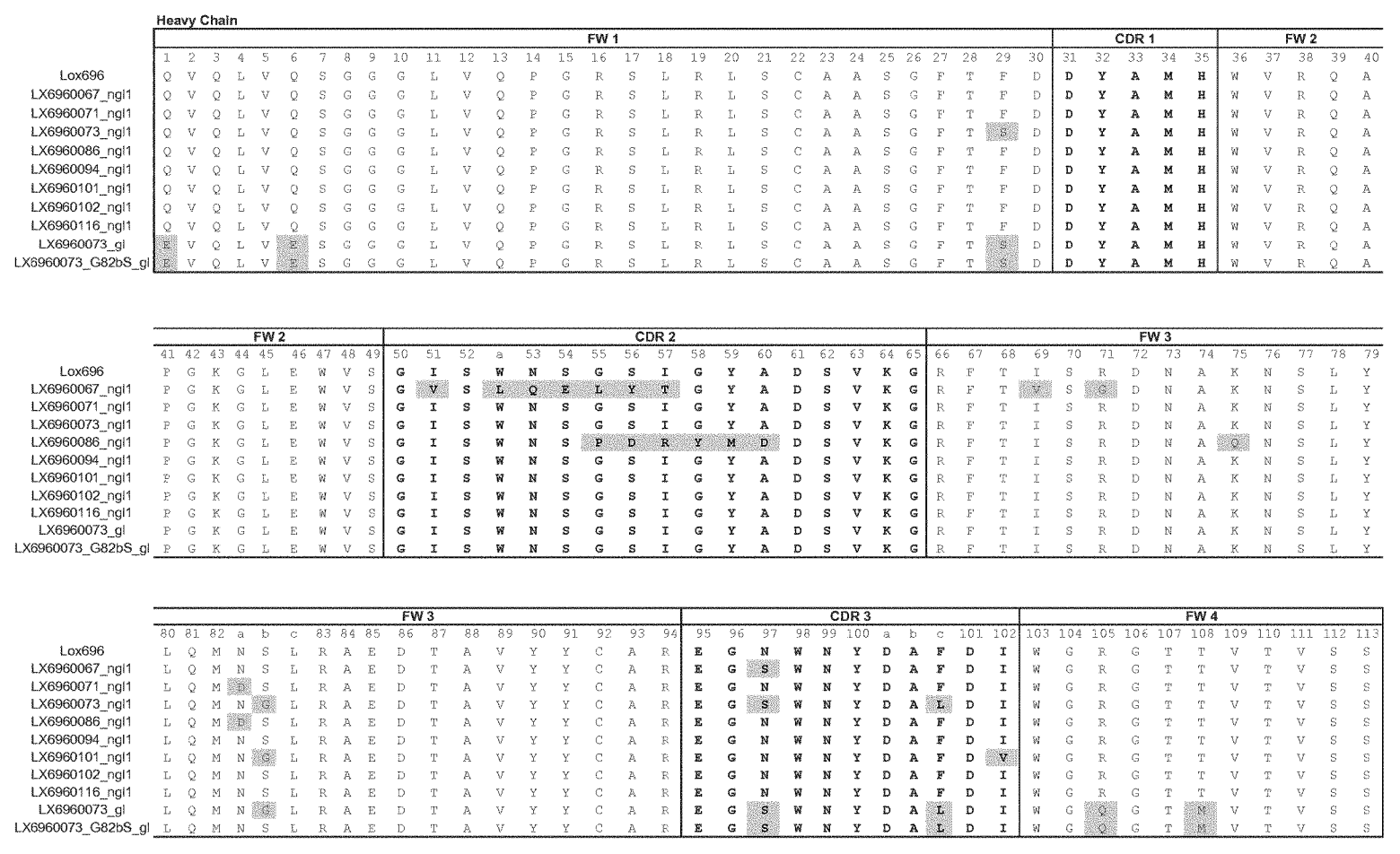
Figure 5B:
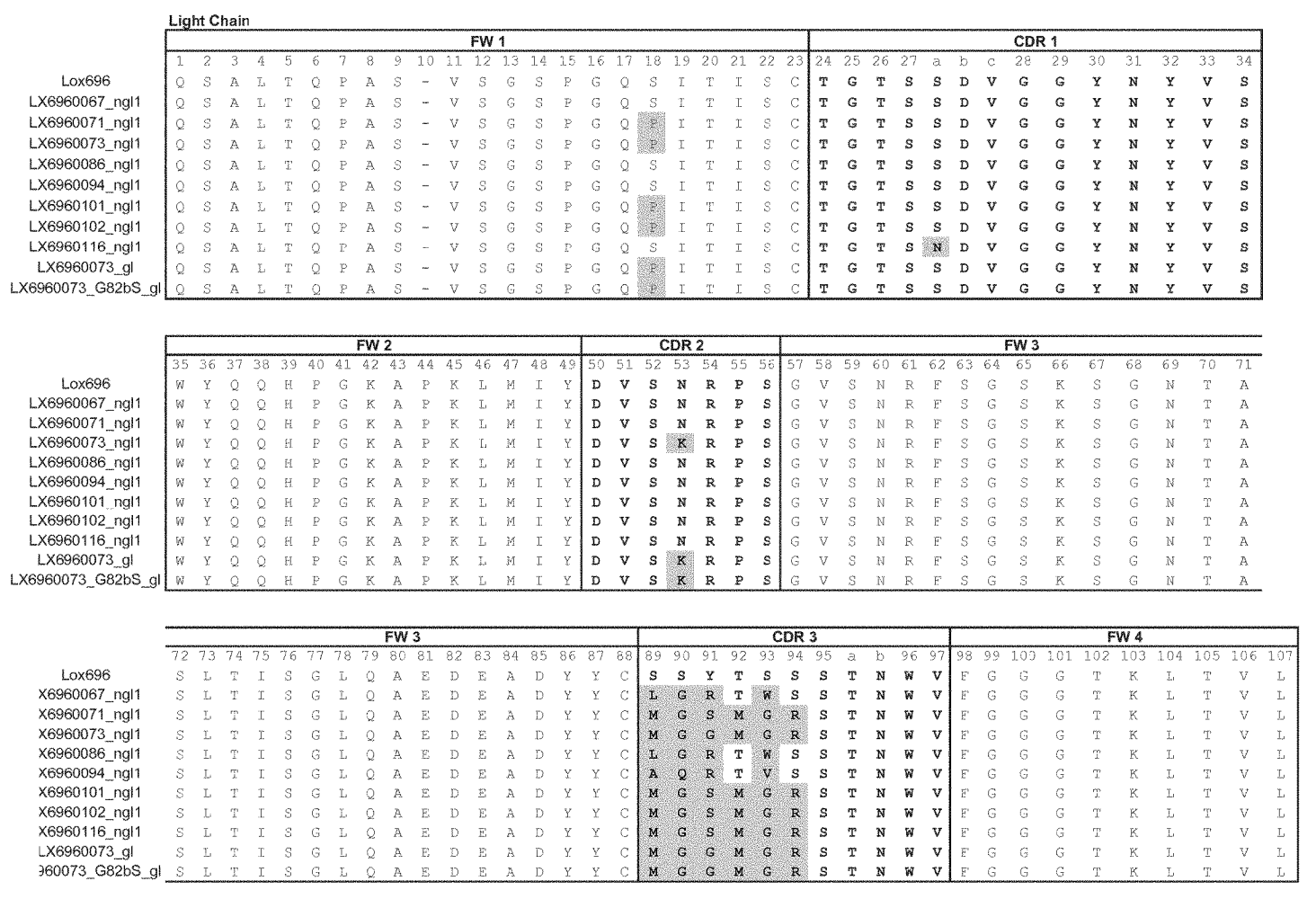

FIG. 5 shows a comparison between LOX696 and several optimized LOX696 antibodies. Amino acid sequence alignments of the heavy chain variable region (VH) (FIG. 5A) or the light chain variable region (VL) (FIG. 5B) between LOX696 and optimized LOX696 antibodies are shown. Differences from LOX696 VH or VL are highlighted. FW=framework; CDR=complementary determining regions.

Figure 6:
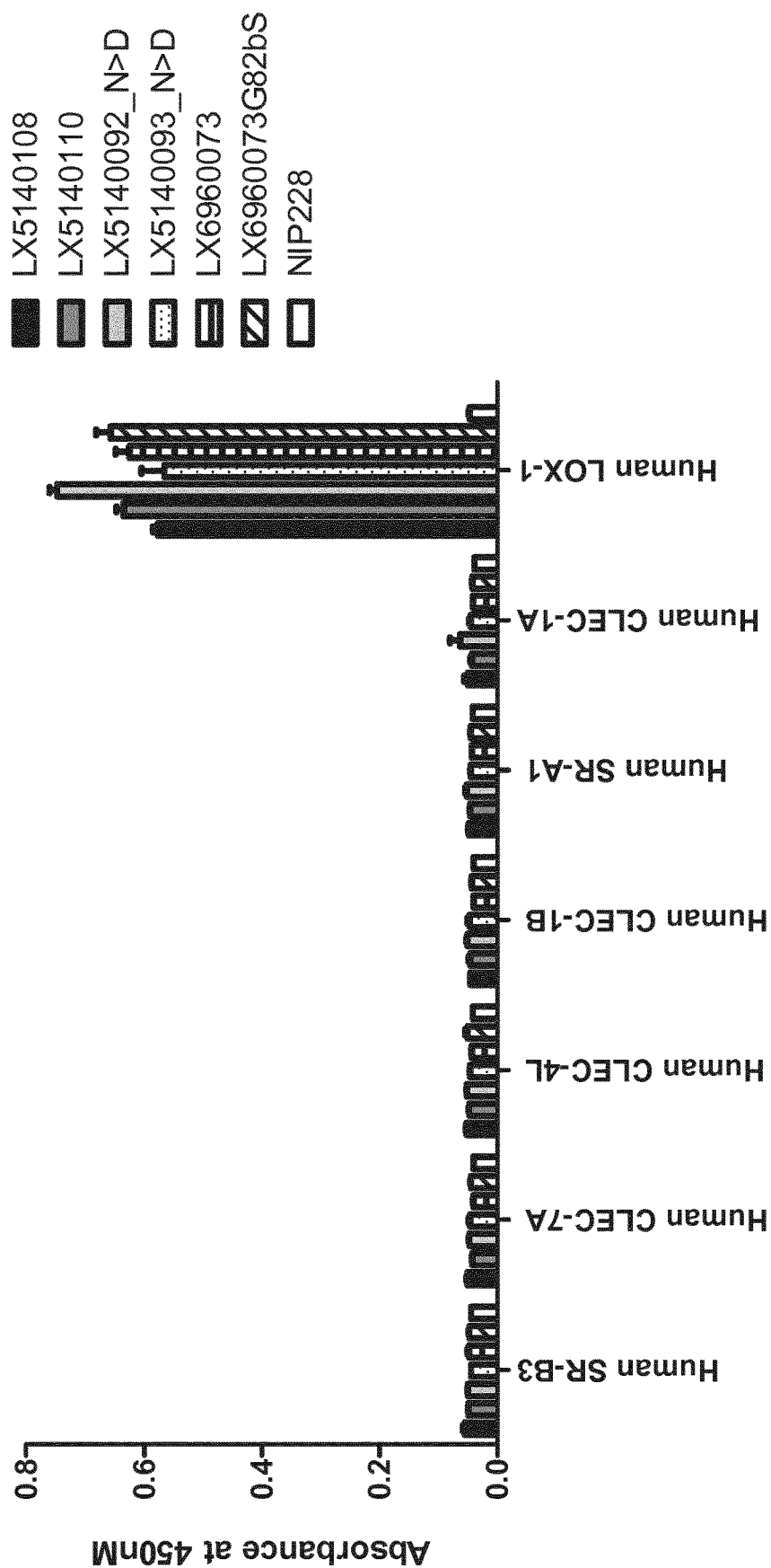

FIG. 6 shows the specificity of anti-LOX1 antibodies for human LOX1 compared to several human C type lectin and scavenger receptors related to LOX-1. The specificity of anti-LOX1 antibodies LX5140108, LX5140110, LX5140092_N>D, LX5140093_N>D, LX6960073_gl ("LX6960073") and LX6960073_G82bS_gl ("LX6960073G82bS") in an IgG1-TM format to human LOX-1 and other human C type lectin and scavenger receptors related to LOX-1 was assessed using an IgG binding ELISA. LX5140108, LX5140110, LX5140092_N>D, LX5140093_N>D, LX6960073_gl and LX6960073_G82bS_gl bind only to human LOX1 and do not bind to human CLEC-7A, CLEC-1A, CLEC-4L, CLEC-1B, SR-A1 or SR-B3. NIP228, an isotype human IgG1-TM control antibody, did not bind to human LOX-1 or any of the human C type lectin and scavenger receptors tested. CLEC-7A=C-type lectin domain family 7 member A (also known as Dectin-1); CLEC-1A=C-type lectin domain family 1 member A; CLEC-4L=C-type lectin domain family 4 member L (also known as DC-SIGN); CLEC-1B=C-type lectin domain family 1 member B (also known as CLEC-2); SR-A1=Macrophage scavenger receptor types I and II (also known as MSR); SR-B3=Platelet glycoprotein 4 (also known as CD36). Bars denote standard error.

Figure 7A:
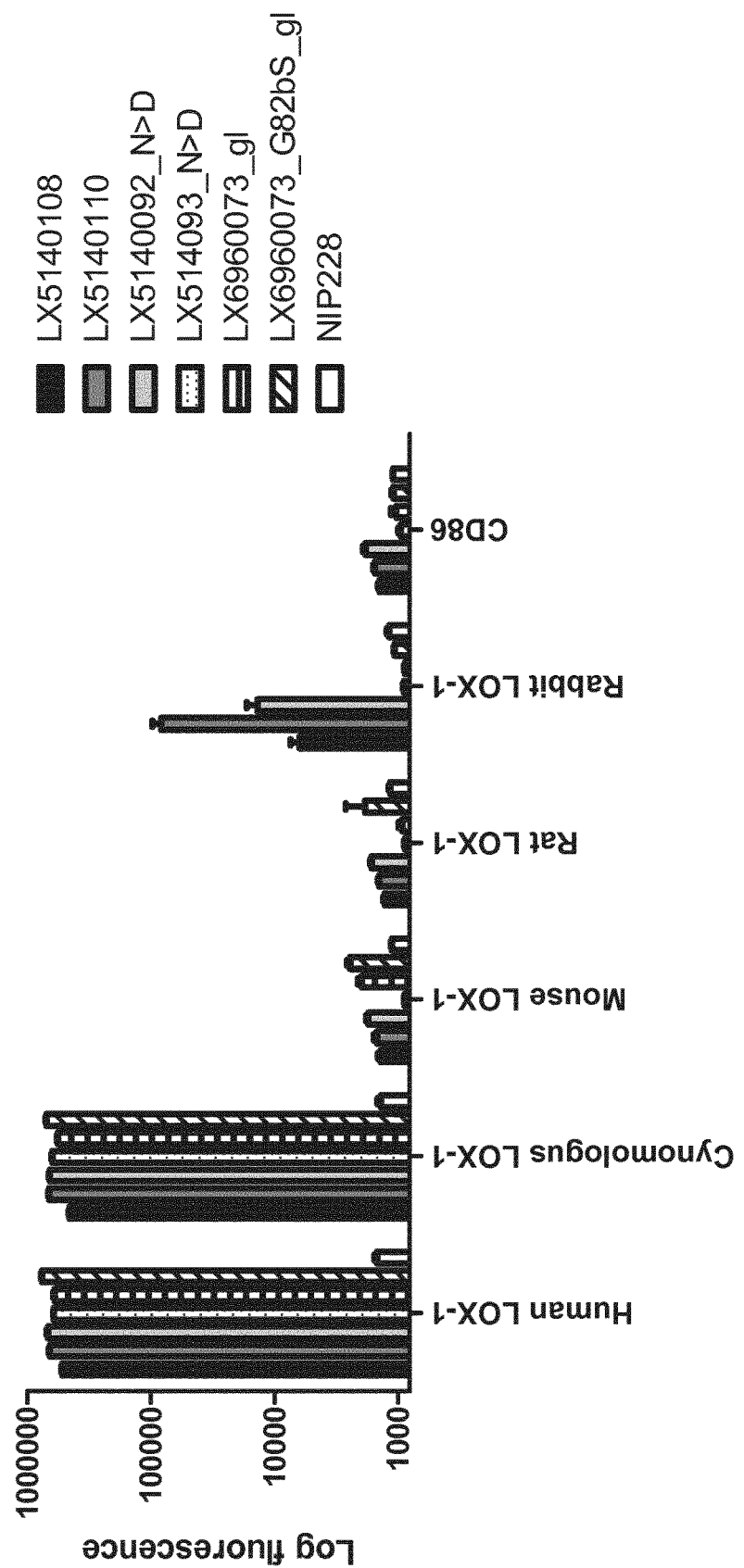
Figure 7B:
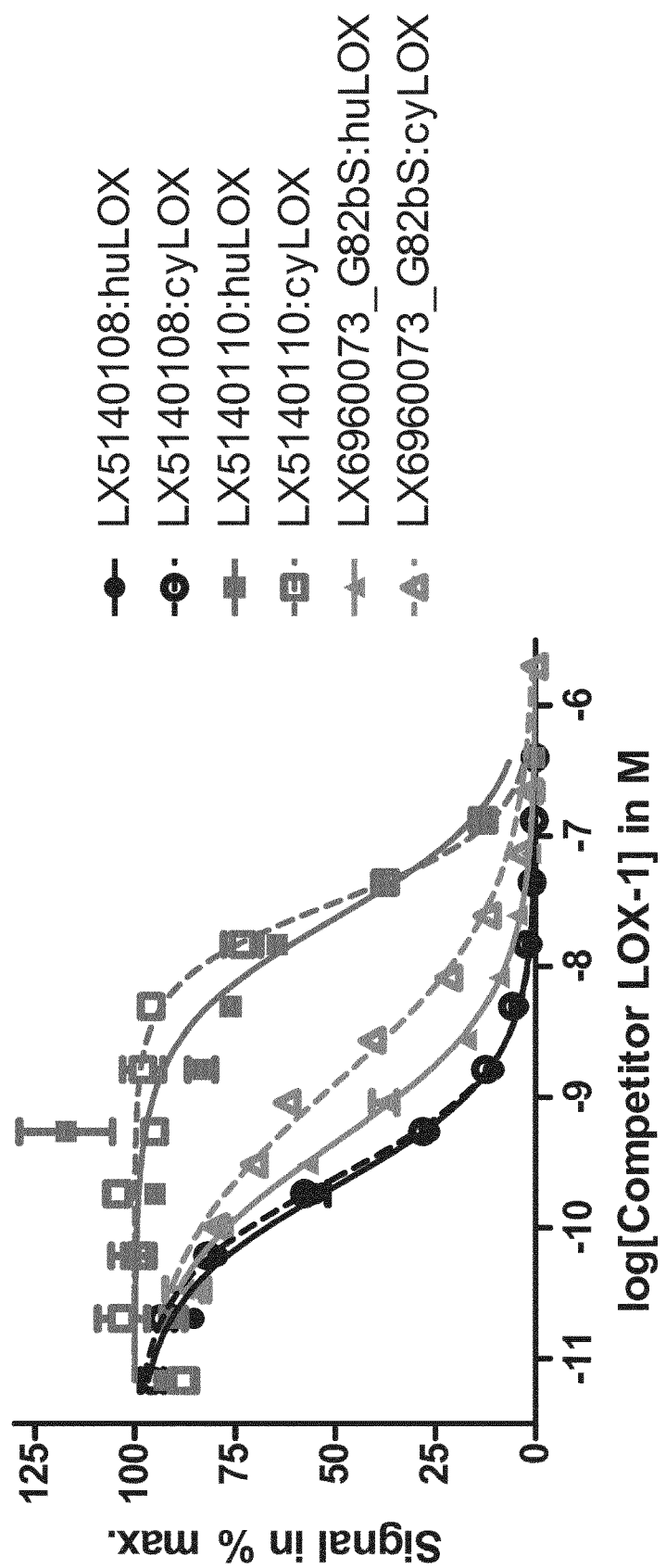

FIG. 7 shows the cross reactivity of anti-LOX1 antibodies to various LOX1 species orthologs. Cross-reactivity of anti-LOX1 antibodies LX5140108, LX5140110, LX5140092_N>D, LX5140093_N>D, LX6960073_gl and LX6960073_G82bS_gl in an IgG1-TM format to various LOX1 species orthologs was assessed using an IgG binding ELISA. As shown in FIG. 7A, anti-LOX1 antibodies LX5140108, LX5140110, LX5140092_N>D, LX5140093_N>D, LX6960073_gl and LX6960073_G82bS_gl bind to human and cynomolgus LOX1 but not to mouse or rat LOX1 orthologs or CD86 (negative control). Only LX5140108, LX5140110 and LX5140092_N>D also bind rabbit LOX-1. NIP228, an isotype human IgG1-TM control antibody, did not bind CD86 or any of the LOX-1 orthologs tested. In addition, cross reactivity characterization between human (huLOX) and cynomolgus (cyLOX) LOX1 were performed for the anti-LOX1 IgG1-TM antibodies LX5140108, LX5140110 and LX6960073_G82bS_gl ("LX6960073_G82bS") using a competition ELISA. As shown in FIG. 7B, LX5140108 (circles), LX5140110 (squares) and LX6960073_G82bS_gl (triangles) compete with both cynomolgus LOX1 and human LOX1 further confirming the cynomolgus cross-reactivity of anti-LOX1 antibodies LX5140108, LX5140110 and LX6960073_G82bS_gl. Bars denote standard error.

FIG. 8 shows inhibition of oxLDL, AGE-BSA and CRP binding to human LOX1 (hLOX1), inhibition of oxLDL internalization and inhibition of oxLDL-dependent LOX-1 signaling by antibodies LX5140110 and LX6960073_G82bS_gl. Binding of DyLight 649 labeled ox-LDL (FIG. 8A) or DyLight 649 labeled AGE-BSA (FIG. 8B) to hLOX1 transfected cells or binding of biotin labeled C-Reactive Protein (CRP) to recombinant hLOX1 (FIG. 8C) was measured in the presence of LX5140110-IgG1-TM ("LOX514_110"; circles FIGS. 8A and 8C, squares FIG. 8B), or LX6960073_G82bS_gl-IgG1-TM ("LX6960073_G82bS"; squares FIGS. 8A and 8C, circles FIG. 8B). Representative plots are shown in FIGS. 8A, 8B and 8C illustrating dose-dependent inhibition of oxLDL, AGE-BSA and CRP binding to hLOX1, respectively, by LX5140110 and LX6960073_G82bS_gl. In addition, LX5140110 and LX6960073_G82bS_gl also block the binding of DyLight 649 labeled ox-LDL to hLOX1 K167N transfected cells (FIG. 8D) confirming that these antibodies bind and block oxLDL binding to the LOX1 SNP K167N variant. To examine the ability of LX5140110 and LX6960073_G82bS_gl to block oxLDL internalization and oxLDL-dependent LOX-1 signaling, cypher 5E labeled ox-LDL internalization (FIG. 8E) or oxLDL-dependent ROS generation (FIG. 8F) in human LOX1 transfected cells was measured in the presence of LX5140110-IgG1-TM ("514_110", circles FIG. 8E; & "LOX10514_110", diamonds FIG. 8F), or LX6960073_G82bS_gl-IgG1-TM ("LX6960073_G82bS", squares FIG. 8E; & "LOX10696_73", squares FIG. 8F). Representative plots are shown in FIGS. 8E and 8F illustrating dose-dependent inhibition of oxLDL internalization and oxLDL-dependent ROS production, respectively, by LX5140110 and LX6960073_G82bS_gl. These results demonstrate: (1) specific, multi-ligand inhibition of LOX1 binding to oxLDL, AGE-BSA and CRP by antibodies LX5140110 and LX6960073_G82bS_gl; (2) LX5140110 and LX6960073_G82bS_gl functionally cross react with the common LOX1 SNP K167N variant; and (3) LX5140110 and LX6960073_G82bS_gl inhibit oxLDL internalization and oxLDL-dependent LOX-1 signaling. M=molar concentration of antibody; bars denote standard error.

Figure 9A:
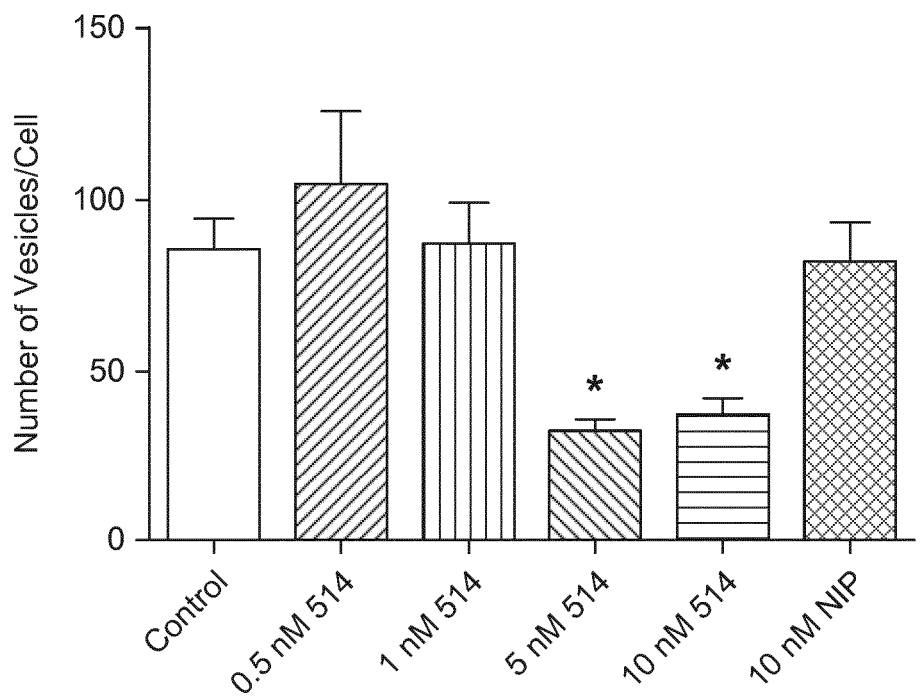

FIG. 9A shows the inhibition of OxLDL uptake in human aortic endothelial cells (HAECs) by LX5140110. AlexaFluor568-OxLDL uptake by HAECs incubated with 0, 0.5, 1, 5, or 10 nM of anti-LOX1 antibody LX5140110 ("514") or 10 nM of control antibody (NIP) was measured using fluorescence microscopy to test the ability of LX5140110 to block binding and internalization of oxidized low density lipoprotein (OxLDL) by HAECs. Approximately 12 images for each set were analyzed and the average number of Alexafluor-568-conjugated-OxLDL red fluorescent vesicles in each cell following an 1 hour incubation was determined. Number of vesicles per cell with 1 standard derivation is reported. These results demonstrate that 5 nM or 10 nM LX5140110 significantly inhibits OxLDL uptake by HAECs ($p=0.0003$ or $p=0.0002$ for 5 nM and 10 nM, respectively). * indicates that $P<0.05$ as compared with untreated controls (cells incubated only with Alexa-Fluor tagged OxLD, and without antibody); bars denote standard deviation.

Figure 9B:
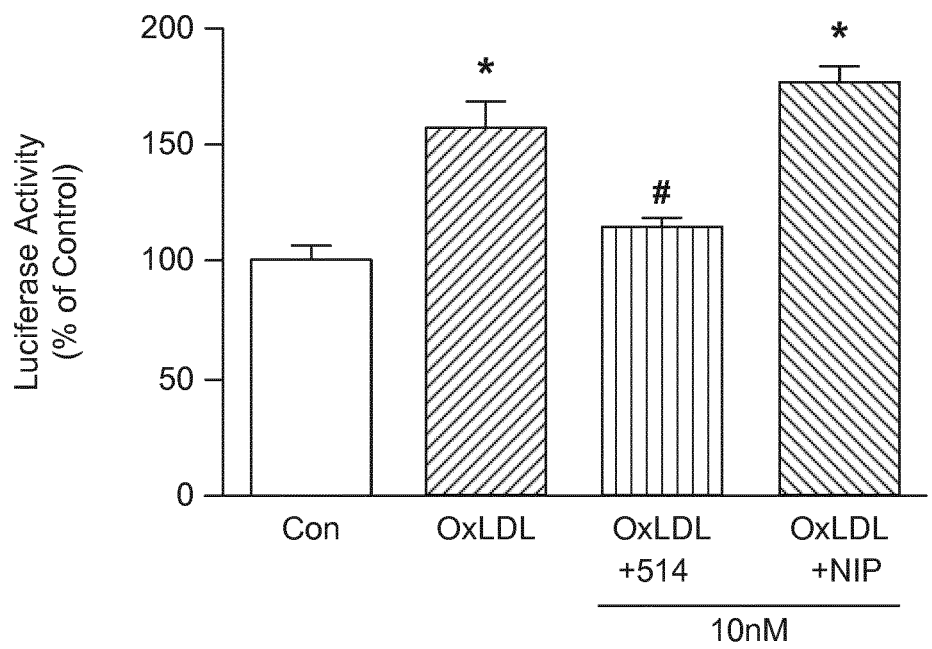

FIG. 9B shows reduction of OxLDL-dependent NFkB signaling in human aortic endothelial cells (HAECs) by LX5140110. HAECs co-expressing NFκB-luciferase and GFP were serum starved for 24 hours and incubated for 8 hours with: vehicle (control); OxLDL alone (50 μg/ml); OxLDL (50 μg/ml)+LX5140110 ("514") (10 nM); or OxLDL (50 μg/ml)+NIP (10 nM). Luciferase activity and luminescence were measured, while GFP fluorescence was used as a normalization control. These results demonstrate that addition of 10 mM LX5140110, but not NIP (control antibody), significantly reduces OxLDL-dependent NFkB signaling in HAECs. N=5 for each group; * indicates $P<0.05$ (compared with vehicle-only control); # indicates $P<0.05$ (compared with OxLDL alone); bars denote standard error.

Figure 9C:
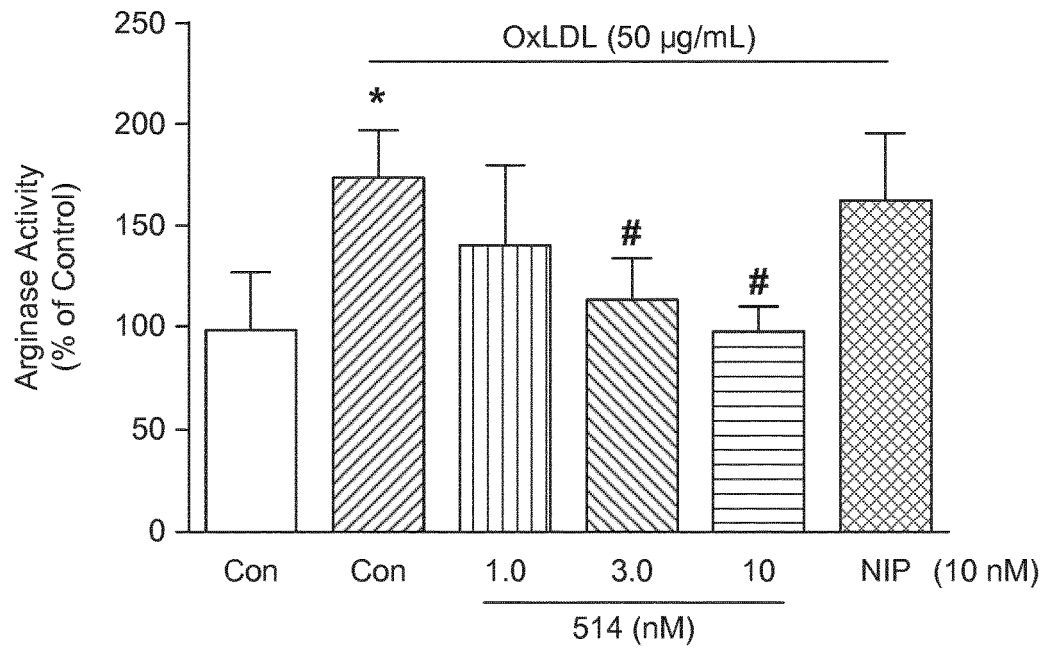

FIG. 9C shows inhibition of OxLDL-dependent augmentation of arginase activity in human aortic endothelial cells (HAECs) by LX5140110. HAECs were serum starved for 24 hours and incubated for 3 hours with: vehicle alone (control); OxLDL (50 μg/ml); OxLDL (50 μg/ml)+LX5140110 ("514") (1 nM); OxLDL (50 μg/ml)+LX5140110 ("514") (3 nM); OxLDL (50 μg/ml)+LX5140110 ("514") (10 nM); or OxLDL (50 μg/ml)+NIP (10 nM). Cells were lysed and arginase activity was determined using the urea assay. These results demonstrate that addition of 3 nM or 10 nM LX5140110, but not 10 nM NIP (control antibody), significantly reduces OxLDL-dependent arginase activity in HAECs in a dose-dependent manner. N=3 for each group; * indicates that $P<0.05$ as compared with vehicle-only controls; # indicates that $P<0.05$ as compared with OxLDL (50 μg/ml) control (without antibody); bars denote standard error.

Figure 9D:
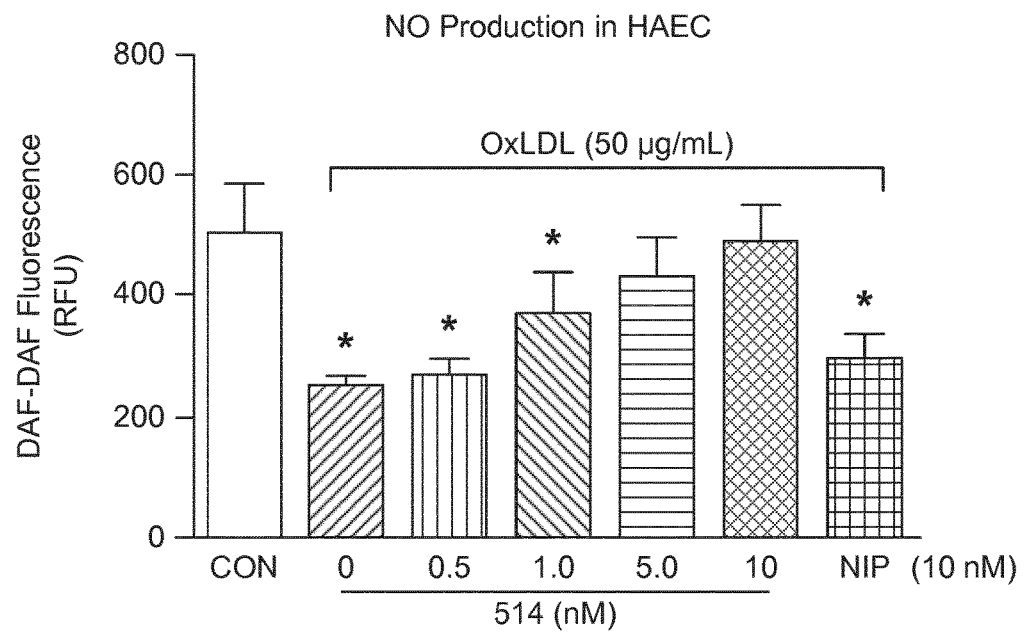

FIG. 9D shows that LX5140110 blocks OxLDL-dependent reduction in nitric oxide production by HAECs. HAECs were serum starved (1% serum) overnight and incubated for 24 hours with: vehicle (control); OxLDL (50 μg/ml); OxLDL (50 μg/ml)+LX5140110 ("514") (0.5 nM); OxLDL (50 μg/ml)+LX5140110 ("514") (1 nM); OxLDL (50 μg/ml)+LX5140110 ("514") (5 nM); OxLDL (50 μg/ml)+LX5140110 ("514") (10 nM); or OxLDL (50 μg/ml)+NIP (10 nM) prior to adding DAF-FM DA (504) in fresh media and measuring total fluorescence of DAF-FM DA. These results demonstrate that addition of 5 nM or 10 nM LX5140110, but not 10 nM NIP (control antibody), significantly inhibits OxLDL-dependent reduction in nitric oxide production of HAECs in a dose-dependent manner. To confirm that nitric oxide (NO) was produced by eNOS, the NOS inhibitor L-NAME was used as a control (data not shown). N=5 for each group; * indicates that $P<0.05$ (compared with vehicle-only control); bars denote standard error.

FIG. 9E shows that LX5140110 blocks OxLDL-dependent increased reactive oxygen species (ROS) production by HAECs. HAECs were serum starved (1% serum) overnight and incubated for 24 hours with: vehicle (control); OxLDL (50 μg/ml); OxLDL (50 μg/ml)+LX5140110 ("514") (0.5 nM); OxLDL (50 μg/ml)+LX5140110 ("514") (1 nM); OxLDL (50 μg/ml)+LX5140110 ("514") (5 nM); OxLDL (50 μg/ml)+LX5140110 ("514") (10 nM); or OxLDL (50 μg/ml)+NIP (10 nM), prior to incubating the cells with fresh phenol-free media containing 400 μM of the luminol analogue L-012. Relative light units (RLU) quantified from the luminescence of the luminol analogue L-012 indicate changes in production of ROS. These results demonstrate that addition of 0.5 nM, 1 nM, 5 nM or 10 nM LX5140110, but not 10 nM NIP (control antibody), inhibits OxLDL-dependent ROS production in HAECs. To confirm that superoxide was produced by eNOS, the NOS inhibitor L-NAME was used as a control (data now shown). N=5 for each group; * indicates $P<0.05$ as compared with vehicle-only controls; # indicates $P<0.05$ as compared with OxLDL (50 μg/ml) control (without antibody); bars denote standard error.

Figure 9F:
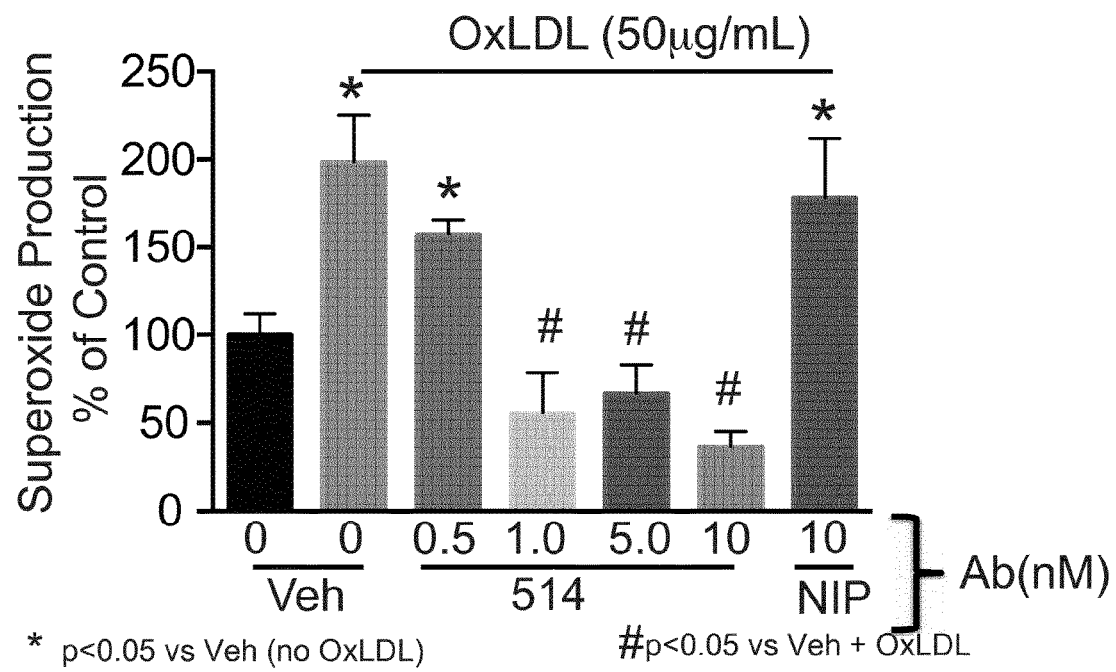
Figure 9F:
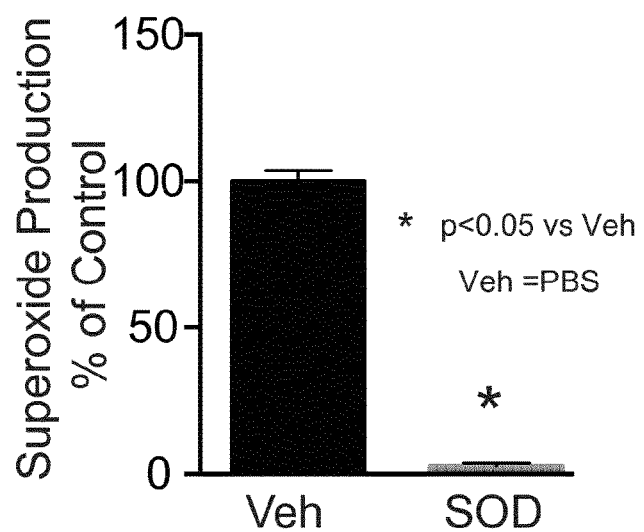

FIG. 9F shows that the luminol analogue L-012 is specific for reactive oxygen species (ROS). HAECs were serum starved (1% serum) overnight and incubated for 24 hours with: vehicle (Veh) or superoxide scavenger SOD (5 mM). As shown, addition of the superoxide scavenger SOD resulted in virtually undetectable levels of luminescence thereby confirming the specificity of L-012 for measuring superoxide (ROS) in FIG. 9E. * indicates that P<0.05 (compared with vehicle); bars denote standard error.

Figure 9G:
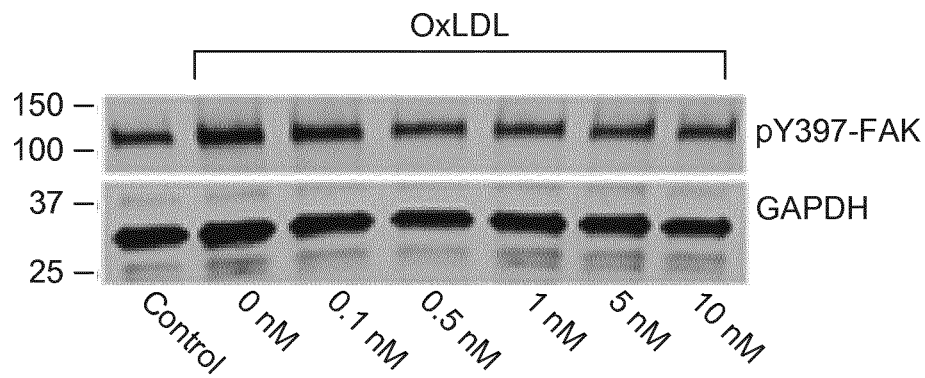
Figure 9H:
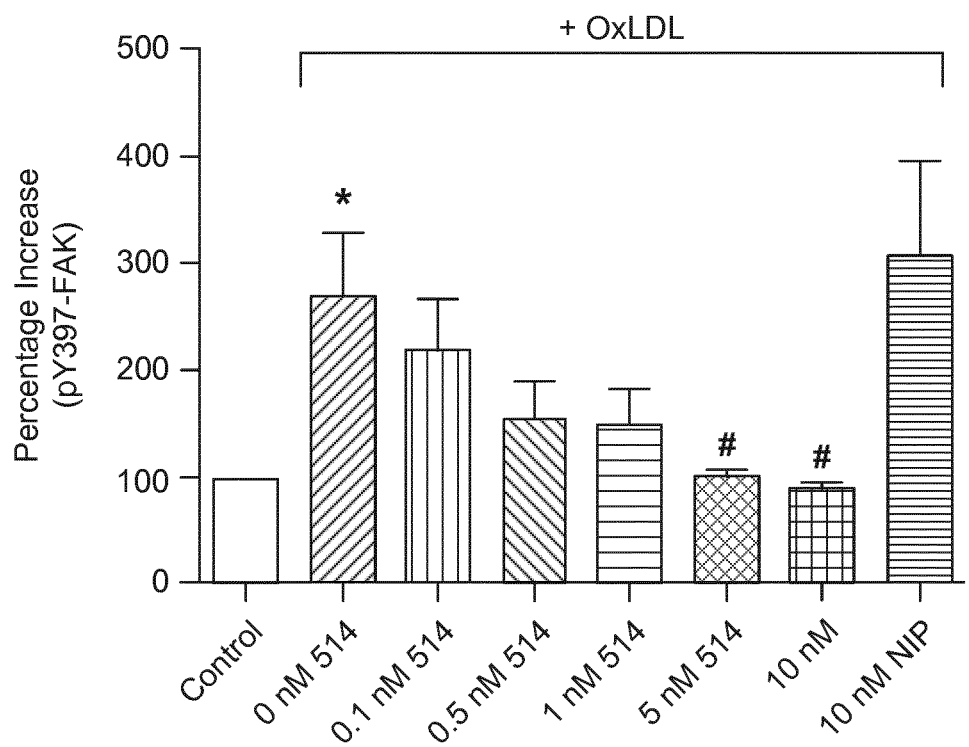

FIGS. 9G and 9H show that LX5140110 blocks OxLDL-mediated phosphorylation of Focal Adhesion Kinase (FAK) at tyrosine (Y) 397. HAECs were serum starved for 18 hours and incubated for 1 hour with: 0, 0.1, 0.5, 1, 5, or 10 nM of anti-LOX1 antibody LX5140110 (514) or 10 nM of control antibody (NIP), prior to incubating cells for 1 hour in fresh media with 50 µg/ml of OxLDL and running 10 µg of protein lysates on 4-15% gradient polyacrylamide gels. Protein samples subjected to SDS-PAGE were transferred to nitrocellulose membranes for Western blotting. A representative blot showing changes in FAK phosphorylation at Tyr397 and expression of GAPDH is shown in FIG. 9G, while quantification of the percentage increase of FAK phosphorylation at Tyr397 (pY397-FAK) normalized to GAPDH expression is shown in FIG. 9H. These results demonstrate that addition of 5 nM or 10 nM LX5140110, but not 10 nM NIP (control antibody), inhibits OxLDL-mediated FAK phosphorylation at Tyr397 in HAECs. * indicates that P<0.05 (compared with untreated control); # indicates that P<0.05 as compared with 0 nM LX5140110 (514); bars denote standard error.

Figure 9I:
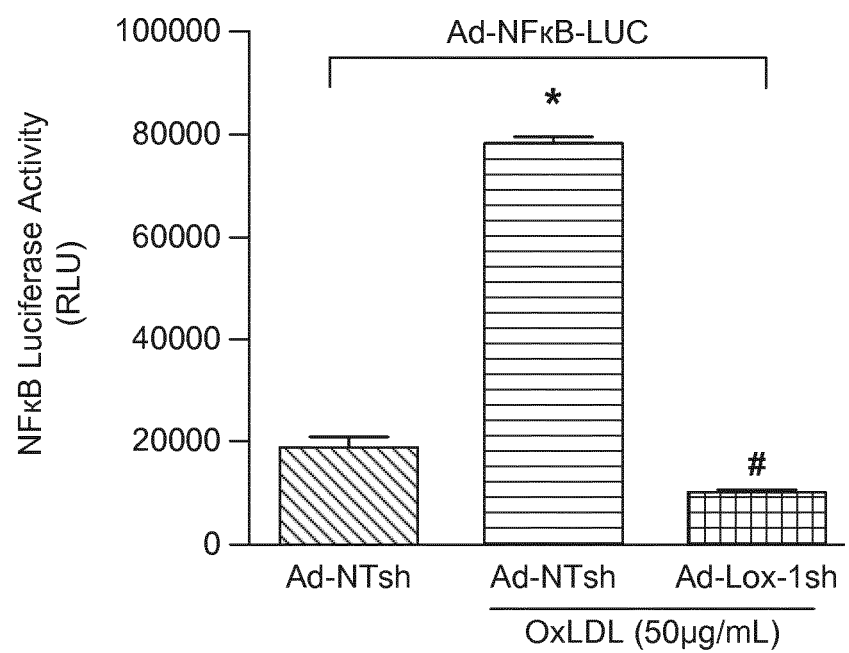

FIG. 9I shows that LOX1 is necessary for OxLDL signaling in HAECs. Human Aortic Endothelial Cells (HAECs) were co-transduced with adenoviruses encoding NFKB-LUC and either a non-targeted shRNA (Ad-NTsh) or Lox-1 shRNA (Ad-Lox-1sh) to specifically inhibit LOX1 expression. 24 hours post-transduction, cells were treated with or without OxLDL (50 µg/mL) and incubated at 37° C. for 24 hours. Firefly Luciferase activity was measured in cell lysates using chemiluminescence. Ad-LOX-1sh significantly inhibited OxLDL-mediated NFkB signaling in HAECs compared to cells incubated with a control, non-targeted shRNA (Ad-NTsh) virus. * indicates P<0.05 (compared with untreated control); # indicates P<0.05 as compared with OxLDL+Ad-NTsh.

Figure 9J:
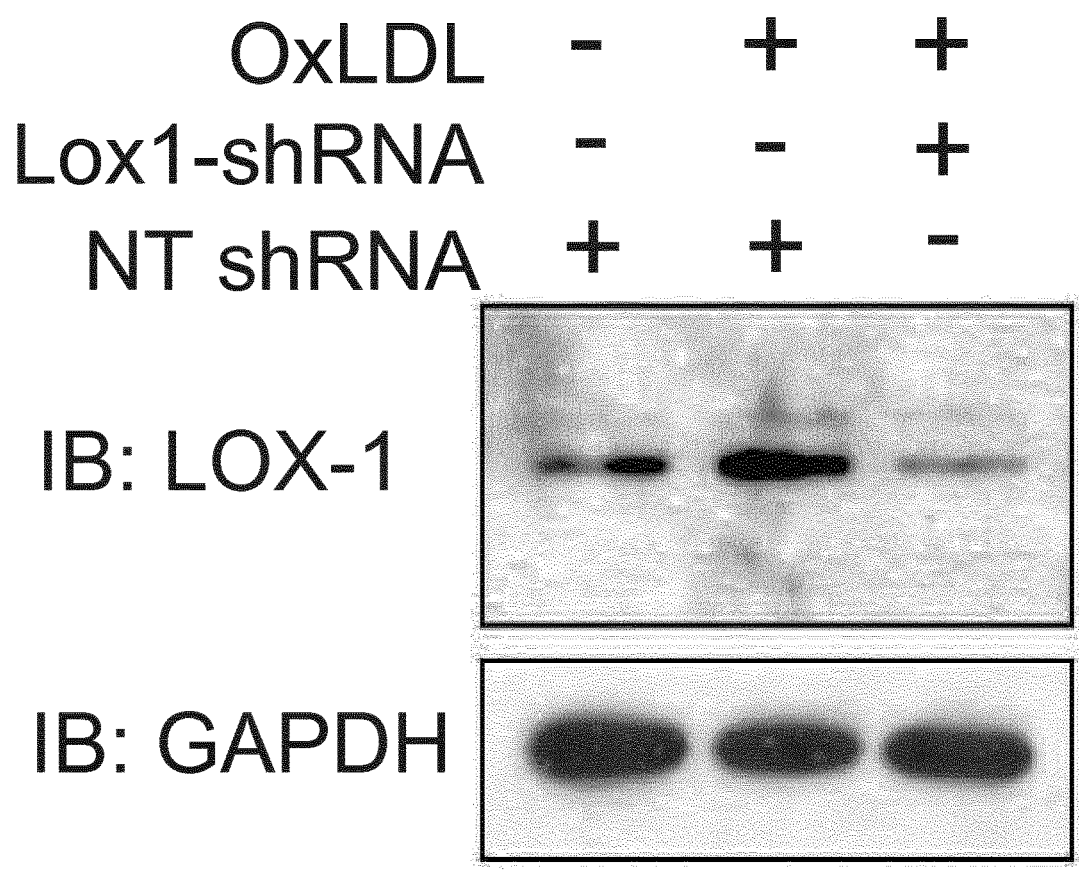

FIG. 9J shows that a viral vector expressing interfering short hairpin RNAs (shRNA) directed to the 5'UTR region of Human LOX1 gene (LOX1-shRNA) reduces LOX1 protein expression. LOX1 protein expression was monitored by immunoblotting using anti-Lox1 (IB:LOX-1) and anti-GAPDH (IB:GAPDH, used here as protein loading control) antibodies from the following samples: HAEC lysates transduced with non-targeted shRNA (NT shRNA) (lanes 1 and 2), or HAEC lysates transduced with Lox-1 shRNA (lane 3). Lysates in lanes 2 and 3 were treated with OxLDL (50 µg/mL), while lysates in lane 1 were not exposed to OxLDL. Addition of LOX1-shRNA significantly reduced LOX1 protein expression (lane 3) compared to levels that were measured in lysates from cells treated with non-targeted shRNA (lanes 1 and 2). These data confirm that LOX1-shRNA effectively inhibits LOX1 expression in HAECs.

Figure 9K:
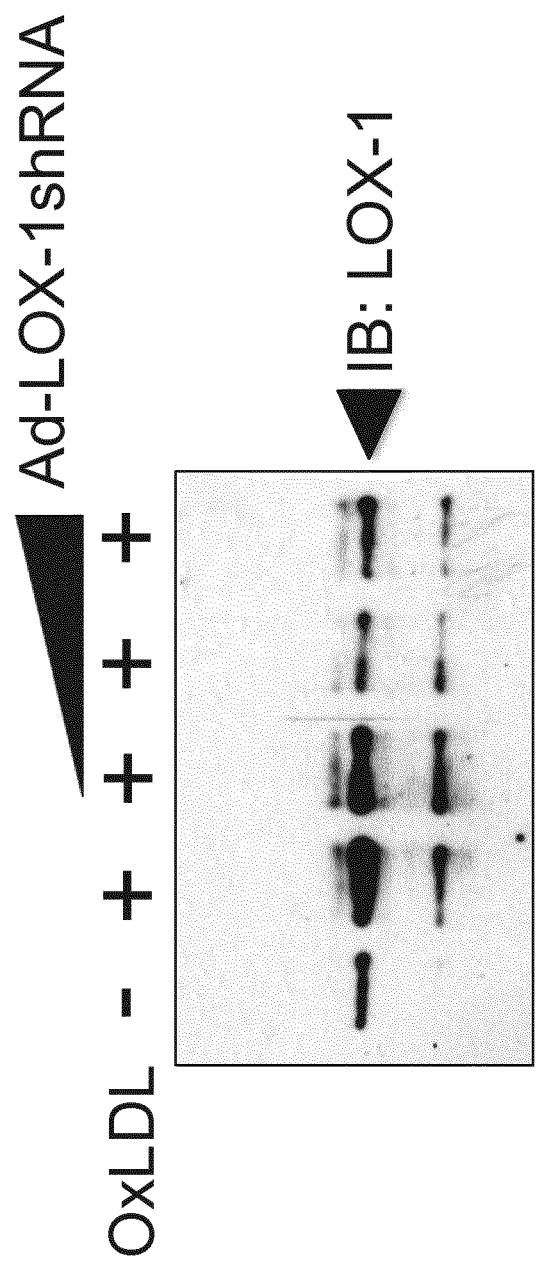

FIG. 9K shows that a viral vector expressing interfering short hairpin RNAs (shRNA) directed to the 5'UTR region of Human LOX1 gene (Ad-LOX-1shRNA) reduces LOX1 protein expression in a dose-dependent manner. HAECs transduced with increasing concentrations of Lox-1 shRNA (Ad-LOX-1shRNA) (0, 10, 20, 30 and 100 MOI for lanes 1-5, respectively) were stimulated with OxLDL (50 µg/mL) (with the exception of the control, unstimulated sample shown in lane 1). Cell lysates were obtained and subjected to immunoblotting with anti-Lox-1 antibody. Data are representative of at least 3 independent experiments. Ad-LOX-1shRNA significantly reduced LOX1 protein expression in a dose-dependent manner.

Figure 10:
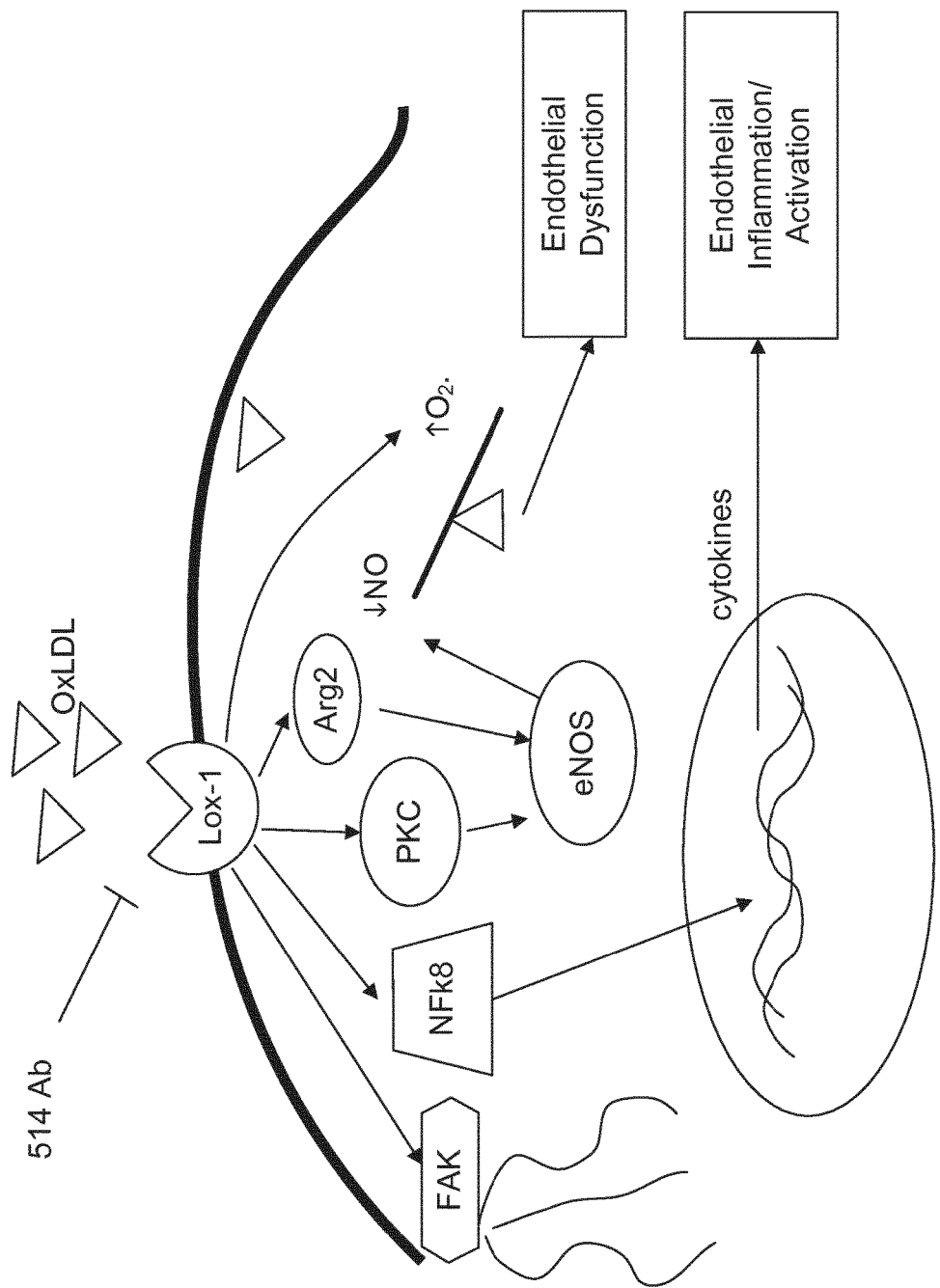

FIG. 10 shows some of the signaling pathways involved in LOX1 receptor signaling that are blocked by the anti-LOX1 antibodies disclosed herein, including LX5140110 ("514Ab").

DETAILED DESCRIPTION OF THE INVENTION

The present disclosure provides LOX1-binding proteins. In some aspects, the disclosure provides antagonists of LOX1 activity that are anti-LOX1 antibodies such as, full length anti-LOX1 antibodies, LOX1-binding antibody fragments, and variants and derivatives thereof. Related nucleic acids, compositions comprising LOX1-binding proteins, and methods of making the LOX1-binding proteins are also provided. Methods of using the LOX1-binding proteins in, for example, improving the LOX1-binding protein associated diseases or conditions such as: atherosclerosis, thrombosis, coronary artery disease (CAD), ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia or cancer in a subject and diagnostic uses, are further provided.

In order that the present disclosure can be more readily understood, certain terms are first defined. Additional definitions are set forth throughout the detailed description.

I. Definitions

As used in this specification and the appended claims, the singular forms "a", "an" and "the" include plural referents unless the context clearly dictates otherwise. The terms "a" (or "an"), as well as the terms "one or more," and "at least one" can be used interchangeably herein.

The term "about" is used herein to mean approximately, in the region of, roughly, or around. When the term "about" is used in conjunction with a numerical value or range, it modifies that value or range by extending the boundaries above and below the numerical values or ranges set forth. In general, the term "about" is used herein to modify a numerical value or range above and below the stated value or range by a variance of 10%.

Furthermore, "and/or" is to be taken as specific disclosure of each of the two specified features or components with or without the other. Thus, the term "and/or" as used in a phrase such as "A and/or B" is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

Wherever aspects are described with the language "comprising," otherwise analogous aspects described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

The term "LOX1" and "Lectin-like oxidized low density lipoprotein receptor-1" are used interchangeably herein and refer to LOX1 and/or biologically active fragments of LOX1. The cDNA and amino acid sequences of three hLOX1 isoforms are provided at GenBank Acc. Nos.: NP_002534.1, NP_001166103.1, and NP_001166104.1, each of which is incorporated herein by reference in its entirety.

The terms "inhibit," "block," "reduce," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in LOX1 biological activity. Accordingly, when the terms "inhibition" or "suppression" are applied to describe for example, an effect on a LOX1-mediated signal transduction pathway in a cell expressing cell surface LOX1 (e.g., an endothelial cell, smooth muscle cell, macrophage, and platelet) and in the presence of a LOX1 ligand (e.g., oxLDL, CRP and AGEs), the terms refer to the ability of a LOX1-binding protein, e.g., an anti-LOX1 antibody, to decrease a LOX1-mediated induced signal transduction in the cell at a statistically significant level (e.g., with a p value less than or equal to 0.05). In some aspects, the LOX1-mediated signal transduction pathway is a member selected from RhoA/Rac1, nitrogen monoxide, p38MAPK, protein kinase B and C, ERK1/2, and/or NFκB. In additional aspects, the inhibited or blocked LOX1-mediated biological activity is programmed cell death (i.e., apoptosis). In further embodiments, the decreased, inhibited or blocked LOX1-mediated biological activity is LOX1-mediated increased caspase 8, caspase 9, and/or decreased BAX activity. The cell which expresses cell surface LOX1 can be a naturally occurring cell (e.g., human endothelial cells, smooth muscle cells, and macrophage), a cell from a cell line or a recombinant cell produced by introducing a nucleic acid encoding LOX1 into the host cell.

The terms "antibody" or "immunoglobulin," as used interchangeably herein, include whole antibodies and any antigen-binding fragment or single chains thereof. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, Cl. The VH and VL regions can be further subdivided into regions of hypervariability, termed Complementarity Determining Regions (CDRs), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include typical antibodies, scFvs, and combinations thereof where, for example, an scFv is covalently linked (for example, via peptidic bonds or via a chemical linker) to the N-terminus of either the heavy chain and/or the light chain of a typical antibody, or intercalated in the heavy chain and/or the light chain of a typical antibody.

The term "antibody" can refer to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. The term "antibody" includes monoclonal antibodies, recombinant antibodies, human antibodies, humanized antibodies, chimeric antibodies, bi-specific antibodies, multi-specific antibodies, or antibody fragments thereof.

The term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

The term "germlining" means that amino acids at specific positions in an antibody are mutated back to those amino acids occurring at the same position as found in the germ line.

The term "antigen-binding antibody fragment" or "LOX1-binding antibody fragment" refers to a portion of an intact antibody and refers to the complementarity determining variable regions of an intact antibody. Examples of antibody fragments include, but are not limited to Fab, Fab', F(ab')2, and Fv fragments, linear antibodies, single chain antibodies (e.g., ScFvs), and multispecific antibodies formed from antibody fragments. The disclosure further provides LOX1-binding antibody fragments wherein the antibody fragment is a Fab fragment, a Fab' fragment, a F(ab')$_2$ fragment, a Fv fragment, a diabody, or a single chain antibody molecule.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., *Nature*, 321:522-525 (1986); Riechmann et al., *Nature*, 332:323-327 (1988); Verhoeyen et al., *Science*, 239:1534-1536 (1988)). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity-determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., *J. Molec. Biol.* 273:927-948 (1997)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991) herein incorporated by reference). The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See, e.g., Lefranc, M. P. et al., *Dev. Comp. Immunol.* 27: 55-77 (2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, etc.) with the desired specificity, affinity, and capability while the constant regions are homologous to the sequences in antibodies derived from another (usually human) to avoid eliciting an immune response in that species.

The terms "TM" or "TM mutant" refer to a mutation in the IgG1 constant region that results in a decreased effector function (e.g., ADCC) of an antibody having the mutation. A TM mutant comprises a combination of three mutations L234F/L235E/P331S resulting in an effector null human IgG1 (EU numbering Kabat et al. (1991) Sequences of Proteins of Immunological Interest, U.S. Public Health Service, National Institutes of Health, Washington, D.C.), introduced into the heavy chain of an IgG1.

The terms "YTE" or "YTE mutant" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., *J. Biol. Chem.* 281:23514-24 (2006)). See also U.S. Pat. No. 7,083,784, which is incorporated by reference herein in its entirety.

The terms "LOX1-binding protein", "anti-LOX1 antibody," or "an antibody that specifically binds LOX1" refer to a LOX1-binding protein such as an anti-LOX1 antibody that is capable of binding LOX1 with sufficient affinity such that the antibody is useful as a therapeutic agent or diagnostic reagent in targeting LOX1. The extent of binding of an anti-LOX1 antibody to an unrelated, non-LOX1 protein is less than about 10% of the binding of the antibody to LOX1 as measured, e.g., by a radioimmunoassay (RIA), BIACORE® (using recombinant LOX1 as the analyte and antibody as the ligand, or vice versa), Kinetic Exclusion Assay (KINEXA®), or other binding assays known in the art. In certain aspects, the LOX1-binding protein is a full-length antibody or a LOX1-binding antibody fragment that has a dissociation constant (KD) of ≤1 nM, ≤0.5 nM, ≤0.1 nM, ≤10 pM, or ≤1 pM, or in some instances, a KD of about 150 pM to about 600 pM or about 400 pM to about 600 pM. In certain aspects, the LOX1-binding protein is a full-length antibody or a LOX1-binding antibody fragment that has a dissociation constant (KD) of ≤1 µM, ≤100 nM, ≤10 nM, ≤1 nM, ≤0.1 nM, ≤10 pM, ≤1 pM, or ≤0.1 pM, or in some instances, a KD of about 150 pM to about 600 pM.

An "antagonist" or "blocking" LOX1-binding protein is one that inhibits or reduces the biological activity of LOX1. In some aspects, the antagonist LOX1-binding protein inhibits the ability of LOX1 to bind oxLDL, AGEs, and/or CRP. In some aspects, the LOX1-binding protein inhibits the ability of LOX1 to bind oxHDL, HSP60, leukocytes and/or activated platelets. In certain aspects a LOX1-binding protein substantially or completely inhibits the biological activity of LOX1. Desirably, the LOX1 biological activity is reduced by 10%, 20%, 30%, 50%, 70%, 80%, 90%, 95%, or even 100%. In particular aspects, the LOX1-binding protein is an anti-LOX1 antibody, such as a full length antibody or a LOX1-binding antibody fragment. In further aspects, the anti-LOX1 antibody inhibits or reduces the biological activity of LOX1 by 10%, 20%, 30%, 50%, 70%, 80%, 90%, 95%, or even 100%.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

"Potency" is normally expressed as an $IC_{50}$ value, in nM or pM unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by means known in the art.

The fold improvement in potency for the LOX1-binding protein disclosed herein (e.g., an antibody such as, a full length LOX1-antibody and a LOX1-binding antibody fragment, and variants and derivatives thereof) as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A LOX1-binding protein (e.g., a LOX1 antibody, including an antigen-binding fragment, variant, and derivative thereof), polynucleotide, vector, cell, or composition that is "isolated" is a polypeptide, antibody, polynucleotide, vector, cell, or composition that is in a form not found in nature. Isolated polypeptides (e.g., anti-LOX1 antibodies including full-length antibodies and LOX1-binding antibody fragments), polynucleotide, vector, polynucleotides, vectors, cells or compositions include those which have been purified to a degree that they are no longer in a form in which they are found in nature. In some aspects, an antibody, polynucleotide, vector, cell, or composition that is isolated is substantially pure.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation which is in such form as to permit the biological activity of the active ingredient (e.g., a LOX1-binding protein disclosed herein) to be effective, and which contains no additional components which are unacceptably toxic to a subject to which the composition would be administered. Such composition can be sterile.

An "effective amount" or "pharmaceutically effective amount" of a LOX1-binding protein such as, an anti-LOX1 antibody, or another therapeutic agent, is an amount sufficient to carry out a specifically stated purpose. An "effective amount" can be determined empirically and in a routine manner, in relation to the stated purpose. The disclosure provides therapeutics to treat, prevent or ameliorate diseases and conditions associated with LOX1 and/or decreased HDL-mediated signaling. These diseases and conditions include, for example, atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and cancer.

The word "label" when used herein refers to a detectable compound or composition that is conjugated directly or indirectly to the antibody so as to generate a "labeled" antibody. The label can be detectable by itself (e.g., radioisotope labels or fluorescent labels) or, in the case of an enzymatic label, can catalyze chemical alteration of a substrate compound or composition that is detectable.

Terms such as "treating" or "treatment" or "to treat" or "ameliorating" or "to ameliorate" refer to both (1) therapeutic measures that cure, slow down, lessen conditions associated with, and/or halt progression of a diagnosed disease or condition and (2) prophylactic or preventative measures that prevent and/or slow the development of a targeted disease or condition. Thus, those in need of treatment include those already with the disease or condition; those at risk of developing the disease or condition; and those in whom the disease or condition is to be prevented. In certain aspects, a subject is successfully "treated" according to the methods provided herein if the subject shows, e.g., total, partial, or transient amelioration or elimination of a symptom associated with the disease or condition. Such diseases or conditions include, for example, atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and cancer.

A "nucleic acid" or "polynucleotide," as used herein can include one or more "polynucleotides," "polynucleotide molecules," or "polynucleotide sequences," and refers to a polymer of nucleotides of any length, and includes DNA (genomic or cDNA) and RNA. The nucleic acids can be deoxyribonucleotides, ribonucleotides, modified nucleotides or bases, and/or their analogs, or any substrate that can be incorporated into a polymer by DNA or RNA polymerase. A "nucleic acid" or "polynucleotide," can comprise modified nucleotides, such as methylated nucleotides and their analogs. The preceding description applies to all polynucleotides referred to herein, including RNA and DNA (genomic or cDNA).

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and non-amino acids can interrupt it. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain aspects, the polypeptides can occur as single chains or associated chains.

The terms "identical" or percent sequence "identity" in the context of two or more nucleic acids or proteins, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., *Proc. Natl. Acad. Sci.*, 87:2264-2268 (1990), as modified in Karlin et al., *Proc. Natl. Acad. Sci.* 90:5873-5877 (1993), and incorporated into the NBLAST and XBLAST programs (Altschul et al., *Nucleic Acids Res.*, 25:3389-3402 (1991)). In certain aspects, Gapped BLAST can be used as described in Altschul et al., *Nucleic Acids Res.* 25:3389-3402 (1997), BLAST-2, WU-BLAST-2 (Altschul et al., *Methods in Enzymology* 266:460-480 (1996)), ALIGN, ALIGN-2 (Genentech, South San Francisco, Calif.) or Megalign (DNASTAR) are additional publicly available software programs that can be used to align sequences. In certain aspects, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative aspects, the GAP program in the GCG software package, which incorporates the algorithm of Needleman and Wunsch (*J. Mol. Biol.* (48):444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain aspects, the percent identity between nucleotide or amino acid sequences is determined using the algorithm of Myers and Miller (*CABIOS*, 4:11-17 (1989)). For example, the percent identity can be determined using the ALIGN program (version 2.0) and using a PAM120 with residue Table, a gap length penalty of 12 and a gap penalty of 4. One skilled in the art can determine appropriate parameters for maximal alignment by particular alignment software. In certain aspects, the default parameters of the alignment software are used.

In certain aspects, the percent sequence identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain aspects, conservative substitutions in the sequences of the LOX1-binding proteins of the disclosure do not abrogate the binding of the protein containing the substituted amino acid sequence to LOX1. Methods of identifying nucleotide and amino acid conservative substitutions which do not eliminate antigen-binding are well-known in the art (see, e.g., Brummell et al., *Biochem*. 32: 1180-1 187 (1993); Kobayashi et al., *Protein Eng*. 12(10):879-884 (1999); and Burks et al., *Proc. Natl. Acad. Sci. USA* 94:412-417 (1997)).

The term "epitope" as used herein refers to a LOX1, e.g., human LOX1 (hLOX1) or monkey LOX1 (e.g. *M. cynomolgus*), protein determinant capable of binding to a LOX1-binding protein (e.g., an antibody) of the disclosure. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. Such LOX1-binding proteins can be identified based on their ability to cross-compete (e.g., to competitively inhibit the binding of, in a statistically significant manner) with antibodies comprising for example, a VH sequence of SEQ ID NO:4 and a VL sequence of SEQ ID NO:33, or a VH sequence of SEQ ID NO:41 and a VL sequence of SEQ ID NO:58 in standard antigen-binding or activity assays.

A LOX1-binding protein (e.g., an antibody) is said to "compete" with a reference molecule for binding to LOX1 if it binds to LOX1 to the extent that it blocks, to some degree, binding of the reference molecule to LOX1. The ability of proteins to compete for binding to LOX1 can be determined by any method known in the art including, for example, a competition ELISA assay. As used herein, LOX1-binding protein may be said to competitively inhibit binding of the reference molecule to LOX1, for example, by at least 90%, at least 80%, at least 70%, at least 60%, or at least 50%.

II. LOX1-Binding Proteins

The present disclosure provides LOX1-binding proteins that specifically bind LOX1. In some aspects, a LOX1-binding protein is an antibody (e.g., a full length LOX1-antibody, an antigen-binding antibody fragment, and a variant and derivative thereof). In further aspects, the antibody is a monoclonal antibody, a recombinant antibody, a human antibody, a humanized antibody, a chimeric antibody, a bi-specific antibody, a multi-specific antibody, or an antibody fragment thereof. In certain aspects, the LOX1-antibody is a full-length antibody.

In some aspects, the LOX1-antibody is a LOX1-binding antibody fragment. In some aspects, the LOX1-binding antibody fragment is a: Fab, Fab', F(ab')$_2$, Fv fragment, diabody, or single chain antibody molecule. In additional aspects, the LOX1-antibody is a Fd, single chain Fv(scFv), disulfide linked Fv, V-NAR domain, IgNar, intrabody, IgGΔCH2, minibody, F(ab')$_3$, tetrabody, triabody, diabody, single-domain antibody, DVD-Ig, Fcab, mAb$^2$, (scFv)$_2$, or a scFv-Fc.

In additional aspects, the LOX1 binding protein is an antibody that includes a VH and a VL. In some aspects, the LOX1 binding protein (e.g. a LOX1 antibody or fragment thereof) further includes a heavy chain constant region or fragment thereof. In some aspects, the antibody comprises a heavy chain immunoglobulin constant region selected from the group consisting of: (a) a human IgA constant region, or fragment thereof; (b) a human IgD constant region, or fragment thereof; (c) a human IgE constant domain, or fragment thereof; (d) a human IgG1 constant region, or fragment thereof; (e) a human IgG2 constant region, or fragment thereof; (f) a human IgG3 constant region, or fragment thereof; (g) a human IgG4 constant region, or fragment thereof; and (h) a human IgM constant region, or fragment thereof. In further aspects, the LOX1-binding protein (e.g. a LOX1 antibody or fragment thereof) comprises a heavy chain immunoglobulin constant domain that has, or has been mutated to have, reduced ADCC activity. In particular aspects, the LOX1-binding protein (e.g. a LOX1 antibody or fragment thereof) comprises an IgG1 heavy chain constant region containing a mutation that decreases effector function. In some aspects, the IgG1 constant region comprises a mutation at positions 234, 235 and 331, wherein the position numbering is according to the EU index as in Kabat. In further aspects, the IgG1 constant region comprises triple mutations L234F/L235E/P331S (TM), wherein the position numbering is according to the EU index as in Kabat, resulting in an effector null human IgG1. In some aspects, the IgG1 constant region comprises the triple mutation mutant YTE, as disclosed supra in the Definitions section. In further aspects, the LOX1-binding protein is an antibody containing an IgG1 constant region that comprises both the triple Mutation™ and the triple mutation YTE.

In certain aspects a heavy chain constant region or fragment thereof, e.g., a human IgG constant region or fragment thereof, can include one or more amino acid substitutions relative to a wild-type IgG constant domain wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In certain aspects the IgG constant domain can contain one or more of a substitution of the amino acid at Kabat position 252 with Tyrosine (Y), Phenylalanine (F), Tryptophan (W), or Threonine (T), a substitution of the amino acid at Kabat position 254 with Threonine (T), a substitution of the amino acid at Kabat position 256 with Serine (S), Arginine (R), Glutamine (Q), Glutamic acid (E), Aspartic acid (D), or Threonine (T), a substitution of the amino acid at Kabat position 257 with Leucine (L), a substitution of the amino acid at Kabat position 309 with Proline (P), a substitution of the amino acid at Kabat position 311 with Serine (S), a substitution of the amino acid at Kabat position 428 with Threonine (T), Leucine (L), Phenylalanine (F), or Serine (S), a substitution of the amino acid at Kabat position 433 with Arginine (R), Serine (S), Isoleucine (I), Proline (P), or Glutamine (Q), or a substitution of the amino acid at Kabat position 434 with Tryptophan (W), Methionine (M), Serine (S), Histidine (H), Phenylalanine (F), or Tyrosine. More specifically, the IgG constant domain can contain amino acid substitutions relative to a wild-type human IgG constant domain including as substitution of the amino acid at Kabat position 252 with Tyrosine (Y), a substitution of the amino acid at Kabat position 254 with Threonine (T), and a substitution of the amino acid at Kabat position 256 with Glutamic acid (E).

In additional aspects, the LOX1-binding protein (e.g. a LOX1 antibody or fragment thereof) comprises a light chain immunoglobulin constant domain selected from the group consisting of: (a) a human Ig kappa constant domain; and (b) a human Ig lambda constant domain. In additional aspects, the LOX1-binding protein e.g. a LOX1 antibody or fragment thereof) comprises a human heavy chain IgG1 constant domain containing triple mutations L234F/L235E/P331S ("IgG-TM") resulting in an effector null human IgG1 and a human light chain lambda constant domain.

The disclosure provides an isolated LOX1-binding protein comprising a VH and/or a VL which has a total of one, two, three, four, five, six, seven, eight or fewer amino acid substitutions, deletions, and/or insertions from a reference VH or VL disclosed herein. In some aspects, the LOX1-binding protein has a VH and/or VL as shown in Table 1.

Exemplary LOX-1 binding proteins are provided in Table 1.

TABLE 1

| Exemplary LOX-1 binding proteins | |
|---|---|
| Lox514 | |
| VH CDR1 | ELSMH (SEQ ID NO: 1) |
| VH CDR2 | GFDPEDGETIYAQKFQG (SEQ ID NO: 5) |
| VH CDR3 | PNGQQGKGVRGWDYYYGMDV (SEQ ID NO: 14) |
| VH | QVQLVQSGAEVKKPGASVKVSCKVSGYTLTELSMHWVRQA PGKGLEWMGGFDPEDGETIYAQKFQGRVTMTEDTSTDTAY MELSSLRSEDTAVYYCATPNGQQGKGVRGWDYYYGMDVWG RGTTVTVSS (SEQ ID NO: 29) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQ LPGTAPKLLIYGNSNRPSGVPDRFSGSKSGTSASLAITGL QAEDEADYYCQSYDSSLSGWVFGGGTKLTVL (SEQ ID NO: 33) |
| LX5140011 | |
| VH CDR1 | ELSMH (SEQ ID NO: 1) |
| VH CDR2 | GFDPEDWEYAYDQKFQG (SEQ ID NO: 6) |
| VH CDR3 | PNGQQGKGVRGWDYYYGMDV (SEQ ID NO: 14) |
| VH | QVQLVQSGAEVKKPGASVKVSCKVSGYTLTELSMHWVRQA PGKGLEWMGGFDPEDWEYAYDQKFQGRVTMTEDTSTDTAY MELSSLRSEDTAVYYCATPNGQQGKGVRGWDYYYGMDVWG QGTTVTVSS (SEQ ID NO: 19) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQ LPGTAPKLLIYGNSNRPSGVPDRFSGSKSGTSASLAITGL QAEDEADYYCQSYDSSLSGWVFGGGTKLTVL (SEQ ID NO: 33) |
| LX5140014 | |
| VH CDR1 | ELSMH (SEQ ID NO: 1) |
| VH CDR2 | GFDPEDYTIRVGQKFQG (SEQ ID NO: 7) |
| VH CDR3 | PNGQQGKGVRGWDYYYGMDV (SEQ ID NO: 14) |
| VH | QVQLVQSGAEVKKPGASVKVSCKVSGYTLTELSMHWVRQA PGKGLEWMGGFDPEDYTIRVGQKFQGRVTMTEDTSTDTAY MELSSLRSEDTAVYYCATPNGQQGKGVRGWDYYYGMDVWG QGTTVTVSS (SEQ ID NO: 20) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQ LPGTAPKLLIYGNSNRPSGVPDRFSGSKSGTSASLAITGL QAEDEADYYCQSYDSSLSGWVFGGGTKLTVL (SEQ ID NO: 33) |
| LX5140016 | |
| VH CDR1 | ELSMH (SEQ ID NO: 1) |
| VH CDR2 | GFDPEDWQTHTAQKFQG (SEQ ID NO: 8) |
| VH CDR3 | PNGQQGKGVRGWDYYYGMDV (SEQ ID NO: 14) |
| VH | QVQLVQSGAEVKKPGASVKVSCKVSGYTLTELSMHWVRQA PGKGLEWMGGFDPEDWQTHTAQKFQGRVTMTEDTSTDTAY MELSSLRSEDTAVYYCATPNGQQGKGVRGWDYYYGMDVWG QGTTVTVSS (SEQ ID NO: 21) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQ LPGTAPKLLIYGNSNRPSGVPDRFSGSKSGTSASLAITGL QAEDEADYYCQSYDSSLSGWVFGGGTKLTVL (SEQ ID NO: 33) |

TABLE 1-continued

Exemplary LOX-1 binding proteins

LX5140038

| | |
|---|---|
| VH CDR1 | ELSMH (SEQ ID NO: 1) |
| VH CDR2 | GFDPEDWTIHVDQKFQG (SEQ ID NO: 9) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEWMGGFDPEDWTIHVDQKFQGRVTMTEDTSTDTAYMELSSLRSEDTAVYYCATPNGQQGKGVRGWDYYYGMDVWGQGTTVTVSS (SEQ ID NO: 22) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGWVFGGGTKLTVL (SEQ ID NO: 33) |

LX5140094

| | |
|---|---|
| VH CDR1 | ELSMH (SEQ ID NO: 1) |
| VH CDR2 | GFDPEDWQYHVSQKFQG (SEQ ID NO: 10) |
| VH CDR3 | PNGQQGKGVRGWDYYYGMDV (SEQ ID NO: 14) |
| VH | QVQLVQSGAEVKKPGASVKVSCKVSGYTLTELSMHWVRQAPGKGLEWMGGFDPEDWQYHVSQKFQGRVTMTEDTSTDTAYMELSSLRSEDTAVYYCATPNGQQGKGVRGWDYYYGMDVWGQGTTVTVSS (SEQ ID NO: 23) |
| VL CDR1 | TGSSSNIGAGYDVH (SEQ ID NO: 30) |
| VL CDR2 | GNSNRPS (SEQ ID NO: 31) |
| VL CDR3 | QSYDSMYRFG (SEQ ID NO: 34) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSMYRFGFGGGTKLTVL (SEQ ID NO: 36) |

LX5140108

| | |
|---|---|
| VH CDR1 | ELSMH (SEQ ID NO: 1) |
| VH CDR2 | GFDPEDWSNHVSQKFQG (SEQ ID NO: 11) |
| VH CDR3 | STGRQGKGVRGWDYYYGMDV (SEQ ID NO: 15) |
| VH | QVQLVQSGAEVKKPGASVKVSCKVSGYTLTELSMHWVRQAPGKGLEWMGGFDPEDWSNHVSQKFQGRVTMTEDTSTDTAYMELSSLRSEDTAVYYCLTSTGRQGKGVRGWDYYYGMDVWGQGTTVTVSS (SEQ ID NO: 24) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGWVFGGGTKLTVL (SEQ ID NO: 33) |

LX5140110

| | |
|---|---|
| VH CDR1 | ELSMH (SEQ ID NO: 1) |
| VH CDR2 | GFDPEDFKYHTHQKFQG (SEQ ID NO: 2) |
| VH CDR3 | VWGTQGKGVRGWDYYYGMDV (SEQ ID NO: 3) |
| VH | QVQLVQSGAEVKKPGASVKVSCKVSGYTLTELSMHWVRQAPGKGLEWMGGFDPEDFKYHTHQKFQGRVTMTEDTSTDTAYMELSSLRSEDTAVYYCALVWGTQGKGVRGWDYYYGMDVWGQGTTVTVSS (SEQ ID NO: 4) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGWVFGGGTKLTVL (SEQ ID NO: 33) |

LX5140092

| | |
|---|---|
| VH CDR1 | ELSMH (SEQ ID NO: 1) |
| VH CDR2 | GFDPEDWKYHLSQKFQG (SEQ ID NO: 12) |
| VH CDR3 | PNGTHQGGVRGWDYYYGMDV (SEQ ID NO: 17) |
| VH | QVQLVQSGAEVKKPGASVKVSCKVSGYTLTELSMHWVRQAPGKGLEWMGGFDPEDWKYHLSQKFQGRVTMTEDTSTDTAYMELSSLRSEDTAVYYCATPNGTHQGGVRGWDYYYGMDVWGQGTTVTVSS (SEQ ID NO: 26) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGWVFGGGTKLTVL (SEQ ID NO: 33) |

LX5140092_D

| | |
|---|---|
| VH CDR1 | ELSMH (SEQ ID NO: 1) |
| VH CDR2 | GFDPEDWKYHLSQKFQG (SEQ ID NO: 12) |
| VH CDR3 | PDGTHQGGVRGWDYYYGMDV (SEQ ID NO: 16) |
| VH | QVQLVQSGAEVKKPGASVKVSCKVSGYTLTELSMHWVRQAPGKGLEWMGGFDPEDWKYHLSQKFQGRVTMTEDTSTDTAYMELSSLRSEDTAVYYCATPDGTHQGGVRGWDYYYGMDVWGQGTTVTVSS (SEQ ID NO: 25) |
| VL CDR1 | TGSSSNIGAGYDVH (SEQ ID NO: 30) |
| VL CDR2 | GNSNRPS (SEQ ID NO: 31) |
| VL CDR3 | QSYDSSLSGWV (SEQ ID NO: 32) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGWVFGGGTKLTVL (SEQ ID NO: 33 |

LX5140093

| | |
|---|---|
| VH CDR1 | ELSMH (SEQ ID NO: 1) |
| VH CDR2 | GFDPEDWAYHQAQKFQG (SEQ ID NO: 13) |
| VH CDR3 | PNGQQGKGVRGWDYYYGMDV (SEQ ID NO: 14) |

TABLE 1-continued

Exemplary LOX-1 binding proteins

| | |
|---|---|
| VH | QVQLVQSGAEVKKPGASVKVSCKVSGYTLTELSMHWVRQAPGKGLEWMGGFDPEDWAYHQAQKFQGRVTMTEDTSTDTAYMELSSLRSEDTAVYYCATPNGQQKGVRGWDYYYGMDVWGQGTTVTVSS (SEQ ID NO: 27) |
| VL CDR1 | TGSSSNIGAGYDVH (SEQ ID NO: 30) |
| VL CDR2 | GNSNRPS (SEQ ID NO: 31) |
| VL CDR3 | QSYDSSHRAWA (SEQ ID NO: 35) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSHRAWAFGGGTKLTVL (SEQ ID NO: 37) |

LX5140093_D

| | |
|---|---|
| VH CDR1 | ELSMH (SEQ ID NO: 1) |
| VH CDR2 | GFDPEDWAYHQAQKFQG (SEQ ID NO: 13) |
| VH CDR3 | PDGQQKGVRGWDYYYGMDV (SEQ ID NO: 18) |
| VH | QVQLVQSGAEVKKPGASVKVSCKVSGYTLTELSMHWVRQAPGKGLEWMGGFDPEDWAYHQAQKFQGRVTMTEDTSTDTAYMELSSLRSEDTAVYYCATPDGQQKGVRGWDYYYGMDVWGQGTTVTVSS (SEQ ID NO: 28) |
| VL CDR1 | TGSSSNIGAGYDVH (SEQ ID NO: 30) |
| VL CDR2 | GNSNRPS (SEQ ID NO: 31) |
| VL CDR3 | QSYDSSHRAWA (SEQ ID NO: 35) |
| VL | QSVVTQPPSVSGAPGQRVTISCTGSSSNIGAGYDVHWYQQLPGTAPKLLIYGNSNRPSGVPDRFSGSKSGTSASLAITGLQAEDEADYYCQSYDSSHRAWAFGGGTKLTVL (SEQ ID NO: 37) |

Lox696

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQAPGKGLEWVSGISWNSGSIGYADSVKGRFTISRDNAKNSLYLQMNSLRAEDTAVYYCAREGNWNYDAFDIWGRGTTVTVSS (SEQ ID NO: 54) |
| VL CDR1 | TGTSSDVGGYNYVS (SEQ ID NO: 55) |
| VL CDR2 | DVSNRPS (SEQ ID NO: 60) |
| VL CDR3 | SSYTSSSTNWV (SEQ ID NO: 61) |
| VL | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTNWVFGGGTKLTVL (SEQ ID NO: 70) |

LX6960067_ng11

| | |
|---|---|
| VH CDR1 | DYAMH (SEQ ID NO: 38) |
| VH CDR2 | GVSLQELYTGYADSVKG (SEQ ID NO: 42) |
| VH CDR3 | EGSWNYDAFDI (SEQ ID NO: 45) |
| VH | QVQLVQSGGGLVQPGRSLRLSCAASGFTFDDYAMHWVRQAPGKGLEWVSGVSLQELYTGYADSVKGRFTVSGDNAKNSLYLQMNSLRAEDTAVYYCAREGSWNYDAFDIWGRGTTVTVSS (SEQ ID NO: 48) |
| VL CDR1 | TGTSSDVGGYNYVS (SEQ ID NO: 55) |
| VL CDR2 | DVSNRPS (SEQ ID NO: 60) |
| VL CDR3 | LGRTWSSTNWV (SEQ ID NO: 62) |
| VL | QSALTQPASVSGSPGQSITISCTGTSSDVGGYNYVSWYQQHPGKAPKLMIYDVSNRPSGVSNRFSGSKSGNTASLTISGLQAEDEADYYCLGRTWSSTNWVFGGGTKLTVL (SEQ ID NO: 65) |

LX6960071_ng11

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQAPGKGLEWVSGISWNSGSIGYADSVKGRFTISRDNAKNSLYLQMDSLRAEDTAVYYCAREGNWNYDAFDIWGRGTTVTVSS (SEQ ID NO: 49) |
| VL CDR1 | TGTSSDVGGYNYVS (SEQ ID NO: 55) |
| VL CDR2 | DVSNRPS (SEQ ID NO: 60) |
| VL CDR3 | MGGMGRSTNWV (SEQ ID NO: 57) |
| VL | QSALTQPASVSGSPGQPITISCTGTSSDVGGYNYVSWYQQHPGKAPKLMIYDVSNRPSGVSNRFSGSKSGNTASLTISGLQAEDEADYYCMGSMGRSTNWVFGGGTKLTVL (SEQ ID NO: 66) |

LX6960073_ng11

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGSWNYDALDI (SEQ ID NO: 46) |
| VH | QVQLVQSGGGLVQPGRSLRLSCAASGFTSDDYAMHWVRQAPGKGLEWVSGISWNSGSIGYADSVKGRFTISRDNAKNSLYLQMNGLRAEDTAVYYCAREGSWNYDALDIWGRGTTVTVSS (SEQ ID NO: 50) |
| VL CDR1 | TGTSSDVGGYNYVS (SEQ ID NO: 55) |
| VL CDR2 | DVSKRPS (SEQ ID NO: 56) |
| VL CDR3 | MGGMGRSTNWV (SEQ ID NO: 57) |
| VL | QSALTQPASVSGSPGQPITISCTGTSSDVGGYNYVSWYQQHPGKAPKLMIYDVSKRPSGVSNRFSGSKSGNTASLTISGLQAEDEADYYCMGGMGRSTNWVFGGGTKLTVL (SEQ ID NO: 67) |

LX6960086_ng11

| | |
|---|---|
| VH CDR1 | DYAMH (SEQ ID NO: 38) |
| VH CDR2 | GISWNSPDRYMDDSVKG (SEQ ID NO: 43) |
| VH CDR3 | EGNWNYDAFDI (SEQ ID NO: 44) |
| VH | QVQLVQSGGGLVQPGRSLRLSCAASGFTFDDYAMHWVRQAPGKGLEWVSGISWNSPDRYMDDSVKGRFTISRDNAQNSLYLQMDSLRAEDTAVYYCAREGNWNYDAFDIWGRGTTVTVSS (SEQ ID NO: 51) |
| VL CDR1 | TGTSSDVGGYNYVS (SEQ ID NO: 55) |
| VL CDR2 | DVSNRPS (SEQ ID NO: 60) |

TABLE 1-continued

Exemplary LOX-1 binding proteins

| | |
|---|---|
| VL CDR3 | LGRTWSSTNWV (SEQ ID NO: 62) |
| VL | QSALTQPASVSGSPGQSITISCTGTSSDVGGYNYVSWYQQ<br>HPGKAPKLMIYDVSNRPSGVSNRFSGSKSGNTASLTISGL<br>QAEDEADYYCLGRTWSSTNWVFGGGTKLTVL<br>(SEQ ID NO: 65) |

LX6960094_ng1l

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQA<br>PGKGLEWVSGISWNSGSIGYADSVKGRFTISRDNAKNSLY<br>LQMNSLRAEDTAVYYCAREGNWNYDAFDIWGRGTTVTVSS<br>(SEQ ID NO: 54) |
| VL CDR1 | TGTSSDVGGYNYVS (SEQ ID NO: 55) |
| VL CDR2 | DVSNRPS (SEQ ID NO: 60) |
| VL CDR3 | AQRTVSSTNWV (SEQ ID NO: 64) |
| VL | QSALTQPASVSGSPGQSITISCTGTSSDVGGYNYVSWYQQ<br>HPGKAPKLMIYDVSNRPSGVSNRFSGSKSGNTASLTISGL<br>QAEDEADYYCAQRTVSSTNWVFGGGTKLTVL<br>(SEQ ID NO: 68) |

LX6960101_ng1l

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDV (SEQ ID NO: 47) |
| VH | QVQLVQSGGGLVQPGRSLRLSCAASGFTFDDYAMHWVRQA<br>PGKGLEWVSGISWNSGSIGYADSVKGRFTISRDNAKNSLY<br>LQMNGLRAEDTAVYYCAREGNWNYDAFDVWGRGTTVTVSS<br>(SEQ ID NO: 52) |
| VL CDR1 | TGTSSDVGGYNYVS (SEQ ID NO: 55) |
| VL CDR2 | DVSNRPS (SEQ ID NO: 60) |
| VL CDR3 | MGGMGRSTNWV (SEQ ID NO: 57) |
| VL | QSALTQPASVSGSPGQPITISCTGTSSDVGGYNYVSWYQQ<br>HPGKAPKLMIYDVSKRPSGVSNRFSGSKSGNTASLTISGL<br>QAEDEADYYCMGGMGRSTNWVFGGGTKLTVL<br>(SEQ ID NO: 67) |

LX6960102_ng1l

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQA<br>PGKGLEWVSGISWNSGSIGYADSVKGRFTISRDNAKNSLY<br>LQMNSLRAEDTAVYYCAREGNWNYDAFDIWGRGTTVTVSS<br>(SEQ ID NO: 54) |
| VL CDR1 | TGTSSDVGGYNYVS (SEQ ID NO: 55) |
| VL CDR2 | DVSNRPS (SEQ ID NO: 60) |
| VL CDR3 | MGGMGRSTNWV (SEQ ID NO: 57) |
| VL | QSALTQPASVSGSPGQSITISCTGTSSDVGGYNYVSWYQQ<br>HPGKAPKLMIYDVSNRPSGVSNRFSGSKSGNTASLTISGL<br>QAEDEADYYCSSYTSSSTNWVFGGGTKLTVL<br>(SEQ ID NO: 70) |

TABLE 1-continued

Exemplary LOX-1 binding proteins

LX6960116_ng1l

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGNWNYDAFDI (SEQ ID NO: 44) |
| VH | QVQLVQSGGGLVQPGRSLRLSCAASGFTFDDYAMHWVRQA<br>PGKGLEWVSGISWNSGSIGYADSVKGRFTISRDNAKNSLY<br>LQMNSLRAEDTAVYYCAREGNWNYDAFDIWGRGTTVTVSS<br>(SEQ ID NO: 54) |
| VL CDR1 | TGTSNDVGGYNYVS (SEQ ID NO: 59) |
| VL CDR2 | DVSNRPS (SEQ ID NO: 60) |
| VL CDR3 | SSYTSSSTNWV (SEQ ID NO: 61) |
| VL | QSALTQPASVSGSPGQSITISCTGTSNDVGGYNYVSWYQQ<br>HPGKAPKLMIYDVSNRPSGVSNRFSGSKSGNTASLTISGL<br>QAEDEADYYCMGSMGRSTNWVFGGGTKLTVL<br>(SEQ ID NO: 69) |

LX6960073_g1

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGSWNYDALDI (SEQ ID NO: 40) |
| VH | EVQLVESGGGLVQPGRSLRLSCAASGFTSDDYAMHWVRQA<br>PGKGLEWVSGISWNSGSIGYADSVKGRFTISRDNAKNSLY<br>LQMNGLRAEDTAVYYCAREGSWNYDALDIWGQGTMVTVSS<br>(SEQ ID NO: 53) |
| VL CDR1 | TGTSSDVGGYNYVS (SEQ ID NO: 55) |
| VL CDR2 | DVSKRPS (SEQ ID NO: 56) |
| VL CDR3 | MGGMGRSTNWV (SEQ ID NO: 57) |
| VL | QSALTQPASVSGSPGQPITISCTGTSSDVGGYNYVSWYQQ<br>HPGKAPKLMIYDVSKRPSGVSNRFSGSKSGNTASLTISGL<br>QAEDEADYYCMGGMGRSTNWVFGGGTKLTVL<br>(SEQ ID NO: 58) |

LX6960073_G82bS_g1

| | |
|---|---|
| VH CDR1 | DYAMH (SEQ ID NO: 38) |
| VH CDR2 | GISWNSGSIGYADSVKG (SEQ ID NO: 39) |
| VH CDR3 | EGSWNYDALDI (SEQ ID NO: 40) |
| VH | EVQLVESGGGLVQPGRSLRLSCAASGFTSDDYAMHWVRQA<br>PGKGLEWVSGISWNSGSIGYADSVKGRFTISRDNAKNSLY<br>LQMNSLRAEDTAVYYCAREGSWNYDALDIWGQGTMVTVSS<br>(SEQ ID NO: 41) |
| VL CDR1 | TGTSSDVGGYNYVS (SEQ ID NO: 55) |
| VL CDR2 | DVSKRPS (SEQ ID NO: 56) |
| VL CDR3 | MGGMGRSTNWV (SEQ ID NO: 57) |
| VL | QSALTQPASVSGSPGQPITISCTGTSSDVGGYNYVSWYQQ<br>HPGKAPKLMIYDVSKRPSGVSNRFSGSKSGNTASLTISGL<br>QAEDEADYYCMGGMGRSTNWVFGGGTKLTVL<br>(SEQ ID NO: 58) |

In some aspects the isolated LOX1-binding protein comprises a VH sequence that has a total of one, two, three, four, five, six, seven, eight or fewer amino acid substitutions, deletions and/or insertions from a reference VH sequence of SEQ ID NO:4. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VH of SEQ ID NO:4. The disclosure also provides nucleic acids encoding the LOX1-binding protein, vectors containing these nucleic acids and host cells transformed with these nucleic acids and vectors, and methods of making and using the LOX1-binding protein.

In some aspects the isolated LOX1-binding protein comprises a VL sequence that has a total of one, two, three, four, five, six, seven, eight or fewer amino acid substitutions, deletions and/or insertions from a reference VL sequence of SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VL of SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a VH selected from a VH containing a VH-CDR1 having the amino acid sequence of SEQ ID NO:1, a VH-CDR2 having the amino acid sequence of SEQ ID NO:2, 5-12 or 13, and a VH-CDR3 having the amino acid sequence of SEQ ID NO:3, 14-17 or 18; and a light chain VL selected from a VL containing a VL-CDR1 having the amino acid sequence of SEQ ID NO:30, a VL-CDR2 having the amino acid sequence of SEQ ID NO:31, and a VL-CDR3 having the amino acid sequence of SEQ ID NO:32, 34, or 35. The disclosure also provides nucleic acids encoding the LOX1-binding protein, vectors containing these nucleic acids and host cells transformed with these nucleic acids and vectors, and methods of making and using the LOX1-binding protein.

The disclosure also provides an isolated LOX1-binding protein comprising a VH and a VL sequence that each have a total of one, two, three, four, five, six, seven, eight or fewer amino acid substitutions, deletions, and/or insertions from a reference VH and VL LOX1-binding proteins disclosed herein. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein has a VH comprising SEQ ID NO:4, 19-28, or 29, and a VL comprising SEQ ID NO:33, 36, or 37. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3 wherein the set of CDRs is identical to, or has a total of 18 or fewer (e.g. 1, 2, 3, 4, 5, 6, 7, 8, 9, 10, 11, 12, 13, 14, 15, 16, 17 or 18) amino acid substitutions, deletions, and/or insertions from a reference set of CDRs in which: (a) VH-CDR1 has the amino acid sequence of SEQ ID NO:1; (b) VH-CDR2 has the amino acid sequence of SEQ ID NO:5; (c) VH-CDR3 has the amino acid sequence of SEQ ID NO:14; (d) VL-CDR1 has the amino acid sequence of SEQ ID NO:30; (e) VL-CDR2 has the amino acid sequence of SEQ ID NO:31; and (f) VL-CDR3 has the amino acid sequence of SEQ ID NO:32 The disclosure also provides nucleic acids encoding the LOX1-binding protein, vectors containing these nucleic acids and host cells transformed with these nucleic acids and vectors, and methods of making and using the LOX1-binding protein.

In further aspects, the LOX1-binding protein comprises a set of CDRs: VH-CDR1, VH-CDR2, VH-CDR3, VL-CDR1, VL-CDR2 and VL-CDR3 wherein: (a) VH-CDR1 has the amino acid sequence of SEQ ID NO:1; (b) VH-CDR2 has the amino acid sequence of SEQ ID NO:2; (c) VH-CDR3 has the amino acid sequence of SEQ ID NO:3; (d) VL-CDR1 has the amino acid sequence of SEQ ID NO:30; (e) VL-CDR2 has the amino acid sequence of SEQ ID NO:31; and (f) VL-CDR3 has the amino acid sequence of SEQ ID NO:32. The disclosure also provides nucleic acids encoding the LOX1-binding protein, vectors containing these nucleic acids and host cells transformed with these nucleic acids and vectors, and methods of making and using the LOX1-binding protein.

The disclosure also provides an isolated LOX1-binding protein comprising a heavy chain variable region (VH) having at least 90, 95, 97, 98 or 99% sequence identity to a reference VH sequence disclosed herein and/or a light chain variable region (VL) having at least 90, 95, 97, 98 or 99% sequence identity to a reference VL sequence disclosed herein (e.g., the VH and VL sequences disclosed in Table 1, FIG. 4 or FIG. 5). In further aspects, the disclosure provides an isolated LOX1-binding protein comprising a VH having at least 90, 95, 97, 98 or 99% sequence identity to SEQ ID NO:4 and/or a VL having at least 90, 95, 97, 98 or 99% sequence identity to SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a heavy chain variable region (VH) having at least 90, 95, 97, 98 or 99% sequence identity and a light chain variable region (VL) having at least 90, 95, 97, 98 or 99% sequence identity to a VH and a VL selected from the group consisting of: (a) a VH having the amino acid sequence of SEQ ID NO:4 and a VL having the amino acid sequence of SEQ ID NO:33; (b) a VH having the amino acid sequence of SEQ ID NO:29 and a VL having the amino acid sequence of SEQ ID NO:33; (c) a VH having the amino acid sequence of SEQ ID NO:41 and a VL having the amino acid sequence of SEQ ID NO:58; and (d) a VH having the amino acid sequence of SEQ ID NO:54 and a VL having the amino acid sequence of SEQ ID NO:70. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a VH having at least 90, 95, 97, 98 or 99% sequence identity and a VL having at least 90, 95, 97, 98 or 99% sequence identity to a VH and a VL selected from the group consisting of: (a) a VH having the amino acid sequence of SEQ ID NO:19 and a VL having the amino acid sequence of SEQ ID NO:33; (b) a VH having the amino acid sequence of SEQ ID NO:20 and a VL having the amino acid sequence of SEQ ID NO:33; (c) a VH having the amino acid sequence of SEQ ID NO:21 and a VL having the amino acid sequence of SEQ ID NO:33; (d) a VH having the amino acid sequence of SEQ ID NO:22 and a VL having the amino acid sequence of SEQ ID NO:33; (e) a VH having the amino acid sequence of SEQ ID NO:23 and a VL having the amino acid sequence of SEQ ID NO:33; (f) a VH having the amino acid sequence of SEQ ID NO:24 and a VL having the amino acid sequence of SEQ ID NO:33; (g) a VH having the amino acid sequence of SEQ ID NO:25 and a VL having the amino acid sequence of SEQ ID NO:33; (h) a VH having the amino acid sequence of SEQ ID NO:26 and a VL having the amino acid sequence of SEQ ID NO:33; (i) a VH having the amino acid sequence of SEQ ID NO:27 and a VL having the amino acid sequence of SEQ ID NO:37; (j) a VH having the amino acid sequence of SEQ ID NO:28 and a VL having the amino acid sequence of SEQ ID NO:37; (k) a VH having the amino acid sequence of SEQ ID NO:48 and a VL having the amino acid sequence of SEQ ID NO:65; (l) a VH having the amino acid sequence of SEQ ID NO:49 and a VL having the amino acid sequence of SEQ ID NO:66; (m) a VH having the amino acid sequence of SEQ ID NO:50 and a VL having the amino acid sequence of SEQ ID NO:67; (n) a VH having the amino acid sequence of SEQ ID NO:51 and a VL having the amino acid sequence of SEQ ID NO:65; (o) a VH having the amino acid sequence of SEQ ID NO:54 and a VL having the amino acid sequence of SEQ ID NO:68; (p) a VH having the amino acid sequence of SEQ ID NO:52 and a VL having the amino acid sequence of SEQ ID NO:67; (q) a VH having the amino acid sequence of SEQ ID NO:54 and a VL having the amino acid sequence of SEQ ID NO:69; (r) a VH having the amino acid sequence of SEQ ID NO:53 and a VL having the amino acid sequence of SEQ ID NO:58; and (s) a VH having the amino acid sequence of SEQ ID NO:41 and a VL having the amino acid sequence of SEQ ID NO:58. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VH-CDR3 having the amino acid sequence of SEQ ID NO:3. In further aspects, the LOX1-binding protein comprises a VH-CDR3 having the amino acid sequence of SEQ ID NO:3 and a VH-CDR2 having the amino acid sequence of SEQ ID NO:2. In other aspects, the LOX1-binding protein comprises a VH-CDR3 having the amino acid sequence of SEQ ID NO:3 and a VH-CDR2 having the amino acid sequence of SEQ ID NO:5-12 or 13. In additional aspects, the LOX1-binding protein comprises a VH-CDR3 having the amino acid sequence of SEQ ID NO:3, 14-17 or 18 and a VH-CDR2 having the amino acid sequence of SEQ ID NO:2. In further aspects, the LOX1-binding protein comprises a VH-CDR3 having the amino acid sequence of SEQ ID NO: 3, 14-17 or 18 and a VH-CDR2 having the amino acid sequence of SEQ ID NO:2, 5-12 or 13. In further aspects, the LOX1-binding protein comprises a VH-CDR3 having the amino acid sequence of SEQ ID NO: 3, 14-17 or 18 and a VH-CDR2 having the amino acid sequence of SEQ ID NO:2, 5-12 or 13 and a VH-CDR1 having the amino acid sequence of SEQ ID NO:1. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VLH-CDR3 having the amino acid sequence of SEQ ID NO:32. In further aspects, the LOX1-binding protein comprises a VL-CDR3 having the amino acid sequence of SEQ ID NO:32 and a VL-CDR2 having the amino acid sequence of SEQ ID NO:31. In other aspects, the LOX1-binding protein comprises a VL-CDR3 having the amino acid sequence of SEQ ID NO:32, a VL-CDR2 having the amino acid sequence SEQ ID NO:31 and a VL-CDR1 having the amino acid sequence of SEQ ID NO:30. In other aspects, the LOX1-binding protein comprises a VL-CDR3 having the amino acid sequence of SEQ ID NO:32, 34, or 35, a VL-CDR2 having the amino acid sequence SEQ ID NO:31. In further aspects, the LOX1-binding protein comprises a VL-CDR3 having the amino acid sequence of SEQ ID NO:32, 34, or 35, a VL-CDR2 having the amino acid sequence SEQ ID NO:31 and a VL-CDR1 having the amino acid sequence of SEQ ID NO:30. The disclosure also provides nucleic acids encoding the LOX1-binding protein, vectors containing these nucleic acids and host cells transformed with these nucleic acids and vectors, and methods of making and using the LOX1-binding protein.

In additional aspects, the LOX1-binding protein comprises one, two, or three VH-CDRs such as a VH-CDR1 identical to, or that has a total of one, two or fewer amino acid substitutions, deletions, or insertions to SEQ ID NO:1, a VH-CDR2 identical to, or that has a total of one, two or fewer amino acid substitutions, deletions, or insertions to SEQ ID NO:2, 5-12 or 13, or a VH-CDR3 identical to, or that has a total of one, two, three, four, or fewer amino acid substitutions, deletions, or insertions to SEQ ID NO:3, 14-17 or 18.

In additional aspects, the LOX1-binding protein comprises one, two, or three VL-CDRs such as a VL-CDR1 identical to, or that has a total of one, two or fewer amino acid substitutions, deletions, or insertions to SEQ ID NO:30, a VL-CDR2 identical to, or that has a total of one, two or fewer amino acid substitutions, deletions, or insertions to SEQ ID NO:31, or a VH-CDR3 identical to, or that has a total of one, two, three, four, or fewer amino acid substitutions, deletions, or insertions to SEQ ID NO:32, 34, or 35.

In some aspects the isolated LOX1-binding protein comprises a VH sequence that has a total of one, two, three, four, five, six, seven, eight or fewer amino acid substitutions, deletions and/or insertions from a reference VH sequence of SEQ ID NO:41. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VH of SEQ ID NO:41. The disclosure also provides nucleic acids encoding the LOX1-binding proteins, vectors containing these nucleic acids and host cells transformed with these nucleic acids and vectors, and methods of making an using the LOX1-binding proteins.

In some aspects the isolated LOX1-binding protein comprises a VL sequence that has a total of one, two, three, four, five, six, seven, eight or fewer amino acid substitutions, deletions and/or insertions from a reference VL sequence of SEQ ID NO:58. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VL of SEQ ID NO:58. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a VH selected from a VH containing a VH-CDR1 having the amino acid sequence of SEQ ID NO:38, a VH-CDR2 having the amino acid sequence of SEQ ID NO:39, 42 or 43, and a VH-CDR3 having the amino acid sequence of SEQ ID NO:40, 44-46 or 47; and a light chain VL selected from a VL containing a VL-CDR1 having the amino acid sequence of SEQ ID NO:55 or 59, a VL-CDR2 having the amino acid sequence of SEQ ID NO:56 or 60, and a VL-CDR3 having the amino acid sequence of SEQ ID NO:57, 61-63, or 64.

In some aspects, the isolated LOX1-binding protein has a VH comprising a sequence of SEQ ID NO:41, 48-53, or 54, and a VL comprising a sequence of SEQ ID NO:58, 65-69, or 70. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3 wherein the set of CDRs is identical to, or has a total of one, two, three, four, five, six, seven, eight or fewer amino acid substitutions, deletions, and/or insertions from a reference set of CDRs in which: (a) VH-CDR1 has the amino acid sequence of SEQ ID NO:38; (b) VH-CDR2 has the amino acid sequence of SEQ ID NO:39; (c) VH-CDR3 has the amino acid sequence of SEQ ID NO:44; (d) VL-CDR1 has the amino acid sequence of SEQ ID NO:55; (e) VL-CDR2 has the amino acid sequence of SEQ ID NO:60; and (f) VL-CDR3 has the amino acid sequence of SEQ ID NO:61. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3 wherein the set of CDRs is identical to, or has a total of one, two, three, four, five, six, seven, eight or fewer amino acid substitutions, deletions, and/or insertions from a reference set of CDRs in which: (a) VH-CDR1 has the amino acid sequence of SEQ ID NO:38, (b) VH-CDR2 has the amino acid sequence of SEQ ID NO:39; (c) VH-CDR3 has the amino acid sequence of SEQ ID NO:40; (d) VL-CDR1 has the amino acid sequence of SEQ ID NO:55; (e) VL-CDR2 has the amino acid sequence of SEQ ID NO:56; and (f) VL-CDR3 has the amino acid sequence of SEQ ID NO:57. The disclosure also provides nucleic acids encoding the LOX1-binding protein, vectors containing these nucleic acids and host cells transformed with these nucleic acids and vectors, and methods of making and using the LOX1-binding protein.

In further aspects, the LOX1-binding protein comprises a set of CDRs: VH-CDR1, VH-CDR2, VH-CDR3, VL-CDR1, VL-CDR2 and VL-CDR3 wherein: (a) VH-CDR1 has the amino acid sequence of SEQ ID NO:38; (b) VH-CDR2 has the amino acid sequence of SEQ ID NO:39; (c) VH-CDR3 has the amino acid sequence of SEQ ID NO:40; (d) VL-CDR1 has the amino acid sequence of SEQ ID NO:55; (e) VL-CDR2 has the amino acid sequence of SEQ ID NO:56; and (f) VL-CDR3 has the amino acid sequence of SEQ ID NO:57. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VH-CDR3 having the amino acid sequence of SEQ ID NO:40. In further aspects, the LOX1-binding protein comprises a VH-CDR3 having the amino acid sequence of SEQ ID NO:40 and a VH-CDR2 having the amino acid sequence of SEQ ID NO:39. In other aspects, the LOX1-binding protein comprises a VH-CDR3 having the amino acid sequence of SEQ ID NO:40 and a VH-CDR2 having the amino acid sequence of SEQ ID NO:42 or 43. In additional aspects, the LOX1-binding protein comprises a VH-CDR3 having the amino acid sequence of SEQ ID NO:40, 44-46, or 47 and a VH-CDR2 having the amino acid sequence of SEQ ID NO:39. In further aspects, the LOX1-binding protein comprises a VH-CDR3 having the amino acid sequence of SEQ ID NO: 40, 44-46, or 47 and a VH-CDR2 having the amino acid sequence of SEQ ID NO:39, 42, or 43. In further aspects, the LOX1-binding protein comprises a VH-CDR3 having the amino acid sequence of SEQ ID NO: 40, 44-46, or 47 and a VH-CDR2 having the amino acid sequence of SEQ ID NO: 39, 42, or 43, and a VH-CDR1 having the amino acid sequence of SEQ ID NO:38. The disclosure also provides nucleic acids encoding the LOX1-binding protein, vectors containing these nucleic acids and host cells transformed with these nucleic acids and vectors, and methods of making and using the LOX1-binding protein.

In further aspects, the disclosure provides an isolated LOX1-binding protein comprising a VLH-CDR3 having the amino acid sequence of SEQ ID NO:57. In further aspects, the LOX1-binding protein comprises a VL-CDR3 having the amino acid sequence of SEQ ID NO:57 and a VL-CDR2 having the amino acid sequence of SEQ ID NO:56. In other aspects, the LOX1-binding protein comprises a VL-CDR3 having the amino acid sequence of SEQ ID NO:57, a VL-CDR2 having the amino acid sequence SEQ ID NO:56 and a VL-CDR3 having the amino acid sequence of SEQ ID NO:55. In other aspects, the LOX1-binding protein comprises a VL-CDR3 having the amino acid sequence of SEQ ID NO:57, a VL-CDR2 having the amino acid sequence SEQ ID NO:56 or 60, and a VL-CDR1 having the amino acid sequence of SEQ ID NO:55 or 59. The disclosure also provides nucleic acids encoding the LOX1-binding protein, vectors containing these nucleic acids and host cells transformed with these nucleic acids and vectors, and methods of making and using the LOX1-binding protein.

In additional aspects, the LOX1-binding protein comprises one, two, or three VH-CDRs such as a VH-CDR1 identical to, or that has a total of one, two or fewer amino acid substitutions, deletions, or insertions to SEQ ID NO:38, a VH-CDR2 identical to, or that has a total of one, two or fewer amino acid substitutions, deletions, or insertions to SEQ ID NO:39, 42 or 43, or a VH-CDR3 identical to, or that has a total of one, two, three, four, or fewer amino acid substitutions, deletions, or insertions to SEQ ID NO:40, 44-46 or 47. The disclosure also provides nucleic acids encoding the LOX1-binding protein, vectors containing these nucleic acids and host cells transformed with these nucleic acids and vectors, and methods of making and using the LOX1-binding protein.

In additional aspects, the LOX1-binding protein comprises one, two, or three VL-CDRs such as a VL-CDR1 identical to, or that has a total of one, two or fewer amino acid substitutions, deletions, or insertions to SEQ ID NO: 55 or 59, a VL-CDR2 identical to, or that has a total of one, two or fewer amino acid substitutions, deletions, or insertions to SEQ ID NO:56 or 60, or a VH-CDR3 identical to, or that has a total of one, two, three, four, or fewer amino acid substitutions, deletions, or insertions to SEQ ID NO: 57, 61-63 or 64. The disclosure also provides nucleic acids encoding the LOX1-binding protein, vectors containing these nucleic acids and host cells transformed with these nucleic acids and vectors, and methods of making and using the LOX1-binding protein.

In some aspects, the LOX1-binding protein comprises a set of CDRs: VH-CDR1, VH-CDR2, VH-CDR3, VL-CDR1, VL-CDR3 and VL-CDR3 as described in Table 1, FIG. 4 or FIG. 5. The disclosure also provides nucleic acids encoding the LOX1-binding protein, vectors containing these nucleic acids and host cells transformed with these nucleic acids and vectors, and methods of making and using the LOX1-binding protein.

In some additional aspects, the LOX1-binding protein comprises a heavy chain variable region (VH) and light chain variable region (VL) as described in Table 1, FIG. 4 or FIG. 5. The disclosure also provides nucleic acids encoding the LOX1-binding protein, vectors containing these nucleic acids and host cells transformed with these nucleic acids and vectors, and methods of making and using the LOX1-binding protein.

In some aspects, the isolated LOX1-binding protein comprises a VH-CDR2 having the amino acid sequence of G F D P E D $HX_1$ $HX_2$ $HX_3$ $HX_4$ $HX_5$ $HX_6$ Q K F Q G (Gly Phe Asp Pro Glu Asp $HX_1$ $HX_2$ $HX_3$ $HX_4$ $HX_5$ $HX_6$ Gln Lys Phe Gln Gly), wherein $HX_1$ is Gly, Trp, Tyr, or Phe; $HX_2$ is Glu, Thr, Gln, Ser, Lys, or Ala; $HX_3$ is Thr, Tyr, Ile, or Asn; $HX_4$ is Be, Ala, Arg, or His; $HX_5$ is Tyr, Val, Thr, Leu, or Gln, and $HX_6$ is Ala, Asp, Gly, Ser, or His (SEQ ID NO:71).

In additional aspects, the isolated LOX1-binding protein comprises a VH-CDR3 having the amino acid sequence of $HX_7$ $HX_8$ G $HX_9$ $HX_{10}$ $HX_{11}$ $HX_{12}$ G V R G W D Y Y Y G M D V ($HX_7$ $HX_8$ Gly $HX_9$ $HX_{10}$ $HX_{11}$ $HX_{12}$ Gly Val Arg Gly Trp Asp Tyr Tyr Tyr Gly Met Asp Val Trp) wherein $HX_7$ is Pro, Ser, or Val; $HX_8$ is Asn, Thr, Trp, or Asp; $HX_9$ is Gln, Arg, or Thr; $HX_{10}$ is Gln or His; $HX_{11}$ is Gly or Gln; $HX_{12}$ is Lys or Gly (SEQ ID NO: 72).

In other aspects, the isolated LOX1-binding protein comprises a VL-CDR3 having the amino acid sequence of Q S Y D S $LX_1$ $LX_2$ $LX_3$ $LX_4$ $LX_5$ $LX_6$ (Gln Ser Tyr Asp Ser $LX_1$ $LX_2$ $LX_3$ $LX_4$ $LX_5$ $LX_6$), wherein $LX_1$ is Ser or Met; $LX_2$ is Leu, Tyr, or His; $LX_3$ is Ser or Arg; $LX_4$ is Gly, Ala, or no amino acid; $LX_5$ is Trp or Phe; and $LX_6$ is Val, Gly, or Ala (SEQ ID NO:73).

In some aspects, the isolated LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3 wherein: (a) VH-CDR1 comprises the amino acid sequence: E L S M H (SEQ ID NO: 1); (b) VH-CDR2 comprises the amino acid sequence: G F D P E D $HX_1$ $HX_2$ $HX_3$ $HX_4$ $HX_5$ $HX_6$ Q K F Q G, wherein HX1 is selected from the group consisting of G, W, Y and F, HX2 is selected from the group consisting of E, T, Q, K, A, and S, HX3 is selected from the group consisting of T, Y, I, and N, HX4 is selected from the group consisting of I, A, R and H, HX5 is selected from the group consisting of Y, V, T, L and Q, and HX6 is selected from the group consisting of A, D, G, S and H (SEQ ID NO: 71); (c) VH-CDR3 comprises the amino acid sequence: $HX_7$ $HX_8$ G $HX_9$ $HX_{10}$ $HX_{11}$ $HX_{12}$ G V R G W D Y Y Y G M D V, wherein HX7 is selected from the group consisting of P, S and V, HX8 is selected from the group consisting of N, W, D, and T, HX9 is selected from the group consisting of Q, R and T, HX10 is selected from the group consisting of Q and H, HX11 is selected from the group consisting of G and Q, and HX12 is selected from the group consisting of K and G (SEQ ID NO: 72); (d) VL-CDR1 comprises the amino acid sequence: T G S S S N I G A G Y D V H (SEQ ID NO: 30); (e) VL-CDR2 comprises the amino acid sequence: G N S N R P S (SEQ ID NO: 31); and (f) VL-CDR3 comprises the amino acid sequence: Q S Y D S $LX_1$ $LX_2$ $LX_3$ $LX_4$ $LX_5$ $LX_6$, wherein LX1 is selected from the group consisting of M and S, LX2 is selected from the group consisting of L, Y and H, LX3 is selected from the group consisting of S and R, LX4 is selected from the group consisting of A and G or is omitted (no amino acid), LX5 is selected from the group consisting of W and F, and LX6 is selected from the group consisting of V, G and A (SEQ ID NO: 73).

In additional aspects, the isolated LOX1-binding protein comprises a VH-CDR2 having the amino acid sequence of G $HX_1$ S $HX_2$ $HX_3$ $HX_4$ $HX_5$ $HX_6$ $HX_7$ $HX_8$ $HX_9$ $HX_{10}$ D S V K G (Gly $HX_1$ Ser $HX_2$ $HX_3$ $HX_4$ $HX_5$ $HX_6$ $HX_7$ $HX_8$ $HX_9$ $HX_{10}$ Asp Ser Val Lys Gly), wherein $HX_1$ is Be or Val; $HX_2$ is Trp or Leu; $HX_3$ is Asn or Gln; $HX_4$ is Ser or Glu; $HX_5$ is Gly, Leu, or Pro; $HX_6$ is Ser, Tyr, or Asp; $HX_7$ is Ile, Thr, or Arg; $HX_8$ is Gly or Tyr; $HX_9$ is Tyr or Met; and $HX_{10}$ is Ala or Asp (SEQ ID NO:74).

In additional aspects, the isolated LOX1-binding protein comprises a VH-CDR3 having the amino acid sequence of E G $HX_{11}$ W N Y D A $HX_{12}$ D $HX_{13}$ (Glu Gly $HX_{11}$ Trp Asn Tyr Asp Ala $HX_{12}$ Asp $HX_{13}$), wherein $HX_{11}$ is Asn or Ser; $HX_{12}$ is Phe or Leu; and $HX_{13}$ is Ile or Val (SEQ ID NO:75).

In additional aspects, the isolated LOX1-binding protein comprises a VL-CDR1 having the amino acid sequence of T G T S $LX_1$ D V G G Y N Y V S (Thr Gly Thr Ser $LX_1$ Asp Val Gly Gly Tyr Asn Tyr Val Ser), wherein $LX_1$ is Ser or Asn (SEQ ID NO:76).

In additional aspects, the isolated LOX1-binding protein comprises a VL-CDR2 having the amino acid sequence of D V S $LX_2$ R P S (Asp Val Ser X4 Arg Pro Ser), wherein $LX_2$ is Asn or Lys (SEQ ID NO:77).

In additional aspects, the isolated LOX1-binding protein comprises a VL-CDR3 having the amino acid sequence of $LX_3$ $LX_4$ $LX_5$ $LX_6$ $LX_7$ $LX_8$ S T N W V ($LX_3$ $LX_4$ $LX_5$ $LX_6$ $LX_7$ $LX_8$ Ser Thr Asn Trp Val), wherein $LX_3$ is Ser, Leu, Met, or Ala; $LX_4$ is Ser, Gly, or Gln; $LX_5$ is Tyr, Arg, Ser, or Gly; $LX_6$ is Thr or Met; $LX_7$ is Ser, Trp, Gly, or Val; and $LX_8$ is Ser or Arg (SEQ ID NO:78).

In some aspects, the isolated LOX1-binding protein comprises a set of complementary determining regions (CDRs): heavy chain variable region (VH)-CDR1, VH-CDR2, VH-CDR3, and light chain variable region (VL)-CDR1, VL-CDR2 and VL-CDR3 wherein: (a) VH-CDR1 comprises the amino acid sequence: D Y A M H (SEQ ID NO: 38); (b) VH-CDR2 comprises the amino acid sequence: G $HX_1$ S $HX_2$ $HX_3$ $HX_4$ $HX_5$ $HX_6$ $HX_7$ $HX_8$ $HX_9$ $HX_{10}$ D S V K G, wherein HX1 is selected from the group consisting of I and V, HX2 is selected from the group consisting of W and L, HX3 is selected from the group consisting of N and Q, HX4 is selected from the group consisting of S and E, HX5 is selected from the group consisting of G, L and P, HX6 is selected from the group consisting of S, Y and D, HX7 is selected from the group consisting of I, T and R, HX8 is selected from the group consisting of G and Y, HX9 is selected from the group consisting of M and Y, and HX10 is selected from the group consisting of A and D (SEQ ID NO:74); (c) VH-CDR3 comprises the amino acid sequence: E G $HX_{11}$ W N Y D A $HX_{12}$ D $HX_{13}$, wherein HX11 is selected from the group consisting of N and S, HX12 is selected from the group consisting of F and L, and HX13 is selected from the group consisting of I and V (SEQ ID NO:75); (d) VL-CDR1 comprises the amino acid sequence: T G T S $LX_1$ D V G G Y N Y V 5, wherein LX1 is selected from the group consisting of N and S (SEQ ID NO:76); (e) VL-CDR2 comprises the amino acid sequence: D V S $LX_2$ R P S, wherein LX2 is selected from the group consisting of N and K (SEQ ID NO:77); and (f) VL-CDR3 comprises the amino acid sequence: $LX_3$ $LX_4$ $LX_5$ $LX_6$ $LX_7$ $LX_8$ S T NW V, wherein LX3 is selected from the group consisting of L, M, A and S, LX4 is selected from the group consisting of S, Q and G, LX5 is selected from the group consisting of Y, S, G and R, LX6 is selected from the group consisting of T and M, LX7 is selected from the group consisting of S, W, G and V, and LX8 is selected from the group consisting of S and R (SEQ ID NO:78).

In some aspects, the set of CDRs of a LOX1-binding protein disclosed herein is provided within antibody framework regions or other protein scaffolds known in the art. Exemplary antibody framework regions include: germline framework regions, such as VH1-24 (DP-5), JH6, VH3-09 (DP-31), and JH3 for the antibody framework region of the heavy chain and Vλ1e (DPL-8), Vλ2a2 (DPL-11), and JL3 for the antibody framework region of the light chain and/or any suitable framework regions well known to one of skilled in the art.

In some aspects, the LOX1-binding protein contains one or more framework regions from a heavy chain variable region (VH) and/or a light chain variable region (VL) that is a germline framework. Frameworks regions of the heavy chain domain may be selected from VH1-24 (DP-5), JH6, VH3-09 (DP-31), JH3 frameworks and/or any suitable framework regions or protein scaffolds well known in the art. Framework regions of the light chain may be selected from Vλ1e (DPL-8), Vλ2a2 (DPL-11), and JL3 frameworks, and/or any suitable framework regions or protein scaffolds well known in the art. One or more CDRs may be taken from the LOX1-binding proteins disclosed herein (e.g. a LOX1-binding protein described in Table 1, FIG. 4 or FIG. 5) and incorporated into a suitable framework and/or protein scaffold.

In additional aspects, the disclosure provides an isolated LOX1-binding protein that binds to the same LOX1 epitope as an antibody comprising a VH and VL of SEQ ID NO:4 and SEQ ID NO:33, respectively.

In other aspects, the disclosure provides LOX1-binding proteins (e.g., antibodies such as, full length LOX1-antibodies, LOX1-binding antibody fragments, and variants and derivatives thereof) that compete or cross-compete for binding to LOX1 with an antibody comprising a VH sequence of SEQ ID NO:4 and a VL sequence of SEQ ID NO:33. In a particular aspect, the LOX1-binding protein is able to competitively inhibit an antibody comprising a VH of SEQ ID NO:4 and a VL of SEQ ID NO:33, to bind to LOX1.

Also provided is a LOX1-binding protein such as a LOX1 antibody (e.g., a full length anti-LOX1 antibody, a LOX1-binding antibody fragment, and variants, and derivatives thereof) which can bind to LOX1 with a greater affinity than a LOX1-binding protein (e.g. a LOX1 antibody or fragment thereof) comprising the VH of SEQ ID NO:29 and the VL of SEQ ID NO:33. The disclosure also provides nucleic acids encoding the LOX1-binding protein, vectors containing these nucleic acids and host cells transformed with these nucleic acids and vectors, and methods of making and using the LOX1-binding protein.

In additional aspects, the disclosure provides an isolated LOX1-binding protein that binds to the same LOX1 epitope as an antibody comprising a VH and VL of SEQ ID NO:41 and SEQ ID NO:58, respectively.

In other aspects, the disclosure provides LOX1-binding proteins (e.g., antibodies such as, full length LOX1-antibodies and LOX1-binding antibody fragments, and variants and derivatives thereof) that compete or cross-compete for binding to LOX1 with an antibody comprising a VH sequence of SEQ ID NO:41 and a VL sequence of SEQ ID NO:58. In a particular aspect, the LOX1-binding protein is able to competitively inhibit an antibody comprising a VH of SEQ ID NO:41 and a VL of SEQ ID NO:58 to bind to LOX1.

Also provided is a LOX1-binding protein such as, a LOX1 antibody (e.g., a full length anti-LOX1 antibody and a LOX1-binding antibody fragment, and variants, and derivatives thereof), which can bind to LOX1 with a greater affinity than a full-length antibody comprising the VH of SEQ ID NO:54 and the VL of SEQ ID NO:70. The disclosure also provides nucleic acids encoding the LOX1-binding protein, vectors containing these nucleic acids and host cells transformed with these nucleic acids and vectors, and methods of making and using the LOX1-binding protein.

In some aspects, the anti-LOX1 antibody provided herein is a murine antibody, a human antibody, a humanized antibody, a chimeric antibody, a monoclonal antibody, a polyclonal antibody, a recombinant antibody, a bi-specific antibody, a multispecific antibody, or any combination thereof. In some aspects the anti-LOX1 antibody is an Fv fragment, an Fab fragment, an F(ab')2 fragment, an Fab' fragment, a dsFv fragment, an scFv fragment, or an sc(Fv)2 fragment.

The disclosure provides a LOX1-binding protein (e.g., an isolated anti-LOX1 antibody such as, a full length LOX1-antibody, a LOX1-binding antibody fragment, and a variant and derivative thereof) that can bind to LOX1 molecules across species. In some aspects, the LOX1-binding protein binds to human LOX1 (hLOX1) and cynomolgus LOX1 (cynoLOX1). In additional aspects, the LOX1-binding protein binds to human LOX1 (hLOX1) and rabbit LOX1. In further aspects, the LOX1-binding protein binds to hLOX1, cynoLOX1 and rabbit LOX1. In certain aspects provided herein, a LOX1-binding protein (e.g., an anti-LOX1 antibody) specifically binds to LOX1 (e.g., hLOX1, cynoLOX1 and/or rabbit LOX1) and does not bind to one or more of: CLEC-7A, CLEC-1A, CLEC-4L, CLEC-1B, SR-A1 and/or SR-B3. See, e.g., FIGS. 3, 6 and 7.

In some aspects, the LOX1-binding protein (e.g., an isolated anti-LOX1 antibody or thereof) further comprises a human IgG1 TM mutant heavy chain, wherein the heavy chain variable region (VH) comprises an amino acid sequence having at least 70%, 75%, 80%, 85%, 90%, 95%, 96%, 97%, 98% 99%, or 100% sequence identity to the reference amino acid sequence SEQ ID NO:4, 19-28 or 29.

In some aspects, the LOX1-binding protein (e.g., an isolated anti-LOX1 antibody or thereof) further comprises a human IgG1 TM mutant heavy chain, wherein the heavy chain variable region (VH) comprises an amino acid sequence having at least 70%, 75%, 80%, 85%, 90%, 95%, 96%, 97%, 98% 99%, or 100% sequence identity to the reference amino acid sequence SEQ ID NO:41, 48-53 or 54.

In some aspects, the LOX1-binding protein (e.g., a full length LOX1-antibody, a LOX1-binding antibody fragment, and a variant and derivative thereof) includes in addition to a heavy chain variable region (VH) and a light chain variable region (VL), and optionally a heavy chain constant region or fragment thereof, a light chain constant region or fragment thereof. In certain aspects the light chain constant region is a kappa lambda light chain constant region, e.g., a human kappa constant region or a human lambda constant region. In a specific aspect, the light chain constant region is a human kappa constant region.

In additional aspects, the LOX1-binding protein (e.g., a full length LOX1-antibody, a LOX1-binding antibody fragment, and a variant and derivative thereof) has a light chain variable region (VL) that contains a human kappa constant region, e.g., the VL comprises a VL amino acid sequence having at least 70%, 75%, 80%, 85%, 90%, 95%, or 100% sequence identity to the reference amino acid sequence SEQ ID NO:33, 36, or 37. In certain aspects, the disclosure provides a LOX1-binding protein (e.g., an anti-LOX1 antibody or fragment thereof) further comprising a human IgG1 TM mutant heavy chain and a human kappa light chain, wherein the heavy chain variable region (VH) and the light chain variable region (VL) comprise: SEQ ID NO:4 and SEQ ID NO:33; SEQ ID NO:29 and SEQ ID NO:33; SEQ ID NO:41 and SEQ ID NO:58; or SEQ ID NO:54 and SEQ ID NO:70, respectively.

In additional aspects, the LOX1-binding protein (e.g., a full length LOX1-antibody, a LOX1-binding antibody fragment, and a variant and derivative thereof) has a light chain variable region (VL) that further comprises a human kappa constant region, e.g., the light chain can comprise a light chain amino acid sequence having at least 70%, 75%, 80%, 85%, 90%, 95%, or 100% sequence identity to the reference amino acid sequence SEQ ID NO:58, 65-69 or 70. In certain aspects, the disclosure provides a LOX1-binding protein (e.g., an anti-LOX1 antibody or fragment thereof) further comprising a human IgG1 TM mutant heavy chain and a human kappa light chain, wherein the heavy chain variable region (VH) and the light chain variable region (VL) comprise: SEQ ID NO:41 and SEQ ID NO:58, SEQ ID NO:48 and SEQ ID NO:65, SEQ ID NO:49 and SEQ ID NO:66, SEQ ID NO:50 and SEQ ID NO:67, or SEQ ID NO:53 and SEQ ID NO:58, respectively.

In some aspects, the disclosure provides an isolated LOX1-binding protein such as an anti-LOX1 antibody (e.g., a full length LOX1-antibody, a LOX1-binding antibody fragment, and a variant and derivative thereof), wherein the LOX1-binding protein has at least one property selected from the group consisting of: (a) reduces or inhibits binding of oxLDL, C-reactive protein (CRP) and/or advanced glycation end products (AGEs) to LOX1 as determined by any suitable assay including an assay disclosed herein (see, e.g., Example 10, assays 1, 2 and/or 3 or Example 11); (b) decreases or inhibits RhoA/Rac1, nitrogen monoxide (NO), p38MAPK, protein kinase B and C, ERK1/2, and/or NFκB signaling in an endothelial cell expressing cell surface LOX1 as determined by any suitable assay including an assay disclosed herein (see, e.g., Example 11); (c) decreases or inhibits caspase-8, caspase-9, and/or BAX activity in an endothelial cell expressing cell surface LOX1 as determined by any suitable assay including an assay disclosed herein; (d) binds to LOX1 having the single nucleotide polymorphism K167N as determined by any suitable assay including an assay disclosed herein (see, e.g., Example 10, assays 1, 2 and/or 3 or Example 11); (e) reduces or inhibits oxLDL internalization as determined by any suitable assay including an assay disclosed herein (see, e.g., Example 10, assay 4 or Example 11); (f) reduces or inhibits oxLDL-induced LOX1 signaling as determined by any suitable assay including an assay disclosed herein (see, e.g., Example 10, assay 5 or Example 11); (g) binds to LOX1 with a dissociation constant (KD) of about 150 pM to about 600 pM (e.g. about 400 pM) as determined by BIACORE or KinExA; (h) binds to LOX1 with a Kon rate of about $1\times10^5$ $M^{-1}$ $s^{-1}$ to about $6\times10^6$ $M^{-1}$ $s^{-1}$ (e.g. about $5\times10^5$ $M^{-1}$ $s^{-1}$) as determined by BIACORE; and (i) binds to LOX1 with a Koff rate of about $1\times10^{-4}$ $s^{-1}$ to about $3\times10^{-4}$ $s^{-1}$ (e.g. about $2.3\times10^{-4}$ $s^{-1}$) as determined by BIACORE.

In certain aspects, the blocking of LOX1 biological activity by a LOX1-binding protein (e.g., an anti-LOX1 antibody or fragment thereof) described herein, reduces atherosclerosis and/or decreases one or more conditions associated with atherosclerosis. In particular aspects, the LOX1 antagonist (e.g. an anti-LOX1 antibody or fragment thereof) inhibits or decreases LOX1-mediated development of atherosclerotic lesions, coronary artery disease, stroke, ischemia, infarction, peripheral vascular disease, reperfusion, injury, or other clinical symptoms, associated with the development of atherosclerosis.

In certain aspects, a LOX1-binding protein such as, an anti-LOX1 antibody (e.g., a full length LOX1-antibody, a LOX1-binding antibody fragment, and a variant and derivative thereof) can specifically bind to LOX1, e.g., human LOX1 (hLOX1) and/or cynomolgus LOX1 (cynoLOX1), and antigenic fragments thereof with a dissociation constant or $K_D$ of less than $10^{-6}$ M, or of less than $10^{-7}$ M, or of less than $10^{-8}$ M, or of less than $10^{-9}$ M, or of less than $10^{-10}$ M, or of less than $10^{-11}$ M, of less than $10^{-12}$ M, of less than $10^{-13}$ M, of less than $10^{-14}$ M, or of less than $10^{-15}$ M as measured, e.g., by KINEXA® or BIACORE®. In one aspect, the anti-LOX1 antibody can bind to hLOX1 and cynoLOX1 with a $K_D$ of less than about $1\times10^{-8}$ M to about $1\times10^{-10}$ M as measured by BIACORE®.

In another aspect, a LOX1-binding protein such as, an anti-LOX1 antibody (e.g., a full length LOX1-antibody, a LOX1-binding antibody fragment, and a variant and derivative thereof) can bind to LOX1 with a $K_{off}$ of less than $1\times10^{-3}$ $s^{-1}$, or less than $2\times10^{-3}$ $s^{-1}$. In other aspects, the LOX1-binding protein binds to LOX1 with a $K_{off}$ of less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$ as measured, e.g., by KINEXA® or BIACORE®. In one aspect, the anti-LOX1 antibody can bind to hLOX1 and cynLOX1 with a $K_{off}$ of 1 to $10\times10^{-4}$ $s^{-1}$ as measured by BIACORE®.

In another aspect, a LOX1-binding protein such as, an anti-LOX1 antibody (e.g., a full length LOX1-antibody, a LOX1-binding antibody fragment, and a variant and derivative thereof) can bind to LOX1, e.g., human LOX1 (hLOX1) and/or cynomolgus LOX1, with an association rate constant or $k_{on}$ rate of at least $10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, or at least $10^8$ $M^{-1}$ $s^{-1}$, or at least $10^9$ $M^{-1}$ $s^{-1}$ as measured, e.g., by KINEXA® or BIACORE®. In one aspect, the anti-LOX1 antibody can bind to hLOX1 and cynLOX1 with a $k_{on}$ rate of about $1\times10^5$ $M^{-1}$ $s^{-1}$ to about $20\times10^5$ $M^{-1}$ $s^{-1}$ as measured by BIACORE®.

As noted above, a LOX1-binding protein (e.g., a full length LOX1-antibody, a LOX1-binding antibody fragment, and a variant and derivative thereof) containing a VH and/or VL amino acid sequence that binds LOX1 can have at least 85%, 90%, 95%, 96%, 97%, 98% or 99% sequence identity to a sequence set forth herein (see, e.g., Table 1, FIG. 4 or FIG. 5). In some aspects, the VH and/or VL amino acid sequence(s) that binds LOX1 comprise 15 or fewer (e.g., 1, 2, 3, 4, 5, 6, 7, 8, 9, 10, 11, 12, 13, 14 or 15) amino acid additions, substitutions (e.g., conservative substitutions) or deletions relative to a sequence set forth herein. In some aspects, the VH and/or VL amino acid sequence(s) that binds LOX1 comprise 8 or fewer (e.g., 1, 2, 3, 4, 5, 6, 7 or 8) amino acid additions, substitutions (e.g., conservative substitutions) or deletions relative to a sequence set forth herein. In additional aspects, the VH and/or VL amino acid sequence that binds LOX1 comprise 5 or fewer (e.g., 1, 2, 3, 4 or 5) amino acid additions, substitutions (e.g., conservative substitutions) or deletions relative to a sequence set forth herein. A LOX1-binding protein (e.g. an anti-LOX1 antibody or fragment thereof) containing VH and VL regions having a certain percent similarity to a VH region or VL region, or having one or more substitutions, deletions and/or insertions (e.g., conservative substitutions) can be obtained by mutagenesis (e.g., site-directed or PCR-mediated mutagenesis) of nucleic acid molecules encoding VH and/or VL regions described herein, followed by testing of the encoded altered antibody for binding to LOX1 and optionally testing for retained function using the functional assays described herein or an assay known in the art that can be routinely modified to test the retained function.

The affinity or avidity of a LOX1-binding protein such as, an anti-LOX1 antibody (e.g., a full length LOX1-antibody, a LOX1-binding antibody fragment, and a variant and derivative thereof), for LOX1 can be determined experimentally using any suitable method known in the art, e.g., flow cytometry, enzyme-linked immunosorbent assay (ELISA), or radioimmunoassay (RIA), or kinetics (e.g., KINEXA® or BIACORE® analysis). Direct binding assays as well as competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein). The measured affinity of a particular antibody-antigen interaction can vary if measured under different conditions (e.g., salt concentration, pH, temperature). Thus, measurements of affinity and other LOX1-binding parameters (e.g., $K_D$ or Kd, $K_{on}$, $K_{off}$) are made with standardized solutions of LOX1-binding proteins and LOX1, and a standardized buffer, as known in the art such as, the buffer described herein.

The disclosure further provides a LOX1-binding protein such as, an anti-LOX1 antibody (e.g., a full length LOX1-antibody, a LOX1-binding antibody fragment, and a variant and derivative thereof), as described herein (see, e.g., Table 1, FIG. 4 or FIG. 5), wherein the antibody is conjugated to a heterologous agent. In certain aspects the agent is an antimicrobial agent, a therapeutic agent, a prodrug, a peptide, a protein, an enzyme, a lipid, a biological response modifier, a pharmaceutical agent, a lymphokine, a heterologous antibody or antibody fragment, a detectable label, or a polyethylene glycol (PEG). Heteroconjugate LOX1-binding proteins are discussed in more detail elsewhere herein.

In certain aspects, the LOX1-binding protein is not an anti-LOX1 antibody. A variety of methods for identifying and producing non-antibody polypeptides that bind with high affinity to a protein target are known in the art. See, e.g., Skerra, *Curr. Opin. Biotech.* 18:295-304 (2007), Hosse et al., *Protein Science* 15:14-27 (2006), Gill et al., *Curr. Opin. Biotechnol.* 17:653-658 (2006), Nygren, *FEBS J.* 275:2668-76 (2008), and Skerra, *FEBS J.* 275:2677-83 (2008), each of which is incorporated by reference herein in its entirety. In certain aspects, phage display technology can been used to identify/produce a LOX1-binding protein. In certain aspects, the polypeptide comprises a protein scaffold of a type selected from the group consisting of ankyrin, protein A, a lipocalin, a fibronectin domain, an ankyrin consensus repeat domain, and thioredoxin.

Proteins that Bind the Same Epitope as a LOX1-Binding Protein

In certain aspects the disclosure provides LOX1-binding proteins (e.g., anti-LOX1 antibodies such as, full length anti-LOX1 antibodies, LOX1-binding antibody fragments, and variants and derivatives thereof) that bind to the same epitope as one or more LOX1-binding proteins disclosed herein (see, e.g., Table 1, FIG. 4 or FIG. 5). The term "epitope" as used herein refers to a target protein determinant capable of binding to an antibody of the disclosure. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. Such antibodies can be identified based on their ability to cross-compete (e.g., to competitively inhibit the binding of, in a statistically significant manner) with antibodies comprising a VH sequence of SEQ ID NO:4 and a VL sequence of SEQ ID NO:33, and/or antibodies comprising a VH sequence of SEQ ID NO:41 and a VL sequence of SEQ ID NO:58, in standard antigen-binding or activity assays.

The disclosure also provides LOX1-binding proteins such as, anti-LOX1 antibodies (e.g., full length LOX1-antibodies, LOX1-binding antibody fragments, and variants and derivatives thereof), that bind the same epitope as an isolated LOX1-binding protein disclosed herein (see, e.g., Table 1, FIG. 4 or FIG. 5).

The ability of a test LOX1-binding protein to inhibit the binding of, e.g., an antibody comprising a VH sequence of SEQ ID NO:4 and a VL sequence of SEQ ID NO:33 and/or antibodies comprising a VH sequence of SEQ ID NO:41 and a VL sequence of SEQ ID NO:58, demonstrates that the test LOX1-binding protein can compete with that antibody for binding to LOX1; such a LOX1-binding protein can, according to non-limiting theory, bind to the same or a related (e.g., a structurally similar or spatially proximal) epitope on LOX1 as the LOX1-binding proteins (e.g., anti-LOX1 antibodies such as, full length anti-LOX1 antibodies, LOX1-binding antibody fragments, and variants and derivatives thereof) with which it competes. In one aspect, the LOX1-binding protein binds to the same epitope on LOX1 as an antibody comprising a VH sequence of SEQ ID NO:4 and a VL sequence of SEQ ID NO:33. In another aspect, the LOX1-binding protein binds to the same epitope on LOX1 as an antibody comprising a VH sequence of SEQ ID NO:41 and a VL sequence of SEQ ID NO:58.

In one aspect, the disclosure provides LOX1-binding proteins (e.g., antibodies such as, full length LOX1-antibodies, LOX1-binding antibody fragments, and variants and derivatives thereof), that compete for binding to LOX1 with an antibody comprising a VH sequence of SEQ ID NO:4 and a VL sequence of SEQ ID NO:33. In another aspect, the disclosure provides LOX1-binding proteins (e.g., antibodies such as, full length LOX1-antibodies, LOX1-binding antibody fragments, and variants and derivatives thereof), that compete for binding to LOX1 with an antibody comprising a VH sequence of SEQ ID NO:41 and a VL sequence of SEQ ID NO:58.

IV. Activity of LOX1-Binding Proteins

In some aspects, a LOX1-binding protein (e.g., an anti-LOX1 antibody such as, a full length LOX1-antibody, a LOX1-binding antibody fragment, and variants and derivatives thereof) has at least one property selected from the group consisting of: (a) reduces or inhibits binding of oxLDL, C-reactive protein (CRP) and/or advanced glycation end products (AGEs) to LOX1 as determined by any suitable assay including an assay disclosed herein (see, e.g., Example 10, assays 1, 2 and/or 3 or Example 11); (b) decreases or inhibits RhoA/Rac1, nitrogen monoxide (NO), p38MAPK, protein kinase B and C, ERK1/2, and/or NFκB signaling in an endothelial cell expressing cell surface LOX1 as determined by any suitable assay including an assay disclosed herein (see, e.g., Example 11); (c) decreases or inhibits caspase-8, caspase-9, and/or BAX activity in an endothelial cell expressing cell surface LOX1 as determined by any suitable assay including an assay disclosed herein; (d) binds to LOX1 having the single nucleotide polymorphism K167N as determined by any suitable assay including an assay disclosed herein (see, e.g., Example 10, assays 1, 2 and/or 3 or Example 11); (e) reduces or inhibits oxLDL internalization as determined by any suitable assay including an assay disclosed herein (see, e.g., Example 10, assay 4 or Example 11); (f) reduces or inhibits oxLDL-induced LOX1 signaling as determined by any suitable assay including an assay disclosed herein (see, e.g., Example 10, assay 5 or Example 11); (g) binds to LOX1 with a dissociation constant (KD) of about 150 pM to about 600 pM (e.g. about 400 pM) as determined by BIACORE or KinExA; (h) binds to LOX1 with a Kon rate of about $1\times10^5$ $M^{-1}$ $s^{-1}$ to about $6\times10^6$ $M^{-1}$ $s^{-1}$ (e.g. about $5\times10^5$ $M^{-1}$ $s^{-1}$) as determined by BIACORE; and (i) binds to LOX1 with a Koff rate of about $1\times10^{-4}$ $s^{-1}$ to about $3\times10^{-4}$ $s^{-1}$ (e.g. about $2.3\times10^{-4}$ $s^{-1}$) as determined by BIACORE.

In some aspects, a LOX1-binding protein (e.g., an anti-LOX1 antibody such as, a full length LOX1-antibody, a LOX1-binding antibody fragment, and variants and derivatives thereof) can suppress, inhibit or reduce LOX1-mediated signal transduction in cells expressing LOX1. In some aspects, a LOX1-binding protein can suppress, inhibit or reduce LOX1-mediated activation of the RhoA/Rac1, nitrogen monoxide, p38MAPK, protein kinase B and C, ERK1/2, and/or NFκB signal transduction pathway as measured using a cell-based assay for example as described herein, with an $IC_{50}$ lower than about 500 pM, lower than about 450 pM, lower than about 450 pM, lower than about 350 pM, lower than about 300 pM, lower than about 250 pM, lower than about 150 pM, lower than about 100 pM, lower than about 75 pM, lower than about 100 nM, lower than about 75 nM, lower than about 50 nM, lower than about 30 nM, lower than about 20 pM, lower than about 10 nM, or lower than about 5 nM.

In certain aspects, a LOX1-binding protein (e.g., an anti-LOX1 antibody such as, a full length anti-LOX1 antibody, LOX1-binding antibody fragment, and variants and derivatives thereof) can suppress, inhibit or reduce cynomolgus LOX1-mediated activation of the RhoA/Rac1, nitrogen monoxide, p38MAPK, protein kinase B and C, ERK1/2, and/or NFκB signaling pathway in cynomolgus endothelial cells, smooth muscle cells, and/or macrophages expressing LOX1 with an $IC_{50}$ of about 700 pM, about 550 pM, about 500 pM, about 300 pM, about 250 pM, about 220 pM, about, 100 pM, about 1 pM, about 0.1, about 1 nM, about 10 nM, about 20 nM, about 30 nM, about 50 nM or about 100 nM. In certain aspects, a LOX1-binding protein can suppress, inhibit or reduce cynomolgus LOX1-mediated activation in cynomolgus endothelial cells, smooth muscle cells, and/or macrophages expressing LOX1 with an $IC_{50}$ of about 1 nM to about 500 pM.

In additional aspects, an antagonist LOX1-binding protein (e.g., an anti-LOX1 antibody such as, a full length anti-LOX1 antibody, LOX1-binding antibody fragment, and variants and derivatives thereof) can suppress, inhibit or reduce human LOX1-mediated activation of the RhoA/Rac1, nitrogen monoxide, p38MAPK, protein kinase B and C, ERK1/2, and/or NFκB signal transduction pathway as measured using a cell-based assay for example as described herein, in endothelial cells, smooth muscle cells, and/or macrophages expressing LOX1 with an $IC_{50}$ of about 300 pM, about 250 pM, about 100 pM, about 55 pM, about 44 pM, about 1 pM, about 0.1 pM, about 100 nm, about 50 nm about 44 nM, about 10 nM, or about 3 nM.

In some aspects, a LOX1-binding protein (e.g., an anti-LOX1 antibody such as, a full length LOX1-antibody, a LOX1-binding antibody fragment, and variants and derivatives thereof) inhibits or reduces LOX1-binding to oxLDL. In some aspects the LOX1-binding protein inhibits or reduces LOX1-binding to multiple LOX1 ligands. In some aspects the LOX1-binding protein inhibits or reduces LOX1-binding to oxLDL and AGEs. In some aspects the LOX1-binding protein inhibits or reduces LOX1-binding to oxLDL and CRP. In some aspects the LOX1-binding protein inhibits or reduces LOX1-binding to oxLDL, AGEs and CRP. In further aspects, the LOX1-binding protein inhibits or reduces LOX1-binding to oxLDL, CRP, phosphatidylserine, advanced AGEs, small dense lipoproteins (sdLDL), oxidized HDL, N4-oxononanoyl lysine (ONL), heat shock proteins (hsp, e.g., HSP60), *Chlamydia pneumoniae*, platelets, leukocytes and/or apoptotic cells. Methods of measuring inhibition or reduction of LOX-1 binding to one or more ligands include those described herein in the Examples and any other suitable method known in the art.

V. Preparation of Anti-LOX1 Antibodies

In certain aspects, the LOX1-binding proteins are anti-LOX1 antibodies such as, a full length anti-LOX1 antibody, LOX1-binding antibody fragments, and variants, and derivatives thereof.

Monoclonal anti-LOX1 antibodies can be prepared using hybridoma methods, such as those described by Kohler and Milstein, *Nature* 256:495 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against LOX1 such as hLOX1, as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively anti-LOX1 monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, Per.C6 cells, or myeloma cells (e.g. NS0 cells) that do not otherwise produce immunoglobulin protein, monoclonal antibodies are generated by the host cells. Also, recombinant anti-LOX1 monoclonal antibodies can be isolated from phage display libraries expressing CDRs of the desired species as described (McCafferty et al., *Nature* 348:552-554 (1990); Clackson et al., *Nature* 352:624-628 (1991); and Marks et al., *J. Mol. Biol.* 222:581-597 (1991)).

The nucleic acid(s) encoding an anti-LOX1 antibody, such as a full length anti-LOX1 antibody and a LOX1-binding antibody fragment, and variants and derivatives thereof, can further be modified in a number of different manners using recombinant DNA technology to generate alternative antibodies. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-LOX1-binding protein binds human LOX1 such as, a full length anti-hLOX1 antibody and a hLOX1-binding human antibody fragment, and variants, and derivatives thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., *J. Immunol.* 147 (1):86-95 (1991); and U.S. Pat. No. 5,750, 373).

Also, the anti-LOX1 human antibody (e.g., a LOX1-binding human antibody fragment) can be selected from a phage library, where that phage library expresses human antibodies, as described, for example, in Vaughan et al., *Nat. Biotech.*, 14:309-314 (1996), Sheets et al., *Proc. Nat'l. Acad. Sci.* 95:6157-6162 (1998), Hoogenboom and Winter, *J. Mol. Biol.* 227:381 (1991), and Marks et al., *J. Mol. Biol.* 222:581 (1991)). Techniques for the generation and use of antibody phage libraries are also described in U.S. Pat. Nos. 5,969, 108, 6,172,197, 5,885,793, 6,521,404; 6,544,731; 6,555, 313; 6,582,915; 6,593,081; 6,300,064; 6,653,068; 6,706, 484; and 7,264,963; and Rothe et al., *J. Mol. Biol.* 376(4): 1182-200 (2008) (each of which is incorporated by reference herein in its entirety).

Affinity maturation strategies and chain shuffling strategies (Marks et al., *Bio/Technology* 10:779-783 (1992), which is incorporated by reference herein in its entirety) are known in the art and can be employed to generate high affinity anti-LOX1 human antibodies.

In some aspects, a LOX1 antibody, such as a full length anti-LOX1 antibody and a LOX1-binding antibody fragment, and variants and derivatives thereof), can be a humanized antibody. Methods for engineering, humanizing or resurfacing non-human or human antibodies can also be used and are known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing LOX1 binding. Accordingly, part or all of the non-human or human CDR sequences are maintained while the non-human sequences of the variable and constant regions can be replaced with human or other amino acids.

Anti-LOX1 antibodies can also optionally be humanized, resurfaced, engineered or human antibodies engineered with retention of high affinity for the antigen LOX1 and other favorable biological properties. To achieve this goal, humanized (or human) or engineered LOX1 antibody, such as a full length anti-LOX1 antibody and a LOX1-binding antibody fragment, and variants, and derivatives thereof such as, resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as LOX1. In this way, framework (FW) residues can be selected and combined from the consensus and import sequences so that the desired antibody characteristic, such as increased affinity for the target antigen(s), is achieved.

Humanization, resurfacing or engineering of anti-LOX1 antibodies of the disclosure can be performed using any known method including, but not limited to, those described in Jones et al., *Nature* 321:522 (1986); Riechmann et al., *Nature* 332:323 (1988); Verhoeyen et al., *Science* 239:1534 (1988)), Sims et al., *J. Immunol.* 151: 2296 (1993); Chothia and Lesk, *J. Mol. Biol.* 196:901 (1987), Carter et al., *Proc. Natl. Acad. Sci. U.S.A.* 89:4285 (1992); Presta et al., *J. Immunol.* 151:2623 (1993), U.S. Pat. Nos. 5,639,641, 5,723, 323; 5,976,862; 5,824,514; 5,817,483; 5,814,476; 5,763, 192; 5,723,323; 5,766,886; 5,714,352; 6,204,023; 6,180, 370; 5,693,762; 5,530,101; 5,585,089; 5,225,539; 4,816, 567, 7,557,189; 7,538,195; and 7,342,110; Intl. Appl. Nos. PCT/US98/16280; PCT/US96/18978; PCT/US91/09630; PCT/US91/05939; PCT/US94/01234; PCT/GB89/01334; PCT/GB91/01134; PCT/GB92/01755; Intl. Appl. Publ. Nos. WO90/14443; WO90/14424; WO90/14430; and EP Pat.

Publ. No. EP 229246; each of which is entirely incorporated herein by reference, including the references cited therein.

Antagonist human anti-LOX1 antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain aspects the anti-LOX1 antibody is a LOX1-binding antibody fragment. Various techniques are known for the production of antibody fragments. Traditionally, these fragments are derived via proteolytic digestion of intact antibodies (for example Morimoto et al., *J. Biochem. Biophys. Meth.* 24:107-117 (1993); Brennan et al., *Science* 229:81 (1985)). In certain aspects, LOX1-binding antibody fragments are produced recombinantly. Fab, Fv, and scFv antibody fragments can all be expressed in and secreted from *E. coli* or other host cells, thus allowing the production of large amounts of these fragments. Such LOX1-binding antibody fragments can also be isolated from the antibody phage libraries discussed above. The LOX1-binding antibody fragments can also be linear antibodies as described in U.S. Pat. No. 5,641,870. Other techniques for the production of antibody fragments are known in the art.

According to the present disclosure, techniques known in the art can be adapted for the production of single-chain antibodies specific to LOX1 (see, e.g., U.S. Pat. No. 4,946,778). In addition, methods can be adapted for the construction of Fab expression libraries (see, e.g., Huse et al., *Science* 246:1275-1281 (1989)) to allow rapid and effective identification of monoclonal Fab fragments with the desired specificity for LOX1. Anti-LOX1-binding antibody fragments can be produced by techniques known in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the anti-LOX1 antibody with papain and a reducing agent, and (d) Fv fragments.

In certain aspects, a LOX1-binding protein (e.g., a LOX1 antibody, such as a full length anti-LOX1 antibody and a LOX1-binding antibody fragment, and variants and derivatives thereof) can be modified in order to increase its serum half-life. This can be achieved, for example, by incorporation of a salvage receptor binding epitope into the LOX1-binding protein by mutation of the appropriate region in the LOX1-binding protein or by incorporating the epitope into a peptide tag that is then fused to the LOX1-binding protein at either end or in the middle (e.g., by DNA or peptide synthesis), or by YTE mutation. Other methods to increase the serum half-life of a LOX1-binding protein (e.g., a LOX1 antibody, such as a full length anti-LOX1 antibody and a LOX1-binding antibody fragment, and variants, and derivatives thereof), e.g., conjugation to a heterologous molecule such as PEG are known in the art.

Heteroconjugate LOX1-binding proteins (e.g., anti-LOX1 antibodies, such as a full length anti-LOX1 antibodies and LOX1-binding antibody fragments, and variants and derivatives thereof) are also within the scope of the disclosure. Heteroconjugate LOX1-binding proteins are composed of two covalently joined proteins. Such proteins have, for example, been proposed to target immune cells to unwanted cells (see, e.g., U.S. Pat. No. 4,676,980). It is contemplated that the heteroconjugate LOX1-binding proteins can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

Modified anti-LOX1 antibodies such as, full length anti-LOX1 antibodies and LOX1-binding antibody fragments, and variants, and derivatives thereof, as provided herein can comprise any type of variable region that provides for the association of the antibody with LOX1. In this regard, the variable region can comprise or be derived from any type of mammal that can be induced to mount a humoral response and generate immunoglobulins against the LOX1 antigen. As such, the variable region of an anti-LOX1 antibody can be, for example, of human, murine, non-human primate (e.g., cynomolgus monkeys, macaques, etc.) or lupine origin. In some aspects both the variable and constant regions of the modified anti-LOX1 antibodies are human. In other aspects the variable regions of compatible antibodies (usually derived from a non-human source) can be engineered or specifically tailored to improve the binding properties or reduce the immunogenicity of the molecule. In this respect, variable regions useful according to the disclosure can be humanized or otherwise altered through the inclusion of imported amino acid sequences.

In certain aspects, the variable domains in both the heavy and light chains of an anti-LOX1 antibody (e.g., a full length anti-LOX1 antibody and a LOX1-binding antibody fragment, and variants and derivatives thereof) are altered by at least partial replacement of one or more CDRs and/or by partial framework region replacement and sequence changing. Although the CDRs can be derived from an antibody of the same class or even subclass as the antibody from which the framework regions are derived, it is envisaged that the CDRs will be derived from an antibody of different class and in certain aspects from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified anti-LOX1 antibodies (e.g., full length anti-LOX1 antibodies and a LOX1-binding antibody fragments, and variants and derivatives thereof) of the disclosure will comprise antibodies in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some aspects, the constant region of the modified anti-LOX1 antibodies will comprise a human constant region. Modifications to the constant region can include additions, deletions or substitutions of one or more amino acids in one or more domains. That is, the modified anti-LOX1 antibodies disclosed herein can comprise alterations or modifications to one or more of the three heavy chain constant domains (CH1, CH2 or CH3) and/or to the light chain constant domain (CL). In some aspects, the modified anti-LOX1 antibodies will comprise constant regions wherein one or more domains are partially or entirely deleted are contemplated. In some aspects, the modified anti-LOX1 antibodies will comprise domain deleted constructs or variants wherein the entire CH2 domain has been removed (ΔCH2 constructs). In some aspects, the omitted constant region domain can be replaced by a short amino acid spacer (e.g., 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors that are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain aspects, an anti-LOX1 antibody (e.g., a full length anti-LOX1 antibody and a LOX1-binding antibody fragment, and variants and derivatives thereof) has an altered effector function that, in turn, affects the biological profile of the administered anti-LOX1 antibody. For example, the deletion or inactivation (through point mutations or other means) of a constant region domain can reduce Fc receptor binding of the circulating modified antibody. In other cases the constant region modifications, can moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this disclosure can easily be made using well-known biochemical or molecular engineering techniques well within the purview of the skilled artisan.

In some aspects, a LOX1-binding protein provided herein is a LOX1 antibody (e.g., a full length anti-LOX1 antibody and a LOX1-binding antibody fragment, and variants, and derivatives thereof) that does not have one or more effector functions. For instance, in some aspects, the anti-LOX1-antibody has no antibody-dependent cellular cytotoxicity (ADCC) activity and/or no complement-dependent cytotoxicity (CDC) activity. In certain aspects, the anti-LOX1 antibody does not bind to an Fc receptor and/or complement factors. In certain aspects, the anti-LOX1 antibody has no effector function.

In some aspects, an anti-LOX1 antibody (e.g., a full length anti-LOX1 antibody and a LOX1-binding antibody fragment, and variants and derivatives thereof) is engineered to fuse the CH3 domain directly to the hinge region of the respective modified antibody. In other constructs a peptide spacer is inserted between the hinge region and the modified CH2 and/or CH3 domains. For example, compatible constructs can be expressed in which the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. Amino acid spacers can, in some cases, prove to be immunogenic and elicit an unwanted immune response against the construct. Accordingly, in certain aspects, any spacer added to the construct can be relatively non-immunogenic, or even omitted altogether, so as to maintain the desired biochemical qualities of the modified anti-LOX1.

Besides the deletion of whole constant region domains, anti-LOX1 antibodies (e.g., full length anti-LOX1 antibodies and LOX1-binding antibody fragments, and variants and derivatives thereof) can be modified by the partial deletion or substitution of a few or even a single amino acid in a constant region. For example, the mutation of a single amino acid in selected areas of the CH2 domain can be enough to substantially reduce Fc binding and thereby. Similarly one or more constant region domains that control the effector function (e.g., complement C1Q binding) can be fully or partially deleted. Such partial deletions of the constant regions can improve selected characteristics of the antagonist anti-LOX1 antibody (e.g., serum half-life) while leaving other desirable functions associated with the corresponding constant region domain intact. Moreover, the constant regions of the anti-LOX1 antibodies provided herein can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified anti-LOX1 antibody. The disclosure also provides an anti-LOX1 antibody that contains the addition of one or more amino acids to the constant region to enhance desirable characteristics such, as decreasing or increasing effector function or providing attachments sites for more cytotoxin, labeling or carbohydrate moieties. In such aspects it can be desirable to insert or replicate specific sequences derived from selected constant region domains.

The disclosure is also directed to variants and equivalents that are substantially homologous in structure and/or similar in one or more functions, to anti-LOX1 antibodies disclosed herein (e.g., murine, chimeric, humanized and human LOX1-binding proteins). These variants can contain, for example, conservative amino acid residue substitution mutations. As generally understood in the art, a conservative amino acid residue substitution refers to the substitution of an amino acid residue with another within the same general class such as, for example, one acidic amino acid with another acidic amino acid, one basic amino acid with another basic amino acid or one neutral amino acid by another neutral amino acid. What is intended by a conservative amino acid substitution is known in the art.

LOX1-binding proteins such as, anti-LOX1 antibodies provided herein can be derivatised to contain additional chemical moieties that are not normally part of the protein. Such derivatization moieties are known in the art and can function to improve for example, the solubility, biological half-life, bioavailability, and to otherwise improve the stability, formulation and/or therapeutic properties of the LOX1-binding protein. A non-exhaustive overview for such moieties can be found for example, in Remington's Pharmaceutical Sciences, 20th ed., Mack Publishing Co., Easton, Pa. (2000).

VI. Nucleic Acids Encoding LOX1-Binding Proteins and their Expression

This disclosure provides nucleic acid molecules that encode LOX1-binding proteins (see, e.g., those described in Table 1, FIG. 4 or FIG. 5) including anti-LOX1 antibodies such as full length anti-LOX1 antibodies, LOX1-binding antibody fragments, and variants and derivatives thereof. The nucleic acid molecules disclosed herein can be in the form of RNA or in the form of DNA. DNA includes cDNA, genomic DNA, and synthetic DNA; and can be double-stranded or single-stranded, and if single stranded can be the coding strand or non-coding (anti-sense) strand. In certain aspects, the nucleic acid molecule is isolated. In additional aspects, a nucleic acid molecule is substantially pure. In some aspects the nucleic acid is cDNA or is derived from cDNA. In some aspects the nucleic acid is recombinantly produced.

In some aspects, the nucleic acid molecule comprises a LOX1-binding protein coding sequence operably linked to a control sequence that controls the expression of the coding sequence in a host cell or in vitro. In particular aspects, the coding sequence is a cDNA. The disclosure also relates to vectors containing nucleic acid molecules comprising a LOX1-binding protein coding sequence operably linked to a control sequence that controls the expression of the coding sequence in a host cell or in vitro.

In some aspects, the nucleic acid molecule comprises a coding sequence for a mature LOX1-binding protein that is fused in the same reading frame to a heterologous polynucleotide sequence. In some aspects, the heterologous polynucleotide sequence encodes a leader peptide sequence that facilitates the secretion of the expressed protein from the host cell transformed with the LOX1-encoding nucleic acid molecule. A protein containing a leader sequence is referred to as a preprotein and can have the leader sequence cleaved by the host cell to form the mature form of the polypeptide. Such leader peptide sequences and their use facilitating the secretion of recombinant proteins in host cells is generally known in the art. In additional aspects, the heterologous polynucleotide sequence encodes additional 5' and/or 3' amino acid residues that can function, for example, to facilitate purification, add or improve protein stability and/or therapeutic or diagnostic properties of the recombinantly expressed LOX1-binding protein.

In some aspects the disclosure provides isolated nucleic acids such as a cDNA molecule sufficient for use as a hybridization probe, PCR primer or sequencing primer.

In certain aspects the disclosure provides an isolated nucleic acid molecule encoding a light chain variable region (VL), wherein the VL comprises VL-CDR1, VL-CDR2, and VL-CDR3 amino acid sequences identical to, or that has a total of one, two, three, four, five, six, seven, eight or fewer amino acid substitutions in one or more of the VL-CDRs to: SEQ ID NO:30; SEQ ID NO:31; or SEQ ID NO:32, 34 or 35, respectively. In other aspects the disclosure provides an isolated nucleic acid molecule encoding a light chain variable region (VL), wherein the VL comprises VL-CDR1, VL-CDR2, and VL-CDR3 amino acid sequences identical to, or that has a total of one, two, three, four, five, six, seven, eight or fewer amino acid substitutions in one or more of the VL-CDRs to: SEQ ID NO:55 or 59; SEQ ID NO:56 or 60; or SEQ ID NO:57, 61-63 or 64, respectively.

The disclosure further provides an isolated nucleic acid molecule encoding a heavy chain variable region (VH), wherein the VH comprises VH-CDR1, VH-CDR2, and VH-CDR3 amino acid sequences identical to, or that has a total of one, two, three, four, five, six, seven, eight or fewer amino acid substitutions in one or more of the VH-CDRs to: SEQ ID NO: 1; SEQ ID NO:2, 5-12 or 13; and SEQ ID NO:3, 14-17 or 18, respectively. In other aspects, the disclosure provides an isolated nucleic acid molecule encoding a heavy chain variable region (VH), wherein the VH comprises VH-CDR1, VH-CDR2, and VH-CDR3 amino acid sequences identical to, or that has a total of one, two, three, four, five, six, seven, eight or fewer amino acid substitutions in one or more of the VH-CDRs to: SEQ ID NO:38; SEQ ID NO:39, 42 or 43; and SEQ ID NO:40, 44-46 or 47, respectively.

The disclosure further provides an isolated nucleic acid such as a cDNA, encoding a light chain variable region (VL), wherein the VL comprises an amino acid sequence having at least 70%, 75%, 80%, 85%, 90%, 95%, 96%, 97%, 98%, 99% or 100% sequence identity to a reference amino acid sequence selected from the group consisting of SEQ ID NO:33, SEQ ID NO:36, and SEQ ID NO:37. In some aspects, the isolated nucleic acid molecule encodes a light chain variable region (VL), wherein the VL comprises an amino acid sequence having at least 90%, 95%, 97%, 98%, 99% sequence identity to the reference amino acid sequence.

Moreover, the disclosure provides an isolated nucleic acid molecule encoding a heavy chain variable region (VH), wherein the VH comprises an amino acid sequence having at least 70%, 75%, 80%, 85%, 90%, 95%, 96%, 97%, 98%, 99% or 100% sequence identity to a reference amino acid sequence selected from the group consisting of SEQ ID NO:4, 19-28 and 29. In some aspects, the isolated nucleic acid molecule encodes a heavy chain variable region (VH), wherein the VH comprises an amino acid sequence having at least 90%, 95%, 97%, 98%, 99% sequence identity to the reference amino acid sequence.

In certain aspects the disclosure provides a nucleic acid molecule or combination of nucleic acid molecules that encode a LOX1-binding protein (e.g. the LOX-1 binding proteins described in Table 1, FIG. 4 or FIG. 5) that specifically binds to LOX1. Further provided is a vector comprising a nucleic molecule such as a cDNA or combination of nucleic acid molecules, as described herein. Suitable vectors are described elsewhere herein and are known in the art.

In certain aspects, the heavy chain variable region (VH) and light chain variable region (VL) are encoded by nucleic acid sequences having at least 70%, 75%, 80%, 85%, 90%, 95%, 96%, 97%, 98%, 99% or 100% sequence identity to reference nucleic acid sequences encoding SEQ ID NO:4 and SEQ ID NO:33, SEQ ID NO:23 and SEQ ID NO:36, or SEQ ID NO:27 and SEQ ID NO:37, respectively. In a particular aspect, the isolated LOX1-binding protein (e.g. an anti-LOX1 antibody or fragment thereof) is encoded by nucleic acid sequences encoding SEQ ID NO:4 and SEQ ID NO:33, respectively.

The disclosure further provides an isolated nucleic acid such as a cDNA, encoding a light chain variable region (VL), wherein the VL comprises an amino acid sequence having at least 70%, 75%, 80%, 85%, 90%, 95%, 96%, 97%, 98%, 99% or 100% sequence identity to a reference amino acid sequence selected from the group consisting of SEQ ID NO:58, 65-69 and 70. In some aspects, the isolated nucleic acid molecule encodes a light chain variable region (VL), wherein the VL comprises an amino acid sequence having at least 90%, 95%, 97%, 98%, 99% sequence identity to the reference amino acid sequence.

The disclosure also provides an isolated nucleic acid molecule encoding a heavy chain variable region (VH), wherein the VH comprises an amino acid sequence having at least 70%, 75%, 80%, 85%, 90%, 95%, 96%, 97%, 98%, 99% or 100% sequence identity to a reference amino acid sequence selected from the group consisting of SEQ ID NO:41, 48-53 and 54. In some aspects, the isolated nucleic acid molecule encodes a heavy chain variable region (VH), wherein the VH comprises an amino acid sequence having at least 90%, 95%, 97%, 98%, 99% sequence identity to the reference amino acid sequence.

In certain aspects, the heavy chain variable region (VH) and light chain variable region (VL) are encoded by nucleic acid sequences having at least 70%, 75%, 80%, 85%, 90%, 95%, 96%, 97%, 98%, 99% or 100% sequence identity to reference nucleic acid sequences encoding SEQ ID NO:54 and SEQ ID NO:70, SEQ ID NO:41 and SEQ ID NO:58, SEQ ID NO:48 and SEQ ID NO:65, SEQ ID NO:49 and SEQ ID NO:66, SEQ ID NO:50 and SEQ ID NO:67, or SEQ ID NO:53 and SEQ ID NO:58, respectively. In a particular aspect, the isolated LOX1-binding protein (e.g. an anti-LOX1 antibody or fragment thereof) is encoded by nucleic acid sequences encoding SEQ ID NO:41 and SEQ ID NO:58, respectively.

In some aspects, the isolated nucleic acid encodes a LOX1-binding protein comprising a set of CDRs: VH-CDR1, VH-CDR2, VH-CDR3, VL-CDR1, VL-CDR3 and VL-CDR3 described in Table 1, FIG. 4 or FIG. 5. In some additional aspects, the isolated nucleic acid encodes a LOX1-binding protein comprising a heavy chain variable region (VH) and light chain variable region (VL) described in Table 1, FIG. 4 or FIG. 5.

In a nucleic acid molecule composition as described above the nucleic acid encoding a VH and the nucleic acid encoding a VL can reside in a single vector, or can be on separate vectors. Accordingly, the disclosure provides one or more vectors comprising the nucleic acid molecule composition or combination of nucleic acid molecules described above.

In some cases, a polynucleotide composition encoding a VH and VL as described above can encode an antibody (including a LOX1-binding antibody fragment) that specifically binds to LOX1, e.g., human and cynomolgus monkey LOX1. In some aspects the polynucleotide composition encodes an antibody that specifically binds to the same epitope as an antibody or antigen-binding fragment comprising the VH and VL of SEQ ID NO:4 and SEQ ID NO:33, respectively. In other aspects the polynucleotide composition encodes an antibody that specifically binds to the same epitope as an antibody or antigen-binding fragment comprising the VH and VL of SEQ ID NO:41 and SEQ ID NO:58, respectively. In some additional aspects, the polynucleotide composition encodes an antibody that specifically binds to the same epitope as a LOX1-binding protein comprising a heavy chain variable region (VH) and light chain variable region (VL) described in Table 1, FIG. 4 or FIG. 5.

In additional aspects, the disclosure provides a host cell comprising a nucleic acid or nucleic acids or vector as provided above, where host cell can, in some instances express a LOX1-binding protein (e.g., an anti-LOX1 antibody such as, a full length LOX1-antibody, a LOX1-binding antibody fragment, and variants and derivatives thereof), that specifically binds to LOX1. Such a host cell can be utilized in a method of making a LOX1-binding protein as provided herein, where the method includes (a) culturing the host cell and (b) isolating the LOX1-binding proteins expressed from the host cell.

The disclosure also provides a method for making a LOX1-binding protein comprising culturing a host cell or hybridoma capable of expressing the LOX1-binding protein under suitable conditions and optionally provides a method for isolating the LOX1-binding protein secreted from the host cell or hybridoma. In addition, the disclosure additionally provides the LOX1-binding protein (e.g., an anti-LOX1 antibody or fragment thereof), isolated after being secreted from the host cell or hybridoma using the disclosed methods.

In certain aspects the polynucleotides comprise the coding sequence(s) for the mature LOX1-binding protein(s) (e.g., an LOX1-antibody, such as a full-length antibody and a LOX1-binding antibody fragment) fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

Nucleic acid variants encoding a LOX1-binding protein such as, an anti-LOX1 antibody and a LOX1-binding antibody fragment, are also provided. Nucleic acid variants can contain alterations in the coding regions, non-coding regions, or both. In some aspects the nucleic acid variants contain alterations that produce silent substitutions, additions, or deletions, but do not alter the properties or activities of the encoded polypeptide. In some aspects, the nucleic acid variants are produced by silent substitutions due to the degeneracy of the genetic code. Nucleic acid variants can be produced for a variety of reasons, e.g., to optimize codon expression for a particular host (change codons in the human mRNA to those preferred by a bacterial host such as *E. coli*). Vectors and cells comprising the nucleic acids described herein are also provided.

In some aspects a nucleic acid sequence encoding a LOX1-binding protein (e.g., an anti-LOX1 antibody such as a full-length antibody and a LOX1-binding antibody fragment) is constructed by chemical synthesis using an oligonucleotide synthesizer. Such oligonucleotides can be designed based on the amino acid sequence of the desired polypeptide and codon optimization based on the host cell preferences. Standard methods can routinely be applied to synthesize an isolate polynucleotide sequences encoding LOX1-binding proteins.

Once assembled (by synthesis, site-directed mutagenesis or another method), the nucleic acid sequences encoding LOX1-binding proteins can routinely be operably linked to a control sequence appropriate for expression of the LOX1-binding proteins in a desired host. In some aspects, the nucleic acid sequences encoding LOX1-binding proteins is inserted into an expression vector and operably linked to a control sequence appropriate for expression of the protein in a desired host. In order to obtain high expression levels of a transfected gene in a host, the gene can be operably linked to or associated with transcriptional and translational expression control sequences that are functional in the chosen expression host.

In certain aspects, recombinant expression vectors are used to amplify and express DNA encoding a LOX1-binding protein, such as, an anti-LOX1 antibody or a LOX1-binding antibody fragment. Recombinant expression vectors are replicable DNA constructs which have synthetic or cDNA-derived DNA fragments encoding a polypeptide chain of a LOX1-binding protein (e.g., an anti-LOX1 antibody such as a full-length antibody and a LOX1-binding antibody fragment) operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final protein. In certain aspects, the disclosure provides a composition, e.g., a pharmaceutical composition, comprising a nucleic acid or vector of as described above or elsewhere herein, optionally further comprising one or more carriers, diluents, excipients, or other additives.

Also provided is a host cell transformed with the nucleic acid molecule or cDNA molecules and/or the vectors disclosed herein. The disclosure also provides host cells transformed with the disclosed nucleic acid molecule or molecules operably linked to a control sequence and optionally inserted into a vector. In some aspects, the host cell is a mammalian host cell. In further aspects, the mammalian host cell is a NS0 murine myeloma cell, a PER.C6® human cell, or a Chinese hamster ovary (CHO) cell. In other aspects, the host cell is a hybridoma.

Additionally host cells expressing nucleic acids encoding LOX1-binding proteins disclosed herein are hybridomas that produce an LOX1-binding protein.

In additional aspects, the disclosure provides a method of making a LOX1-binding protein (e.g., an anti-LOX1 antibody such as, a full length LOX1-antibody and a LOX1-binding antibody fragment, and variants and derivatives thereof) provided herein comprising culturing a transformed host cell or a hybridoma disclosed herein under suitable conditions for producing the LOX1-binding protein. The disclosure optionally provides isolating the LOX1-binding protein secreted from the host cell or hybridoma. The disclosure also optionally provides the LOX1-binding protein produced using this method and pharmaceutical compositions comprising the LOX1-binding protein and a pharmaceutically acceptable carrier.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, and also wider host range plasmids, such as M13 and filamentous single-stranded DNA phages.

Suitable host cells for expression of a LOX1-binding protein (e.g., an anti-LOX1 antibody such as, a full length LOX1-antibody and a LOX1-binding antibody fragment, and variants and derivatives thereof), include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Appl. Publ. No. 2008/0187954, U.S. Pat. Nos. 6,413,746 and 6,660,501, and Intl. Appl. Publ. No. WO 04009823, each of which is hereby incorporated by reference herein in its entirety.

Various mammalian or insect cell culture systems can also be advantageously employed to express recombinant LOX1-binding protein (e.g., an anti-LOX1 antibody such as, a full length LOX1-antibody and a LOX1-binding antibody fragment, and variants and derivatives thereof). Expression of recombinant LOX1-binding proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (*Cell* 23:175 (1981)), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *BioTechnology* 6:47 (1988).

LOX1-binding proteins (e.g., anti-LOX1 antibodies such as, full length anti-LOX1 antibodies and LOX1-binding antibody fragments, and variants and derivatives thereof) produced by a transformed host or hybridoma can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated LOX1-binding proteins can also be physically characterized using such techniques as proteolysis, nuclear magnetic resonance and x-ray crystallography.

For example, supernatants from systems that secrete recombinant LOX1-binding proteins into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an LOX1-binding protein. Some or all of the foregoing purification steps, in various combinations, can also routinely be employed to provide a homogeneous recombinant LOX1-binding proteins.

A recombinant LOX1-binding protein (e.g., an anti-LOX1 antibody such as, a full length LOX1-antibody and a LOX1-binding antibody fragment, and variants and derivatives thereof) produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying target binding proteins such as full-length antibodies and antigen-binding antibody fragments also include, for example, those described in U.S. Appl. Publ. Nos. 2008/0312425, 2008/0177048, and 2009/0187005, each of which is hereby incorporated by reference herein in its entirety.

VII. Treatment Methods Using Therapeutic LOX1-Binding Proteins

Methods are provided for the use of a LOX1-binding protein (e.g., an anti-LOX1 antibody such as, a full length LOX1-antibody, a LOX1-binding antibody fragment, and variants and derivatives thereof) to treat subjects having a disease associated with LOX1, LOX1 activity, and/or LOX1 expression. Methods for detecting LOX1 expression are known in the art and include, but are not limited to, PCR techniques, immunohistochemistry, flow cytometry, Western blot, ELISA, and the like.

In additional aspects, the disclosure provides a pharmaceutical composition containing a LOX1-binding protein provided herein e.g., an anti-LOX1 antibody or fragment thereof) and a pharmaceutically acceptable carrier. In some aspects, the disclosure provides a pharmaceutical composition containing a LOX1-binding protein and a pharmaceutically acceptable carrier, for use as a medicament. The disclosure also provides the use of the pharmaceutical compositions for treating, preventing and/or ameliorating a disease or condition associated with LOX1, LOX1 activity, LOX1 expression and/or reduced HDL-mediated signaling. In some aspects, the disease or condition treated using the pharmaceutical compositions provided herein is atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and/or cancer.

In some aspects, a pharmaceutical composition contains a LOX1-binding protein (e.g., an anti-LOX1 antibody such as, a full length LOX1-antibody and a LOX1-binding antibody fragment, and variants and derivatives thereof), a pharmaceutically acceptable carrier, and further comprises a labeling group or an effector group. As used herein, a "label" refers to one or more elements, isotopes, or chemical compounds attached to enable the detection in a screen. Labels generally fall into three classes: (a) isotopic labels, which may be radioactive or heavy isotopes, (b) small molecule labels, which may include fluorescent and colorimetric dyes, or molecules such as biotin that enable other labeling methods, and (c) immune labels, which may be an epitope incorporated as a fusion partner that is recognized by an antibody. "Labeling group" refers to any detectable label. In some aspects, the labeling group is coupled to the LOX1-binding protein via a spacer (e.g., a peptide spacer) to reduce potential steric hindrance. Labels may be incorporated into the compound at any position and may be incorporated in vitro or in vivo during protein expression. Various methods for labeling proteins are known in the art and may be used in performing the provided methods. In additional aspects, the labeling group is selected from the group consisting of: isotopic labels, magnetic labels, redox active moieties, optical dyes, biotinylated groups and polypeptide epitopes recognized by a secondary reporter. In some aspects, the labeling group is a fluorescent protein such as a Green Fluorescent Protein or derivative thereof (e.g., enhanced GFP, blue fluorescent protein or derivative thereof (e.g., EBFP (Enhanced Blue Fluorescent Protein), EBFP2, Azurite, mKalama1, cyan fluorescent protein or derivative thereof (e.g., ECFP (Enhanced Cyan Fluorescent Protein), Cerulean, CyPet), yellow fluorescent protein or derivative thereof (e.g., YFP, Citrine, Venus, YPet). In some aspects, the polypeptide epitope is a member selected from a biotin signaling peptide, histidine peptide (his), hemagglutinin (HA), Flag, gold binding peptide. In additional aspects the effector group is selected from the group consisting of a radioisotope, radionuclide, a toxin, a therapeutic and a chemotherapeutic agent.

In further aspects, the effector group is selected from the group consisting of a radioisotope, radionuclide, a toxin, a therapeutic and a chemotherapeutic agent.

The following discussion refers to diagnostic methods and methods of treating, preventing and/or ameliorating various diseases and conditions with a LOX1-binding protein (e.g., an anti-LOX1 antibody such as, a full length LOX1-antibody, a LOX1-binding antibody fragment, and variants and derivatives thereof). In some aspects, the LOX1-binding proteins are human, murine, or humanized antibodies.

In one aspect, the disclosure provides for the treatment, prevention or amelioration of a disease or condition comprising administering a LOX1-binding protein (e.g., an anti-LOX1 antibody such as, a full length LOX1-antibody, a LOX1-binding antibody fragment, and variants and derivatives thereof) to a subject that has a disease or condition, or is at risk of developing a disease or condition, associated with LOX1. In another aspect the treatment includes the administration of a LOX1-binding protein to an isolated tissue or cell from a subject, where the subject has a disease or conditions, or is at risk of developing a disease or condition, associated with LOX1.

The disclosure also provides methods for treating, preventing and/or ameliorating a disease or condition associated with atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and cancer in a subject. In some aspects, the method comprises administering to a subject in need thereof, an effective amount of a pharmaceutical composition comprising a LOX1-binding protein (e.g., an anti-LOX1 antibody such as, a full length LOX1-antibody, a LOX1-binding antibody fragment, and variants and derivatives thereof). In additional aspects, the LOX1-binding protein is administered alone or as a combination therapy.

The disclosure also provides methods of reducing or inhibiting LOX1 activity and/or stimulating or increasing HDL-mediated signaling in a subject. In some aspects, the method comprises administering to a subject in need thereof, (e.g. a subject diagnosed with atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and/or cancer), an effective amount of a LOX1-binding protein (e.g., an anti-LOX1 antibody such as, a full length LOX1-antibody, a LOX1-binding antibody fragment, and variants and derivatives thereof).

Additionally provided are methods of treating, preventing, and/or ameliorating atherosclerosis. In some instances, the method comprises administering a LOX1-binding protein (e.g., an anti-LOX1 antibody or fragment thereof in a pharmaceutical composition described herein) to a subject having atherosclerosis. In other aspects, the subject to which the LOX1-binding protein (e.g. an anti-LOX1 antibody or fragment thereof) is administered is at risk of developing atherosclerosis. In some aspects, the subject has a proatherogenic condition. In further aspects, the proatherogenic condition is systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or bacterial infection. Also provided are methods of decreasing atherosclerosis. In some instances, the disclosure provides a method of decreasing atherosclerosis in a subject that comprises administering a LOX1-binding protein to a subject having atherosclerosis.

Also provided are methods of treating, preventing, and/or ameliorating thrombosis. In some instances, the method comprises administering a LOX1-binding protein (e.g. an anti-LOX1 antibody or fragment thereof) to a subject having thrombosis. In other aspects, the subject to which the LOX1-binding protein is administered is at risk of developing thrombosis. In some aspects the thrombosis is an arterial thrombosis. In further aspects, the thrombosis is a deep vein thrombosis.

The disclosure also provides methods of treating, preventing, and/or ameliorating coronary artery disease (CAD) or a condition associated with CAD. In some instances, the method comprises administering a LOX1-binding protein (e.g., an anti-LOX1 antibody or fragment thereof in a pharmaceutical composition described herein) to a subject having CAD. In other aspects, the subject to which the LOX1-binding protein is administered is at risk of developing CAD. In some aspects, the subject has a proatherogenic condition. In further aspects, the proatherogenic condition is systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or bacterial infection.

The disclosure also provides methods of treating, preventing, and/or ameliorating ischemia or a condition associated with ischemia. In some instances, the method comprises administering a LOX1-binding protein (e.g., an anti-LOX1 antibody or fragment thereof in a pharmaceutical composition described herein) to a subject having ischemia. In other aspects, the subject to which the LOX1-binding protein is administered is at risk of developing ischemia. In some aspects, the subject has myocardial ischemia. In other aspects, the subject is at risk of developing myocardial ischemia. In additional aspects, the subject has systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or a bacterial infection.

Also provided are methods of treating, preventing, and/or ameliorating an infarction or a condition associated with an infarction. In some instances, the method comprises administering a LOX1-binding protein (e.g., an anti-LOX1 antibody or fragment thereof in a pharmaceutical composition described herein) to a subject having an infarction. In other aspects, the subject to which the LOX1-binding protein is administered is at risk of developing an infarction. In some aspects, the subject has a myocardial infarction. In other aspects, the subject is at risk of developing a myocardial infarction. In additional aspects, the subject has ischemia, systemic lupus erythematosus (SLE), diabetes, hypertension, hyperglycemia, heart failure, vascular injury, organ transplantation, dyslipidemia (e.g., hyperlipidemia), inflammation (e.g., chronic inflammation and endotoxin induced inflammation) and/or a bacterial infection.

The disclosure also provides methods of treating, preventing, and/or ameliorating acute coronary syndrome (ACS) or a condition associated with ACS. In some instances, the method comprises administering a LOX1-binding protein (e.g., an anti-LOX1 antibody or fragment thereof in a pharmaceutical composition described herein) to a subject having ACS. In other aspects, the subject to which the LOX1-binding protein is administered is at risk of developing ACS. In some aspects, the subject has elevated sLOX serum levels or elevated LOX1 activity. In additional aspects, the subject has atherosclerosis.

The disclosure also provides methods of treating, preventing, and/or ameliorating a stroke or a condition associated with a stroke. In some instances, the method comprises administering a LOX1-binding protein (e.g., an anti-LOX1 antibody or fragment thereof in a pharmaceutical composition described herein) to a subject that has had a stroke. In other aspects, the subject to which the LOX1-binding protein is administered is at risk of having a stroke. In some aspects, the subject has elevated sLOX serum levels or elevated LOX1 activity. In additional aspects, the subject has atherosclerosis.

Also provided are methods of treating, preventing, and/or ameliorating reperfusion injury or a condition associated with reperfusion injury. In some instances, the method comprises administering a LOX1-binding protein (e.g., an anti-LOX1 antibody or fragment thereof in a pharmaceutical composition described herein) to a subject having reperfusion injury. In other aspects, the subject to which the LOX1-binding protein is administered is at risk of developing reperfusion injury. In some aspects, the subject is about to have surgery. In other aspects, the subject has had surgery. In some aspects the surgery is transplantation or coronary bypass surgery. In additional aspects the patient has, or is at risk of developing, myocardial ischemia-reperfusion injury. In further aspects the method decreases myocardial injury, decreases collagen accumulation, reduces serum CK-MB and MDA, reduces cardiomyocyte size, reduces leukocyte infiltration, and/or reduces cardiac dysfunction (e.g., reduced LVP and increased LVEDP). In further aspects, the method increases heart stroke volume, fractional shortening, and/or injection fraction.

The disclosure also provides methods of treating, preventing, and/or ameliorating restenosis or a condition associated with restenosis. In some instances, the method comprises administering a LOX1-binding protein (e.g., an anti-LOX1 antibody or fragment thereof in a pharmaceutical composition described herein) to a subject having restenosis. In other aspects, the subject to which the LOX1-binding protein is administered is at risk of developing restenosis. In some aspects, the subject is about to have surgery. In other aspects, the subject has had surgery. In some aspects the surgery is an endovascular procedure. In further embodiments, the surgery is vascular surgery, cardiac surgery or angioplasty. In additional aspects the procedure is transplantation or coronary bypass surgery. In additional aspects the treated, prevented, and/or ameliorated restenosis is in-stent restenosis or post-angioplasty restenosis.

In additional aspects, the disclosure provides methods of treating, preventing, and/or ameliorating peripheral vascular disease (PVD) or a condition associated with PVD. In some instances, the method comprises administering a LOX1-binding protein (e.g., in a pharmaceutical composition described herein) to a subject having PVD. In other aspects, the subject to which the LOX1-binding protein is administered is at risk of developing PVD. In some aspects, the subject has elevated sLOX serum levels or elevated LOX1 activity. In additional aspects, the subject has atherosclerosis.

The disclosure also provides methods of treating, preventing, and/or ameliorating inflammation or a condition associated with inflammation. In some instances, the method comprises administering a LOX1-binding protein (e.g., an anti-LOX1 antibody or fragment thereof in a pharmaceutical composition described herein) to a subject having inflammation. In further aspects, the subject has chronic inflammation. In some aspects, the subject has elevated oxLDLa and/or sLOX serum levels and/or elevated LOX1 activity. In additional aspects, the subject has atherosclerosis.

The disclosure also provides methods of treating, preventing, and/or ameliorating preeclampsia or a condition associated with preeclampsia. In some instances, the method comprises administering a LOX1-binding protein (e.g., an anti-LOX1 antibody or fragment thereof in a pharmaceutical composition described herein) to a subject having preeclampsia or eclampsia. In further aspects, the subject has high blood pressure and large amounts of protein in the urine. In some aspects, the subject has elevated oxLDL and/or sLOX serum levels and/or elevated LOX1 activity. In additional aspects, the subject has swelling in the feet, legs and/or hands.

In additional aspects, the disclosure provides methods of stabilizing an atherosclerotic plaque in a subject. In some instances, the method comprises administering a LOX1-binding protein (e.g., an anti-LOX1 antibody such as, a full length LOX1-antibody, a LOX1-binding antibody fragment, and variants and derivatives thereof) to a subject in need thereof. In some aspects the method reduces the signaling of the RhoA/Rac1, nitrogen monoxide, p38MAPK, protein kinase B and C, ERK1/2, and/or NFκB signal transduction pathway in the plaque. In other aspects, the method decreases apoptosis in the plaque. In further aspects, the method decreases caspase 8, caspase 9 and/or BAX activity and/or increases BCL-2 activity in the plaque. In other aspects, the method decreases the levels of an adhesion molecule or cytokine produced by the plaque. In further aspects, the method decreases E-selectin, P-selectin, ICAM-1, VCAM-1, MCP1 and/or CD40/CD40L expression by the plaque. In additional aspects, the method decreases atherosclerotic plaque size or formation, macrophage accumulation and/or MMP (e.g., MMP9) expression in the atherosclerotic plaque. In additional aspects, the method results in decreased progression or regression of the plaque.

Also provided are methods of reducing the loss of vascular tone in a subject. In some instances, the method comprises administering a LOX1-binding protein (e.g., an anti-LOX1 antibody such as, a full length LOX1-antibody, a LOX1-binding antibody fragment, and variants and derivatives thereof) to a subject in need thereof. In some aspects the method reduces the loss of vascular tone. In further aspects, the method reduces the loss of vascular tone in a subject through regulating HDL driven nitric oxide (NO) production (ability of antibody to stimulate endothelial NO production).

Additionally provided are methods of improving vascular tone in a subject. In some instances, the method comprises administering a LOX1-binding protein (e.g., an anti-LOX1 antibody or fragment thereof) to a subject in need thereof.

In some aspects the disclosure provides methods of treating, preventing, and/or ameliorating a condition associated with hyperglycemia or hypertension. In some instances, the method comprises administering a LOX1-binding protein to a subject having hyperglycemia or hypertension.

Additionally provided are methods of treating, preventing, and/or ameliorating cancer. In some instances the disclosure provides a method of treating, preventing, and/or ameliorating cancer in a subject that comprises administering a LOX1-binding protein to a subject having cancer. In some aspects, the subject has a cancer selected from the group consisting of: breast cancer, colon cancer, ovarian cancer, melanoma, cervical cancer, lung cancer, uterine cancer, kidney cancer, and pancreatic cancer.

Also provided are methods of inhibiting tumor cell proliferation, migration or invasion. In some instances the disclosure provides a method of antagonizing LOX1 activity that comprises contacting a LOX1-binding protein with a tumor cell expressing LOX1. In some aspects the tumor cell is from a cancer selected from the group consisting of: breast cancer, colon cancer, ovarian cancer, melanoma, cervical cancer, lung cancer, uterine cancer, kidney cancer, and pancreatic cancer. In some aspects the tumor cell is from a cancer line.

The disclosure additionally provides methods of reducing or inhibiting angiogenesis. In some aspects the method of reducing or inhibiting angiogenesis comprises administering a LOX1-binding protein (e.g., an anti-LOX1 antibody or fragment thereof) to a subject in need thereof. In some aspects the subject has a condition associated with pathological angiogenesis. In additional aspects the disclosure provides a method of inhibiting angiogenesis that comprises contacting a LOX1-binding protein with a cell expressing LOX1. In some aspects the cell is an endothelial cell. In further aspects the endothelial cell is a coronary endothelial cell. In some aspects the method is performed in vitro. In other aspects the method is performed in vivo.

Additionally provided are methods of blocking or reducing LOX1 activity. In some aspects the disclosure provides methods of blocking LOX1 activity comprising administering a LOX1-binding protein (e.g., an anti-LOX1 antibody or fragment thereof) that reduces or inhibits the interaction between LOX1 and a LOX1 ligand such as, oxLDL, AGEs, and/or CRP. In some aspects, LOX1 is expressed on the surface of an endothelial cell, macrophage, smooth muscle vascular cell and/or platelet. In some aspects the cell is an endothelial cell such as, a coronary endothelial cell. In additional aspects, the cell is a vascular smooth muscle cell, macrophage, or platelet. In other aspects the cell is part of an atherosclerotic tissue. In some aspects, the method is performed in vivo. In other aspects, the method is performed in vitro. In some aspects the blocked or reduced LOX1 activity is the binding and/or taking up (e.g. internalization) of oxLDL. In additional aspects, the blocked or reduced LOX1 activity is the induction of the p38 (MAPK), p44/42 MAPK, protein kinase C (PKC), protein kinase B (PKB), protein tyrosine kinase (PTK), transcription factor NF-KB and/or AP1 signaling pathway. In additional aspects the blocked or reduced LOX1 activity is the induction of apoptosis. In further embodiments, the induction of apoptosis is mediated by caspase-9, caspase-3 and/or Bcl-2. In additional aspects the blocked or reduced LOX1 activity is the expression of the A and B chains of PDFG and/or heparin-binding EGF-like protein (HB-EGF) in endothelial cells expressing LOX1. In some aspects, the blocked or reduced LOX1 activity is a LOX1 activity induced by oxLDL binding to LOX1.

Additionally provided are methods of blocking or reducing LOX1 activity in a pathological condition associated with increased LOX1 activity levels or LOX1 expression levels (e.g. sLOX1 serum protein levels). In some instances, the method comprises administering a LOX1-binding protein (e.g., an anti-LOX1 antibody or fragment thereof) to a subject having increased LOX1 activity or LOX1 expression levels (e.g. sLOX1 serum protein levels). In some aspects the pathological condition is systemic lupus erythematosus (SLE), diabetes, hypertension, hyperglycemia, heart failure, vascular injury, transplantation, dyslipidemia (hyperlipidemia), inflammation, (e.g., chronic inflammation and endotoxin induced inflammation) or bacterial infection. In some aspects, the subject has elevated serum levels of OxLDL. In some aspects, the subject has elevated serum levels of OxLDL, 15 lipoxygenase modified LDL, 15 lipoxygenase modified HDL, glyoxidized LDL, lysophosphatidylcholinesterase (LPC) and/or palmitic acid. In additional aspects, the subject has elevated serum levels of TNF alpha, IL1, interferon gamma, LPS (lipopolysaccharide), CRP, angiotensin II, endothelin I, and/or AGEs. In additional aspects, the subject has elevated serum levels of soluble LOX1 (sLOX1). In some aspects, the subject has a single nucleotide polymorphism (SNP) in the LOX1 gene. In some aspects, the SNP in the LOX1 gene is the LOX1 K167N variant.

Also provided are methods of agonizing or increasing a high-density lipoprotein (HDL) activity. In some aspects, the disclosure provides a method of increasing or agonizing an HDL activity by administering a LOX1-binding protein (e.g., an anti-LOX1 antibody or fragment thereof) to a subject in need thereof. In some aspects the increased HDL activity is the promotion of HDL-mediated endothelial NO production. In some aspects, the increased HDL activity is the inhibition of the NFKB signaling activity of the endothelial cell. In some aspects, the increase HDL activity is the promotion of endothelial cell repair. In some aspects, the increase HDL activity is the reduction of inflammation.

Also provided is the use of a LOX1-binding protein such as a LOX1-binding protein provided herein for diagnostic monitoring of protein levels (e.g., LOX1 levels) in blood or tissue as part of a clinical testing procedure, e.g., to determine the efficacy of a given treatment regimen. For example, detection can be facilitated by coupling a LOX1-binding protein (e.g., anti-LOX1 antibody) to a detectable substance.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include nptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

VIII. Pharmaceutical Compositions and Administration Methods

Methods of preparing and administering a LOX1-binding protein provided herein to a subject in need thereof are known to or are readily determined by those skilled in the art. The route of administration of the LOX1-binding proteins can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the disclosure, another example of a form for administration would be a solution for injection, in particular for intravenous or intraarterial injection or drip. Usually, a suitable pharmaceutical composition can comprise a buffer (e.g. acetate, phosphate or citrate buffer), a surfactant (e.g. polysorbate), optionally a stabilizer agent (e.g. human albumin), etc. In other methods compatible with the teachings herein, LOX1-binding proteins as provided herein can be delivered directly to the organ and/or site of an atherosclerosis or tumor, thereby increasing the exposure of the diseased tissue to the therapeutic agent. In one aspect, the administration is directly to the airway, e.g., by inhalation or intranasal administration.

As discussed herein, LOX1-binding proteins can be administered in a pharmaceutically effective amount for the in vivo treatment of LOX1-mediated diseases and conditions such as, atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and cancer. In this regard, it will be appreciated that the disclosed LOX1-binding proteins can be formulated so as to facilitate administration and promote stability of the active agent. Pharmaceutical compositions in accordance with the disclosure can comprise a pharmaceutically acceptable, non-toxic, sterile carrier such as physiological saline, non-toxic buffers, preservatives and the like. For the purposes of the instant application, a pharmaceutically effective amount of a LOX1-binding protein, conjugated or unconjugated, means an amount sufficient to achieve effective binding to LOX1 and to achieve a benefit, e.g., to ameliorate symptoms of a disease or condition or to detect a substance or a cell. Suitable formulations for use in the therapeutic methods disclosed herein are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions.

Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a LOX1-binding protein (e.g., an anti-LOX1 antibody such as, a full length LOX1-antibody and a LOX1-binding antibody fragment, and variants and derivatives thereof) that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, a LOX1-binding protein can be administered to a human or other subject in accordance with the aforementioned methods of treatment in an amount sufficient to produce a therapeutic effect. The LOX1-binding proteins provided herein can be administered to such human or other animal in a conventional dosage form prepared by combining the LOX1-binding proteins with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables. A cocktail comprising one or more different LOX1-binding proteins can also be used.

By "therapeutically effective dose or amount" or "effective amount" is intended an amount of a LOX1-binding protein (e.g., an anti-LOX1 antibody such as, a full length LOX1-antibody and a LOX1-binding antibody fragment, and variants and derivatives thereof) that when administered brings about a positive therapeutic response with respect to treatment of a subject with a disease or condition to be treated.

Therapeutically effective doses of LOX1-binding protein compositions for treatment of LOX1-mediated diseases or conditions such as, atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, hypertension, heart failure, inflammation (e.g., chronic inflammation), angiogenesis, preeclampsia and cancer, vary depending upon many different factors, including means of administration, target site, physiological state of the subject, whether the subject is human or an animal, other medications administered, and whether treatment is prophylactic or therapeutic. Usually, the subject is a human, but non-human mammals including transgenic mammals can also be treated. Treatment dosages can be titrated using routine methods known to those of skill in the art to optimize safety and efficacy.

As used herein, to ameliorate the symptoms of a particular disease or condition by administration of a LOX1-binding protein refers to any lessening, whether permanent or temporary, lasting or transient that can be attributed to or associated with administration of the LOX1-binding protein.

The amount of at least one LOX1-binding protein, e.g., antibody or binding fragment to be administered is readily determined by one of ordinary skill in the art without undue experimentation given this disclosure. Factors influencing the mode of administration and the respective amount of at least one LOX1-binding protein includes, but is not limited to, the severity of the disease, the history of the disease, and the age, height, weight, health, and physical condition of the individual undergoing therapy. Similarly, the amount of a LOX1-binding protein to be administered will be dependent upon the mode of administration and whether the subject will undergo a single dose or multiple doses of this agent.

The disclosure also provides for the use of a LOX1-binding protein, such as, an anti-LOX1 antibody (e.g., a full length LOX1-antibody and a LOX1-binding antibody fragment, and a variant and derivative thereof) in the manufacture of a medicament for example, for improving HDL activity, and methods of treating, preventing, and/or ameliorating atherosclerosis, thrombosis, CAD, ischemia (e.g., myocardial ischemia), infarction (e.g., myocardial infarction), acute coronary syndrome (ACS), stroke, reperfusion injury, restenosis, peripheral vascular disease, inflammation (e.g., chronic inflammation), angiogenesis, preeclampsia and cancer.

Combination Therapies

In some aspects, a LOX1-binding protein (e.g., an anti-LOX1 antibody such as, a full length LOX1-antibody and a LOX1-binding antibody fragment, and variants and derivatives thereof) is administered in combination with one or more other therapies. Such therapies include additional therapeutic agents as well as other medical interventions. Exemplary therapeutic agents that can be administered in combination with the LOX1-binding proteins provided herein include, but are not limited to, platelet inhibitors, anti-coagulants, anti-hypertensives, glycoprotein IIb/IIIa receptor inhibitors, beta blockers, calcium channel blockers, HMG CoA reductases inhibitors (statins), ezetimibe, fibrates (e.g., Gemifibrozil and Fenofibrate), Zetia, bile acid sequestrants, nitrates, and thrombolytic agents.

In various aspects, a LOX1-binding protein is administered to a subject before, during, and/or after a surgical procedure. In some aspects the surgery is an endovascular procedure. In further embodiments, the surgery is vascular surgery, cardiac surgery or angioplasty. In additional aspects the procedure is transplantation or coronary bypass surgery.

IX. Diagnostics

This disclosure further provides a diagnostic method useful during diagnosis of LOX1-mediated diseases and conditions such as, atherosclerosis, thrombosis, coronary artery disease (CAD), ischemia (e.g., myocardial ischemia), infarction (e.g., myocardial infarction), acute coronary syndrome (ACS), stroke, reperfusion injury, restenosis, peripheral vascular disease, hypertension, heart failure, inflammation, angiogenesis, preeclampsia and cancer, which involves measuring the expression level of LOX1 (including sLOX1) protein in tissue or body fluid such as serum from an individual and comparing the measured expression level with a standard LOX1 expression level in normal tissue or body fluid, whereby an increase in the expression level compared to the standard is indicative of a disorder treatable by a LOX1-binding protein provided herein, such as a full-length anti-LOX1 antibody and antigen-binding antibody fragment as provided herein.

The LOX1-binding proteins provided herein such as, anti-LOX1 antibodies (e.g., full length LOX1-antibodies and LOX1-binding antibody fragments, and variants and derivatives thereof) can be used to assay LOX1 protein levels in a biological sample using classical immunohistological methods known to those of skill in the art (see, e.g., Jalkanen, et al., *J. Cell. Biol.* 101:976-985 (1985); Jalkanen et al., *J. Cell Biol.* 105:3087-3096 (1987)). Other antibody-based methods useful for detecting LOX1 protein expression include immunoassays, such as the enzyme linked immunosorbent assay (ELISA), immunoprecipitation, or Western blotting.

By "assaying the expression level of LOX1 protein" is intended qualitatively or quantitatively measuring or estimating the level of LOX1 protein in a first biological sample either directly (e.g., by determining or estimating absolute protein level) or relatively (e.g., by comparing to the disease associated polypeptide level in a second biological sample). The LOX1 protein expression level in the first biological sample can be measured or estimated and compared to a standard LOX1 protein level, the standard being taken from a second biological sample obtained from an individual not having the disorder or being determined by averaging levels from a population of individuals not having the disorder. As will be appreciated in the art, once the "standard" LOX1 protein level is known, it can be used repeatedly as a standard for comparison.

By "biological sample" is intended any biological sample obtained from an individual, cell line, tissue culture, or other source of cells potentially expressing LOX1. Methods for obtaining tissue biopsies and body fluids from mammals are known in the art.

X. Kits Comprising LOX1-Binding Proteins

This disclosure further provides kits that include a LOX1-binding protein (e.g., an anti-LOX1 antibody such as, a full length LOX1-antibody, a LOX1-binding antibody fragment, and variants and derivatives thereof) in suitable packaging, and written material and that can be used to perform the methods described herein.

The written material can include any of the following information: instructions for use, discussion of clinical studies, listing of side effects, scientific literature references, package insert materials, clinical trial results, and/or summaries of these and the like. The written material can indicate or establish the activities and/or advantages of the composition, and/or describe dosing, administration, side effects, drug interactions, or other information useful to the health care provider. Such information can be based on the results of various studies, for example, studies using experimental animals involving in vivo models and/or studies based on human clinical trials. The kit can further contain another therapy (e.g., another agent) and/or written material such as that described above that serves to provide information regarding the other therapy (e.g., the other agent).

In certain aspects, a kit comprises at least one purified LOX1-binding protein in one or more containers. In some aspects, the kits contain all of the components necessary and/or sufficient to perform a detection assay, including all controls, directions for performing assays, and any necessary software for analysis and presentation of results.

XI. Immunoassays

LOX1-binding proteins (e.g., anti-LOX1 antibodies and LOX1-binding fragments, variants, or derivatives thereof) can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and known in the art (see, e.g., Ausubel et al., eds, (1994) Current Protocols in Molecular Biology (John Wiley & Sons, Inc., NY) Vol. 1, which is incorporated by reference herein in its entirety).

LOX1-binding proteins (e.g., anti-LOX1 antibodies or LOX1-binding fragments, variants, or derivatives thereof) provided herein can be employed histologically, as in immunofluorescence, immunoelectron microscopy or non-immunological assays, for in situ detection of LOX1 or conserved variants or peptide fragments thereof. In situ detection can be accomplished by removing a histological specimen from a subject, and applying thereto labeled LOX1-binding proteins by overlaying the labeled LOX1-binding proteins onto a biological sample. Through the use of such a procedure, it is possible to determine not only the presence of LOX1, or conserved variants or peptide fragments, but also its distribution in the examined tissue. Using the present disclosure, those of ordinary skill will readily perceive that any of a wide variety of histological methods (such as staining procedures) can be modified in order to achieve such in situ detection.

The binding activity of a given lot of LOX1-binding protein (e.g., an anti-LOX1 antibody such as, a full length LOX1-antibody and a LOX1-binding antibody fragment, and variants and derivatives thereof) can be determined according to methods known in the art. Those skilled in the art will be able to determine operative and optimal assay conditions for each determination by employing routine experimentation.

Methods and reagents suitable for determination of binding characteristics of an isolated LOX1-binding protein are known in the art and/or are commercially available. Equipment and software designed for such kinetic analyzes are commercially available (e.g., BIACORE®, BIAevaluation® software, GE Healthcare; KINEXA® Software, Sapidyne Instruments).

Unless otherwise indicated, the practice of the disclosure employs conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell et al., (eds) (1980) Selected Methods in Cellular Immunology (W.H. Freeman & Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyzes (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach et al., (2003) PCR Primer (Cold Spring Harbor Press).

The following examples are offered by way of illustration and not by way of limitation.

EXAMPLES

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

Example 1. Isolation and Identification of Anti-LOX1 scFv Antibodies

A large single chain Fv (scFv) human antibody library derived from bone marrow from adult naïve donors and cloned into a phagemid vector based on filamentous phage M13 was used for selections (Hutchings, C., Generation of Naïve Human Antibody Libraries, in Antibody Engineering, R. Kontermann and S. Dubel, Editors. 2001, Springer Laboratory Manuals, Berlin. p. 93). LOX1-specific scFv antibodies were isolated from the phage display library in a series of repeated selection cycles on recombinant mammalian expressed human LOX1 (R&D Systems) essentially as previously described (Vaughan et al., Nat. Biotechnol. 14:309 (1996)). While several antigen-specific scFvs were obtained from different variations of this protocol, the parental clones LOX514 (SEQ ID NO:29 (VH) and SEQ ID NO:33 (VL); also referred herein as "LOX10514") and LOX696 (SEQ ID NO:54 (VH) and SEQ ID NO:70 (VL); also referred herein as "LOX10696") were isolated as follows: 10 µg/ml human LOX1 was immobilized on MAX-ISORP™ plates (Nunc) and incubated with the phage display library. Unbound phage was washed away in a series of wash cycles. The phage particles retained on the antigen were eluted, infected into bacteria and rescued for the next round of selection. Three rounds of selection were performed in this way. A representative number of individual clones from the round 2 and round 3 selection output were grown up in 96-well plates. ScFvs were expressed in the bacterial periplasm and screened for their inhibitory activity in a human LOX1:oxLDL binding assay as described in Example 10, Assay 1.

Screening hits, i.e. scFv clones which showed an inhibitory effect on LOX1:oxLDL interaction, as crude periplasmic extracts, were subjected to DNA sequencing (Vaughan et al., Nat. Biotechnol. 14:309 (1996), and Osbourn et al., Immunotechnology 2:181 (1996)). Unique scFvs were re-expressed in bacteria and purified by affinity chromatography (as described in Example 3 of Intl. Appl. Publ. No. WO01/66754), and $IC_{50}$ values were determined by testing dilution series of purified scFvs in the above assay.

The most potent scFv clones were converted to whole immunoglobulin G1 triple mutant (IgG1-TM, human IgG1 Fc sequence incorporating mutations L234F, L235E and P331S) antibody format essentially as described in Persic et al., Gene 187:9 (1997) with the following modifications. An OriP fragment was included in the expression vectors to facilitate use with CHO cells and to allow episomal replication. The VH domain was cloned into a vector containing the human heavy chain constant domains and regulatory elements to express whole IgG1-TM heavy chain in mammalian cells. Similarly, the VL domain was cloned into a vector for the expression of the human light chain constant domains and regulatory elements to express whole IgG light chain in mammalian cells. To obtain IgGs, the heavy and light chain IgG expressing vectors were transfected into CHO mammalian cells. IgGs were expressed and secreted into the medium. Harvests were pooled and filtered and IgG was purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralized by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG (Mach et al., Anal Biochem, 200:74 (1992)). The purified IgG were analyzed for aggregation and degradation using SEC-HPLC and by SDS-PAGE.

Figure 1B:
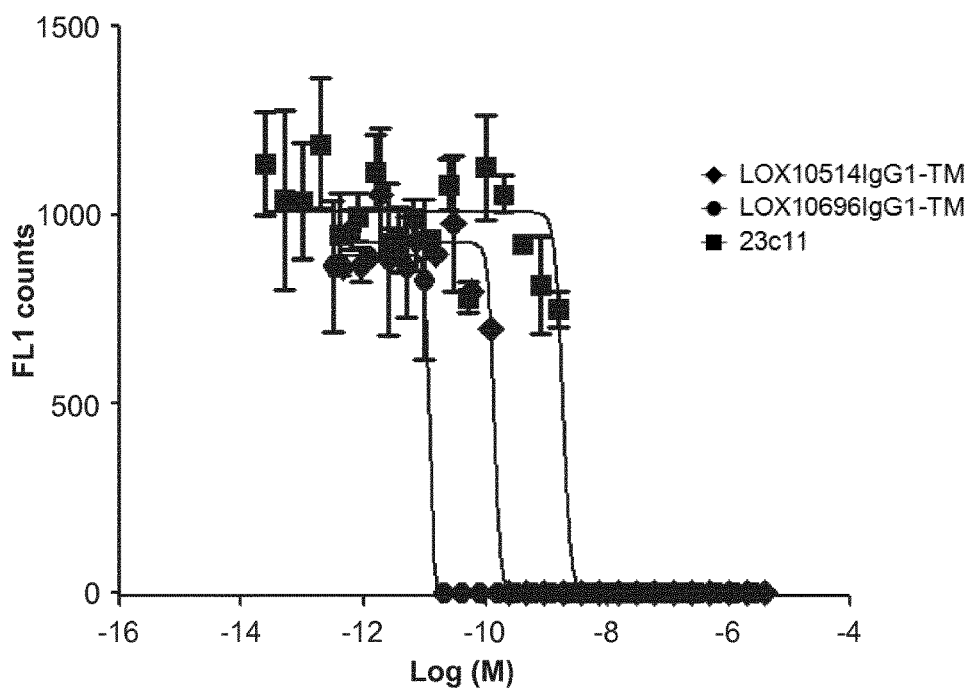
Figure 1C:
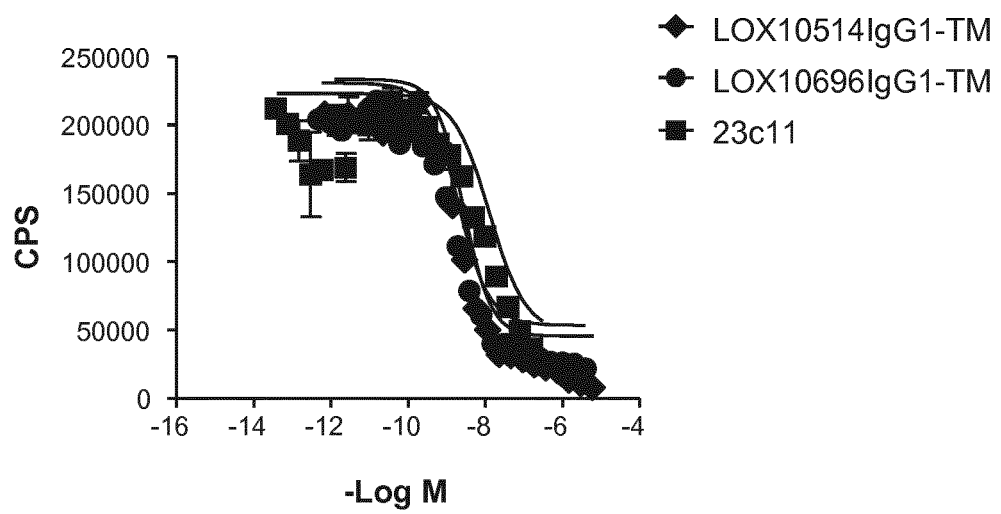
Figure 1D:
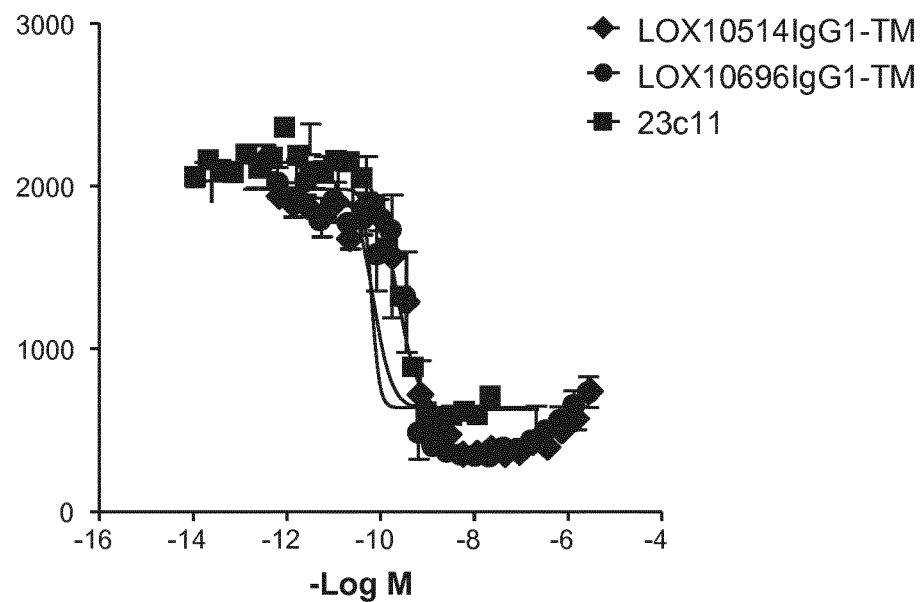

Example 2—Anti-LOX1 Antibodies Inhibit Multi-Ligand Binding, oxLDL Internalization and oxLDL Induced Signaling Purified IgGs were tested for their ability to specifically inhibit oxidized low-density lipoprotein ("oxLDL"), advanced glycation end product of bovine serum albumin ("AGE-BSA") and C-reactive protein ("CRP") binding to LOX1 as described in Example 10, Assays 1, 2 and 3. A number of isolated clones including LOX10514 and LOX10696, and commercially available mouse anti-LOX1 antibody (23C11) were tested for their ability to block oxLDL, AGE-BSA and CRP binding to LOX1. Representative plots are shown in FIGS. 1A, 1B and 1C showing inhibition of oxLDL, AGE-BSA and CRP binding, respectively, by LOX514 and LOX696. To confirm the antibodies cross react and had functional activity on the LOX1 SNP K167N the antibodies were tested for their ability to block oxLDL binding to LOX1 SNP K167N. LOX1 SNP K167N (GenBank Accession No. AB102861) is a naturally occurring human LOX1 variant originally discovered in a family of patients with ischemic heart disease and is believed to be associated with an increased risk of myocardial infarction. See, e.g., Tatsuguchi et al., *Biochem Biophys Res Commun.* 28; 303(1):247-50 (2003). Representative plots are shown in FIG. 1D showing that both LOX514 and LOX696 block oxLDL binding to the LOX1 SNP K167N variant. In addition to inhibition of binding, a number of isolated clones including LOX10514 and LOX10696 were tested for their ability to block oxLDL internalization on LOX1 expressing cells (as described in Example 10, Assay 4) and oxLDL induced LOX1 signaling (as described in Example 10, Assay 5). Representative plots are shown in FIGS. 2A and 2B for inhibition of oxLDL internalization and signaling respectively. The results from these studies are summarized in Table 2.

TABLE 2

Inhibition of oxLDL internalization

|  | LOX10696 | 23C11 | LOX10514 |
|---|---|---|---|
| Mean | 1.31E-10 | 2.20E-09 | 6.42E-10 |
| SD | 1.14E-10 | 6.49E-10 | 8.54E-11 |
| n | 8 | 5 | 4 |
| Mean | 2.46E-10 | 1.31E-09 | 7.03E-10 |
| SD | 1.11E-10 |  | 2.82E-10 |
| n | 2 | 1 | 3 |
| Mean | 3.50E-10 | 2.85E-09 | 7.72E-10 |
| SD | 7.68E-11 | 8.38E-10 | 1.11E-10 |
| n | 2 | 3 | 3 |
| Mean | 8.73E-11 | 1.15E-09 | 2.07E-10 |
| SD | 8.23E-11 | 1.07E-09 | 1.61E-10 |
| n | 2 | 2 | 3 |
| Mean | 4.69E-09 | 1.11E-08 | 1.98E-09 |
| SD | 4.02E-09 | 9.62E-10 | 7.31E-10 |
| n | 2 | 2 | 2 |
| Mean | 6.22E-09 | 1.01E-08 | 8.28E-09 |
| SD | 2.13E-09 |  | 2.84E-09 |
| n | 6 | 1 | 8 |

These results demonstrate: (1) specific inhibition of LOX1 binding to oxLDL, AGE-BSA and CRP by antibodies LOX514 and LOX696; (2) both LOX514 and LOX696 functionally cross react with the common LOX1 SNP K167N variant; (3) LOX514 and LOX696 inhibit oxLDL internalization; and (4) LOX514 and LOX696 inhibit oxLDL-induced LOX1 signaling.

Example 3—Anti-LOX1 Antibodies Species Cross-Reactivity and Specificity for Human LOX1 Over a Panel of Human Related Family Members Cross-reactivity of anti-human LOX1 antibodies to various LOX1 species orthologs was assessed by a scFv binding ELISA. Extracellular domain constructs for human (Uniprot: P78380), mouse (Uniprot: Q9EQ09), rat (Uniprot: O70156), rabbit (Uniprot: Q9XTA8) and cynomolgus monkey LOX1 were designed with either N or C terminal Flag and histidine tags and cloned into Gateway destination vectors (Invitrogen). The constructs were then transfected into mammalian HEK293 EBNA cells for protein expression. The proteins then underwent standard affinity and size exclusion chromatography purification. Briefly, human (His-Flag)-LOX1, cynomolgus LOX1-(FlagHis), mouse LOX1-(FlagHis), rat LOX1-(FlagHis) and rabbit LOX1-(FlagHis) were coated at 10, 10, 5, 5 and 5 µg/mL in PBS buffer respectively on MAXISORP™ plates. Efficient antigen coating using such concentrations was first checked by ELISA using commercial anti-human LOX1 (23C11 from Hycult) or anti-His (Europium-labeled from Perkin Elmer) antibodies. After blocking the wells with PBS containing 3% dried milk, purified anti-LOX1 scFvs in PBS plus 3% dried milk were incubated with the different coated antigens for 1 hour. Bound scFv molecules were detected using a secondary Europium labeled anti-Myc tag antibody (Perkin Elmer) at 100 ng/mL. Plates were read for fluorescence using a 340 nm excitation and 615 nm emission. Non-specific binding was determined on bovine serum albumin (New England Biolabs) coated at 10 µg/mL.

As shown in FIG. 3A, LOX514 ("LOX10514") and LOX696 ("LOX10696") bind to human and cynomolgus LOX1 but not to mouse, rat or rabbit LOX1 orthologs. The lack of antibody cross-reactivity to mouse LOX1 is not surprising given the low homology across the C type lectin domain between these species (~62% identity between human and mouse).

The specificity of the anti-human LOX1 antibody molecules to other human C type lectin and scavenger receptor related molecules was assessed by an IgG binding ELISA as described in Example 10, Assay 6. As shown in FIG. 3B, LOX514 ("LOX10514") and LOX696 ("LOX10696") bind only to human LOX1 and do not bind to human CLEC-7A, CLEC-1A, CLEC-4L, CLEC-1B, SR-A1 and SR-B3. That result demonstrates the specificity of LOX514 and LOX696 to LOX1.

Example 4—Isolation and Identification of Potency Optimized Anti-LOX1 scFv Antibodies by Targeted CDR Randomization and Recombination of LOX514

LOX514 was optimized using affinity-based phage selections. Large scFv libraries derived from the LOX514 scFv sequence were created by oligonucleotide-directed mutagenesis of the variable heavy (VH) complementarity determining regions 2 or 3 (VH-CDR2 or VH-CDR3) or variable light (VL) chain complementarity determining regions 3 (VL-CDR3) using standard molecular biology techniques as described (Clackson, T. and Lowman, H. B. Phage Display—A Practical Approach, 2004. Oxford University Press). The libraries were subjected to affinity-based phage display selections in order to select variants with a higher affinity to human LOX1. These were expected to show an improved inhibitory activity for LOX1 binding to oxLDL and the others LOX1 ligands. The selections were performed essentially as described previously (Thompson et al., J Mol Biol. 256(1):77-88, (1996)). In brief, the scFv-phage particles were incubated with recombinant biotinylated human LOX1 in solution (biotinylated via free amines using EZ LINK™ Sulfo-NHS-LC-Biotin (Thermo/Pierce, product: 21335)). ScFv bound to antigen were then captured on streptavidin-coated paramagnetic beads (DYNABEADS® M-280) following manufacturer's recommendations. The selected scFv-phage particles were then rescued as described previously (Osbourn et al., Immunotechnology, 2(3):181-96, (1996)), and the selection process was repeated in the presence of decreasing concentrations of biotinylated human LOX1 (a typical example would be 50 nM to 20 pM over four rounds).

Crude scFv-containing periplasmic extracts were prepared for a representative number of individual scFvs from the CDR-targeted selection outputs and screened in an epitope competition HTRF® (Homogeneous Time-Resolved Fluorescence) assay format against the parent antibody LOX514 as described in Example 10, Assay 7. Screen hits, i.e. scFv variants which showed a significantly improved inhibitory effect when compared to parent LOX514, were subjected to DNA sequencing, and unique variants from variable heavy CDR2 or CDR3 and variable light library CDR3 outputs were produced as purified scFv and tested. Some scFvs were then selected and converted to IgG1-TM for further characterization. Typical examples of optimized LOX514 antibodies obtained following this approach include: LX5140011, LX5140014, LX5140016 and LX5140038 (as described in Table 1 or FIG. 4).

To generate further improvement, CDR-randomized selection outputs comprising of large numbers of scFv variants with the ability to inhibit the binding of parent LOX514 to human LOX1 were recombined to form libraries in which clones contained randomly paired individually randomized VH CDR2 with VH or VL CDR3 sequences.

Crude scFv-containing periplasmic extracts were prepared of a representative number of individual scFvs from the recombined VH2/VH3 or VH2/VL3 libraries in the epitope competition HTRF® assay. Screen hits, i.e. scFv variants which showed a significantly improved inhibitory effect when compared to parent scFv and leads generated pre-recombination, were subjected to DNA sequencing, and unique recombed variants were produced as purified scFv and tested. The most active scFvs were then selected and converted to IgG1 TM for further characterization. Typical examples of optimized LOX514 antibodies obtained from these recombined libraries were: LX5140092, LX5140093, LX5140094, LX5140108 and LX5140110 (as described in Table 1 or FIG. 4).

Alignments of the amino acid sequence of optimized heavy chains for the selected antibodies from the LOX514 lineage are shown in FIG. 4A. Alignments of the amino acid sequence of optimized light chains for the selected antibodies from the LOX514 lineage are shown in FIG. 4B.

Example 5—Isolation and Identification of Potency Optimized Anti-LOX1 scFv Variants Derived from LOX696

LOX696 was first optimized using affinity-based ribosome display selection essentially as described by EP494955, U.S. Pat. No. 5,658,754 and Hanes et al (Thompson et al., *J. Mol. Biol.* 256(1):77-88 (1996)).

Large scFv libraries, in ribosome display format, derived from the LOX696 scFv sequence were created by oligonucleotide-directed mutagenesis of the variable heavy (VH) complementarity determining regions 2 or 3 (VH-CDR2 or VH-CDR3) or variable light (VL) chain complementarity determining regions 3 (VL-CDR3) using standard molecular biology techniques as described (Thompson et al., *J. Mol. Biol.* 256(1):77-88 (1996)). On the DNA level, a T7 promoter was added at the 5'-end for efficient transcription to mRNA. On the mRNA level, the construct contained a prokaryotic ribosome-binding site (Shine-Dalgarno sequence). At the 3'-end of the single chain, the stop codon was removed and a portion of M13 bacteriophage gIII (gene III) was added to act as a spacer between the nascent scFv polypeptide and the ribosome (Thompson et al., *J. Mol. Biol.* 256(1):77-88 (1996)).

The libraries were subjected to affinity-based ribosome display selections in order to select variants with a higher affinity to human LOX1. These were expected to show an improved inhibitory activity for LOX1 binding to oxLDL and the others LOX1 ligands. The scFvs were expressed in vitro using the RIBOMAX™ Large Scale RNA Production System (T7) (Promega) following the manufacturer's protocol and a cell-free translation system. The produced scFv antibody-ribosome-mRNA (ARM) complexes were incubated in solution with biotinylated human LOX1 (biotinylated via free amines using EZ LINK™ Sulfo-NHS-LC-Biotin (Thermo/Pierce, product: 21335)). The specifically bound tertiary complexes (LOX1:ARM) were captured on streptavidin-coated paramagnetic beads (DYNABEADS® M-280) following the manufacturer's recommendations (Dynal) whilst unbound ARMs were washed away. The mRNA encoding the bound scFvs were then recovered by reverse transcription-PCR (RT-PCR). The selection process was repeated on the obtained population for further rounds of selections with decreasing concentrations of biotinylated human LOX1 (1 µM to a minimum of 2 nM over 4 rounds) in order to enrich for clones with higher affinity for LOX1. The outputs from selection rounds 2, 3 and 4 were subcloned into pCantab6 (1) for bacterial expression as scFvs, and improved clones were identified as periplasmic extracts in an LOX696 epitope competition (see Example 10, Assay 7) as described in Example 4.

Second-generation phage display libraries were constructed based on the LOX696 CDR randomized ribosome display outputs or variants. A total of four libraries were generated: (1) By recombining VH CDR2 sequences with VL CDR3 sequences both from round 2 outputs; (2) By performing an additional error-prone PCR on the recombinated VH CDR2×VL CDR3 library (see above) to incorporate further sequence diversity using the DIVERSIFY™ PCR Random Mutagenesis Kit (BD Biosciences) following the manufacturer's recommendations; (3) By random mutagenesis on the entire scFv sequence using error-prone PCR as described above using as template a pool of 9 scFv DNA hits coming from the early ribosome display libraries plus parental scFv DNA of LOX696 at equimolar ratio; (4) By soft randomization of the entire VH CDR3 as described in Gallop M A et al., J Med Chem, 37(9):1233-51 (1994) using as template a pool of 6 scFv DNA hits coming from the early ribosome display VL CDR3 libraries plus parental scFv DNA of LOX696 at equimolar ratio.

Phage display selections were performed as described in Example 4 using decreasing concentrations of biotinylated LOX1 (typically from 100 nM to 2 pM in four rounds). Crude scFv-containing periplasmic extracts were prepared of a representative number of individual scFvs from the different 2nd generation libraries and tested in the epitope competition HTRF® (as described in Example 10, Assay 7). ScFv variants giving the greatest competition of binding were again sequenced, and purified scFvs were prepared as in Example 1 for testing. The most potent scFvs from those second generation libraries were converted to IgG1 TM format for further characterization as described in later examples.

Typical examples of optimized LOX696 antibodies obtained from these 2nd generation libraries include: LX6960067_ng1, LX6960071_ng1, LX6960073_ng1, LX6960086_ng1, LX6960094_ng1, LX6960101_ng1, LX6960102_ng1 and LX6960116_ng1 (as described in Table 1 or FIG. 5).

Alignments of the amino acid sequence of optimized VH for the selected antibodies from the LOX696 lineage are shown in FIG. 5A. Alignments of the amino acid sequence of optimized VL for the selected antibodies from the LOX696 lineage are shown in FIG. 5B.

Example 6—Germlining and Stability Engineering Anti-LOX1 Antibodies as IgG1-TM

The amino acid sequence of LOX514 VH and VL were aligned to the known human germline sequences in the VBASE database (Tomlinson, I., VBASE. 1997, MRC Centre of Protein Engineering, Cambridge, UK) and the closest germline was identified by sequence similarity. For the VH domain this was VH1-24 (DP-5) and JH6, for the VL domain it was Vλ1-e (DPL-8) and JL3. There is only one difference in the two alignments located in the framework 4 of the heavy chain. That single residue (R105—Kabat numbering) has been reverted to the germline residue (Q) during the IgG conversion process by standard molecular biology meaning that all optimized IgGs from the LOX514 lineage were de-facto produced in the germlined format. Additionally, a heavy chain N96D mutatagenesis (Kabat numbering) was performed to remove a potential N-deamidation motif in the CDR3 of both LX5140092 and LX5140093. Variants were named LX5140092_N>D and LX5140093_N>D respectively (see Table 1 or FIG. 4). An alignment of the heavy and light chain amino acid sequences for LX5140092_N>D and LX5140093_N>D is provided in FIGS. 4A and 4B respectively.

Similarly, germline analysis of LOX696 antibody was also performed. The closest germline was identified as VH3-09 (DP-31) and JH3 for the heavy chain and Vλ2a2 (DPL-11) and JL3 for the light chain. Excluding Vernier residues (Foote, et al., *J Mol. Biol.*, 224:487 (1992)), a total of five differences, all in the VH, were detected: two in framework 1, one in framework 3 and two in framework 4. Differences in optimized LOX696 IgG1-TM sequences were reverted to the closest germline residues at the exception of V89 by standard molecular biology techniques: Q1E, Q6E, R105Q and T108M. Additionally, a heavy chain G82bS mutagenesis (Kabat numbering) was performed to remove a potential N-deamidation motif in the framework 3 of germlined LX6960073_gl (see Table 1 or FIG. 5). The variant was named LX6960073_G82bS_gl (see Table 1 or FIG. 5). An alignment of the heavy and light chain amino acid sequences for the non germlined LX6960073_ng1, germlined LX6960073_gl and LX6960073_G82bS_gl is provided in FIGS. 5A and 5B respectively.

Example 7—Specificity and Species Cross Reactivity of Optimized Anti-LOX1 Antibodies The specificity of optimized anti-human LOX1 antibodies as IgG1-TM to other human C type lectin and scavenger receptor related molecules was assessed by an IgG binding ELISA (as described in Example 10, Assay 7). The panel of related molecules included human CLEC-7A (Dectin-1), human CLEC-1A, human CLEC-4L (DC-SIGN), human CLEC-1B (CLEC-2), human SR-A1 and human SR-B3 (CD36). Human LOX1 was also coated as positive control for binding. The following optimized antibodies were tested: LX5140108, LX5140110, LX5140092_N>D, LX5140093_N>D, LX6960073_gl and LX6960073_G82bS_gl. The isotype human IgG1-TM control antibody NIP228 was included in the panel of antibodies to test for determining nonspecific background level.

As shown in FIG. 6, all optimized anti-LOX1 antibodies bind human LOX1 but do not bind human CLEC-7A, CLEC-1A, CLEC-4L, CLEC-1B, SR-A1 or SR-B3, thus demonstrating the specificity of LX5140108, LX5140110, LX5140092_N>D, LX5140093_N>D, LX6960073_gl and LX6960073_G82bS_gl for human LOX1.

Cross-reactivity of anti-human LOX1 antibodies to various LOX1 species orthologs was assessed by an IgG binding ELISA (as described in Example 10, Assay 7). Briefly, human (HisFlag)-LOX1, cynomolgus LOX1-(FlagHis), mouse LOX1-(FlagHis), rat LOX1-(FlagHis) and rabbit LOX1-(FlagHis) were coated at 5 µg/mL in PBS buffer on MAXISORP™ plates. After blocking with PBS containing 3% dried milk, purified anti-LOX1 IgG1-TM at 10 µg/mL in blocking buffer were incubated with the different coated antigens. Bound IgG molecules were detected using a secondary Europium labeled anti-human IgG antibody (Perkin Elmer) at 100 ng/mL. Plates were read for fluorescence using a 340 nm excitation and 615 nm emission. Non-specific binding was determined on CD86 FlagHis antigen also coated at 5 µg/mL. The following optimized LOX1 antibodies were tested as well as NIP228 human IgG1-TM as a negative control: LX5140108, LX5140110, LX5140092_N>D, LX5140093_N>D, LX6960073_gl and LX6960073_G82bS_gl. As shown in FIG. 7A, all of the tested antibodies (LX5140108, LX5140110, LX5140092_N>D, LX5140093_N>D, LX6960073_gl and LX6960073_G82bS_gl) bind to human and cynomolgus LOX1 but not to mouse or rat LOX1 proteins. Some of those antibodies (LX5140108, LX5140110 and LX5140092_N>D) also bind to rabbit LOX1 but to a lesser extent than to human or cynomolgus LOX1 as demonstrated by the smaller fluorescence count.

Further cross reactivity characterization between human and cynomolgus LOX1 were performed for the optimized anti-LOX1 IgG1-TM antibodies LX5140108, LX5140110 and LX6960073_G82bS_gl by competition ELISA.

Briefly, biotinylated human LOX1 was coated at 0.125 µg/mL in PBS on Streptavidin plates (Abgene). After blocking with PBS containing 3% dried milk, purified anti-LOX1 IgG1-TM at 12.5 ng/mL in blocking buffer were co-incubated with competitor human or cynomolgus LOX1 proteins. A 1:3 titration of competitor in blocking buffer was used starting at 400 nM for LX5140108 and LX5140110 and at 2 µM for LX6960073_G82bS_gl. Bound anti-LOX1 IgG molecules were detected using a secondary Europium labeled anti-human IgG antibody (Perkin Elmer) at 100 ng/mL. Plates were read for fluorescence using a 340 nm excitation and 615 nm emission.

As shown in FIG. 7B and in Table 3 below, all three optimized anti-LOX1 IgG1-TM (LX5140108, LX5140110 and LX6960073_G82bS_gl) compete with cynomolgus LOX1 and exhibit IC50 within 5-fold of the IC50 for a human LOX1 competition, demonstrating that cynomolgus cross-reactivity of anti-LOX1 antibodies LX5140108, LX5140110 and LX6960073_G82bS_gl is strong.

TABLE 3

Optimized Antibody binding to cynomolgus LOX1 and human LOX1

| Anti-LOX1 antibodies | IC50 for huLOX1 competition (M) | IC50 for cynoLOX1 competition (M) |
|---|---|---|
| LX5140108 | $2.2 \times 10^{-10}$ | $2.5 \times 10^{-10}$ |
| LX5140110 | $2.8 \times 10^{-8}$ | $4.4 \times 10^{-8}$ |
| LX6960073_G82bS_gl | $5.5 \times 10^{-10}$ | $1.8 \times 10^{-9}$ |

Example 8—Affinity of Optimized Anti-LOX1 Antibodies for hLOX1 as Determined by BIACORE™ and KinExA™

The affinity of the anti-LOX1 antibody for recombinant Human and Cynomolgus orthologs LOX1 extracellular domain (ECD) was determined at 37° C. using real time interaction monitoring by Biacore (for Human and Cyno) and at equilibrium using KinExA (for Human LOX1 affinity measurements).

In the Biacore assay recombinant protein G+the anti-LOX1 antibody captured by the protein G were immobilized via amine linking to a CM5 chip surface, and the association and dissociation profiles of the LOX1 orthologs passed over the surface collected. The assays were performed with the IFC temperature set at 37° C. and the sample compartment left at ambient temperature. All the experiments were performed with the HBSEP running buffer passing through the IFC at a constant 30 ul/min. At the end of each LOX1 application any bound antibody and antibody-complex were removed from the protein G by two 40 seconds pulses of 10 mM glycine pH 1.5. The amount of anti-LOX1 antibody captured on the protein G surface was tailored to firstly avoid mass transport limitations and secondly to ensure that sufficient dissociation could be observed for accurate modeling. The concentration range of the LOX1 interactant was sufficient to ensure that the entire binding range from saturation of the antibody to no detectable binding was observed. The data was analyzed using the BiaEval evaluation software following double reference subtraction of an antibody body only profile.

The in-solution equilibrium assay was performed at a single concentration of anti LOX1 antibody in which a titration of recombinant Human LOX1 ECD was made from 100 times above to 100 times below the antibody concentration. Free antibody concentrations were determined via the capture of unoccupied antibody that was subsequently detected by a fluorescently labeled human-Fc specific probe. Table 4 details the observed rate-constants and overall affinities.

TABLE 4

LX5140110 affinity and rate constants

| Ligand/LOX1 | Assay | On-rate (1/Ms) | Off-rate (1/s) | KD (pM) |
|---|---|---|---|---|
| Human | Biacore | 5.75e5 | 2.30e−4 | 401 |
| Cynomolgus | Biacore | 1.09e6 | 1.68e−4 | 154 |
| Human | KinExA | n/a | n/a | 378 to 587 pM |

Figure 8A:
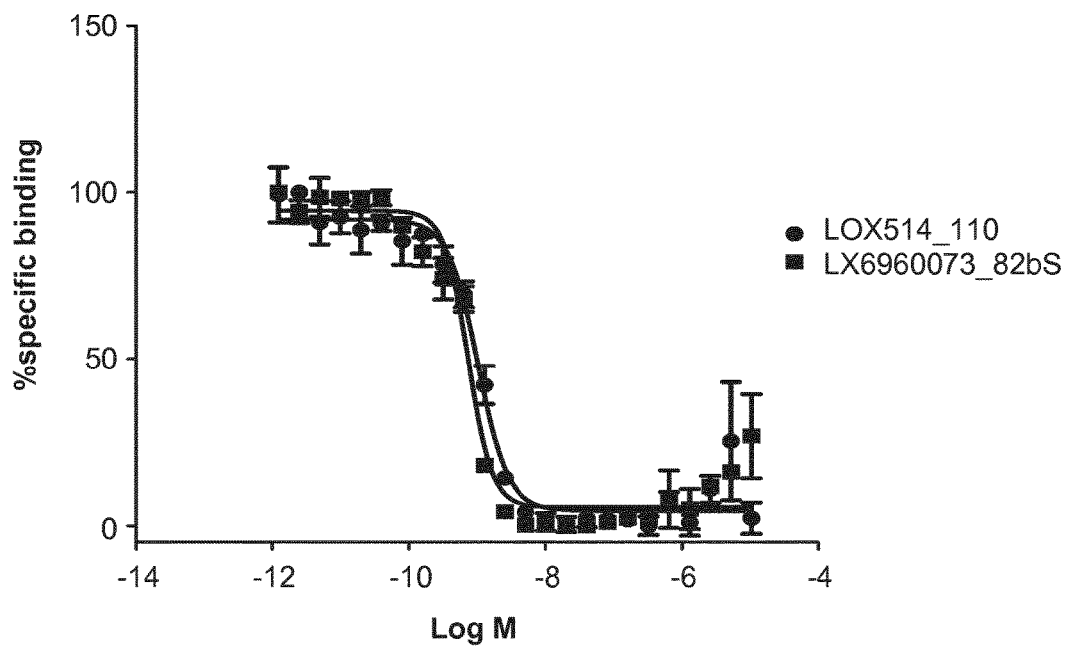
Figure 8B:
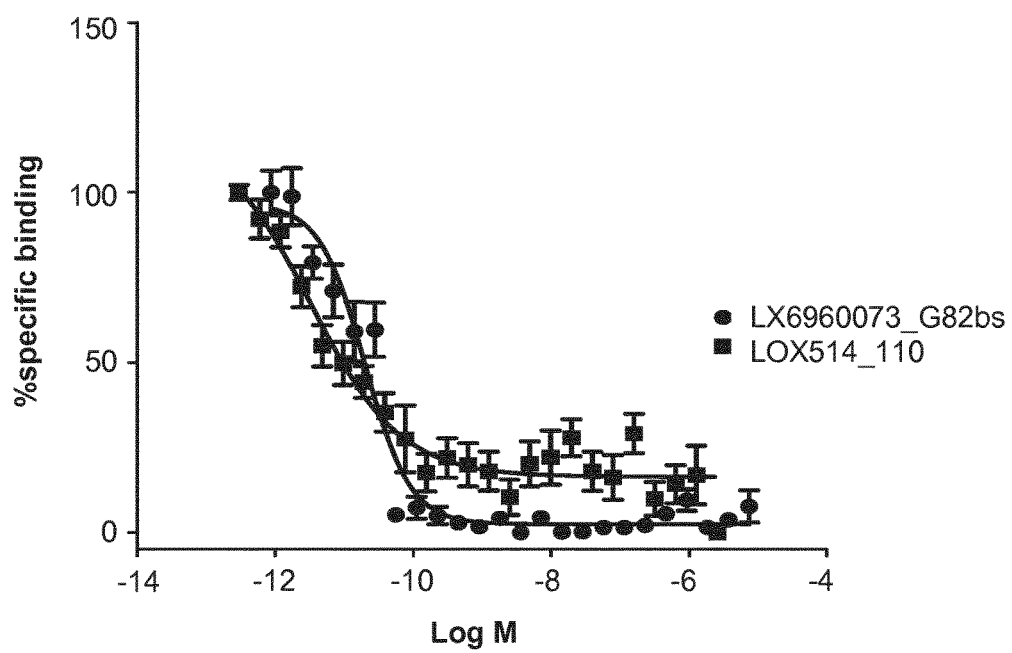
Figure 8C:
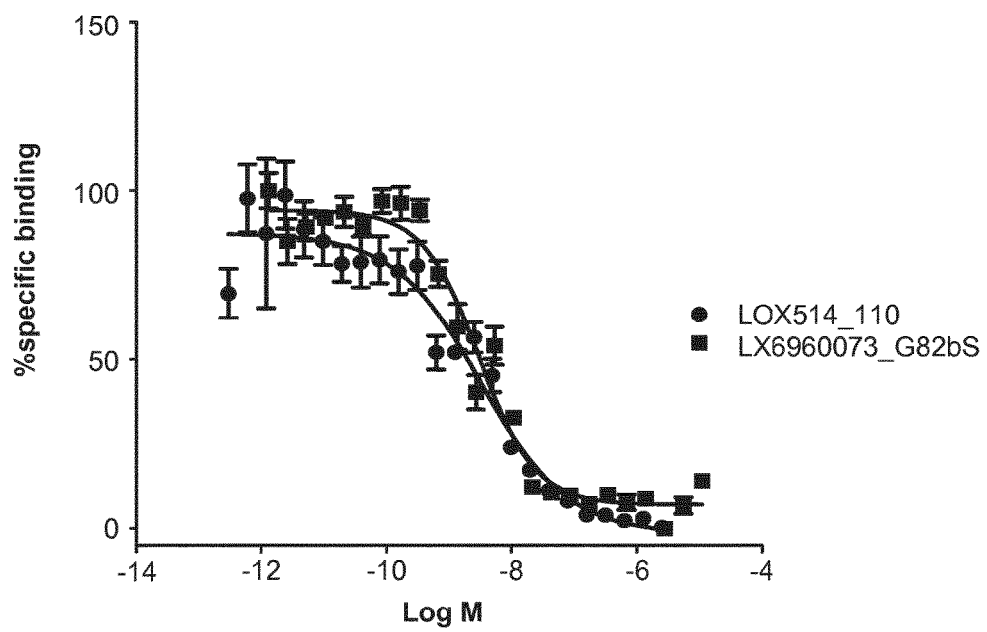
Figure 8D:
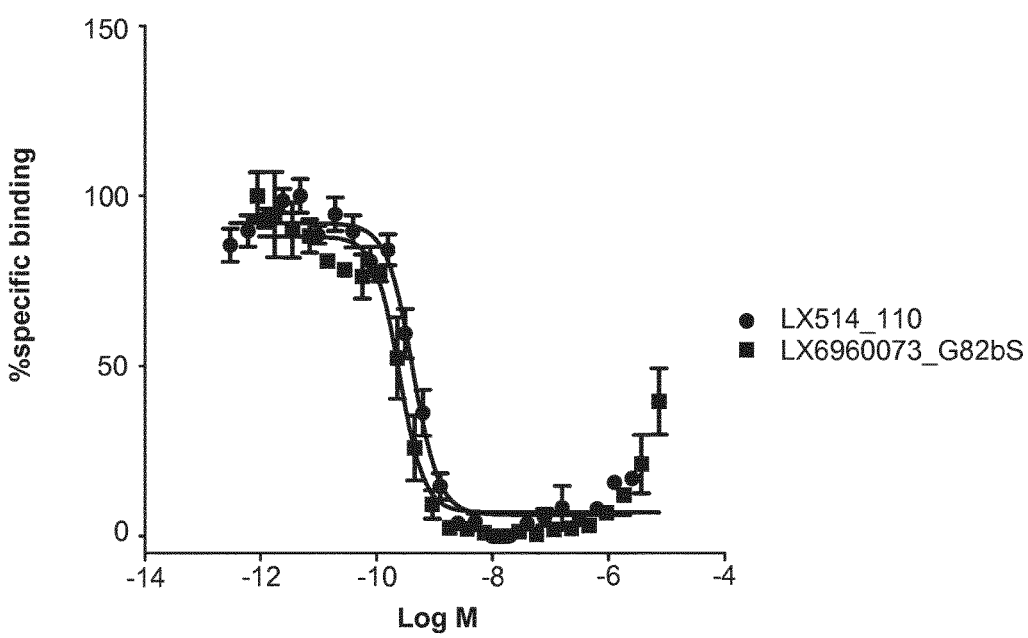
Figure 8E:
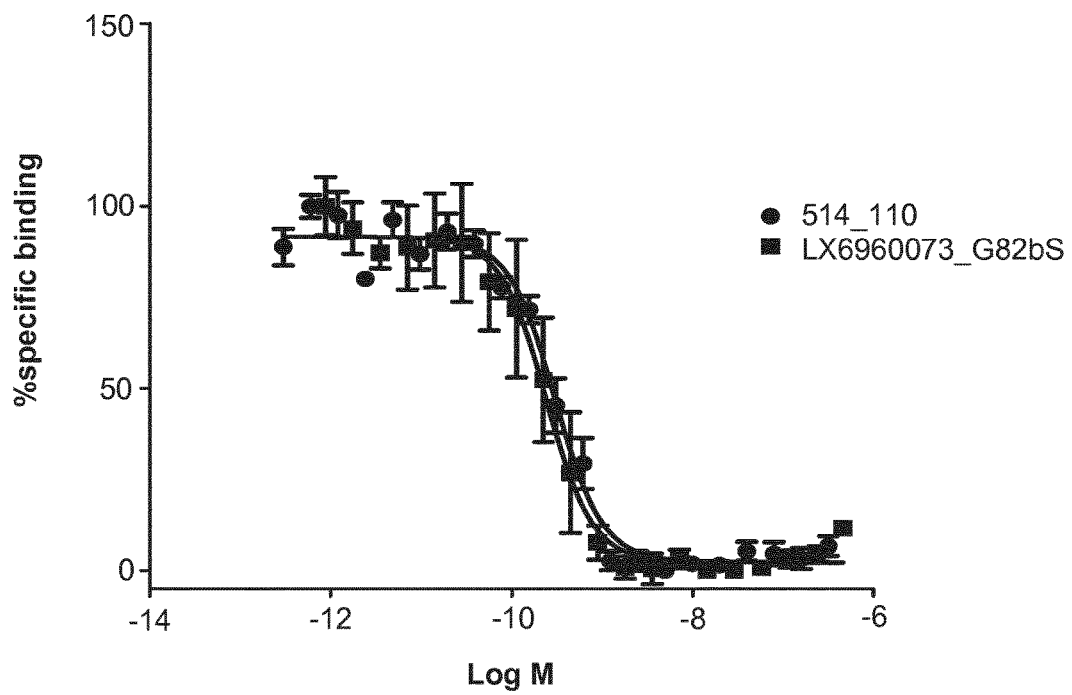
Figure 8F:
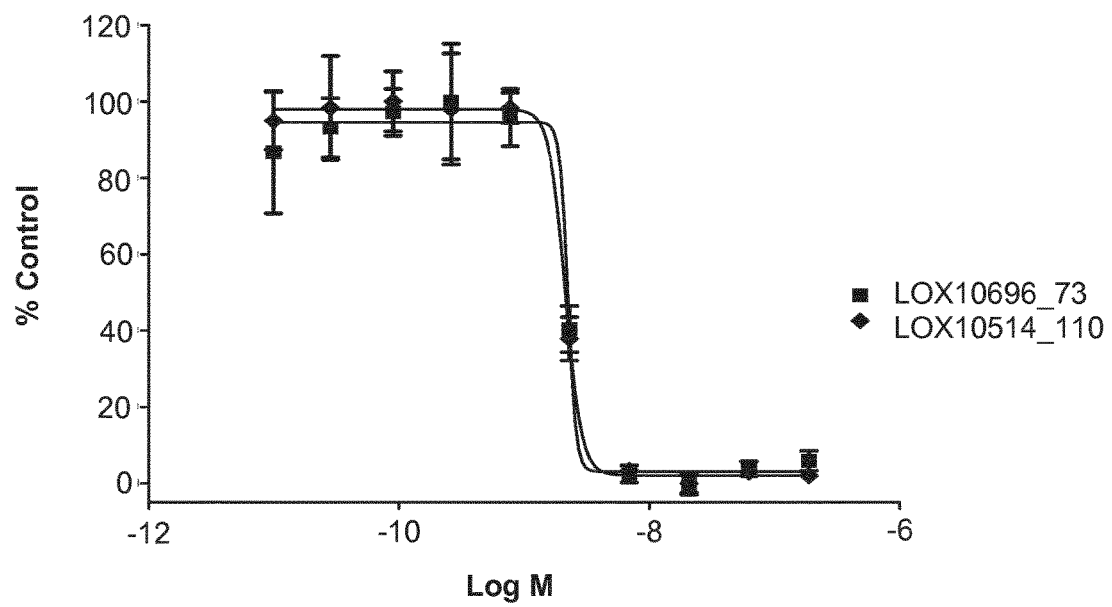

Example 9 Optimized Anti-LOX1 Antibodies Demonstrate Inhibition of Multi-Ligand Binding, oxLDL Internalization and oxLDL Induced Signaling Purified IgGs were tested for their ability to specifically inhibit oxLDL, AGE-BSA and CRP binding to LOX1 (see Example 10; assays 1, 2 and 3). A number of isolated clones including LX5140110 and LX6960073_G82bS_gl were tested for their ability to block oxLDL, AGE-BSA and CRP binding to LOX1. Representative plots are shown in FIGS. 8A, 8B and 8C showing inhibition of oxLDL, AGE-BSA and CRP binding, respectively, by LX5140110 and LX6960073_G82bS_gl. To confirm the antibodies cross react and had functional activity on the LOX1 SNP K167N the antibodies were tested for their ability to block oxLDL binding to LOX1 SNP K167N. Representative plots are shown in FIG. 8D showing that both LX5140110 and LX6960073_G82bS_gl block oxLDL binding to the LOX1 SNP K167N variant. In addition to inhibition of binding, a number of isolated clones including LX5140110 and LX6960073_G82bS_gl were tested for their ability to block oxLDL internalization on LOX1 expressing cells (see Example 10, Assay 4) and oxLDL induced LOX1 signaling (see Example 10, Assay 5). Representative plots are shown in FIGS. 8A and 8F showing inhibition of oxLDL internalization and oxLDL induced LOX1 signaling, respectively, by LX5140110 and LX6960073_G82bS_gl. The results from these studies are summarized in Table 5.

TABLE 5

Optimized anti-LOX1 antibody inhibition of oxLDL internalization and signaling

| | | LOX514_110 | LX6960073_G82bS |
|---|---|---|---|
| oxLDL/hLOX1 CHO Competition | Mean | 1.04663E−10 | 2.00052E−11 |
| | SD | 1.91372E−10 | 6.29934E−12 |
| | n | 3 | 3 |
| oxLDL/K167N hLOX1 CHO Competition | Mean | 4.92E−10 | 1.04531E−10 |
| | SD | 5.40E−10 | 2.37936E−10 |
| | n | 7 | 5 |
| oxLDL/hLOX1 CHO Internalisation | Mean | 3.1223E−10 | 3.80346E−10 |
| | SD | 1.12532E−10 | 3.32497E−10 |
| | n | 3 | 3 |
| AGE BSA/hLOX1 CHO Competition | Mean | 2.07257E−11 | 1.76549E−11 |
| | SD | 1.27853E−10 | 1.34571E−11 |
| | n | 3 | 3 |
| CRP/hLOX1 Competition | Mean | 5.01529E−09 | 2.99815E−09 |
| | SD | 6.37843E−09 | 1.64015E−09 |
| | n | 3 | 3 |
| ROS ASSAY | Mean | 1.98E−09 | 2.21E−09 |
| | SD | 4.47E−10 | 2.50E−10 |
| | n | 3 | 3 |

These results demonstrate specific multi-ligand inhibition of LOX1 binding to oxLDL, AGE-BSA and CRP by antibodies LX5140110 and LX6960073_G82bS_gl and that both LX5140110 and LX6960073_G82bS_gl functionally cross react with the common LOX1 SNP K167N variant and inhibit oxLDL internalization and oxLDL induced LOX1 signaling.

Example 10 Assays and Methods

The following materials and methods were used in the experiments described in Examples 1-9.

Materials

Doxycycline hyclate (Sigma #D9891-1G); CarboxyH2DCFDA (MolecularProbes #C400); Hoechst stain (Molecular probes #33342); AGE-BSA (Biovision #2221-10); PBS (Gibco #14190); Recombinant C-reactive protein (R&D #1707-CRCF); BSA 30% (SIGMA #A9576); Lightning Link biotin conjugation kit (Innova Biosciences #704-0010); DyLight 649 NHS ESTER (Thermo Scientific #46416); Cypher 5E Mono NHS; Ester (GE healthcare #PA15401); HBSS (1×) (GIBCO #14025); Corning 384

Cell; Bind black assay plate (Corning Costar #3683); Delfia Enhancement solution (Perkin Elmer #4001-0010); Europium Streptavidin (Perkin Elmer #1244-360); 0.5 mL Zeba desalt columns (Pierce #89883); CHO-TREx (Invitrogen #R718-07); oxLDL (Intracel #RP049); DiI-oXLDL (Intracel #RP-173); Anti-LOX1 antibody (Biovision #3659); Hoechst stain (Molecular probes #33342); PBS (Gibco #14190); Growth Medium: Hams:F12-GlutaMax-I (Gibco #31765-027); supplemented with 10% Fetal Bovine Serum (Invitrogen #16000-044); Blasticidin (Invitrogen #46-1120); Zeocin (Invitrogen # R25001); Lipofectamin (Invitrogen #11668-019); Doxycycline hyclate (Sigma #D9891-1G).

Reagent Modifications

Cypher 5E Labelling of oxLDL

The pH of ox-LDL (1 mg/mL) was adjusted to pH 8.5 using ⅒th volume of 0.5M Sodium Borate buffer and oxLDL was labeled in accordance with the manufacturers kit instruction's at a molar ratios of protein:dye of 40:1 (1 hour at room temperature in the dark). Un-reacted dye was removed using Zeba spin columns according to manufacturer's instructions (Cypher 5E Mono NHS Ester from GE healthcare) and buffer exchanged into PBS. The labeled protein was kept at 4° C. in the dark. For calculation purposes it is assumed that over 95% of protein was recovered, and there are no dilution factors to consider.

DyLight 649 Labelling of oxLDL and AGE-BSA

The pH of ox-LDL or AGE-BSA (1 mg/mL) was adjusted to pH 8.5 using ⅒th volume of 0.5M Sodium Borate buffer and was labeled in accordance with the manufacturer's instructions (DyLight 649 NHS ester from Thermo Scientific for 1 hour at room temperature in the dark). Un-reacted dye was removed using Zeba spin columns according to manufacturer's instructions and buffer exchanged into PBS. For calculation purposes it is assumed that over 95% of protein is recovered, and there are no dilution factors to consider.

Dylight 649 Labelling of Human Anti-LOX1 Antibodies

The pH of the human anti-LOX1 antibody (1 mg/mL) was adjusted to pH 8.5 using ⅒th volume of 0.5M sodium borate buffer and was labeled in accordance with the manufacturer's instructions (DyLight 649 NHS Ester from Thermo Scientific for 1 hour at room temperature in the dark). Un-reacted dye was removed using Zeba spin columns according to manufacturer's instructions and buffer exchanged into PBS. For calculation purposes it is assumed that over 95% of protein is recovered, and there are no dilution factors to consider.

Biotin Labelling of CRP

C-reactive protein CRP (R&D systems; Carrier free) was reconstituted in distilled water to a concentration of 4 mg/mL and biotinylated according to the kit instructions supplied with the Lightning-Link™ Biotin conjugation kit (Type A).

Human LOX1 CHO-TREX Cell Line 3A9

The human LOX1 gene (NM 002543) was used to generate the recombinant plasmid pcDNA4/TO-LOX1 (pAM2037), which was synthesized and delivered by Geneart. The LOX1 gene was synthesizes with addition of Afl II restriction site and a Kozak sequence at the 5'-end, and EcoRI restriction site at the 3'-end. pAM2037 was then transfected into Chinese hamster ovary cells expressing the tetracycline repressor (CHO-TREx cells) using lipfectamine2000. CHO-TREx, is a CHO-K cell line that contains pcDNA6/TR that has the gene for the tetracycline (Tet) repressor, that will block the expression of genes cloned into the pcDNA4/TO. When these cells are treated with tetracycline the repression is released and the LOX1 gene will be expressed.

The transfected mixed population of cells was sorted using a FACS machine into 96 well plates to obtain a single cell in each well. The pcDNA6/TR was selected with 10 µg/ml blasticidin, and 300 µg/ml zeocin was used to select for the pcDNA4TO-LOX1 plasmid, and 200 µg/ml for maintenance. The individual cells were propagated and stable clones were selected by their ability to bind and internalize DiI-labeled oxLDL, using a High Content Analysis approach to quantify the fluorescence taken up by the cells. One clone was selected for uptake of DiI-oxLDL and stability over several growth passages. LOX1 protein surface expression was verified by immunostaining using an anti-LOX1 specific antibody from Biovision. Functional activity of the LOX1 protein was demonstrated by oxLDL uptake and generation of an oxLDL mediated ROS response in the CHO-TREx-LOX1 cells.

Assays 1 and 2—LOX1: oxLDL and LOX1:AGE-BSA Binding Assays

Saturation Binding Curve

Both DyLight 649 labeled oxLDL and AGE-BSA (1 mg/mL) were diluted 1:50 in HBSS and titrated across a 384 well plate using a 1+1 serial dilution over 16 points in triplicate. For the determination of total binding 10 µL of HBSS was added to all wells, followed by the addition of 10 µL of human LOX1 transfected CHO TREX cells (4000 cells per well). For the determination of nonspecific binding, 10 µL of HBSS was replaced by 10 µL of unlabeled oxLDL (1 mg/mL). The assay plate was incubated for 1 hour at room temperature. Following incubation, plates were read on an Applied Biosystems 8200 cellular detection system (FMAT plate reader) using PMT1 setting of 422 with a minimum count set to 10; Colour<0.4 and FL1<5600. Specific binding was determined by subtracting the mean total binding signal from the mean non-specific binding signal and plotting the resulting binding isotherm in Prism Graphpad software using a one site specific binding algorithm. The calculated concentration at which KD was determined, was used for subsequent high-throughput screening and antibody competition experiments.

Evaluation of Anti-hLOX1 Monoclonal Antibodies

The competition between anti-LOX1 antibodies and DyLight 649 labeled ligand (oxLDL; AGE-BSA) for binding to LOX1 receptor expressed on CHO TREX cells was performed as follows.

Competitor antibodies were used without any pre-dilution and were titrated across a 384 well plate using a 1+1 serial dilution in assay buffer (HBSS) over 24 points in duplicate (10 µL per well). Dylight 649 labeled ligands (at their respective KD concentrations) were added to all antibody containing wells (10 µL per well) followed by the addition of human LOX1 transfected CHO TREX cells (4000 cells per well in 10 µL) or K167N SNP transfected CHO TREX cells.

The assay plates were incubated for 1 hour at room temperature. Following incubation, plates were read on an Applied Biosystems 8200 cellular detection system (FMAT plate reader) using PMT1 setting of 422 with a minimum count set to 10; Colour<0.4 and FL1<5600. The data was analyzed using a 4-parameter logistic equation with GRAPHPAD™ Prism version 5 (GraphPad Inc, California) to determine apparent IC50 values. Y=Bottom+(Top-Bottom)/(1+10^((Log IC50−X)*HillSlope)) where X is the logarithm of concentration and Y is the % specific binding.

The IC50 is the sample concentration that produces 50% inhibition of specific binding.

TABLE 6

Stock concentrations used in oxLDL and AGE-BSA binding assays
Assay conditions for both HTS and IC$_{50}$ Assays

| | Working Solution Con. | Final Assay Con. |
|---|---|---|
| DyLight 649 labeled oxLDL | 8.7 nM | 2.9 nM |
| DyLight 649 labeled AGE BSA | 7.5 µg/mL | 2.5 µg/mL |
| hLOX1 transfected CHO TREX cells | 4 × 10$^5$ cells/mL | 4000 cells/well |
| Peri-prep material for HTS (oxLDL binding assay) | 100% | 30% |
| Purified scFv/IgG samples for IC$_{50}$ analysis | Serial 1 + 1 dilution of purified proteins over 24 points | 30% |

Assay 3—LOX1:CRP Binding Assay

Saturation Binding Curve

LOX1 (R&D systems) was immobilized on the surface of a 384 well Nunc Maxisorp plate at a concentration of 3 µg/mL in PBS, overnight at 4° C. (25 µL per well). The following day the assay plate was washed 12× in PBS (without calcium and magnesium). A working solution of biotinylated CRP was prepared at 20 µg/mL (769 nM) in PBS/0.1% BSA/0.01% tween 20, and titrated across a 384 well plate using a 1+1 serial dilution over 16 points in triplicate (12.5 µL per well). A further 12.5 µL of assay buffer (in PBS/0.1% BSA/0.01% tween 20) was added to each well, and the assay plate was incubated for 2 hours at room temperature. The plate was washed 16× in PBS/0.01% Tween 20, followed by the addition of 50 µL of Europium labeled streptavidin (1:1000 dilution). The assay plate was incubated for a further 1 hour at room temperature followed by washing 16× in PBS/0.01% Tween 20. The plate was developed by adding 100 µL/well of DELFIA enhancement solution, and reading on a Wallac Victor V plate reader using factory installed DELFA europium protocol. The resulting binding isotherm was plotted in Prism Graphpad software using a one site specific binding algorithm. The calculated concentration, at which the apparent K$_D$ was determined, was used for subsequent high-throughput screening and antibody competition experiments.

Evaluation of Anti-Human LOX1 Monoclonal Antibodies

The competition between antibody and biotin labeled CRP for binding to recombinant human LOX1 was performed as follows: LOX1 (R&D systems) was immobilized on the surface of a 384 well Nunc Maxisorp assay plate at a concentration of 3 µg/mL in PBS, overnight at 4° C. (25 µL per well). The following day the assay plate was washed 12× in PBS (without calcium and magnesium). Competitor antibodies were used without any pre-dilution and were titrated across a 384 well dilution plate using a 1+1 serial dilution in assay buffer (PBS/0.1% BSA/0.01% tween 20) over 24 points in duplicate (30 µL per well). Biotin labeled CRP (304, per well at K$_D$ concentration) was then added to all antibody containing wells. Samples (50 µL) were then transferred using a 384 MiniTrak liquid handling robot from the dilution plate to the assay plate containing immobilized recombinant human LOX1. Plates were incubated for 2 hours at room temperature. The plate was washed 16× in PBS/0.01% Tween 20, followed by the addition of 50 µL of Europium labeled streptavidin (1:1000 dilution). The assay plate was incubated for a further 1 hour at room temperature followed by washing 16× in PBS/0.01% Tween 20. The plate was developed by adding 100 µL/well of DELFIA enhancement solution, and reading on a Wallac Victor V plate reader using factory installed DELFA europium protocol. The data was analyzed using a 4-parameter logistic equation with GRAPHPAD™ Prism version 5 (GraphPad Inc, California) to determine apparent IC$_{50}$ values. Y=Bottom+(Top-Bottom)/(1+10^((Log IC50−X)*HillSlope)) where X is the logarithm of concentration and Y is the % specific binding. The IC$_{50}$ is the sample concentration that produces 50% inhibition of specific binding.

TABLE 7

Stock concentrations used in CRP binding assays
Assay conditions for both HTS and IC$_{50}$ Assays

| | Working Solution Con. | Final Assay Con. |
|---|---|---|
| Biotin labeled CRP | 784 nM | 6.12 nM |
| Recombinant LOX1 | 39.2 µM | 0.11 µM |
| Europium Labeled Streptavidin | 0.1 mg/mL | 0.1 µg/mL |
| Purified scFv/IgG samples for IC$_{50}$ analysis | Serial 1 + 1 dilution of purified proteins over 24 points | 50% |

Assay 4—LOX1:oxLDL Internalization Assay

Saturation Binding Curve

Cypher 5E labeled oxLDL (40:1 Molar ratio at 1 mg/mL) was diluted 1:50 in HBSS and titrated across a 384 well plate using a 1+1 serial dilution over 16 points in triplicate. For the determination of total binding, 10 µL of HBSS was added to all wells, followed by the addition of 10 µL of human LOX1 transfected CHO TREX cells (4000 cells per well). For the determination of nonspecific binding, 10 µL of HBSS was replaced by 104, of unlabeled oxLDL (1 mg/mL).

The assay plate was incubated for 1 hour at 37° C. A parallel experiment was performed where all reagents are kept at 4° C. in order to demonstrate that internalization was a metabolically active process. Following incubation, plates were read on an Applied Biosystems 8200 cellular detection system (FMAT plate reader) using PMT1 setting of 422 with a minimum count set to 10; Colour<0.4 and FL1<5600. Specific binding was determined by subtracting the mean total binding signal from the mean non-specific binding signal and plotting the resulting binding isotherm in Prism Graphpad software using a one site specific binding algorithm. The calculated concentration at which K$_D$ was determined, was used for subsequent high-throughput screening and antibody competition experiments.

Evaluation of Anti-hLOX1 Monoclonal Antibodies

The competition between anti-LOX1 antibodies and Cypher5E labeled ox-LDL for internalization in CHO TREX cells expressing LOX1 receptor was performed as follows.

Competitor antibodies were used without any pre-dilution and were titrated across a 384 well plate using a 1+1 serial dilution in assay buffer (HBSS) over 24 points in duplicate (10 µL per well). Dylight 649 labeled ligands (at their respective K$_D$ concentrations) were added to all antibody containing wells (10 µL per well) followed by the addition of human LOX1 transfected CHO TREX cells (4000 cells per well in 10 µL) or K167N SNP transfected CHO TREX cells.

The assay plates were incubated for 1 hour at room temperature. Following incubation, plates were read on an Applied Biosystems 8200 cellular detection system (FMAT plate reader) using PMT1 setting of 422 with a minimum count set to 10. Colour<0.4 and FL1<5600. The data was analyzed using a 4-parameter logistic equation with GRAPHPAD™ Prism version 5 (GraphPad Inc, California)

to determine apparent $IC_{50}$ values. Y=Bottom+(Top-Bottom)/(1+10^((Log IC50−X)*HillSlope)) where X is the logarithm of concentration and Y is the % specific binding. The $IC_{50}$ is the sample concentration that produces 50% inhibition of specific binding.

TABLE 8

Stock concentrations used in oxLDL Internalization assays
Assay conditions for both HTS and $IC_{50}$ Assays

| | Working Solution Con. | Final assay Con. |
|---|---|---|
| Cypher5E labeled oxLDL | 9.6 nM | 3.2 nM |
| Human LOX1 transfected CHO TREX cells | 4 × 10⁵ cells/mL | 4000 cells per well |
| Purified scFv/IgG samples for $IC_{50}$ analysis | Serial 1 + 1 dilution of purified proteins over 24 points | 30% |

Assay 5—ROS Induction in Recombinant CHO-LOX1 Cells

Preparation of Cells

Human LOX1 transfected CHO TREX cells were induced 24 hours prior to conducting experiments with a 1 µg/mL (final concentration) of doxycycline. On the day of the experiment, cells were scraped and centrifuged for 5 minutes at 1200 rpm. Supernatant was discarded and the cell pellet was re-suspended in 50 mLs of PBS and centrifuged at 1200 rpm for 5 minutes. This procedure was repeated twice. Supernatant was discarded and the cell pellet was re-suspended in 5 mLs of HBSS. Cells were counted on a haemocytometer using the Trypan Blue exclusion method. The number of cells was adjusted to give $4\times10^5$ cells total. Cells were kept on ice until use.

Saturation Binding Curve

Cypher 5E labeled oxLDL (40:1 Molar ratio at 1 mg/mL) was diluted 1:50 in HBSS and titrated across a 384 well plate using a 1+1 serial dilution over 16 points in triplicate. For the determination of total binding, 10 µL of HBSS was added to all wells, followed by the addition of 10 µL of human LOX1 transfected CHO TREX cells (4000 cells per well). For the determination of nonspecific binding, 10 µL of HBSS was replaced by 10 µL of unlabeled oxLDL (1 mg/mL).

The assay plate was incubated for 1 hour at 37° C. A parallel experiment was performed where all reagents were kept at 4° C. in order to demonstrate that internalization was a metabolically active process.

Following incubation, plates were read on an Applied Biosystems 8200 cellular detection system (FMAT plate reader) using PMT1 setting of 422 with a minimum count set to 10; Colour<0.4 and FL1<5600.

Specific binding was determined by subtracting the mean total binding signal from the mean non-specific binding signal and plotting the resulting binding isotherm in Prism Graphpad software using a one site specific binding algorithm. The calculated concentration at which $K_D$ was determined, was used for subsequent high-throughput screening and antibody competition experiments.

CHO-TREx-LOX1 transfected cells were seeded in assay plates at 7000 cells/well (100 l/well in media+10% FCS (tetracycline free)), and incubated overnight 37° C., 5% $CO_2$. The following day doxycycline was added at a final concentration of 50 ng/ml per well in order to induce LOX expression and plates were incubated overnight at 37° C. in a 95% $O_2$/5% $CO_2$ atmosphere. For each screening experiment three separate plates were prepared, and the anti-LOX antibodies were run in triplicates with one replicate per plate. The following day, the anti LOX1 antibodies were prepared by serially diluting the antibodies in warm cell culture media as 2× concentrated solutions in a separate dilution plate. All media was removed from the assay plates, and 25 µL aliquots of a dilution series of the anti-LOX1 antibodies (2× concentrated solution) were added to each well of the assay plate and incubated for 20 min at 37° C., in a 95% $O_2$/5% $CO_2$ atmosphere. This was followed by the addition of 25 µL per well of oxLDL (at a fixed final concentration of 25 µg/ml) and plates were incubated for 60 min at 37° C. in 95% $O_2$/5% $CO_2$.

Wells were then washed carefully with 1×100 µl warm HBSS/Ca/Mg and 50 µl/well of carboxy-$H_2$DCFDA (1.5 µM in warm HBSS/Ca/Mg) was thereafter added, and assay plates were incubated for 30 minutes. During the last 5 min of incubation with carboxy-$H_2$DCFDA, cells were counter stained with Hoechst stain (final concentration of 8.3 µg/ml) in warm HBSS/Ca/Mg, by adding 10 µl 50 µg/ml Hoechst in warm HBSS/Ca/Mg to the carboxy-$H_2$DCFDA already present in the wells.

Assay plates were then washed 2× with warm HBSS+Ca/Mg and read immediately on an Arrayscan high content plate reader (ThernoFischerScientific, Cellomics) using XF53-Hoechst (Ch1) and XF53-FITC (Ch2) settings. For image analysis, the Compartemental BioApplication Algorithm was used, and the fluorescence generated by the ROS probe was quantified by the CircSpotAvgIntensity parameter. The competitive data, and resulting IC50s were plotted and calculated in ExcelFit v.5.1 using a sigmoidal dose-response one-site-zero model using a 4 parameter logistic model (Model 903).

Assay 6—LOX1 Specificity ELISAs

The IgG specificity ELISAs were performed essentially as follows on the LOX1 and LOX1-related molecules listed in Table 9 below. MAXISORB™ (NUNC) plates were coated with antigen at 5 µg/mL in PBS and incubated over night at 4° C., except 10 µg/mL was used for human SR-B3. Plates were washed 3× with PBS and blocked with 200 µL/well blocking buffer (PBS+3% dried milk) for 1 hour. After plates were washed 3× with PBS, IgGs were diluted to 0.2 µg/mL in blocking buffer, added at 50 µL/well, and 1 incubated for 1 hour. Plates were then washed 3× with PBS-Tween, the detection reagent (anti-human IgG lambda light chain peroxidase conjugate (Sigma A5175, diluted at 0.23 µg/mL) or kappa light chain (Sigma A7164, diluted at 0.8 µg/mL)) was added (50 µL/well in blocking buffer), and plates were incubated for 1 hour. Plates were washed 3× with PBS-Tween, 50 µL/well of TMB was added, and the plates were left to develop for 5-15 minutes. The reaction was quenched with 50 µL/well 0.1M $H_2SO_4$, and plates were read on an ENVISION™ plate reader, or similar equipment, at 450 nm.

TABLE 9

Reagents used in LOX1 specificity ELISAs

| Reagent | Supplier | Catalogue |
|---|---|---|
| Human HisFlag tagged LOX1 | MedImmune | N/A |
| Human CLEC-7A (Dectin-1) | R&D Systems | 1859-DC |
| Human CLEC-1A | R&D Systems | 1704-CL |
| Human CLEC-4L (DC-SIGN) | R&D Systems | 161-DC |
| Human CLEC-1B (CLEC-2) | R&D Systems | 1718-CL |
| Human SR-A1 (MSR) | R&D Systems | 2708-MS |
| Human SR-B3 (CD36) | R&D Systems | 1955-CD |

Assay 7—Epitope Competition

LOX514 and LOX696 were labeled with DyLight 649 as described above in the protein modifications section and used as competitor molecules for both high throughput screening and profiling alongside ligand binding assays. Labeled antibodies were used at several concentrations above their respective $K_D$ concentrations in order to make it more difficult for higher affinity unlabeled antibodies to compete against.

Determining the $K_D$ of DyLight 649 Labeled LOX514 and LOX696

Dylight 649 labeled human anti-LOX1 antibodies were diluted 1:50 in HBSS and titrated across a 384 well plate using a 1+1 serial dilution over 16 points in triplicate. For the determination of total binding, 10 μL of HBSS was added to all wells, followed by the addition of 10 μL of human LOX1 transfected CHO TREX cells (4000 cells per well). For the determination of nonspecific binding, 10 μL of HBSS was replaced by 10 μL of unlabeled human anti-LOX1 antibody (1 mg/mL).

The assay plate was incubated for 1 hour at room temperature.

Following incubation, plates were read on an Applied Biosystems 8200 cellular detection system (FMAT plate reader) using PMT1 setting of 422 with a minimum count set to 10; Colour<0.4 and FL1<5600.

Specific binding was determined by subtracting the mean total binding signal from the mean non-specific binding signal and plotting the resulting binding isotherm in Prism Graphpad software using a one site specific binding algorithm. Antibodies were used at multiples over and above the calculated $K_D$ concentration.

TABLE 10

Stock concentrations for LOX514 and LOX696 epitope competition assays
Assay conditions for both HTS and $IC_{50}$ Assays

|  | $K_D$ | Final assay concentration (x$K_D$) |
|---|---|---|
| DyLight 649 labeled LOX10514 | 0.8 nM | 6.5 nM (×8) |
| DyLight 649 labeled LOX10696 | 3.3 nM | 20.8 nM (×6.3) |
| Human LOX1 transfected CHO TREX cells | 4 × 10⁵ cells/mL | 4000 cells per well |
| Peri-prep material for HTS (oxLDL binding assay) | 100% | 30% |
| Purified scFv/IgG samples for $IC_{50}$ analysis | Serial 1 + 1 dilution of purified proteins over 24 points | 30% |

Example 11—Effects of Anti-LOX1 Antibodies on Endothelial Lipid Uptake, Cell Signaling and Nitric Oxide Homeostasis in Tissue Culture and in Human Blood Vessels The LOX1 receptor acts as one of the proximate causes of the atherogenic process by specific ligation and internalization of OxLDL with subsequent activation of multiple intracellular signal transduction cascades. See, e.g., Twigg et al., *Cardiol Res Pract.* 2012: 632408 (2012). Activation of the LOX1 receptor in endothelial cells contributes to endothelial dysfunction including increased ROS production and impaired nitric oxide (NO) signaling induced, in part, by arginase 2 upregulation. (See, e.g., Ryoo et al., *Atherosclerosis* 214(2):279-287 (2011), Ryoo et al., *Circ Res.* 102(8): 923-932 (2008); and Ryoo et al., *Circ Res.* 99(9):951-60 (2006). Additionally, LOX1 receptor activation leads to initiation and perpetuation of an inflammatory process in the vascular wall with increased cytokine production and adhesion molecule expression. The development of a biological inhibitor of the LOX1 receptor would therefore likely be an effective way of attenuating the development of the atherogenic process. Here, we demonstrate that LX5140110, blocks uptake of OxLDL by human aortic endothelial cells (HAECs) in a dose-dependent manner. Additionally, LX5140110 prevents arginase 2 activation, a process previously demonstrated to be LOX1 dependent. Furthermore, LX5140110 prevents an Ox-LDL-dependent decrease in NO production and increase in superoxide (ROS) production. Additionally, using an NFkB luciferase reporter construct, we demonstrate that LX5140110 significantly attenuates the activation of NFkB—a master inflammatory regulator in atherogenesis. See, e.g., Pamukcu et al., *Thrombosis Res.* 128(2):117-23 (2011). Finally, the LX5140110 antibody prevents the phosphorylation and activation of Focal Adhesion Kinase (FAK), a process critical in barrier function in endothelial cells. Thus, we show that LX5140110 blocks a number of LOX1-dependent processes that lead to activation of the endothelium and initiate and promote atherogenesis. The results of these experiments are discussed in turn.

A. LX5140110 Blocks the Uptake of OxLDL in HAECs (FIG. 9A)

Methods:

OxLDL Conjugation with Alexa Fluor-568

500 microliters of human oxidized LDL (1 mg/ml, Intracel, Frederick, Md.) was labeled with Alexafluor-568 using the Alexafluor-568 protein labeling kit (Molecular probes, Eugene, Oreg.) following the manufacturer's protocol. Briefly, OxLDL was incubated with Alexafluor-568 in 0.1 M bicarbonate (pH 8.3) at room temperature for one hour. Alexafluor-568-conjugated-OxLDL was then purified with purification resin column.

Alexa Fluor-568-Conjugated-OxLDL Uptake by HAEC

HAEC were seeded onto fibronectin-coated (10 μg/ml) coverslips for eight hours in serum-containing media before serum starvation for 18 hours.

Cells were then incubated with 0, 0.5, 1, 5, or 10 nM of LX5140110 (("514") or 10 nM of control antibody NIP for one hour in serum free media. Antibody was washed off completely with fresh serum-free media before approximately 50 ng/ml of AlexaFluor568-OxLDL was added to the media for uptake for one hour. Cells were then permeabilized for 2 min with 0.5% Triton X-100 (Fisher Scientific) in 3% paraformaldehyde (Sigma) followed by fixation with 3% paraformaldehyde for 20 min. Fixed cells were labeled with fluorescein phalloidin (Life Technologies, Grand Island, N.Y.) and DAPI (Life Technologies) and were observed on an epifluorescence Nikon TE-200 microscope. Images were captured with a Rolera EMCCD camera (QImaging, Vancouver, Canada) with Volocity software (PerkinElmer, Lexington, Mass.). Images were further analyzed with Volocity software by counting the Alexafluor-568-conjugated-OxLDL red fluorescent particles (exclusion of particles with size smaller than 0.1 μm2) inside HAEC cells (images not shown). Approximately 12 images for each set were acquired and analyzed for the average number of Alexafluor-568-conjugated-OxLDL red fluorescent particles in each cell. Dose response data are shown in FIG. 9A (number of vesicles per cell with standard derivation). As shown in FIG. 9A, 5 nM or 10 nM LX5140110 significantly inhibited OxLDL uptake by HAECs (p=0.0003 or p=0.0002, respectively).

B. LX5140110 Attenuates NFkB Signaling in HAECs (FIG. 9B)

Methods: Confluent 6 well plates of HAECs that were co-expressing NFκB-LUCIFERASE and GFP were serum starved for 24 hours before they were subjected to following conditions (numbers indicate the bars in FIG. 9B from left to right): 1. Control; 2. OxLDL alone (50 µg/ml); 3. OxLDL+LX5140110 ("514") (10 nM); 4. OxLDL+NIP (control antibody) (10 nM).

Antibodies were added 1 hour before OxLDL (50 µg/ml). The incubation with OxLDL was for an additional 8 hours. Cells were lysed and subjected to a Luciferase activity assay (Promega), and luminescence was determined with a FlexStation 3 microplate reader (Molecular Devices). Briefly, HAECs were lysed with Promega 5× lysis buffer and supernatants were plated in white plate containing 50 µl of Promega substrate in each well. 48 hours after transfection, cells were lysed in ice-cold modified lysis buffer consisting of 20 mM Tris-HCl at pH 7.5, 150 mM NaCl, 1 mM EDTA, 1 mM EGTA, 1% NP40, 1% sodium deoxycholate, 1 mM $Na_3VO_4$, 2.5 mM sodium pyrophosphate, 1 mM β-glycerophosphate, 1 µg/mL leupeptin, and 1:1000 diluted protease inhibitor cocktail (Sigma). Loading buffer was added to a final concentration of 2×, boiled for 5 min, spun for 3 minutes and loaded in a gel. GFP fluorescence was used as normalization control. N=5 for each group; * indicates P<0.05 (compared with untreated control); # indicates P<0.05 (compared with OxLDL+0 nM ab 514 (LX5140110). As shown in FIG. 9B, addition of 10 mM LX5140110, but not NIP (control antibody), significantly reduced OxLDL-dependent NFkB signaling in HAECs. This suggests that LX5140110 is capable of inhibiting LOX1-dependent NFkB activation, a signaling pathway that is well established to be downstream of the LOX-1 receptor. See, e.g., Zhao W, et al., "Lipopolysaccharide induced LOX-1 expression via TLR4/MyD88/ROS activated p38MAPK-NF-κB pathway." Vascul Pharmacol. (2014).

C. LX5140110 Inhibits the Activation of Arginase in HAEC (FIG. 9C)

Methods: Confluent 6 well plates of HAEC were serum-starved for 24 hours before they were subjected to following conditions (numbers indicate the bars in FIG. 9C from left to right): 1. Control; 2. OxLDL (50 µg/ml); 3. OxLDL+LX5140110 ("514") (1 nM); 4. OxLDL+LX5140110 ("514") (3 nM); 5. OxLDL+LX5140110 ("514") (10 nM); 6. OxLDL+NIP (10 nM). Antibodies were added 1 hour before HAEC were incubated in OxLDL (50 µg/ml) for another 3 hours. Cells were lysed and arginase activity was determined using the urea assay using α-isonitrosopropiophenone. Briefly, supernatants of extracted cell lysates were prepared following incubation with lysis buffer (50 mM Tris-HCl, pH7.5, 0.1 mM EDTA and protease inhibitors) for 30 min at 4° C. and centrifugation for 20 minutes at 14,000×g at 4° C. Supernatants were then incubated with 150 mM L-arginine for 1 hour at 37° C. After 1 hour the reaction was stopped using 400 µl acid solution mixture (H2SO:H3PO4:H2O 1:3:7) and then 25 µl 9% α-isonitrosopropiophenone (in 100% EtOH) was added and heated for 30 min 95° C., and read after 10 min at 540 nm. N=3 for each group; * indicates that P<0.05 as compared with untreated controls; # indicates that P<0.05 as compared with 0 nM ab 514 (LX5140110). As shown in FIG. 9C, addition of 3 nM or 10 nM LX5140110, but not 10 nM NIP (control antibody), significantly reduced OxLDL-dependent arginase activity in HAECs in a dose-dependent manner. This further suggests that LX514110 inhibits LOX1-dependent activation of arginase 2, a downstream signaling pathway that has recently been shown to be coupled to LOX-1 in vascular endothelium. See, e.g., Ryoo et al., Atherosclerosis 214:279-87 (2011).

D. LX5140110 Blocks OxLDL-Dependent Reduction in Nitric Oxide Production (FIG. 9D)

Methods: NO production was determined using DAF fluorescence. Briefly, to measure NO, HAEC cells were plated into white 96-well plates (ThermoLabsystems) at a density of approximately 5×104 cells per well and serum-starved (1% serum) overnight. Cells investigated in 7 experimental groups (numbers indicate the bars in FIG. 9D from left to right): 1. Control; 2. OxLDL (50 µg/ml); 3. OxLDL+LX5140110 ("514") (0.5 nM); 4. OxLDL+LX5140110 ("514") (1 nM); 5. OxLDL+LX5140110 ("514") (5 nM); 6. OxLDL+LX5140110 ("514") (10 nM); 7. OxLDL+NIP (10 nM). Antibodies were added 1 hour before HAEC were incubated in OxLDL (50 µg/ml) for 24 hours. Medium was then removed and the cells were placed at 37° C. in EBM2 media containing DAF-FM DA (504) for 30 min at 37° C. Medium was then replaced with fresh media and the cells were incubated for another 20 min prior to measuring total fluorescence with a FlexStation 3 microplate reader (Molecular Devices) at excitation 495 nm and emission 515 nm. To confirm that NO was produced by eNOS, the NOS inhibitor L-NAME was used as a control (data not shown). N=5 for each group; * indicates that P<0.05 (compared with untreated control). As shown in FIG. 9D, addition of 5 nM or 10 nM LX5140110, but not 10 nM NIP (control antibody), significantly inhibited in a dose-dependent manner OxLDL-dependent reduction in nitric oxide production of HAECs.

E. LX5140110 Blocks OxLDL-Dependent Increases in ROS Production (FIGS. 9E and 9F)

Methods: Superoxide production was determined using the Luminol analog L-012. To measure superoxide (ROS), HAEC cells were plated into white TC-treated 96-well plates (ThermoLabsystems) at a density of approximately $5 \times 10^4$ cells per well and serum starved (1% serum) for overnight. The 7 study populations were as follows (numbers indicate the bars in FIG. 9E from left to right): 1. Control; 2. OxLDL (50 µg/ml); 3. OxLDL+LX5140110 ("514") (0.5 nM); 4. OxLDL+LX5140110 ("514") (1 nM); 5. OxLDL+LX5140110 ("514") (5 nM); 6. OxLDL+LX5140110 ("514") (10 nM); 7. OxLDL+NIP (10 nM). Antibodies were added 1 hour before HAEC were incubated in OxLDL (50 µg/ml) for 24 hours. Medium was then removed and the cells were further incubated at 37° C. in phenol free DMEM (Sigma) containing 400 µM of the luminol analogue L-012 (Wako) for a minimum of 20 minutes prior to the addition of agonists. Luminescence was quantified over time using a FlexStation 3 microplate reader (Molecular Devices). The specificity of L-012 for reactive oxygen species was confirmed by co-incubation with the superoxide scavenger SOD (5 mM), and this yielded virtually undetectable levels of luminescence under control or OxLDL-stimulated conditions (see FIG. 9F). Relative light units (RLU) quantified from the luminescence of L-012 therefore indicate changes in production of superoxide. To confirm that superoxide was produced by eNOS, the NOS inhibitor L-NAME was used as a control. N=5 for each group. As shown in FIGS. 9E and 9F, addition of 0.5 nM, 1 nM, 5 nM or 10 nM LX5140110, but not 10 nM NIP (control antibody), inhibited OxLDL-dependent ROS production in HAECs. Thus, LX5140110 prevents OxLDL-mediated eNOS uncoupling and subsequent increase in ROS production by preventing LOX-1 activation and downstream activation of arginase 2. See, e.g., Ryoo et al., Atherosclerosis 214:279-87 (2011).

F. LX5140110 Blocks OxDL Mediated Phosphorylation of Focal Adhesion Kinase (FAK), Y397 (FIGS. 9G and 9H).

Methods: HAECs were cultured with ECM media (ScienCell, Carlsbad, Calif.) with 5% serum for one day before serum-starvation for 18 hours. LX5140110 or the control antibody NIP was then added to cells at the concentration indicated in FIG. 9G and incubated for one hour. Cells were washed with fresh media to remove antibodies before they were incubated with 50 µg/ml of OxLDL for one hour. Cells were washed with ice-cold PBS buffer and then protein was extracted using modified RIPA buffer (0.1% DOC, 0.1% Trition X-100, 2 mM EDTA, 1 mM PMSF, 2 mM sodium vanadate, 20 mg/ml leupeptin, and 20 mg/ml aprotinin in PBS). Cell lysates were clarified by centrifugation at 15,000×g at 4° C. for 10 minutes. Protein concentration was then quantified by the bicinchoninic assay (Pierce, Rockford, Ill.). 10 µg of protein lysates were mixed with 2× Laemmli sample buffer, boiled, and then subjected to SDS-PAGE using 4-15% gradient polyacrylamide gels, followed by transfer to nitrocellulose membranes for Western blotting.

Primary antibodies used in the experiments described in FIGS. 9G and 9H include anti-pY397-FAK (rabbit polyclonal, Life Technologies, Grand Island, N.Y.) and anti-GAPDH (mouse monoclonal, Novus Biologicals, Littleton, Colo.). Horseradish peroxidase-conjugated anti-mouse and anti-rabbit secondary antibodies were obtained from ICN Biochemicals, Inc. (Costa, Mesa, Calif.).

A Student t-test was used to analyze the differences in FAK phosphorylation on Tyr397 in control, OxLDL-treated, and antibody-preincubated cells. P values are supplied in FIG. 9H and significance (*) was adjudged to be present at p values less than 0.05 for all data. The figures include standard error bars. A representative blot showing changes in FAK phosphorylation at Tyr397 and expression of GAPDH in HAECs is shown in FIG. 9G, while quantification of the percentage increase of FAK phosphorylation at Tyr397 (pY397-FAK) normalized to GAPDH expression is shown in FIG. 9H. These results demonstrate that addition of 5 nM or 10 nM LX5140110, but not 10 nM NIP (control antibody), significantly inhibited OxLDL-dependent mediated FAK phosphorylation at Tyr397 in HAECs. * indicates that $P<0.05$ (compared with untreated control); # indicates that $P<0.05$ as compared with 0 nM LX5140110 (514). This data suggests that LX5140110 inhibits OxLDL-mediated induction of LOX-1 dependent FAK phosphorylation, a process that regulates endothelial cytoskeletal functions including cell-cell and cell-matrix adhesion with subsequent effects on endothelial barrier function.

G. LOX1 is the Primary Receptor Responsible for OxLDL Signaling in HAECs (FIGS. 9I, 9J and 9K).

Methods: Construction of LOX1 shRNA Adenoviruses:

Ad-shNontargeted- and Ad shLOX1-encoded viruses were generated using a pAdBLOCK-iT kit (Life Sciences). Briefly, oligonucleotides that were nontargeted, and other targeting 5'UTR region of Human LOX1 were designed with proprietary software from Life Sciences and cloned into pU6-ENTR. Sequences used were as follows. Non targeted: Top, 5'-CAC CGA TGG ATT GCA CGC AGG TTC TCG AAA GAA CCT GCG TGC AAT CCA TC-3' (SEQ ID NO:79); Bottom, 5'-AAA AGA TGG ATT GCA CGC AGG TTC TTT CGA GAA CCT GCG TGC AAT CCA TC-3' (SEQ ID NO:80). LOX1sh: Top, 5'-CAC CGC TTC ACT CTC TCA TTC TTA GCG AAC TAA GAA TGA GAG AGT GAA GC-3' (SEQ ID NO:81); Bottom, 5'-AAA AGC TTC ACT CTC TCA TTC TTA GTT CGC TAA GAA TGA GAG AGT GAA GC-3' (SEQ ID NO:82).

The resulting pU6-sh-Nontargeted and pU6-LOX1shRNA plasmids were tested for function in transient transfection experiments with HAEC cells. The constructs showing the greatest inhibition were recombined with pAD/BLOCK-iTDEST (Invitrogen) to generate pAd-Nontargeted and Ad-shLOX1. Viruses were amplified, purified, and concentrated using a Millipore Kit.

To confirm that LOX1 is necessary for OxLDL signaling in HAECs, LOX1 RNA expression was inhibited using a viral vector expressing interfering short hairpin RNAs (shRNA) directed to the 5'UTR region of the human LOX1 gene (LOX1shRNA). Briefly, 60 percent confluent HAECs were transduced with 25 MOI (multiplicity of infection, a measure of virulence) of adenovirus expressing LOX1shRNA ("LOX1-shRNA" or "Ad-LOX-1shRNA"). 24 hours later, media was replaced with low serum media (1%) containing NFKB-LUC encoding viruses. The day after viral transduction, cells were treated with 50 µg/mL of OxLDL and incubated for an additional 8 hours, followed by luciferase activity measurement by chemiluminescence. Cell lysates were then subjected to immunoblotting with anti-Lox-1 or anti-GAPDH antibodies. As shown in FIGS. 9J and 9K, addition of LOX1shRNA significantly reduced LOX1 protein expression (see, e.g., lane 3 of FIG. 9J as compared to lanes 1 and 2) confirming that LOX1shRNA effectively inhibited LOX1 expression in HAECs. In addition, as shown in FIG. 9I, AdshLOX1 significantly inhibited OxLDL-mediated NFkB signaling in HAECs compared to cells incubated with OxLDL and a control, non-targeted shRNA (Ad-NTsh) construct. * indicates $P<0.05$ (compared with untreated control); # indicates $P<0.05$ as compared with OxLDL+Ad-NTsh.

A summary of signaling pathways involved in LOX1 receptor signaling and blocked by the anti-LOX1 antibodies disclosed herein (including e.g. LX5140110; "514 Ab") is shown in FIG. 10.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

All publications, patents, patent applications, and/or other documents cited herein are incorporated by reference in their entirety for all purposes to the same extent as if each individual publication, patent, patent application, and/or other document were individually indicated to be incorporated by reference for all purposes.

The invention claimed is:

1. An isolated Lectin-like oxidized low density lipoprotein receptor-1 (LOX1) antibody comprising a set of complementary determining regions (CDRs): heavy chain variable region (VH)-CDR1, VH-CDR2, VH-CDR3, and light chain variable region (VL)-CDR1, VL-CDR2 and VL-CDR3, wherein:
   (a) (i) VH-CDR1 has the amino acid sequence of SEQ ID NO:1;
      (ii) VH-CDR2 has the amino acid sequence of SEQ ID NO:2;
      (iii) VH-CDR3 has the amino acid sequence of SEQ ID NO:3;
      (iv) VL-CDR1 has the amino acid sequence of SEQ ID NO:30;
      (v) VL-CDR2 has the amino acid sequence of SEQ ID NO:31; and
      (vi) VL-CDR3 has the amino acid sequence of SEQ ID NO:32;
   (b) (i) VH-CDR1 has the amino acid sequence of SEQ ID NO:1;
      (ii) VH-CDR2 has the amino acid sequence of SEQ ID NO:5;
      (iii) VH-CDR3 has the amino acid sequence of SEQ ID NO:14;
      (iv) VL-CDR1 has the amino acid sequence of SEQ ID NO:30;
      (v) VL-CDR2 has the amino acid sequence of SEQ ID NO:31; and
      (vi) VL-CDR3 has the amino acid sequence of SEQ ID NO:32;
   (c) (i) VH-CDR1 has the amino acid sequence of SEQ ID NO:38;
      (ii) VH-CDR2 has the amino acid sequence of SEQ ID NO:39;
      (iii) VH-CDR3 has the amino acid sequence of SEQ ID NO:44;
      (iv) VL-CDR1 has the amino acid sequence of SEQ ID NO:55;
      (v) VL-CDR2 has the amino acid sequence of SEQ ID NO:60; and
      (vi) VL-CDR3 has the amino acid sequence of SEQ ID NO:61; or
   (d) (i) VH-CDR1 has the amino acid sequence of SEQ ID NO:38;
      (ii) VH-CDR2 has the amino acid sequence of SEQ ID NO:39;
      (iii) VH-CDR3 has the amino acid sequence of SEQ ID NO:40;
      (iv) VL-CDR1 has the amino acid sequence of SEQ ID NO:55;
      (v) VL-CDR2 has the amino acid sequence of SEQ ID NO:56; and
      (vi) VL-CDR3 has the amino acid sequence of SEQ ID NO:57.

2. The isolated LOX1 antibody of claim 1, wherein the LOX1 antibody comprises a heavy chain variable region (VH) and a light chain variable region (VL) selected from the group consisting of:
   (a) a VH having the amino acid sequence of SEQ ID NO:4 and a VL having the amino acid sequence of SEQ ID NO:33;
   (b) a VH having the amino acid sequence of SEQ ID NO:29 and a VL having the amino acid sequence of SEQ ID NO:33;
   (c) a VH having the amino acid sequence of SEQ ID NO:41 and a VL having the amino acid sequence of SEQ ID NO:58 and
   (d) a VH having the amino acid sequence of SEQ ID NO:54 and a VL having the amino acid sequence of SEQ ID NO:70.

3. The isolated LOX1 antibody of claim 2, wherein the LOX1 antibody comprises a heavy chain variable region (VH) comprising SEQ ID NO:4 and a light chain variable region (VL) comprising SEQ ID NO:33.

4. The isolated LOX1 antibody of claim 1, wherein the LOX1 antibody reduces, inhibits or antagonizes LOX1 activity.

5. The isolated LOX1 antibody of claim 1, wherein the antibody is a monoclonal antibody, a recombinant antibody, a human antibody, a humanized antibody, a chimeric antibody, a bi-specific antibody, a multi-specific antibody, or a LOX1-binding antibody fragment.

6. The isolated LOX1 antibody of claim 5, wherein the LOX1-binding antibody fragment is selected from the group consisting of a Fab fragment, a Fab' fragment, a F(ab')2 fragment, a Fv fragment, a diabody, or a single chain antibody molecule.

7. The isolated LOX1 antibody of claim 1, wherein the LOX1 antibody further comprises a heavy chain immunoglobulin constant domain selected from the group consisting of:
   (a) a human IgA constant domain
   (b) a human IgD constant domain;
   (c) a human IgE constant domain;
   (d) a human IgG1 constant domain;
   (e) a human IgG2 constant domain;
   (f) a human IgG3 constant domain;
   (g) a human IgG4 constant domain; and
   (h) a human IgM constant domain.

8. The isolated LOX1 antibody of claim 1, wherein the LOX1 antibody further comprises a light chain immunoglobulin constant domain selected from the group consisting of:
   (a) a human Ig kappa constant domain; and
   (b) a human Ig lambda constant domain.

9. The isolated LOX1 antibody of claim 1, wherein the LOX1 antibody further comprises a human IgG1 heavy chain constant domain and a human lambda light chain constant domain.

10. The isolated LOX1 antibody of claim 9, wherein the IgG1 heavy chain constant domain contains a mutation at positions 234, 235 and 331, wherein the position numbering is according to the EU index as in Kabat.

11. The isolated LOX1 antibody of claim 10, wherein the IgG1 heavy chain constant domain contains the mutations L234F, L235E and P331S, wherein the position numbering is according to the EU index as in Kabat.

12. An isolated nucleic acid molecule or set of nucleic acid molecules encoding a LOX1 antibody according to claim 1.

13. A vector comprising the nucleic acid molecule according to claim 12.

14. A pharmaceutical composition comprising a LOX1 antibody according to claim 1 and a pharmaceutically acceptable carrier.

15. A method for treating, preventing and/or ameliorating a cardiovascular disease or condition associated with LOX1 in a subject, comprising administering to a subject in need thereof an effective amount of a composition comprising a LOX1 antibody of claim 1.

16. The method of claim 15, wherein the cardiovascular disease or condition is selected from the group consisting of atherosclerosis, thrombosis, coronary artery disease (CAD), ischemia, infarction, acute coronary syndrome (ACS), stroke, reperfusion injury, restenosis, peripheral vascular disease, hypertension, heart failure, and angiogenesis.

17. A method of reducing or inhibiting LOX1 activity in a subject having a cardiovascular disease or condition associated with LOX1 comprising administering an effective amount of a LOX1 antibody according to claim 1.

18. A method for treating, preventing and/or ameliorating a cardiovascular disease or condition associated with LOX1 in a subject, comprising administering to a subject in need thereof an effective amount of a composition comprising a LOX1 antibody of claim 3.

19. The method of claim 18, wherein the cardiovascular disease or condition is selected from the group consisting of atherosclerosis, thrombosis, coronary artery disease (CAD), ischemia, infarction, acute coronary syndrome (ACS), stroke, reperfusion injury, restenosis, peripheral vascular disease, hypertension, heart failure, and angiogenesis.

20. A method of reducing or inhibiting LOX1 activity in a subject having a cardiovascular disease or condition associated with LOX1 comprising administering an effective amount of a LOX1 antibody according to claim 3.

* * * * *